(12) United States Patent
Purcell et al.

(10) Patent No.: US 10,863,729 B2
(45) Date of Patent: *Dec. 15, 2020

(54) **RODENTS HAVING A HUMANIZED *TMPRSS* GENE**

(71) Applicant: REGENERON PHARMACEUTICALS, INC., Tarrytown, NY (US)

(72) Inventors: Lisa Purcell, Garnerville, NY (US); Alexander O. Mujica, Elmsford, NY (US); Yajun Tang, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/052,700

(22) Filed: Aug. 2, 2018

(65) Prior Publication Data

US 2018/0332831 A1 Nov. 22, 2018

Related U.S. Application Data

(63) Continuation of application No. 15/442,857, filed on Feb. 27, 2017, now Pat. No. 10,070,632.

(60) Provisional application No. 62/301,023, filed on Feb. 29, 2016.

(51) Int. Cl.
| | |
|---|---|
| *A01K 67/027* | (2006.01) |
| *C07K 14/00* | (2006.01) |
| *C07K 14/435* | (2006.01) |
| *C07K 14/47* | (2006.01) |
| *C12N 9/00* | (2006.01) |
| *C12N 9/64* | (2006.01) |
| *C12N 15/00* | (2006.01) |
| *C12N 15/09* | (2006.01) |
| *C12N 15/63* | (2006.01) |
| *C12N 5/0735* | (2010.01) |
| *C12N 15/86* | (2006.01) |
| *A61K 48/00* | (2006.01) |

(52) U.S. Cl.
CPC ...... *A01K 67/0275* (2013.01); *A01K 67/0278* (2013.01); *C07K 14/47* (2013.01); *C12N 5/0606* (2013.01); *C12N 9/6424* (2013.01); *C12N 15/63* (2013.01); *C12N 15/86* (2013.01); *A01K 2207/15* (2013.01); *A01K 2217/072* (2013.01); *A01K 2227/10* (2013.01); *A01K 2227/105* (2013.01); *A01K 2267/0337* (2013.01); *A61K 48/00* (2013.01); *C07K 2319/00* (2013.01); *C12N 15/09* (2013.01); *C12N 2710/10332* (2013.01)

(58) Field of Classification Search
CPC ............. A01K 67/027; A01K 67/0275; A01K 67/0278; A01K 2207/00; A01K 2207/15; A01K 2217/072; A01K 2227/10; A01K 2227/105; A01K 2267/03; A01K 2267/0337; C07K 14/00; C07K 14/435; C07K 14/47; C07K 2319/00; C12N 5/06; C12N 5/0602; C12N 5/0606; C12N 9/00; C12N 9/64; C12N 9/6421; C12N 9/6429; C12N 15/00; C12N 15/09; C12N 15/63
See application file for complete search history.

(56) References Cited

U.S. PATENT DOCUMENTS

| | | | |
|---|---|---|---|
| 6,586,251 B2 | 7/2003 | Economides et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 10,070,631 B2 | 9/2018 | Purcell et al. | |
| 10,070,632 B2* | 9/2018 | Purcell | C07K 14/47 |
| 2004/0132156 A1 | 7/2004 | Parry et al. | |
| 2005/0003416 A1 | 1/2005 | Wu | |
| 2005/0022256 A1 | 1/2005 | Laferia | |
| 2005/0026255 A1 | 2/2005 | Morser et al. | |
| 2006/0101531 A1 | 5/2006 | Vasioukhin et al. | |
| 2008/0078000 A1 | 3/2008 | Poueymirou et al. | |
| 2013/0273070 A1 | 10/2013 | Purcell | |
| 2014/0235933 A1 | 8/2014 | Lee et al. | |
| 2014/0310828 A1 | 10/2014 | Lee et al. | |
| 2015/0106961 A1 | 4/2015 | Rojas et al. | |
| 2015/0143558 A1 | 5/2015 | McWhirter et al. | |
| 2015/0143559 A1 | 5/2015 | McWhirter et al. | |
| 2017/0245482 A1 | 8/2017 | Purcell et al. | |

FOREIGN PATENT DOCUMENTS

| | | |
|---|---|---|
| RU | 2 425 880 C2 | 2/2011 |
| WO | 2011/044050 A2 | 4/2011 |
| WO | 2012/112544 A2 | 8/2012 |
| WO | 2013/063556 A1 | 5/2013 |
| WO | 2013/158516 A1 | 10/2013 |
| WO | 2013/192030 A1 | 12/2013 |

(Continued)

OTHER PUBLICATIONS

NCBI NG_047085.1, 2017.*

(Continued)

*Primary Examiner* — Kevin K Hill

(74) *Attorney, Agent, or Firm* — Scully, Scott, Murphy & Presser, P.C.; Brian A. Cocca

(57) ABSTRACT

Genetically modified rodents such as mice and rats, and methods and compositions for making and using the same, are provided. The rodents comprise a humanization of at least one endogenous rodent Tmprss gene, such as an endogenous rodent Tmprss2, Tmprss4, or Tmprss11d gene.

16 Claims, 16 Drawing Sheets

Specification includes a Sequence Listing.

(56) References Cited

FOREIGN PATENT DOCUMENTS

| WO | 2014/039782 A2 | 3/2014 |
| WO | 2015/042557 A1 | 3/2015 |
| WO | 2015/196051 A1 | 12/2015 |
| WO | 2016/089692 A1 | 6/2016 |
| WO | 2016/094481 A1 | 6/2016 |
| WO | 2015/171861 A1 | 11/2016 |

OTHER PUBLICATIONS

Anderson P., "Post-Transcriptional Control of Cytokine Production", Nature Immunology 9(4):353-359 (Apr. 2008).
Bahgat M.M. et al., "Inhibition of Lung Serine Proteases in Mice: A Potentially New Approach to Control Influenza Infection", Virology Journal 8:27 (15 pagers) (2011).
Bertram S. et al., "TMPRSS2 and TMPRSS4 Facilitate Trypsin-Independent Spread of Influenza Virus in Caco-2 Cells", Journal of Virology 84(19):10016-10025 (Oct. 2010).
Bertram S. et al., "Novel Insights into Proteolytic Cleavage of Influenza Virus Hemagglutinin", Rev. Med. Virol. 20:298-310 (2010).
Bodewes R. et al., "Animal Models for the Preclinical Evaluation of Candidate Influenza Vaccines", Expert Reviews Vaccines 9(1):59-72 (2010).
Böttcher-Friebertshäuser E. et al., "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology 85(4):1554-1562 (Feb. 2011).
Böttcher-Friebertshäuser E. et al., "Cleavage of Influenza Virus Hemagglutinin by Airway Proteases TMPRSS2 and HAT Differs in Subcellular Localization and Susceptibility to Protease Inhibitors", Journal of Virology 84 (11):5605-5614 (Jun. 2010).
Böttcher E. et al., "MDCK Cells that Express Proteases TMPRSS2 and HAT Provide a Cell System to Propagate Influenza Viruses in the Absence of Trypsin and to Study Cleavage of HA and its Inhibition", Vaccine 27:6324-6329 (2009).
Böttcher E. et al., "Proteolytic Activation of Influenza Viruses by Serine Proteases TMPRSS2 and HAT from Human Airway Epithelium", Journal of Virology 80(19):9896-9898 (Oct. 2006).
Bugge T.H. et al., "Type II Transmembrane Serine Proteases", The Journal of Biological Chemistry 284 (35)23177-23181 and Supplementary Tables (Aug. 28, 2009).
Devoy A. et al., "Genomically Humanized Mice: Technologies and Promises", Nature Reviews Genetics 13:14-20 (Jan. 2012).
Guipponi M. et al., "The Transmembrane Serine Protease (TMPRSS3) Mutated in Deafness DFNB8/10 Activates the Epithelial Sodium Channel (ENaC) In Vitro", Human Molecular Genetics 11(23):2829-2836 (2002).
Hooper J.D. et al., "Type II Transmembrance Serine Proteases", The Journal of Biological Chemistry 276 (2):857-860 (Jan. 12, 2001).
Kühn N. et al., "Studies on the Host Response to Influenza A Virus Infections in Mouse Knock-Out Mutants", Thesis-University of Veterinary Medicine Hannover pp. 1-74 (2015).
Macchiarini F. et al., "Humanized Mice: Are We There Yet?", JEM 202(10):1307-1311 (Nov. 21, 2005).
MacDonald L.E. et al., "Precise and In Situ Genetic Humanization of 6 Mb of Mouse Immunoglobulin Genes", PNAS 111(14):5147-5152 (Apr. 8, 2014).
Murphy A.J. et al., "Mice With Megabase Humanization of Their Immunoglobulin Genes Generate Antibodies as Efficiently as Normal Mice", PNAS 111(4):5153-5158 (Apr. 8, 2014).
Radigan K.A. et al., "Modeling Human Influenza Infection in the Laboratory", Infection and Drug Resistance 8:311-320 (2015).
Rajagowthamee R. et al., "Animal Models for Influenza Virus Pathogenesis, Transmission, and Immunology", Journal of Immunological Methods 410:60-79 (2014).
Rongvaux A. et al., "Human Thrombopoietin Knockin Mice Efficiently Support Human Hematopoiesis In Vivo", PNAS 108(6):2378-2383 (Feb. 8, 2011).
Sun Y., "Characterization of the TMPRSS2 Protease as a Modulator of Prostate Cancer Metastasis", Defense Technical Information Center, pp. 1-12 (Mar. 2009).
Szabo R. et al., "Type II Transmembrane Serine Proteases in Development and Disease", The International Journal of Biochemistry & Cell Biology 40:1297-1316 (2008).
Tong C. et al., "Generating Gene Knockout Rats by Homologous Recombination in Embryonic Stem Cells", Nature Protocols 6(6):827-844 (Jun. 2011).
Tong C. et al., "Production of p53 Gene Knockout Rats by Homologous Recombination in Embryonic Stem Cells", Nature 467:211-215 (Sep. 2010).
Valenzuela D.M. et al., "High-Throughput Engineering of the Mouse Genome Coupled With High-Resolution Expression Analysis", Nature Biotechnology 21(6):652-659 (Jun. 2003).
Vuagniaux G. et al., "Synergistic Activation of ENaC by Three Membrane-Bound Channel-Activating Serine Proteases (mCAP1, mCAP2, and mCAP3) and Serum- and Glucocorticoid-Regulated Kinase (Sgk1) in Xenopus Oocytes", J. Gen. Physiol. 120:191-201 (Aug. 2002).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Willinger T. et al., Improving Human Hemato-Lymphoid-System Mice by Cytokine Knock-in Gene Replacement, Trends in Immunology 32(7):321-327 (Jul. 2011).
GenBank NCBI Reference Sequence No. NG_047085.1 (13 pages) (Sep. 13, 2017).
GenBank NCBI Reference Sequence No. NM_005656.3 (5 pages) (Apr. 30, 2017).
GenBank NCBI Reference Sequence No. NM_015775.2 (5 pages) (Apr. 25, 2017).
GenBank NCBI Reference Sequence No. NM_001173551.1 (5 pages) (Apr. 17, 2017).
GenBank NCBI Reference Sequence No. NM_004262.2 (4 pages) (Sep. 9, 2016).
GenBank NCBI Reference Sequence No. NM_145403.2 (4 pages) (Sep. 4, 2016).
GenBank NCBI Reference Sequence No. CH471057.1 (4 pages) (Mar. 23, 2015).
GenBank NCBI Reference Sequence No. NP_004253.1 (3 pages) (Mar. 15, 2015).
GenBank NCBI Reference Sequence No. NM_145561.2 (3 pages) (Feb. 15, 2015).
GenBank NCBI Reference Sequence No. NG_0118582 (13 pages) (May 4, 2014).
NCBI CCDS Report for TMPRSS11D, https://www.ncbi.nlm.nih.gov/CCDS/CcdsBrowse.cgi?REQUEST=CCDS&DATA=CCDS3518; downloaded Dec. 7, 2017 (2 pages).
ENSG00000153802, https://www.ensembl.org/Homo_sapiens/Gene/Summary?g=ENSG00000153802; downloaded Dec. 7, 2017 (2 pages).
International Search Report and Written Opinion dated Jun. 19, 2017 received in International Application No. PCT/US2017/019574.
Harari D. et al., "Bridging the Species Divide: Transgenic Mice Humanized for Type-I Interferon Response", PLoS ONE 9(1):e84259, XP055553720, DOI:10.1371/journal.pone.0084259 (Jan. 9, 2014).
Brevini T.A.L. et al., "No Shortcuts to Pig Embryonic Stem Cells", Theriogenology 74:544-550 (2010).
Cao S. et al., "Isolation and Culture of Primary Bovine Embryonic Stem Cell Colonies by a Novel Method", Journal of Experimental Zoology 311A:368-376 (2009).
Dennis, Jr. M.B., "Welfare Issues of Genetically Modified Animals", ILAR Journal 43(2):100-109 (2002).
Hofker M.H. et al., "Transgenic Mouse Methods and Protocols", Methods in Molecular Biology 209:51-67 (2002-2003).
Houdebine L-M, "Methods to Generate Transgenic Animals", Genetic Engineering in Livestock, New Applications and Interdisciplinary Perspectives, Engelhard M. et al., XVI, 1 46, p. 8, illu. pp. 31-47 (2009).

(56) References Cited

OTHER PUBLICATIONS

Kühn N. et al., "The Proteolytic Activation of (H3N2) Influenza A Virus Hemagglutinin is Facilitated by Different Type II Transmembrane Serine Proteases", Journal of Virology 90(9):4298-4307 (May 2016).
Paris D.B.B.P. et al., "Equine Embryos and Embryonic Stem Cells: Defining Reliable Markers of Pluripotency", Theriogenology 74:516-524 (2010).
Rybchin V.N., "Fundamentals of Genetic Engineering", Textbook for High Schools, Saint-Petersburg, Publishing House SPbSTU 522:411-413 (2002), cited in Russian Office Action dated Jul. 13, 2020 received n Russian Patent Application No. 2018131152.
Zhou H. et al., "Developing ITA Transgenic Rats for Inducible and Reversible Gene Expression", International Journal of Biological Sciences 5(2):171-181 (2009).
Russian Office Action dated Jul. 13, 2020 received in Russian Patent Application No. 2018131152, together with an English-language translation.

* cited by examiner

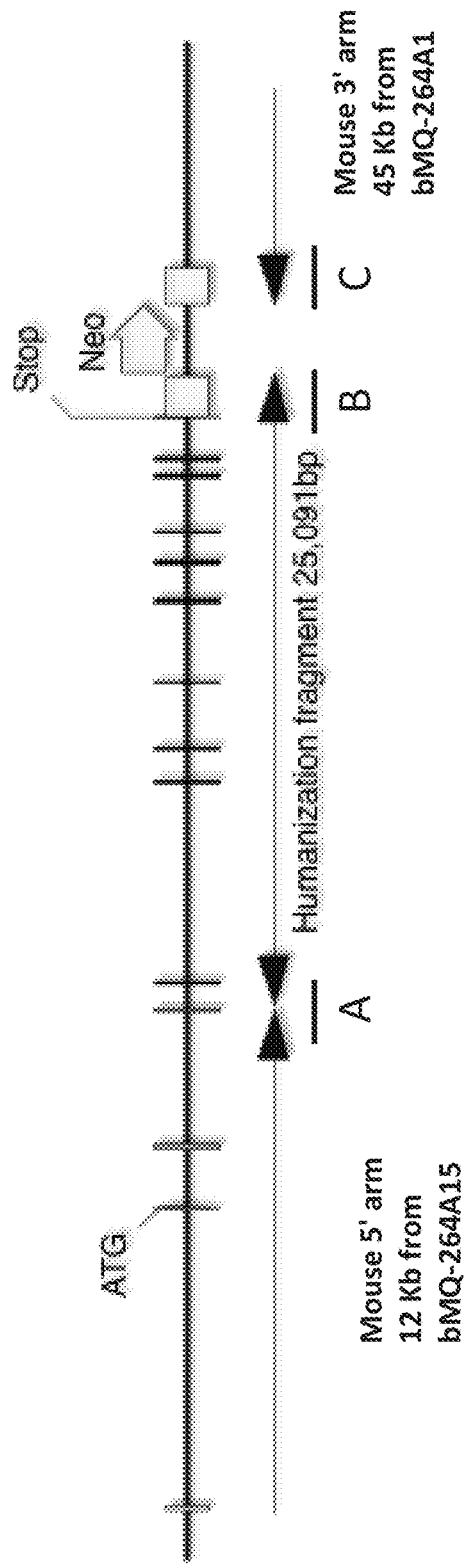

| A. 5' mouse // 5' human (SEQ ID NO:22) | AGCACCCCTC TCTTCCGCAG AGTCTAAGAA ATCGCTGTGT TTAGCCCTCG CCCTGGGCAC TGTCCTCACG GGAGCTGCTG TGGCTGCTGT CTTGCTTTGG // AAGTTCAGTA AGTGCAGGGA GCCTCGATCC CACCATGTGC TCCTGCAGTC CCCAGTGCTC TGAGCCAGAC CCTGCTCTCT GGGCTATTGA GACCTCTGGA GGCCCTCCGT GAGGTTCCTC TCTTACATAA CGAGGCTGTC TCTCTTCCCT TCTCTTG |
| B. human/XhoI/(*loxP*) Cassette (SEQ ID NO:23) | GGTCAGAGGA CCAAAGGTGA GGCAAGGCCA GACTTGGTGC TCCTGTGGTT// CTCGAG//*ATAACTTCG TATAATGTAT GCTATACGAA GTTAT* ATGCATGCC TCCGGCGCGG GTTTTGGCGC CTCCCGCGGG CGCCCCCCTC CTCACGGCGA GGGCTGCCAC GTCAGAACGAA GGGCGCAGCG AGCGTCCTGA |
| C. Cassette (*loxP*)/ICEU1/NheI// mouse (SEQ ID NO:24) | ATTGTTTTGC CAAGTTCTAA TTCCATCAGA CCTCGACCTG CAGCCCCTAG *ATAACTTCGT ATAATGTATG CTATACGAAG TTAT*/GCTAGTAACTATAACGGTCCTAAGGTAGCGA // GCTAGC // TCCACGTGGC TTTGTCCCAG ACTTCCTTTG TCTTCAACAA CCTTCTGCAA |

Figure 1B

Tmprss2 protein alignment

```
                       310        320        330        340        350        360
hTMPRSS2         PLNNPWHWTAFAGILRQSFMFYGAGYQVEKVISHPNYDSKTKNNDIALMKLQKPLTFNDL
mTmprss2         PLSSPRYWTAFAGILRQSLMFYGSRHQVEKVISHPNYDSKTKNNDIALMKLQTPLAFNDL
7010 mutant pro  PLNNPWHWTAFAGILRQSFMFYGAGYQVEKVISHPNYDSKTKNNDIALMKLQKPLTFNDL
                 ** **:*******:****:****. :********************** **:****

370        380        390        400        410        420
hTMPRSS2         VKPVCLPNPGMMLQPEQLCWISGWGATEEKGKTSEVLNAAKVLLIETQRCNSRYVYDNLI
mTmprss2         VKPVCLPNPGMMLDLDQECWISGWGATYEKGKTSDVLNAAMVPLIEPSKCNSKYIYNNLI
7010 mutant pro  VKPVCLPNPGMMLQPEQLCWISGWGATEEKGKTSEVLNAAKVLLIETQRCNSRYVYDNLI
                 *************: :*:********* ******:*****:* ***..:***:*:*:***

430        440        450        460        470        480
hTMPRSS2         TPAMICAGFLQGNVDSCQGDSGGPLVTSKNNIWWLIGDTSWGSGCAKAYRPGVYGNVMVF
mTmprss2         TPAMICAGFLQGNVDSCQGDSGGPLVTSKNNIWWLIGDTSWGSGCAKALRPGVYGNVTVF
7010 mutant pro  TPAMICAGFLQGNVDSCQGDSGGPLVTSKNNIWWLIGDTSWGSGCAKAYRPGVYGNVMVF
                 ***********************************************:********:**

490
hTMPRSS2         TDWIYRQMRADG
mTmprss2         TDWIYQQMRANS
7010 mutant pro  TDWIYRQMRADG
                 *****:****:.
``` solid line: TM
solid box: LDLRa
dotted box: SRCR domain
dotted line: peptidase S1

Tmprss4 protein alignment

```
                    310        320        330        340        350        360
hTMPRSS4        TFSGTVRPICLPFFDEELTPATPLWIIGWGFTKQNGGKMSDILLQASVQVIDSTRCNADD
mTmprss4        TFSGSVRPICLPFSDEVLVPATPVWVIGWGFTEENGGKMSDMLLQASVQVIDSTRCNAED
7224 mutant pro TFSGTVRPICLPFFDEELTPATPLWIIGWGFTKQNGGKMSDILLQASVQVIDSTRCNADD
                ****.********.**::*.***::*****.::*******.********:***:**:
                    370        380        390        400        410        420
hTMPRSS4        AYQGEVTEKMMCAGIPEGGVDTCQGDSGGPLMYQSDQWHVVGIVSWGYGCGGPSTPGVYT
mTmprss4        AYEGEVTAEMLCAGTPQGGKDTCQGDSGGPLMYHSDKWQVIVSWGHGCGGPSTPGVYT
7224 mutant pro AYQGEVTEKMMCAGIPEGGVDTCQGDSGGPLMYQSDQWHVVGIVSWGYGCGGPSTPGVYT
                **:**** :*:*** *:**:*************:**:*:*:*****:***********
                    430
hTMPRSS4        KVSAYLNWIYNVWKAEL
mTmprss4        KVTAYLNWIYNVRKSEM
7224 mutant pro KVSAYLNWIYNVWKAEL
                **:*********.*:*:
``` solid line: TM
solid box: LDLRa
doted box: SRCR domain
dotted line: peptidase S1

Figure 2D (Continued)

Tmprss11d protein alignment

```
                       310        320        330        340        350        360
hTMPRSS11D      PPGSTAYVTGWGAQEYAGHTVPELRQGQVRIISNDVCNAPHSYNGAILSGMLCAGVPQGG
mTmprss11d      IPGSVAYVTGWGSLITYGGNAVTNLRQGEVRIISSEECNTPAGYSGSVLPGMLCAGMRSGA
7226 mutant pro PPGSTAYVTGWGAQEYAGHTVPELRQGQVRIISNDVCNAPHSYNGAILSGMLCAGVPQGG
                 **.*:*******. :.*. .. :*** ***:* :  ** ..* * *:**:***: .

370        380        390        400        410
hTMPRSS11D      VDACQGDSGGPLVQEDSRRLWFIVGIVSWGDQCGLPDKPGVYTRVTAYLDWIRQQTGI
mTmprss11d      VDACQGDSGGPLVQEDSRRLWFIVGIVSWGYQCGLPNKPGVYTRVTAYRNWIRQQTGI
7226 mutant pro VDACQGDSGGPLVQEDSRRLWFIVGIVSWGDQCGLPDKPGVYTRVTAYLDWIRQQTGI
                ****************************** *****:*********** :*******
``` solid line: TM
solid box: SEA domain
dotted line: peptidase S1

Figure 3D (Continued)

SEQUENCE LISTING

<160> NUMBER OF SEQ ID NOS: 72

<210> SEQ ID NO 1
<211> LENGTH: 3175
<212> TYPE: DNA
<213> ORGANISM: Mus musculus

<400> SEQUENCE: 1

| | | | | | |
|---|---|---|---|---|---|
| gcctttcctg | gccgttccct | ccttctggcc | gaggtgcctg | cgtttagggg | tgtcaccctg | 60 |
| gctcccggga | cgccgcctcc | ggagatttaa | gcgagaactg | gagtaggtcg | tgtacttgga | 120 |
| gcggacgagg | aagccaagag | ctcggacaga | ggcgagagg | ggcgggaagc | gcaacaggtc | 180 |
| acctggagga | agccccatac | tgacctcctc | atgctgctga | cacaggcagg | atggcattga | 240 |
| actcagggtc | acctccagga | atcggacctt | gctatgagaa | ccacgggtat | cagtctgagc | 300 |
| acatctgtcc | tccgagacca | ccagtggctc | ccaatggcta | caacttgtat | ccagcccagt | 360 |
| actacccatc | tccagtgcct | cagtatgctc | cgaggattac | aacgcaagcc | tcaacatctg | 420 |
| tcatccacac | acatcccaag | tcctcaggag | cactgtgcac | ctcaaagtct | aagaaatcgc | 480 |
| tgtgtttagc | cctcgccctg | gcactgtcc | tcacgggagc | tgctgtggct | gctgtcttgc | 540 |
| tttggaggtt | ctgggacagc | aactgttcta | cgtctgagat | ggagtgtggg | tcttcaggca | 600 |
| catgcatcag | ctcttctctc | tggtgtgacg | gggtagcaca | ttgtcccaac | ggagaagatg | 660 |
| agaaccgttg | tgttcgtctc | tacggacaaa | gcttcatcct | ccaggtttac | tcatctcaga | 720 |
| ggaaagcctg | gtatcccgtg | tgccaggatg | attggagtga | gagctacggg | agagcagcat | 780 |
| gtaaagacat | gggatacaag | aacaatttt | attctagcca | agggatacca | gaccagagcg | 840 |
| gggcaacgag | ctttatgaag | ctgaatgtga | gctcaggcaa | cgttgacctc | tataaaaaac | 900 |
| tctaccacag | tgactcatgt | tcatcccgca | tggtggtttc | tttgcgctgt | atagaatgcg | 960 |
| gggttcgctc | agtgaaacgc | cagagcagga | ttgtgggtgg | attgaatgcc | tcaccaggag | 1020 |
| actggccctg | gcaggtcagc | ctgcacgtcc | aaggcgtcca | cgtctgcgga | ggctccatca | 1080 |
| tcaccccga | gtggattgtg | acggccgccc | actgtgtgga | agaacccctc | agcagcccga | 1140 |
| ggtactggac | ggcatttgcg | ggaattctga | cacagtctct | catgttctat | ggaagtagac | 1200 |
| accaggtaga | aaaagtaatt | tcccatccaa | attacgactc | taagaccaag | ataacgaca | 1260 |
| ttgctctcat | gaagctgcag | acacctttgg | cttttaatga | tctagtgaag | ccagtgtgtc | 1320 |
| tgccgaaccc | aggcatgatg | ctagacctag | accaggaatg | ctggatttcg | ggtgggggg | 1380 |
| ccacctatga | gaagggaag | acctcggacg | tgttgaatgc | tgccatggta | cccttgatcg | 1440 |
| agccctccaa | atgtaatagt | aaatacatat | acaacaacct | aatcacacca | gccatgatct | 1500 |
| gtgccggctt | cctccagggg | tctgtcgact | cttgccaggg | agacagtgga | gggccgctgg | 1560 |
| ttactttgaa | gaatgggatc | tggtggctga | ttgggacac | gagctggggc | tcgggctgtg | 1620 |
| ccaaggcact | cagacctgga | gtatacggga | acgtgacggt | atttacagat | tggatctacc | 1680 |
| agcaaatgag | ggcgaacagc | taatccacgt | ggctttgtcc | cagacttcct | ttgtcttcaa | 1740 |
| caaccttctg | caagaaaacc | aagggcctga | attttaactt | cctgtgcaca | atgtaccttt | 1800 |
| tgagatgatt | cgaagggcct | ttcactttta | ttaaacagtg | acttgtttga | ctgtgctccc | 1860 |
| tggtcctgtg | agggcttcag | tgccccaccc | ctgggccact | tctgcagctc | ccaccagaat | 1920 |
| ggatgaccag | attctgttgg | gtttgggcac | atagggccaa | aggcagagga | gggtggcact | 1980 |
| ctcatgttgg | aacttctttt | gggctcatgc | tcaggccttt | tttggatcac | taaggactat | 2040 |
| gacctctgag | taacctgatg | acctgagaaa | gagtaaggag | gccaggcagg | gccttgggcc | 2100 |

-continued

```
caggaacagg taccttgaga gtgagagcta cccattgcct gtggcctaaa tctgctgtgc    2160
aggttgggct ggtcatactg tcatgatttc attaacagcc tgggtgaaca tggctgggag    2220
taaagggctt gctctcctgc atgttgacat gacggccctt tccaagggtg atggaggctt    2280
tcccaagcta agggcctagg cagatctctc agagcaagaa gctaatgccg gcatgtccct    2340
tgggtgagct ctacatggtg ttattcagtc tggttcttgg ctccccacta ctgtttctct    2400
cagcctctca gagcctgaaa cttacctctt agctttggct acaggcatgg cctagtacct    2460
gatggagcct gtatagctca gctaatcaaa tggaggctca ggtccatcag aatcagggac    2520
ttgtgatttc agtcaccttg cttctgggtt gtgtttcttc tcttactacc tcactgcacc    2580
tggacactag agtggatgaa tgtctggagt tcacctgcat ttggactgtg tgattgtgcc    2640
tcagacacta gacctcttcc agatggttag gttgttctgt agactggcaa tgagattaga    2700
agttcctagc ttcagataaa gatgaaagag aggagatcat tgtcttctgt cttcttctgg    2760
ccctgggttt ataccaggaa agccatgcca gaattaccaa atatgaagta tgaatgtctt    2820
acccacggtg aggctctgcc tccttctctc tgcctggttc ttcagaaggc agtgaatggg    2880
tcataactgg gactccatct ttgctgggga agtctcccca cctagggaat ggttaccact    2940
ccatgtaaag aaaactccct catgcgtcct ctgggacctt cttagatgct gtaaggtacc    3000
tacatacaga ctaaatgtgc aagcaccttg aagtgtgaga acctgtcccc tccttagctc    3060
tccttgtctt tgctgttggt tggttatttc ctgctttgtg tctgttctga gctgtgagat    3120
tccactgtga aatatatgaa taaagtatat aattctttta aaaaaaaaaa aaaaa    3175
```

<210> SEQ ID NO 2
<211> LENGTH: 490
<212> TYPE: PRT
<213> ORGANISM: Mus musculus

<400> SEQUENCE: 2

```
Met Ala Leu Asn Ser Gly Ser Pro Gly Ile Gly Pro Cys Tyr Glu
1               5                  10                  15

Asn His Gly Tyr Gln Ser Glu His Ile Cys Pro Pro Arg Pro Val
            20                  25                  30

Ala Pro Asn Gly Tyr Asn Leu Tyr Pro Ala Gln Tyr Tyr Pro Ser Pro
        35                  40                  45

Val Pro Gln Tyr Ala Pro Arg Ile Thr Thr Gln Ala Ser Thr Ser Val
    50                  55                  60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Arg Phe Trp Asp Ser Asn Cys
            100                 105                 110

Ser Thr Ser Glu Met Glu Cys Gly Ser Ser Gly Thr Cys Ile Ser Ser
        115                 120                 125

Ser Leu Trp Cys Asp Gly Val Ala His Cys Pro Asn Gly Glu Asp Glu
    130                 135                 140

Asn Arg Cys Val Arg Leu Tyr Gly Gln Ser Phe Ile Leu Gln Val Tyr
145                 150                 155                 160

Ser Ser Gln Arg Lys Ala Trp Tyr Pro Val Cys Gln Asp Asp Trp Ser
                165                 170                 175

Glu Ser Tyr Gly Arg Ala Ala Cys Lys Asp Met Gly Tyr Lys Asn Asn
```

180                 185                 190
Phe Tyr Ser Ser Gln Gly Ile Pro Asp Gln Ser Gly Ala Thr Ser Phe
                    195                 200                 205
Met Lys Leu Asn Val Ser Ser Gly Asn Val Asp Leu Tyr Lys Lys Leu
                210                 215                 220
Tyr His Ser Asp Ser Cys Ser Ser Arg Met Val Val Ser Leu Arg Cys
225                 230                 235                 240
Ile Glu Cys Gly Val Arg Ser Val Lys Arg Gln Ser Arg Ile Val Gly
                    245                 250                 255
Gly Leu Asn Ala Ser Pro Gly Asp Trp Pro Trp Gln Val Ser Leu His
                260                 265                 270
Val Gln Gly Val His Val Cys Gly Gly Ser Ile Ile Thr Pro Glu Trp
            275                 280                 285
Ile Val Thr Ala Ala His Cys Val Glu Glu Pro Leu Ser Ser Pro Arg
            290                 295                 300
Tyr Trp Thr Ala Phe Ala Gly Ile Leu Arg Gln Ser Leu Met Phe Tyr
305                 310                 315                 320
Gly Ser Arg His Gln Val Glu Lys Val Ile Ser His Pro Asn Tyr Asp
                    325                 330                 335
Ser Lys Thr Lys Asn Asn Asp Ile Ala Leu Met Lys Leu Gln Thr Pro
                340                 345                 350
Leu Ala Phe Asn Asp Leu Val Lys Pro Val Cys Leu Pro Asn Pro Gly
            355                 360                 365
Met Met Leu Asp Leu Asp Gln Glu Cys Trp Ile Ser Gly Trp Gly Ala
            370                 375                 380
Thr Tyr Glu Lys Gly Lys Thr Ser Asp Val Leu Asn Ala Ala Met Val
385                 390                 395                 400
Pro Leu Ile Glu Pro Ser Lys Cys Asn Ser Lys Tyr Ile Tyr Asn Asn
                    405                 410                 415
Leu Ile Thr Pro Ala Met Ile Cys Ala Gly Phe Leu Gln Gly Ser Val
                420                 425                 430
Asp Ser Cys Gln Gly Asp Ser Gly Gly Pro Leu Val Thr Leu Lys Asn
                435                 440                 445
Gly Ile Trp Trp Leu Ile Gly Asp Thr Ser Trp Gly Ser Gly Cys Ala
            450                 455                 460
Lys Ala Leu Arg Pro Gly Val Tyr Gly Asn Val Thr Val Phe Thr Asp
465                 470                 475                 480
Trp Ile Tyr Gln Gln Met Arg Ala Asn Ser
                    485                 490

<210> SEQ ID NO 3
<211> LENGTH: 3212
<212> TYPE: DNA
<213> ORGANISM: Homo sapiens

<400> SEQUENCE: 3
gagtaggcgc gagctaagca ggaggcggag gcggaggcgg agggcgaggg gcggggagcg      60
ccgcctggag cgcggcaggt catattgaac attccagata cctatcatta ctcgatgctg     120
ttgataacag caagatggct ttgaactcag ggtcaccacc agctattgga ccttactatg     180
aaaaccatgg ataccaaccg gaaaacccct atcccgcaca gcccactgtg gtccccactg     240
tctacgaggt gcatccggct cagtactacc gtcccccgt gccccagtac gcccgagggg     300
tcctgacgca ggcttccaac cccgtcgtct gcacgcagcc caaatcccca tccgggacag     360

```
tgtgcacctc aaagactaag aaagcactgt gcatcacctt gaccctgggg accttcctcg    420
tgggagctgc gctggccgct ggcctactct ggaagttcat gggcagcaag tgctccaact    480
ctgggataga gtgcgactcc tcaggtacct gcatcaaccc ctctaactgg tgtgatggcg    540
tgtcacactg ccccggcggg gaggacgaga atcggtgtgt tcgcctctac ggaccaaact    600
tcatccttca ggtgtactca tctcagagga agtcctggca ccctgtgtgc caagacgact    660
ggaacgagaa ctacgggcgg gcggcctgca gggacatggg ctataagaat aattttact    720 ctagccaagg aatagtggat gacagcggat ccaccagctt tatgaaactg aacacaagtg    780
ccggcaatgt cgatatctat aaaaaactgt accacagtga tgcctgttct tcaaaagcag    840
tggtttcttt acgctgtata gcctgcgggg tcaacttgaa ctcaagccgc cagagcagga    900
ttgtgggcgg cgagagcgcg ctcccggggg cctggccctg gcaggtcagc ctgcacgtcc    960
agaacgtcca cgtgtgcgga ggctccatca tcaccccga gtggatcgtg acagccgccc    1020
actgcgtgga aaaacctctt aacaatccat ggcattggac ggcatttgcg gggattttga    1080
gacaatcttt catgttctat ggagccggat accaagtaga aaaagtgatt tctcatccaa    1140
attatgactc caagaccaag aacaatgaca ttgcgctgat gaagctgcag aagcctctga    1200 cttttcaacga cctagtgaaa ccagtgtgtc tgcccaaccc aggcatgatg ctgcagccag    1260
aacagctctg ctggatttcc gggtgggggg ccaccgagga gaaagggaag acctcagaag    1320
tgctgaacgc tgccaaggtg cttctcattg agacacagag atgcaacagc agatatgtct    1380
atgacaacct gatcacacca gccatgatct gtgccggctt cctgcagggg aacgtcgatt    1440
cttgccaggg tgacagtgga gggcctctgg tcacttcgaa gaacaatatc tggtggctga    1500
taggggatac aagctggggt tctggctgtg ccaaagctta cagaccagga gtgtacggga    1560
atgtgatggt attcacggac tggatttatc gacaaatgag ggcagacggc taatccacat    1620
ggtcttcgtc cttgacgtcg ttttacaaga aaacaatggg gctggttttg cttccccgtg    1680
catgatttac tcttagagat gattcagagg tcacttcatt tttattaaac agtgaacttg    1740
tctggctttg gcactctctg ccattctgtg caggctgcag tggctcccct gcccagcctg    1800
ctctccctaa ccccttgtcc gcaaggggtg atggccggct ggttgtgggc actggcggtc    1860
aagtgtggag gagaggggtg gaggctgccc cattgagatc ttcctgctga gtcctttcca    1920
ggggccaatt ttggatgagc atggagctgt cacctctcag ctgctggatg acttgagatg    1980
aaaaaggaga gacatggaaa gggagacagc caggtggcac ctgcagcggc tgccctctgg    2040
ggccacttgg tagtgtcccc agcctacctc tccacaaggg gattttgctg atgggttctt    2100
agagccttag cagccctgga tggtggccag aaataaaggg accagccctt catgggtggt    2160
gacgtggtag tcacttgtaa ggggaacaga aacattttg ttcttatggg gtgagaatat    2220
agacagtgcc cttggtgcga gggaagcaat tgaaaaggaa cttgccctga gcactcctgg    2280
tgcaggtctc cacctgcaca ttgggtgggg ctcctgggag ggagactcag ccttcctcct    2340 catcctcct gaccctgctc ctagcaccct ggagagtgca catgccctt ggtcctggca    2400 gggcgccaag tctggcacca tgttggcctc ttcaggcctg ctagtcactg gaaattgagg    2460
tccatggggg aaatcaagga tgctcagttt aaggtacact gtttccatgt tatgtttcta    2520
cacattgcta cctcagtgct cctggaaact tagcttttga tgtctccaag tagtccacct    2580
tcatttaact ctttgaaact gtatcatctt tgccaagtaa gagtggtggc ctatttcagc    2640
tgctttgaca aaatgactgg ctcctgactt aacgttctat aaatgaatgt gctgaagcaa    2700
agtgcccatg gtggcggcga agaagagaaa gatgtgtttt gttttggact ctctgtggtc    2760
```

```
cctteccaatg ctgtgggttt ccaaccaggg gaagggtccc ttttgcattg ccaagtgcca    2820
taaccatgag cactactcta ccatggttct gcctcctggc caagcaggct ggtttgcaag    2880
aatgaaatga atgattctac agctaggact taaccttgaa atggaaagtc atgcaatccc    2940
atttgcagga tctgtctgtg cacatgcctc tgtagagagc agcattccca gggaccttgg    3000
aaacagttgg cactgtaagg tgcttgctcc ccaagacaca tcctaaaagg tgttgtaatg    3060
gtgaaaacgt cttccttctt tattgccct tcttatttat gtgaacaact gtttgtcttt     3120
ttttgtatct tttttaaact gtaaagttca attgtgaaaa tgaatatcat gcaaataaat    3180
tatgcaattt ttttttcaaa gtaaaaaaaa aa                                  3212
```

<210> SEQ ID NO 4
<211> LENGTH: 492
<212> TYPE: PRT
<213> ORGANISM: Homo sapiens

<400> SEQUENCE: 4

```
Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285
```

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
                340                 345                 350

Lys Pro Leu Thr Phe Asn Asp Leu Val Lys Pro Val Cys Leu Pro Asn
            355                 360                 365

Pro Gly Met Met Leu Gln Pro Glu Gln Leu Cys Trp Ile Ser Gly Trp
370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
                420                 425                 430

Asn Val Asp Ser Cys Gln Gly Asp Ser Gly Gly Pro Leu Val Thr Ser
            435                 440                 445

Lys Asn Ile Trp Trp Leu Ile Gly Asp Thr Ser Trp Gly Ser Gly
450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490

<210> SEQ ID NO 5
<211> LENGTH: 27947
<212> TYPE: DNA
<213> ORGANISM: Artificial Sequence
<220> FEATURE:
<223> OTHER INFORMATION: Recombinant polynucleotide

<400> SEQUENCE: 5

```
gcagagtcta agaaatcgct gtgtttagcc ctcgccctgg gcactgtcct cacgggagct      60
gctgtggctg ctgtcttgct ttggaagttc agtaagtgca gggagcctcg atcccaccat     120
gtgctcctgc agtccccagt gctctgagcc agacctgctc tctgggcta ttgagacctc      180
tggaggccct ccgtgaggtt cctctcttac ataacgaggc tgtctctctt cccttctctt     240
gtttagctat gagattgaca catcatgggg aaagcattta gaatgtaccc agtgctttgg     300
ggtgcttggt gccacccagc actgtgagca caggttcttc taccttgggg ccacacccag     360
ttacctgtat ctcactgcac agcagtggct gttggggacc aggcccaccc ctccatgtcc     420
cacctcctgc aactgcagcc tgagccttcc catcagcctg gggtggtgca gacccatgtg     480
ccattgtgga tccttcaagt tacctgtgtg cagagagga cgtgtgagtg ccgtccaaac      540
ccaaacactg agagggtcct tcccattgcc ccacggaag taaggtgccc cagtgctaat      600
tccacttata cttgctggtg gcaaggacac ttctcctcct tattaaagtg ggggattggc     660
tgggtgaggt ggctcacgcc tgttatccca gcactttaag aggccaaggc aggtggacca    720
cctgaggtca ggagtttgag accacaagcc tggccaacat gttgaaactc catctctact   780
aaaaatacaa aaattagtca ggcgtggtgg cgtgcacctg taatcccagc tacttaggag   840
gctggggcag gaggatcact tgaacccagg agttggaggt tgcagtgagc caagattgtg    900
```

```
cccctgcact ccagcctggg tgacagaatg agacttcatc tcaaaaacaa aacaaaacaa   960
aacacagtgg ggccaggagt tggaggctgc agcgagctac agtaatgcca cggtgttcct  1020
cactccatga ggctcattgc gtttctcagc ctgaagggca cctctcttct gttttctctg  1080
caagtgggca gcaagtgctc caactctggg atagagtgcg actcctcagg tacctgcatc  1140
aacccctcta actggtgtga tggcgtgtca cactgccccg gcggggagga cgagaatcgg  1200
tgtggtgagt cagccttgac cttgggaagg gactcctctg ctcaccttgg agacagcagc  1260
cgggtccagg ggcctttggg tgactgggcc tggcgtgcgt ccagtacgct gacacatgat  1320
gtcattgaat ccctgctcca ggctgagccc tgggctcag agaggttgtg tttccggccc  1380
aacctcaccc agcaggtggg agatgacagg gccaccgagg actgtgtcat ggaaccaca  1440
cgtgctctga actgccacag gaagtcagtt aagatgagca aactgtttat aaagttggag  1500
atgcaggcta ggaacggtgg ctcatgcctg taatcccagc actttgggag gccgaggcag  1560
atggatcacc tgaggtcagg agtttgagac cagcctgacc aatatggtga aaccttatct  1620
ccactaaaaa tacaaaaatt agccaagcgc ggtggcgggt gcctgtaatt ccagctattc  1680
aggaggctga ggcaggagaa tcacttgaac ctgggaggcg gaggttgcag tgagctgaga  1740
tcacgccact gcattccagc ctgggagaca gagctggctc aaaaaataaa ttaattaatt  1800
aaaaacaaaa ttggagatgc actatgttat tttcaaaaca agctgccttt aaagatctat  1860
ctgttgtcac agggtgggct catctgtttc attttatttt ctgtggttta tctatttatt  1920
cattttaatg aactaggaag cattgctcct atttatggca taccacatga tgtttggata  1980
cgtgtatgcc tgtggcatgg ctaagtcaag ctagaacatg ggccttacct catatacgtg  2040
tcttattaag aacacataaa acctactctt gtagtgattt tcaaatatgc aacatatagt  2100
ttattaactg cagtcactat gatgtacaat agattgctcg aacttattcc tcctgtctaa  2160
ctaagatttt gtgacctctg accaacatct ccccagtgtt gtcacccccc gcccccagcc  2220
tctgatagct gccttctac tctctgcttc tgtgagtttg atgtttatac attccacatg  2280
taagtggcct catgcagtgt ttctgtctct gtgtctggct tgttcactta gcgtaatgtc  2340
ctccagcttc atctatgttg ttggaaatga caggatttcc ttctttcttg tggctgaata  2400
gtattgcctt gtgcatatac accacatttt ctttatccct tcattcactg atggactctt  2460
aggttgatgt catgtcttgg ctgttgtgaa aaatgccgca gtgagcgtgg gcgtgcaggt  2520
ccctcttcaa cacacggatt tcctttcctt tggatataaa cccagcagtg agattgctgg  2580
atcacatggc agttctgttt ctcacctttt gaggaaactc catactgttt tccataatgg  2640
ctgtagcaac ttccactccc accccacgg tgcaaagtct ccatttctct tctacaacct  2700
caccaactcc tgttatttc catctttctg atagtagcca tttgaagagg tatgagatga  2760
tacctcattg tggttttcat ttgcattttt atttgtattt ttcatgaatt tttgagggtg  2820
atttcaaggg tagttagtga ctcgaacagg gaaacgatcc tgagtatgag ggttgtgcta  2880
atcatccccc tcctgccagc tgcgtacgga atggggctct gcagatggca gggagctggc  2940
tcgtttctct ttaagagctg cctttactt ttcttcctct tccttttaaa cttatttcct  3000
ggccggacgc agtggctcat gcctgtaatc ccagcacttt gggaggccga ggtgggcgga  3060
tcacgaggtc aggaattcca gaccagcctg gccaacatgg tgaaaccccg tctctactaa  3120
aaatacaaaa attagccaga cgtggtggtg cgggcctata gtcccagcta ctcgggaggc  3180
tgaggcagga gaatcacttg aacctgggag gaggggttg cagtgagccg agattgcgcc  3240
actgcactcc agcctgggcg acagagccag actccatctc aaaaaacaaa aaaaagttat  3300
```

```
ttcccaagca cagccatgta ttccaggctt gtggatcagc gttggtggtg gtgtgtgctc   3360
tcatatctta gttccagcta agcacactct gacatgttta cactagaacc atttgttttt   3420
tctagaaata gaaatttcag aattgtagag tcagaggact taccagaaat ctcttaggta   3480
gttctcctcc cctccctcaa gtgcagtcct aacctcctgg agttttctgt agaaaccaca   3540
agcctcagag ctggccgaga attctagcca aagattttc  catgccaaag taatcccccc   3600
tctcctaagg gccatccttg gtggggactg gtttcctgtt aagccctcgc tgtcagtcct   3660
ggctgtggaa tttcctggtg aggagcactg gcccgtggag ctcggccctc gtgccggcct   3720
tgagcaggcc caagtgttcc gtgttcttga tacctttcct ccagcacagt cttgcttccc   3780 agaaaaggt  ttgcacttga aaatgatgca tttgctgatt aaacatagtt cttttgcttt   3840
atttggtttc taaaataaag tgggagtttt tgagattgag taacgtgagg ttaagatagc   3900
acgtggaatg gctttttctt ttctttctat tttttttttt ttttcctgg  agacagggtt   3960 tcactctgtt gcccaggctg gagtgcagag gcatgaccat ggctcactgc aacttcgatg   4020
tcctggggtt aagcgatccc ccagcctcag ccccccaagt ggctgggact acaggtgctc   4080
gccaccacac ctggctaatt tttgtatttt ttgtagaaaa tgggtttcat caatgttgtc   4140
cagactggtc tcgaactcct gacctcaagc aattctcctg cctcagcctc ccagactgct   4200
gggattacag gcgtgaacta ccacgcctgg cctggaatgg cttttgatgt tctcctatgt   4260
gcacatgtgg gtgaataaac accaacaaag tccttatgtt acctgaagag ttgctctctt   4320
cttaatattt aagtcgtatt tatttaaata ctttaatagt tgtacactat taaagtatta   4380
ttaggtcaaa atcaaggaag tacaaaaggg tatgctgtga aaaatctctt cttccttgct   4440
ctgcttactt acctaccccg catcccccca tacaccccag acacacacac acacacacac   4500
acacacacac acacacgcat cactcccata catgcccacc tgtttaccag ccaatcacat   4560 ttcttgggc  aactcatctg agttgcttct cttttccagag agttttttgca taaagaagca   4620 caggtatttc tgcgttacca tgaccctatt tcccagtggt tcctagccag ttgactctcc   4680
tgcactggat accatcctgg acagcattcc ttagggaaat gagccccctg ttttttccca   4740
ccatggcaca gttggtcctt tgcatggacg caccattatt gccctgtct  cttcttggtg   4800 gaccttaagg ttttctccat cctttgctg  taacacacac tgctccaagt gtgtgagcat   4860
atcagtagga aacgcttcca ggagtagaac tgctaggtca gagggcgtgt ggatctgtaa   4920
cctgacagac ctagaccggc ttcagtttgg ttttatccag tttccatatt gattattcat   4980
ataaaaggaa acagacaaac ataacgctgt gcatgtattc tctcttagac cagaacaggc   5040 ataggtgca  cttttaattt gtccatttcg tagagtagaa attgttttg  ctgaaatgaa   5100 caccttagga tgctgaagaa tatgacccgt cccatgaaaa acattcaaaa atgtgtgtag   5160
cgctttcttc ccaagggtgt gtgtgcgcat attttaacac taattcactt tctacttccg   5220
ttgctatcct ttctgtgagt cttttctcaga atctcagaaa agaaactaaa ttgttcactc   5280
tagttatcaa tgctgtactc tatacctgga atttgctaaa agggcagatt ttaagtattc   5340
tcaccacaga aaagagaaaa gaaaatggta attatgtgac gtggtggaca tgttaactag   5400
ctttattatg gtgagcattt cacagcggat atccagtcat cacgctgtac acattaaaca   5460
tgtacaattg ggtttttttg agacaaggtc tccttctgtc acccagtctg gagtgcagtg   5520
gctcagtcat ggctcattgc agcctcgacc tcctgggctc aatccatcct tcccctcag   5580 cctcctgaaa agctggggcc acaggcatgt accatcatgc caggctaatg catatatatt   5640
```

```
tatatttttt ggtggagatg gggttggtct cgaactctgg gctcaagtga tcctcccgcc    5700
ttgcccttcc aaagtgctga gattacaggc atgaaccaca gcaccaggcc tacatgtaaa    5760
atttttattt gtcaactata ctttgacaaa gctgagaaaa aaaatcctaa tatttaaaaa    5820
aaaaaaaaaa aggactagct tgagacccttt tccagctctc tggcttatca gctgccgtct    5880
cttccgggtg cagatagctg aagggaaag aaaatcccta aaattaccca caagccaaga    5940
atgaagtgtc tcccttttgag ccacagtggc agttttgttt ttaatcatag aagtgtattt    6000
tgagccgggt gtgctggctc acgcctgtaa tccccgcact ttgggaggcc gaggtgggg    6060 gcggagggg tggggatcgc ctgaggtcag gagttcgaga ccagcctgac caacatggag    6120 aaacccgtc tctactaaaa atacaaaatt agccggcgtg gtggtgcatg cctgtaatcc    6180
cagctactca tgaggctgag tcaggagaat ctcttgaacc caggaggtgg aggttgcggt    6240
gagctgagat catgccattg cactccagcc tgggaacaag aaaaaaaag aagaagaaga    6300 agaagtgtat tcatttcagt tacttttaaa aaagtgaaca gactttatat tttagagcgg    6360
ttttaggttt acagaaaatg aaacagacag ggcagcgagc tccttgtact cctcccagc    6420 acacagttgc cctgttatga acatcccaca tcagtgctgt gcgttcatta acaccgatga    6480
acctgatgca tacattatga tgaactgaag tcctggactt cacccttctct cttgtacagt    6540 tctgtgggat ttgacaaatg cataatgctg tacagccaca atgatagtat cgtccagagt    6600
agttctcctg ccttaaaacc tcttttgctg cacctgtttc tctctcccca ctcaccccag    6660
ctatctgatc ttcttagtgc ctccgaagtt ttggtctttt caggatgttg tagcgttgga    6720
atcatggagt atgtagcctt caccacatac accttcttc actttgttgg cttcctttac    6780
ttagtaatat gcattcaagt ttcctccatg ccttttcatg gcttgatagc tcatttcttt    6840
ttagcaccaa ataatattcc gttgtccaga tgtagcacaa tgtttatcca ttcatgtaac    6900
ctgtgaccga ctcacagata ggatgtggaa tcactcacca cagaggcatt agacaataat    6960
cagacccaag tcatttcatg ggggaacaag cccacaggta ccagactgtc cagtgagtca    7020
gggccactcg taggaagtaa aagagaggc tagagcatag ccaggtcctc actttatact    7080
ttaagcccat gtgtatttct cccaaaccac acagcattgt ttccatgctt tcagctttgc    7140
atgaataacg tgatacttga acgcatcatt tatcacttgc tctcttttccc acagcgctgt    7200 tttcaagctt cttcctgttc atgatgctct gcttaaccct taagctgcat gggattctgt    7260
tctgtgaata cgcccacccc atgtattatc ctgcccagca aaaagtcccc aaaactctgg    7320
atggtggtta cctctaggga gggagagaag agattgggaa tagggagcga cttcaacggt    7380
gtttgtaatg ttttgtttct ttaaataaaa gagctgagat catttcagca gaatgttgat    7440
ttagagtctc ctggacaatt tgttgctcaa agtgctctct taaagagcac tttaaaaaaa    7500
aaaacctttt atcttattat ttatttattt atttattgag acggagtttt gctctgtcac    7560
ccaggctgga gtggagtggt gtgatctcag ctcactgcaa cctttacctc ctgggttcaa    7620
gcaattcccc tgcctcagcc tcccaagtag gtgggattac agatgcgtgc caccacactt    7680
ggctaatttt tgcattttag tagagatcgg tttctccatg ttggccaggc tgatctcaaa    7740
cgcctgacct caggtgatct gcccgccttg gcctcccaaa gtgctggtat tacaggcgtg    7800
agctaccatg cctggcttat cttatatatt tttaaaaaca gcttattgag atctaattta    7860
tgtaccataa aattcaagta tataattcag tgctttata tataaaacat atatatgaaa    7920
tagcttattg agatataatt ttttatataa aacagcttat tgatatgtaa tgtatgtacc    7980
ataaaattta aatatataat tcactggctt ttatatattc acgaatatgt gcaactatca    8040
```

```
ccacagtcaa ttttagcata ttttcatcag ctcataaaga aaccccaagc ccttgaacta    8100
tcaccccata tccctcctcc cagcccgtcc ctcctactca taagcaacca ctaatctact    8160
tagtgtctat agatttccta ctctaggcat tccatgtgag cgggatcatg caatacgtgg    8220
gctcacacaa tataagtggc attccatgtg agtcggctca tgcagtatgt ccggctcctt    8280
tcactgagca taaggtcttc agcactcatc caggttgcag cctgtgtctg aatttcattc    8340
cctcttctgg ctgaatcgta ttccattgtg tatcttggac atatcctatt ctgctcaccc    8400
agccgttggt gggcgtttgg agtgttttcg cctttcagct gttttaagag ggttgcagtg    8460
aacatttgta caagttttgg acccaatgcc tgttttcaat tctcttgtgt agagagcact    8520
ttttagcaga aaaagaatag atttgtggcc tcccttgtgt gcggtcagt gccttgagaa      8580 gagtgaactg tgctgccacc tccggagccg tggagagcgc ggggcttggg tagcagctag    8640
gacgatacaa gttgggacaa ggccaggtgc aatggctcac gcctgtaatt ccaacacttt    8700
gggagaccga ggcaggggga tcacctgagg tcaggagttc aagaccagcc tggccaacat    8760
ggtgaaaccc catctctaat aaaacagaaa aattaactgg acggggtggt ggacgcctgt    8820
aatcccagct actcgggagg ctgaggcagg agaatcactt gaacctggga ggcggaggct    8880
gcagtgagtg gagatcagac cactgcactt cagcctaggt gacagagcga gactccgtct    8940 caaaaaaag aaaaaaaag aaagaaactc atggataatc ctccctctcg tgcagttcgc      9000
ctctacggac caaacttcat ccttcaggtg tactcatctc agaggaagtc ctggcaccct    9060
gtgtgccaag acgactggaa cgagaactac gggcgggcgg cctgcaggga catgggctat    9120
aagtgagtat ggggcagcac ccgccgagtg acagtaacag acagcagaaa cacgagaaga    9180
ccctctctct gcctcccgt gaaagcaccg gcacatgagt gctggggaca attgtcacct      9240
tccaaaagct gagccctata accagcaggt ggaatttgtc ctgctagggc tgtgcccagc    9300
acacagacct tggctcactg ccaccttgcc ctgcctcctc cttggcctct atagactcct    9360
ggttgctcgg gagtgcccag tgctgtggtc atctggtcag aggggtaggc tgagggcgtt    9420
aggtgcctct ttttccaagg tgcctctcag ccagggtcca ttcacctccc tgggtagagg    9480
ttggaccaga acagctggcg aggaggggttg ggctggggag agcagcagag acaaatcctg    9540
tgccagtttc acttcattcg ggagccatgg aagccttttg agctggggag agaatcaatc    9600
aatcagactg atacttaaaa aatgtcattc ctgctcgtag ctctgaggga aggtgggaag    9660
gcttaacagg gtgtgtgtcg cctgacagtg attcctaacg ggggtggggc ggtggttacc    9720
atttaccagc actgcctggg gagatgcggc agccctcagg catcggggga gagggtggta    9780
ggatgctact gccactttgt tttccatggg agggtcccca ggtgatttct atgcaacttt    9840
agggtattca atatgccagt tttcagaatg aattaccact cggtgagaaa gttggcatct    9900
tagctagtca ctgtgacatc cctaaacagc aggggtgaat tacacagcaa agcccccca    9960 tcacagtcca ggaacctggt ggaattgata actggggcca tgttaacatc tgtacccttt    10020
attagattaa atgtgtgtat gattatacaa tcctatgtcc ttctcatagt ttcttgatcc    10080
taacctggat aagaaacacg accaatgaag gaatttttgtc tgacactta gggttattga    10140 atcgaaaaat cgttacaata ttctagcact tggttagaac gtgtgatttt ttttcctaaa    10200
tgctaaggtt tttcccctct tattctgaatg tcgtatgagc ggtattatga catagtatag    10260
gatttgtgtt tgcttatgcc ttaaccatta tcacaaataa ggttttcttt tttaggaata    10320
atttttactc tagccaagga atagtggatg acagcggatc caccagcttt atgaaactga    10380
```

```
acacaagtgc cggcaatgtc gatatctata aaaaactgta ccacaggtat gcagcaattt    10440
cttcttgaaa aattttggaa tgaaatcaac taggagacac catggggaat cgttgtcctg    10500
agtctgattt ctctgagctg caatactcgg tctggatggg ttttgcattg ggaggagatt    10560
agagtctgac caggcctggt tactctaagc agcccttggt ttattcatag gaagtggctg    10620
aggtttctct gctatttcat tttcagcctc taccgtctgc ccttgttggt agcggctcac    10680
acttgcaaca tcgacattca actctattta gttttctttc ctcttcagac atttagaggt    10740
gtacctattt tgtcagggcg tggttctagg aatccaagat aatgtctcag tgtcccagcc    10800
agggtgaccg gctcattcca gtttgccagg gacttcactg gcttgagcaa gggaagtcct    10860
gctccattcc aggcagctgg gctggctggt cccgttagcc ccaaccccgg gacagcagtg    10920
ccagagggtg ctctgtgagg gatgggcagc attctggcgg cctgggaatg agttgtggtg    10980
tttccagggg gtagaagtgg gtacaagcca caggtcacat gatgagtggc tgacctggct    11040
gggagggcag aagaggggat ggacttaggc tcttcctttt gctttgcaca tatttaggat    11100
gtttgcagac ttgctatgat tgttgctgtt atgtgttttc tgatgtgaaa gatacacagt    11160
gtcctttgcc catgagctct ccttgcctcc caggtcccca gggcttatgc tggtgtcta    11220 ggcatcacct ccctgcctgc caggtgccag gtgctgcatt tcggggagg atgaactaat    11280 caccccgcgc cacctttcct ctgagtggga gcctggggca ggtttgcatt cctggaggcc    11340
gctggtggag gggtctgggg gcctgacttc cactgcagcc tgctgtcctg gggaatgtgg    11400
cagggcaagc ccagtgggga gggctgtgca cggccaggtg cacccatcaa acagcaggg    11460 ctgcggtttg tccctgtgga gaagctaaac acagctgcct gggcactttg taaatgctga    11520
gtggttcttt gtcttctctgg gttacacacg gaatcaggga gccaagtcca gccgggcagg    11580
gacgggggga ggggaggagg tgctgccgtc ccttggcaag agccttggga actcacaagg    11640
aggctggagg gcttggaaga aagaagagaa ggccattgtc tggtaggctc tattctatct    11700
cggtggtggt ggtgggggga ggcgcacttc ttttcctctt tctgtgcagc agttgccctt    11760
tgatgcctga gttcttggct tgtttttctgt cgggcttctg tgaataacca catgtgccct    11820
ggcgctgtga ccacacaggg ctatccctac cgaccttagg attcttagga aatgtcttct    11880
cttaaagggg acatgtcttc acttggccgt gtcagtgccc cagagccaga gtccacctgg    11940
aatgcacctg tagtcactga gaacccgggg ggtgtgcctt agtaagaagg tgtcaggaag    12000
gacctattat tgtagggcct gggctcctgc aaggtggttt gggggtggtt ggaggaagca    12060
gagatttgct ctggattgga tgctgtcagg aagcaggggg aattctgtga ggctgcttta    12120 ttatttttt tctaggagga ggttggaatg aggctaggct aaagctgtga ttggtaaaga    12180
aacgtccgtc gctcaagtta gccaggacag gaggagacat cagatcgtga ttttgtggtt    12240
gtgagcacaa ggttcctgtt ctgtctgttc agacatcatt tcggaggagg ctccttgtgt    12300
cttgccccat ctcaggcatg gaggggccta gtccgatatt gacgctcagt gaaataattc    12360
aggttccgca gagcacacgg cccagctatc agggcgggcc agctctgcat gccagggcc    12420 gcgtcttccc ttctcagcat agcctgggaa attcactgca ggacaaaatg catcagttac    12480
ttcctcttca tccataacct gggatgtttg actcccaaat gagtaactct tacgtttctt    12540
ctaatcctag ggaaactatt ggttatattg ctttcaacac tacaaattta aagcagttat    12600
aggagcccag aggtttccaa atggcttcct taaaaattag aagatgattt taaattccaa    12660
gaggaaaaac aaaactagca ttattgtata cttaccctca caaccgtcct aggagctggt    12720 acaatttta gagaggttaa gtaacttgcc caaggtcaca ctgtggggat gtgagccgcg    12780
```

```
taccttggct cagtgtctgg tctttgccac tgtccctata tggatttact taccttattg    12840
gagttgtaac tagcagaccc ttctatgtct cagaagacag gagagggaac atcggaagaa    12900
atgactgatt tctaagcatg tgagaggcag gtgactccgc actatcgtga ccagaatttc    12960
ccctgttctt tttgcagtga tgcctgttct tcaaaagcag tggtttcttt acgctgtata    13020
ggtaagttca tctggagtcc ccctttgat acttctaact aggaaaagct ctctactttc     13080
agaacagtac tccctgtgtc tctggggcg tgggagggaa gaaggtgggg tcacgggttg     13140
gaatgtgccc agcggcgtct cgctctttcc aaggagctcc tggtttagat ttccatggcc    13200
tgtagacacc ttcagccttg ggtccaaggg acaccccctg agatcaggca cgctcaagaa    13260
gctgacaaag ccctacactt tatgccaccc atgagctgga ggcccggcag gtctctttct    13320
ccagaaagca aagggggtg gcgttagtga gccctggcag ccacctaacg tggacttgga     13380
gcatctgcgg ggctgtggtc cagcaccacc gtgtggccac caggtgctca tcagccagtg    13440
ggacccggga ggagggacaa gaccagagaa caacagtgct cttgcctctt ctctcctgaa    13500
ttttggacgg tggcttagac ttgggtgtcc ccatctctgt gtttagagtg cttacagttt    13560
ccaaactgtt tgcaaatgtg gaagccaccg tccctctcct ctgggatggc ccagtgctgt    13620
cgtggggccg tggtcctgag ctcagctttt catttgaaga ggtggaagga gctgacaccg    13680
tcccatcccg gcagggctgg ctcaggtctt ctttaggtcc tgagtggggg tccagcacag    13740
ccccaagggt gcgtggcacc cgccctgccc tctgcccatg cactcatctc ctggtggaga    13800
agacactcac acacaggaag cagggaaggc agcagacctc actcacccct cacccccctca    13860
ctcaccccct actcaccccc tcaacctctc attcaccacc caccccctcg cccctcact    13920
caccccctca ctccctcaac cctcactcac ctcctcactc cctcaaccct cactcacctc    13980
ctcacctcct cactctcccc ctcatccctc cctcacccca cccgtcacc tcctcactca    14040
cctcctcacc ccctcactca cccttcaccc cctcactcac cacctcacct cctcactcac    14100
cccctactca acccctcatt caccccctcac ccctcactc accctgcac cccctcactc    14160
accccttcat ccactcaccc acctgctcac ctcctcactc aaccccctcac ccctcacta    14220
atccctcact ccctcacccc ctcacgccct cactcacacc ttcacctcct cactcacccc    14280
ctcaccccct caacccctta cttaccccct cactcatccc ttcacccctc actcacccc    14340
tctctcaccc attcaccccc tcactcatgc cttcaccccc tcactcacct cctcactcac    14400
accttcaccc ctcagtcacc ccctcactca ccccttcacc ccctcaatca tgccttcact    14460
ccctcactca ccccttcacc ctctgaatta ctccctcatc ccctcactca ccccctcact    14520
cacccttca ccccctcacc caccacctca cccacccctc acccacccc tcacctcctt     14580
acccctcacc ccctcactc accctcacc cctcactca ccacctcacc cacccctcac      14640
ccaccccctc actcactccc tcatcccctc actcacccccc tcacccctc actcaccccc    14700
tcacccaccc ctcacccacc ccctcacccc ctcactcacc ccttcacccc ctcactcacc    14760
ccctcactca cccttcacc ccctcactca ccacctcacc cacccctcac ccacccctc      14820
actcactccc tcaccccctc actcaccccc tcacccctc actcaccccc tcatctcctc    14880
actcacccccc tcacctcctc actcaccgc tcacctcctc actcaccccc tcgcccctc    14940
actcaccccct cacccctca ccccctcact cacccctcac ccctcgccc cctcactcac    15000
ccctcgcccc cctcactcac ccctcaccccc ctcaccccct cactcatccc ctcacctcct    15060
cactcaccccc ctcacctcct cactcaccccc ctcacctcct cactcaccccc ctcacctcct    15120
```

```
cacccacccc ctcactcact ccctcacccc ctcaccccct cactcacccc ctcacctcct    15180
cactcacccc ctcacctcct cacccacccc ctcactcact ccctcacccc ctcaccccct    15240
cactcacccc ctcacctcct cactcacccc ctcacctcct cactcacccc ctcacctcct    15300
cactcatgcc ctcaccccct cactcaccct ttcacctcct tgctcatccc ctcacttacc    15360
ccctcacttc gtcaatcacc ccccacctc gtcaatcacc ccctcaccctt ttcactcacc     15420 ccctcactca cccccttact tcctcactta cctcctcacc ccccactcac ccctcacccc    15480
cccactcacc ccctcaccc acactcaccc cctcaccccc cactcaccccc ctcaccctc    15540 tcacctcctc actcaccccc tcacctcctc acttatcccc tcaccccctc aattaccccc    15600
tcaccccctc aattactccc tcatcctttc aattacccac tcaccccctc acctcctcac    15660
tcctcactca ctccctcact caccccttca ccttctcact cacctcctcg tctcctcacc    15720
ccctcactca cttccagccc tgcccctccc atcttccttt tctttgtgtg agaatctggg    15780
gtccctgagt ggtgtcagtc cctccaagac tcaaggagtc cccagggcct tgttatccag    15840
aacaccccca cctgggtccc gggagacccc atgggatcac aggagtgttc agggaagtgg    15900
tgcttcctgg gtctgggtgg gctggagggg catcctccct tccccaagag gagaccccca    15960 ggagcccct aagtccatcc ccagcagtgg tgccctgcc ctgtccttgc agcctgggag      16020
acccttggga ggggcgggcg ctgggtggct gggcggcttc tgctggtctc accccactgg    16080
cctcctgttt gtcatcctca gcctgcgggg tcaacttgaa ctcaagccgc cagagcagga    16140
ttgtgggcgg cgagagcgcg ctcccggggg cctggccctg gcaggtcagc ctgcacgtcc    16200
agaacgtcca cgtgtgcgga ggctccatca tcaccccga gtggatcgtg acagccgccc    16260
actgcgtgga aaagtatgcc aggggcggcg cgggccgggt gggggctcag ggctggccta    16320
cagccaccct gtgaccttga gcaggtctca acccttgcag ccccggcatc cttgtgttta    16380
aatggggaga gtattgcacc tgcttcctag ggctgtgaga catcaagtgc gctcatgcca    16440
ggcagtgcat ggctgtatgc actgagtgtc ccctgcacgc agggcacagg gtgcaggtgg    16500
aacattctcc acgatgtcgc cgtgaccagc gttccttcca gccactgtcc tctgagctct    16560
gtcctgccct tgagcaaagc ccctgccccc tgaggtatcc tgtctccggg acgctagtcc    16620
caggagaggg cacactcaga caggcttcag gctgccctgc tggaaggtcc ctggggttaa    16680
gcgttcttgg ccacagcatt gctcatgcag agggttaggt aggggtgagg ctagccgtga    16740
cagtattagc atttatggac gctaccaccc cctcccctt tccttaaaca catagtgctt     16800
ttggtcacat gctgctttgg aggaggcctc acttggcgga tgtatttttc tgccttagag    16860
agaggctgaa ctgggtttga ctgttggccc agccctctct tgctgcgtgc ccttagacga    16920
ttcactcaac gtctctgatc catggcatgt acaactataa gatgggcatg cccttctcct    16980
ctcgggctgt tatgaaggtc aaggaagcaa gggctgttac ccaagggtgc tcccttctct    17040 cccctcttc acaccccag gtgctctggg ccctctagga actgggtttc tctcaagggc      17100
tgttacccaa gggtgctccc ttctctcccc ctcttcacac cactgggtgc tctgggccca    17160
ctaggagctg ggattctctt aagagggaaa ctcttggata aggaaatgg tttgattgat      17220 atcggacaag tctgttcatt agtatccatt tattaagcac ctaccatgtg ccaggaaatg    17280 cttttggcgta caaaggaaaa taagggccag tcctgctaga aatggccttg aaaccccagg   17340
gagggatgtc ggcccattgt gggtgctgca gattccttga aggtgatgca agagccagaa    17400
agaaggatga tgtgggggc tgaggcaggg agtcggggtt ggggagtgt ggggagaag       17460 gggagaccga gcacctcttc cactatctcc ctgtgtggtt tttggtgaac catcctgcct    17520
```

```
ctgggtgtct tgcctccagc ttctgacgtt ggaagttcat ccactgagag ctctgtgttt   17580
atggctctga gatactgagt ccttcttctc tcccagacct cttaacaatc catggcattg   17640
gacggcattt gcggggattt tgagacaatc tttcatgttc tatggagccg gataccaagt   17700
agaaaaagtg atttctcatc caaattatga ctccaagacc aagaacaatg acattgcgct   17760
gatgaagctg cagaagcctc tgactttcaa cggtacgtgt ggctcaggct tggcaagcag   17820
gttggcagaa tcttaaagag atgttgattg gaaatgacac ttgtgctatg ccaaatggaa   17880
gggaggcatt tgcgttgagc gagggtagcg tgcagcgggt ggccaatggg agaggctcac   17940
agaggctaag agcacctgcc gcattttggg ggaggcagca gccaccacat ctgttctgta   18000
ctgtactgag tggtggtgat tcaagccagg catggaaaag gctagaacag ggctttccca   18060
ctgcagcacc cttgacatct gggtggttct ctgttgtagg gctctcttgt gccttgtagg   18120
atgtttaaca gcgtccccag cctctaccca ctggaggcca gtagctacca agctgtgaca   18180
accagtgttg cctgctgaca ttgccaaaca tccgctttga ggcaaagtca cttccagttg   18240
agaactactg gcctaaaatg tgtaaagatc cttgattttt aaagatacat tctaaaacca   18300
agttgcttaa ttcaggacaa acatgctttc tcttagcctc ttattcggtc ccactctggt   18360
ccatccaagg gtctggaatg ttctagcccc atgtggatac agaagaagca aaacctcagc   18420
cctccctaca gcatgtctgt attcacattg ggaaatggtt cacatataga gagcgaatg    18480 cctgagcaat ggcgtggtgc ctctggggcg aaagctgact ccattgactc catcggcttt   18540
ttggctgttg cctcctgtgt gtcttttccg tcttgatcac ctggagatat gtaattttgg   18600
aagcagagct agcaaataat tcctcttata agcagagcta gcaaataatt ctacttataa   18660
gtagcataac gtcttgcctg ccagaaggag aggtctggca gggggagaaa gtgagaatgt   18720
gggacttgtt gggatgcagg gtcctctggg cagggtggcc agggtgccag gcccagcagc   18780
ctgcatgtgg gaaggccagg tggagacata ggtgataccc gcctggctca ctgtgttttc   18840
tcttcttgaa acagacctag tgaaaccagt gtgtctgccc aacccaggca tgatgctgca   18900
gccagaacag ctctgctgga tttccggggtg ggggccacc gaggagaaag gtgaggctgc   18960
tcctgggcac acaggactgc agggcccaca gatggagcat tgggttcgga agtgggaggt   19020
ccaggtttta atcccagttc tactactcaa tgactggatg actttggttg attccccag    19080 tccttgtgcc tcagtttctc catctgctaa gtgggagaaa tcctgcccag cctacctaat   19140
acactgtgtt cttatcgtga tcacacagag cagcatgtgg aatggctttt gaagtatctg   19200
ggccatacga gtttagaggt gcaggatctc ctgtgttgca ctcattgtga gtttagagct   19260
gccctggaga tcccaccaag gcctgcgtgg ctgagtgaca gggggcttgg tgaggacggg   19320
catcctggac ccatggtggc cacatctaag cctgtcctct gccctgataa ccacagagag   19380
aggctctctc cacccacttc ctttgcaatc tgcatttctc tctgacagtc tttcaaatga   19440
agggagcctg gctgcttcat ttttatggag ggttggaagt gcttagtggc aggcacaaag   19500
gttcatttta catattgttt atatccttct caaaagcgtc taggccatac agacaacaaa   19560
tcctttcaaa caaggggaaa agtacaaagg ttgggtgatt tctggggagc gtcagggaag   19620
gtagtggggg gcatcctggc tcctcatcag cagaaactta ctacagtaga gccacaggct   19680
gggcaaaaga cctcatggaa tccaagatga agggaatatc gacaaatatt tgtgcgcacc   19740
tgcacctagt acaggctggg tgctactcag gtgctgggaa tgcagaagtg aacagagtaa   19800
gacaaatgtc tctgctgtca ggagctttac ctctcttctg gatgtcggtg gtggggacgg   19860
```

-continued

```
ggcaggtgtg gtcagacaga tgggagacaa acaactgagc gaggtacttc caaacatctg    19920
agggtgggga tcacaaggtc ccggctattt tgaaggggtg gtcaggaaag gcttctcgga    19980
agaggtggca tttgagctga gactcaaatg gcaaaaatgt gtacacatca aaaaggctag    20040
tgcatgtatc ttcaggtgtg gtcaaggggc caaggaggtg ggctgggggcc agattgcata   20100
ggtccttgtg gattatggtg aagacaccag cttctcatct gcttgaggtg gggagatcgt    20160
gagccgggga gtgccatgat ctggcagctg cgtgggggagt ggggatgaat ggatggagac    20220
gaggatgatg gtgacaagtc cattgctgtg gttccttgag acaggaagcc agctcatagc    20280
agagtgcggg cgtggatgtg aagagatgag ggtacactag ggctagagcc accagactta    20340
ctgatgggtt gcatgtctgt gggagagaga gtgagaagtc agggacgatg gctttccact    20400
ctgtggctga agccccaggg tggcgggtgg tgccatttttt caagccagga aatattggtt    20460
ggtgagaatt tggggtggga aaggtgtgga cggagggttc tggttttgca cactaagccc    20520
acggtgccca gaagatgccc gaggggaggc agcaaagcga gagtgggaaa tgcagaggtg    20580
gcaagtgcag gccgtgtctt gagaagctct aatgtgcagg ggagccgaga agcaggcggc    20640
ctagggaggg tcacgtgtgc tccagaagag tgtgtgcatg ccagagggga aacaggcgcc    20700
tgtgtgtcct gggtgggggtt cagtgaggag tgggaaattg gttcagcaga accaagccgt    20760
tgggtgaata agagggggat tccatggcac tgatagagcc ctatagtttc agagctggga    20820
atttcttttcc ctgaagctga actccagagc tgcattcagc acaggcaccg ccagttgtaa    20880
ggagaatcca ggtttcccag gagagggggtt ggtgctggga tgagctgacc ggggcagggc    20940
tggaaaatag ggctgtgacc atctgtgtag tgcgtgtgga ggtctcaggg agggaagtgt    21000
gctctccctg cgagagctgc aggcaacact gggagctcaa caagtctccc tgtccttagg    21060
gaagacctca gaagtgctga acgctgccaa ggtgcttctc attgagacac agagatgcaa    21120
cagcagatat gtctatgaca acctgatcac accagccatg atctgtgccg gcttcctgca    21180
ggggaacgtc gattcttgcc aggtaattca acatttttat tctacctttg gtccttacca    21240
gatcctactg aaccccccat gagagagagg gcattcttgg ggtcagcaga gcctcctcag    21300
tgacacggag ccagctcggg gcagtcatgg gaagtgacgg ccacaaacag tgcgaacgct    21360
tctggtggca gaaggaagta cagtcaacaa atcacacaca ccctctgaaa aaccggtatt    21420
tggtaaaagt gccagtggaa cagaaacaag tatttagact attttaaatt atgaacggca    21480
atttatttag taacttttag cttgaacaga ttaaaattca ggatgggggc tatctctttg    21540
ggggttacat ctctgttacc atcacccctt gatggtggag attcgaagcc cacacagtca    21600
ctcgtaactc acactgcgac ccccgccccc caactcctct aggcctggtc agtggtgtgc    21660
ggcagattgt gacttgattt tctgctctct gtaccttgct gtgtcccaca gggtgacagt    21720
ggagggcctc tggtcacttc gaagaacaat atctggtggc tgatagggga tacaagctgg    21780
ggttctggct gtgccaaagc ttacagacca ggagtgtacg ggaatgtgat ggtattcacg    21840
gactggattt atcgacaaat gagggtaact atcctgtcct ccttctgact gtgttctccg    21900
attcctcgag ccaaagccag acatctgtta ggcgtggttc tgctgctgga agctgactgg    21960
tgaccactgg tcagcatgaa gcaaactctg cttcctccag ccacagcccc atcccccag    22020
tgtccaccca ttgcccattg cctctcactg gcttcacttg catatttccc ctggtgtttg    22080
gatgaaaagc gctggggctc agcttgtgtg aaattccttg gtgctctgcc aaccacactt    22140
cgttctggct cagctgactc agctgttcca cccaggccac ctcacatcaa actttttttt    22200
ttttttttg agatggagtc tcactgtgtc gcccaggctg gagtgcagtg cacaatctc     22260
```

```
gactcactgc aacctttgcc tcctgggttc aagtgattct cctgcctcag cctcccaagt    22320
agctgggact acaggcatgc gccaccacgc ccagctactt tttgtatttt tagtagagat    22380
ggggtttctc catgttggcc aggctggtct cgaagccctg acctcaggtg attcacccac    22440
ctcagcctcc cacagtgctg ggattacaag tgtgaaccac ggtgcccggc ctcacatgaa    22500
acttttgatt tatagagagc agagggaaga gccggctgtg cccatccttt tctggggcca    22560
tcgagtggct cctgggcagc ccccaaggtt aggaagggca ggagcagcca gggttctctg    22620
atgccccaga ctcaagcacg agggaaggtc tcaggggttc catgtgagcc tcatggatgt    22680
ctctgcttag cagagccctg gctttgggca ttgtccagat aggggtgag aaccagatct    22740 tctcatctcc aggacctcag acgtatagtt ttctcagatt tctgtgcttt ctggggctgg    22800
gctactagtg gaagaaagca gtctattctg tcttctccca aatctcccag atgcccagtc    22860
tgttgaagga ggagcagaac caggggggcct ttcccgctga ggcccgacct gtgtctcctt    22920
caaatgacac gcgggactca gggccttccc atgaccatgg ggcccagggg gcgtcacctg    22980
gcccagggcc cagtgctaga aacagatgac cccaggagga ggaggcaggg caggagggaa    23040
gctggcaggg ctgggatggt cagccaggct gaggggcgga ctcgcaccag gatggagcta    23100
ggaaatgatc caggtgtgtt tggcggctgc aggtgggtcc gcatggctgt gcagggaggg    23160
aagggctgcg tggcaggaga gcagccgggg gaggcccaga ctctgctgaa gagatgcctg    23220
ttgtgccggc ctccacatcc gctgcccgct ccttccggag ctcctgcccc gccatgctca    23280
gcctgactct gaccaacacg ttggagagaa gaatgatccc tttgtgctat taagcttgct    23340
tatttggttt ctaagtgctt catgcgaacc tagaggaaaa aattattttc cacctttgtt    23400
tgtcttaaga aaataacaca cttttttttt tcctatttga acaggcagac ggctaatcca    23460
catggtcttc gtccttgacg tcgttttaca agaaaacaat ggggctggtt ttgcttcccc    23520
gtgcatgatt tactcttaga gatgattcag aggtcacttc attttttatta aacagtgaac    23580 ttgtctggct ttggcactct ctgccattct gtgcaggctg cagtggctcc cctgcccagc    23640
ctgctctccc taaccccttg tccgcaaggg gtgatggccg gctggttgtg ggcactggcg    23700
gtcaagtgtg gaggagaggg gtggaggctg ccccattgag atcttcctgc tgagtccttt    23760
ccaggggcca atttttggatg agcatggagc tgtcacctct cagctgctgg atgacttgag    23820
atgaaaaagg agagacatgg aaagggagac agccaggtgg cacctgcagc ggctgccctc    23880
tggggccact tggtagtgtc cccagcctac ctctccacaa ggggattttg ctgatgggtt    23940
cttagagcct tagcagccct ggatggtggc cagaaataaa gggaccagcc cttcatgggt    24000
ggtgacgtgg tagtcacttg taaggggaac agaaacattt tgttcttat ggggtgagaa    24060 tatagacagt gcccttggtg cgaggaagc aattgaaaag gaacttgccc tgagcactcc    24120
tggtgcaggt ctccacctgc acattgggtg gggctcctgg gagggagact cagccttcct    24180
cctcatcctc cctgacccctg ctcctagcac cctggagagt gcacatgccc cttggtcctg    24240
gcagggcgcc aagtctggca ccatgttggc ctcttcaggc ctgctagtca ctggaaattg    24300
aggtccatgg gggaaatcaa ggatgctcag tttaaggtac actgtttcca tgttatgttt    24360
ctacacattg ctacctcagt gctcctggaa acttagcttt tgatgtctcc aagtagtcca    24420
ccttcattta actctttgaa actgtatcat cttttgccaag taagagtggt ggcctatttc    24480
agctgctttg acaaaatgac tggctcctga cttaacgttc tataaatgaa tgtgctgaag    24540
caaagtgccc atggtggcgg cgaagaagag aaagatgtgt tttgttttgg actctctgtg    24600
```

```
gtcccttcca atgctgtggg tttccaacca ggggaagggt ccctttttgca ttgccaagtg    24660 ccataaccat gagcactact ctaccatggt tctgcctcct ggccaagcag gctggtttgc    24720
aagaatgaaa tgaatgattc tacagctagg acttaacctt gaaatggaaa gtcatgcaat    24780
cccatttgca ggatctgtct gtgcacatgc ctctgtagag agcagcattc ccagggacct    24840
tggaaacagt tggcactgta aggtgcttgc tccccaagac acatcctaaa aggtgttgta    24900
atggtgaaaa cgtcttcctt ctttattgcc ccttcttatt tatgtgaaca actgtttgtc    24960 ttttttttgta tctttttttaa actgtaaagt tcaattgtga aaatgaatat catgcaaata    25020
aattatgcaa tttttttttc aaagtaacta ctgcatcttt gaagttctgc ctggtgagta    25080
ggaccagcct ccatttcctt ataaggggggt gatgttgagg ctgctggtca gaggaccaaa    25140
ggtgaggcaa ggccagactt ggtgctcctg tggttctcga gataacttcg tataatgtat    25200
gctatacgaa gttatatgca tggcctccgc gccgggtttt ggcgcctccc gcgggcgccc    25260
ccctcctcac ggcgagcgct gccacgtcag acgaagggcg cagcgagcgt cctgatcctt    25320 ccgcccgac gctcaggaca gcggcccgct gctcataaga ctcggcctta gaaccccagt    25380
atcagcagaa ggacatttta ggacgggact tgggtgactc tagggcactg gttttctttc    25440
cagagagcgg aacaggcgag gaaaagtagt cccttctcgg cgattctgcg gagggatctc    25500
cgtggggcgg tgaacgccga tgattatata aggacgcgcc gggtgtggca cagctagttc    25560
cgtcgcagcc gggatttggg tcgcggttct tgtttgtgga tcgctgtgat cgtcacttgg    25620
tgagtagcgg gctgctgggc tggccggggc tttcgtggcc gccgggccgc tcggtgggac    25680
ggaagcgtgt ggagagaccg ccaagggctg tagtctgggt ccgcgagcaa ggttgccctg    25740
aactgggggt tgggggagc gcagcaaaat ggcggctgtt cccgagtctt gaatggaaga    25800
cgcttgtgag gcgggctgtg aggtcgttga aacaaggtgg ggggcatggt gggcggcaag    25860
aacccaaggt cttgaggcct tcgctaatgc gggaaagctc ttattcgggt gagatgggct    25920
ggggcaccat ctggggaccc tgacgtgaag tttgtcactg actggagaac tcggtttgtc    25980
gtctgttgcg ggggcggcag ttatggcggt gccgttgggc agtgcacccg taccctttggg    26040 agcgcgcgcc ctcgtcgtgt cgtgacgtca cccgttctgt tggcttataa tgcagggtgg    26100
ggccacctgc cggtaggtgt gcggtaggct tttctccgtc gcaggacgca gggttcgggc    26160
ctagggtagg ctctcctgaa tcgacaggcg ccggacctct ggtgagggga gggataagtg    26220
aggcgtcagt ttctttggtc ggttttatgt acctatcttc ttaagtagct gaagctccgg    26280
ttttgaacta tgcgctcggg gttggcgagt gtgttttgtg aagttttttta ggcacccttttt    26340 gaaatgtaat catttgggtc aatatgtaat tttcagtgtt agactagtaa attgtccgct    26400
aaattctggc cgttttttggc ttttttgtta gacgtgttga caattaatca tcggcatagt    26460
atatcggcat agtataatac gacaaggtga ggaactaaac catgggatcg gccattgaac    26520
aagatggatt gcacgcaggt tctccggccg cttgggtgga gaggctattc ggctatgact    26580
gggcacaaca gacaatcggc tgctctgatg ccgccgtgtt ccggctgtca gcgcaggggc    26640
gcccggttct ttttgtcaag accgacctgt ccggtgccct gaatgaactg caggacgagg    26700
cagcgcggct atcgtggctg gccacgacgg gcgttccttg cgcagctgtg ctcgacgttg    26760
tcactgaagc gggaagggac tggctgctat tgggcgaagt gccggggcag gatctcctgt    26820
catctcacct tgctcctgcc gagaaagtat ccatcatggc tgatgcaatg cggcggctgc    26880
atacgcttga tccggctacc tgcccattcg accaccaagc gaaacatcgc atcgagcgag    26940
cacgtactcg gatggaagcc ggtcttgtcg atcaggatga tctggacgaa gagcatcagg    27000
```

```
ggctcgcgcc agccgaactg ttcgccaggc tcaaggcgcg catgcccgac ggcgatgatc    27060
tcgtcgtgac ccatggcgat gcctgcttgc cgaatatcat ggtggaaaat ggccgctttt    27120
ctggattcat cgactgtggc cggctgggtg tggcggaccg ctatcaggac atagcgttgg    27180 ctaccccgtga tattgctgaa gagcttggcg gcgaatgggc tgaccgcttc ctcgtgcttt    27240
acggtatcgc cgctcccgat tcgcagcgca tcgccttcta tcgccttctt gacgagttct    27300
tctgagggga tccgctgtaa gtctgcagaa attgatgatc tattaaacaa taaagatgtc    27360
cactaaaatg gaagtttttc ctgtcatact ttgttaagaa gggtgagaac agagtaccta    27420
cattttgaat ggaaggattg gagctacggg ggtgggggtg gggtgggatt agataaatgc    27480 ctgctctttta ctgaaggctc tttactattg ctttatgata atgtttcata gttggatatc    27540
ataatttaaa caagcaaaac caaattaagg gccagctcat tcctcccact catgatctat    27600
agatctatag atctctcgtg ggatcattgt ttttctcttg attcccactt tgtggttcta    27660
agtactgtgg tttccaaatg tgtcagtttc atagcctgaa gaacgagatc agcagcctct    27720
gttccacata cacttcattc tcagtattgt tttgccaagt tctaattcca tcagacctcg    27780
acctgcagcc cctagataac ttcgtataat gtatgctata cgaagttatg ctagtaacta    27840
taacggtcct aaggtagcga gctagctcca cgtggctttg tcccagactt cctttgtctt    27900
caacaacctt ctgcaagaaa accaagggcc tgaattttaa cttcctg                  27947

<210> SEQ ID NO 6
<211> LENGTH: 25333
<212> TYPE: DNA
<213> ORGANISM: Artificial Sequence
<220> FEATURE:
<223> OTHER INFORMATION: Recombinant polynucleotide

<400> SEQUENCE: 6
gcagagtcta agaaatcgct gtgtttagcc ctcgccctgg gcactgtcct cacgggagct      60
gctgtggctg ctgtcttgct ttggaagttc agtaagtgca gggagcctcg atcccaccat     120
gtgctcctgc agtccccagt gctctgagcc agaccctgct ctctgggcta ttgagacctc     180
tggaggccct ccgtgaggtt cctctcttac ataacgaggc tgtctctctt cccttctctt     240
gtttagctat gagattgaca catcatgggg aaagcattta gaatgtaccc agtgctttgg     300
ggtgcttggt gccacccagc actgtgagca caggttcttc taccttgggg ccacacccag     360
ttacctgtat ctcactgcac agcagtggct gttggggacc aggcccaccc ctccatgtcc     420
cacctcctgc aactgcagcc tgagccttcc catcagcctg gggtggtgca gacccatgtg     480
ccattgtgga tccttcaagt tacctgtgtg gcagagagga cgtgtgagtg ccgtccaaac     540
ccaaacactg agagggtcct tcccattgcc cccacgaagt aaggtgccc cagtgctaat     600 tccacttata cttgctggtg gcaaggacac ttctcctcct tattaaagtg gggattggc     660 tgggtgaggt ggctcacgcc tgttatccca gcactttaag aggccaaggc aggtggacca    720
cctgaggtca ggagtttgag accacaagcc tggccaacat gttgaaactc catctctact    780
aaaaatacaa aaattagtca ggcgtggtgg cgtgcacctg taatcccagc tacttaggag    840
gctggggcag gaggatcact tgaacccagg agttggaggt tgcagtgagc caagattgtg    900
cccctgcact ccagcctggg tgacagaatg agacttcatc tcaaaaacaa aacaaaacaa    960
aacacagtgg ggccaggagt tggaggctgc agcgagctac agtaatgcca cggtgttcct   1020
cactccatga ggctcattgc gtttctcagc ctgaagggca cctctcttct gttttctctg   1080
```

```
caagtgggca gcaagtgctc caactctggg atagagtgcg actcctcagg tacctgcatc    1140 aaccccctcta actggtgtga tggcgtgtca cactgccccg gcggggagga cgagaatcgg    1200
tgtggtgagt cagccttgac cttgggaagg gactcctctg ctcaccttgg agacagcagc    1260
cgggtccagg ggcctttggg tgactgggcc tggcgtgcgt ccagtacgct gacacatgat    1320
gtcattgaat ccctgctcca ggctgagccc tggggctcag agaggttgtg tttccggccc    1380
aacctcaccc agcaggtggg agatgacagg gccaccgagg actgtgtcat tggaaccaca    1440
cgtgctctga actgccacag gaagtcagtt aagatgagca aactgtttat aaagttggag    1500
atgcaggcta ggaacggtgg ctcatgcctg taatcccagc actttgggag gccgaggcag    1560
atggatcacc tgaggtcagg agtttgagac cagcctgacc aatatggtga aaccttatct    1620
ccactaaaaa tacaaaaatt agccaagcgc ggtggcgggt gcctgtaatt ccagctattc    1680
aggaggctga ggcaggagaa tcacttgaac ctggaggcg gaggttgcag tgagctgaga    1740
tcacgccact gcattccagc ctgggagaca gagctggctc aaaaaataaa ttaattaatt    1800
aaaaacaaaa ttggagatgc actatgttat tttcaaaaca agctgccttt aaagatctat    1860
ctgttgtcac agggtgggct catctgtttc attttatttt ctgtggttta tctatttatt    1920
cattttaatg aactaggaag cattgctcct atttatggca taccacatga tgtttggata    1980
cgtgtatgcc tgtggcatgg ctaagtcaag ctagaacatg ggccttacct catatacgtg    2040
tcttattaag aacacataaa acctactctt gtagtgattt tcaaatatgc aacatatagt    2100
ttattaactg cagtcactat gatgtacaat agattgctcg aacttattcc tcctgtctaa    2160
ctaagatttt gtgacctctg accaacatct ccccagtgtt gtcaccccccc gcccccagcc    2220 tctgatagct gcctttctac tctctgcttc tgtgagtttg atgtttatac attccacatg    2280
taagtggcct catgcagtgt ttctgtctct gtgtctggct tgttcactta gcgtaatgtc    2340
ctccagcttc atctatgttg ttggaaatga caggatttcc ttctttcttg tggctgaata    2400
gtattgcctt gtgcatatac accacatttt ctttatccct tcattcactg atggactctt    2460
aggttgatgt catgtcttgg ctgttgtgaa aaatgccgca gtgagcgtgg gcgtgcaggt    2520
ccctcttcaa cacacggatt tccttttcctt tggatataaa cccagcagtg agattgctgg    2580
atcacatggc agttctgttt ctcacctttt gaggaaactc catactgttt tccataatgg    2640
ctgtagcaac ttccactccc acccccacgg tgcaaagtct ccatttctct tctacaacct    2700
caccaactcc tgttatttc catctttctg atagtagcca tttgaagagg tatgagatga    2760
tacctcattg tggttttcat ttgcattttt atttgtattt ttcatgaatt tttgagggtg    2820
atttcaaggg tagttagtga ctcgaacagg gaaacgatcc tgagtatgag ggttgtgcta    2880
atcatccccc tcctgccagc tgcgtacgga atggggctct gcagatggca gggagctggc    2940
tcgtttctct ttaagagctg ccttttactt ttcttcctct tcctttaaaa cttatttcct    3000
ggccggacgc agtggctcat gcctgtaatc ccagcacttt gggaggccga ggtgggcgga    3060
tcacgaggtc aggaattcca gaccagcctg ccaacatgg tgaaaccccg tctctactaa    3120
aaatacaaaa attagccaga cgtggtggtg cgggcctata gtcccagcta ctcgggaggc    3180
tgaggcagga gaatcacttg aacctgggag gaggggttg cagtgagccg agattgcgcc    3240
actgcactcc agcctgggcg acagagccag actccatctc aaaaaacaaa aaaagttat    3300 ttcccaagca cagccatgta ttccaggctt gtggatcagc gttggtggtg gtgtgtgctc    3360
tcatatctta gttccagcta agcacactct gacatgtttc cactagaacc atttgttttt    3420
tctagaaata gaaatttcag aattgtagag tcagaggact taccagaaat ctcttaggta    3480
```

```
gttctcctcc cctccctcaa gtgcagtcct aacctcctgg agttttctgt agaaaccaca    3540
agcctcagag ctggccgaga attctagcca aagattttc catgccaaag taatccccc     3600 tctcctaagg gccatccttg gtggggactg gtttcctgtt aagccctcgc tgtcagtcct   3660
ggctgtggaa tttcctggtg aggagcactg gcccgtggag ctcggccctc gtgccggcct   3720
tgagcaggcc caagtgttcc gtgttcttga tacctttcct ccagcacagt cttgcttccc   3780 agaaaaggt ttgcacttga aaatgatgca tttgctgatt aaacatagtt cttttgcttt    3840
atttggtttc taaaataaag tgggagtttt tgagattgag taacgtgagg ttaagatagc   3900
acgtggaatg gcttttttctt ttctttctat tttttttttt tttttcctgg agacagggtt  3960
tcactctgtt gcccaggctg gagtgcagag gcatgaccat ggctcactgc aacttcgatg   4020 tcctgggggtt aagcgatccc ccagcctcag ccccccaagt ggctgggact acaggtgctc  4080
gccaccacac ctggctaatt tttgtatttt ttgtagaaaa tgggtttcat caatgttgtc   4140
cagactggtc tcgaactcct gacctcaagc aattctcctg cctcagcctc ccagactgct   4200
gggattacag gcgtgaacta ccacgcctgg cctggaatgg cttttgatgt tctcctatgt   4260
gcacatgtgg gtgaataaac accaacaaag tccttatgtt acctgaagag ttgctctctt   4320 cttaatatt aagtcgtatt tatttaaata ctttaatagt tgtacactat taaagtatta   4380
ttaggtcaaa atcaaggaag tacaaaaggg tatgctgtga aaatctctt cttccttgct    4440 ctgcttactt acctaccccg catcccccca tacacccccag acacacacac acacacacac 4500
acacacacac acacacgcat cactcccata catgcccacc tgtttaccag ccaatcacat   4560
ttcttggggc aactcatctg agttgcttct cttttccagag agtttttgca taaagaagca  4620
caggtatttc tgcgttacca tgaccctatt tcccagtggt tcctagccag ttgactctcc   4680
tgcactggat accatcctgg acagcattcc ttagggaaat gagccccctg ttttttccca   4740
ccatggcaca gttggtcctt tgcatggacg caccattatt gcccctgtct cttcttggtg   4800
gaccttaagg ttttctccat cctttttgctg taacacacac tgctccaagt gtgtgagcat  4860
atcagtagga aacgcttcca ggagtagaac tgctaggtca gagggcgtgt ggatctgtaa   4920
cctgacagac ctagaccggc ttcagtttgg ttttatccag tttccatatt gattattcat   4980 ataaaggaa acagacaaac ataacgctgt gcatgtattc tctcttagac cagaacaggc    5040
atagggtgca cttttaattt gtccatttcg tagagtagaa attgtttttg ctgaaatgaa   5100
caccttagga tgctgaagaa tatgacccgt cccatggaaa acattcaaaa atgtgtgtag   5160
cgctttcttc ccaagggtgt gtgtgcgcat attttaacac taattcactt tctacttccg   5220
ttgctatcct ttctgtgagt ctttctcaga atctcagaaa agaaactaaa ttgttcactc   5280
tagttatcaa tgctgtactc tatacctgga atttgctaaa agggcagatt ttaagtattc   5340
tcaccacaga aaagagaaaa gaaaatggta attatgtgac gtggtggaca tgttaactag   5400
ctttattatg gtgagcattt cacagcggat atccagtcat cacgctgtac acattaaaca   5460
tgtacaattg ggtttttttg agacaaggtc tccttctgtc acccagtctg gagtgcagtg   5520
gctcagtcat ggctcattgc agcctcgacc tcctgggctc aatccatcct tcccctcag   5580 cctcctgaaa agctggggcc acaggcatgt accatcatgc caggctaatg catatatatt   5640 tatattttt ggtggagatg gggttggtct cgaactctgg gctcaagtga tcctcccgcc   5700
ttgcccttcc aaagtgctga gattacaggc atgaaccaca gcaccaggcc tacatgtaaa  5760 attttatt gtcaactata ctttgacaaa gctgagaaaa aaaatcctaa tatttaaaaa    5820
```

```
aaaaaaaaaa aggactagct tgagaccttt tccagctctc tggcttatca gctgccgtct      5880
cttccgggtg cagatagctg aagggaaag  aaaatcccta aaattaccca caagccaaga      5940
atgaagtgtc tcccttgag  ccacagtggc agttttgttt ttaatcatag aagtgtattt      6000
tgagccgggt gtgctggctc acgcctgtaa tccccgcact tgggaggcc  gaggtggggg      6060
gcggagggg  tggggatcgc ctgaggtcag gagttcgaga ccagcctgac caacatggag      6120
aaacccgtc  tctactaaaa atacaaaatt agccggcgtg gtggtgcatg cctgtaatcc      6180
cagctactca tgaggctgag tcaggagaat ctcttgaacc caggaggtgg aggttgcggt      6240
gagctgagat catgccattg cactccagcc tgggaacaag aaaaaaaag  aagaagaaga      6300
agaagtgtat tcatttcagt tacttttaaa aaagtgaaca gactttatat tttagagcgg      6360
ttttaggttt acagaaaatg aaacagacag ggcagcgagc tccttgtact cctccccagc      6420
acacagttgc cctgttatga acatcccaca tcagtgctgt gcgttcatta acaccgatga      6480
acctgatgca tacattatga tgaactgaag tcctggactt caccctttct cttgtacagt      6540
tctgtgggat ttgacaaatg cataatgctg tacagccaca atgatagtat cgtccagagt      6600
agttctcctg ccttaaaacc tcttttgctg cacctgtttc tctctcccca ctcaccccag      6660
ctatctgatc ttcttagtgc ctccgaagtt ttggtctttt caggatgttg tagcgttgga      6720
atcatggagt atgtagcctt caccacatac accttcctc  actttgttgg cttcctttac      6780
ttagtaatat gcattcaagt ttcctccatg ccttttcatg gcttgatagc tcatttcttt      6840
ttagcaccaa ataatattcc gttgtccaga tgtagcacaa tgtttatcca ttcatgtaac      6900
ctgtgaccga ctcacagata ggatgtggaa tcactcacca cagaggcatt agacaataat      6960
cagacccaag tcatttcatg ggggaacaag cccacaggta ccagactgtc cagtgagtca      7020
gggccactcg taggaagtaa gaagagaggc tagagcatag ccaggtcctc actttatact      7080
ttaagcccat gtgtatttct cccaaaccac acagcattgt ttccatgctt tcagctttgc      7140
atgaataacg tgatacttga acgcatcatt tatcacttgc tctctttccc acagcgctgt      7200
tttcaagctt cttcctgttc atgatgctct gcttaaccct taagctgcat gggattctgt      7260
tctgtgaata cgcccacccc atgtattatc ctgcccagca aaaagtcccc aaaactctgg      7320
atggtggtta cctctaggga gggagagaag agattgggaa tagggagcga cttcaacggt      7380
gtttgtaatg ttttgtttct ttaaataaaa gagctgagat catttcagca gaatgttgat      7440
ttagagtctc ctggacaatt tgttgctcaa agtgctctct taaagagcac tttaaaaaaa      7500
aaaacctttt atcttattat ttatttattt atttattgag acggagtttt gctctgtcac      7560
ccaggctgga gtggagtggt gtgatctcag ctcactgcaa cctttacctc ctgggttcaa      7620
gcaattcccc tgcctcagcc tcccaagtag gtgggattac agatgcgtgc caccacactt      7680
ggctaatttt tgcattttag tagagatcgg tttctccatg ttggccaggc tgatctcaaa      7740
cgcctgacct caggtgatct gcccgccttg gcctcccaaa gtgctggtat tacaggcgtg      7800
agctaccatg cctggcttat cttatatatt tttaaaaaca gcttattgag atctaattta      7860
tgtaccataa aattcaagta tataattcag tgcttttata tataaaacat atatatgaaa      7920
tagcttattg agatataatt ttttatataa aacagcttat tgatatgtaa tgtatgtacc      7980
ataaaattta aatatataat tcactggctt ttatatattc acgaatatgt gcaactatca      8040
ccacagtcaa ttttagcata ttttcatcag ctcataaaga aaccccaagc ccttgaacta      8100
tcaccccata tccctcctcc cagcccgtcc ctcctactca taagcaacca ctaatctact      8160
tagtgtctat agatttccta ctctaggcat tccatgtgag cgggatcatg caatacgtgg      8220
```

```
gctcacacaa tataagtggc attccatgtg agtcggctca tgcagtatgt ccggctcctt    8280
tcactgagca taaggtcttc agcactcatc caggttgcag cctgtgtctg aatttcattc    8340
cctcttctgg ctgaatcgta ttccattgtg tatcttggac atatcctatt ctgctcaccc    8400
agccgttggt gggcgtttgg agtgttttcg cctttcagct gttttaagag ggttgcagtg    8460
aacatttgta caagttttgg acccaatgcc tgttttcaat tctcttgtgt agagagcact    8520
ttttagcaga aaaagaatag atttgtggcc tcccttttgtg tgcggtcagt gccttgagaa    8580
gagtgaactg tgctgccacc tccggagccg tggagagcgc ggggcttggg tagcagctag    8640
gacgatacaa gttgggacaa ggccaggtgc aatggctcac gcctgtaatt ccaacacttt    8700
gggagaccga ggcaggggga tcacctgagg tcaggagttc aagaccagcc tggccaacat    8760
ggtgaaaccc catctctaat aaaacagaaa aattaactgg acggggtggt ggacgcctgt    8820
aatcccagct actcgggagg ctgaggcagg agaatcactt gaacctggga ggcggaggct    8880
gcagtgagtg gagatcagac cactgcactt cagcctaggt gacagagcga gactccgtct    8940
caaaaaaaag aaaaaaaaag aaagaaactc atggataatc ctccctctcg tgcagttcgc    9000
ctctacggac caaacttcat ccttcaggtg tactcatctc agaggaagtc ctggcaccct    9060
gtgtgccaag acgactggaa cgagaactac gggcgggcgg cctgcaggga catgggctat    9120
aagtgagtat ggggcagcac ccgccgagtg acagtaacag acagcagaaa cacgagaaga    9180
ccctctctct gcctccctgt gaaagcaccg gcacatgagt gctggggaca attgtcacct    9240
tccaaaagct gagccctata accagcaggt ggaatttgtc ctgctagggc tgtgcccagc    9300
acacagacct tggctcactg ccaccttgcc ctgcctcctc cttggcctct atagactcct    9360
ggttgctcgg gagtgcccag tgctgtggtc atctggtcag aggggtaggc tgagggcgtt    9420
aggtgcctct ttttccaagg tgcctctcag ccagggtcca ttcacctccc tgggtagagg    9480
ttggaccaga acagctggcg aggagggttg ggctggggag agcagcagag acaaatcctg    9540
tgccagtttc acttcattcg ggagccatgg aagccttttg agctggggag agaatcaatc    9600
aatcagactg atacttaaaa aatgtcattc ctgctcgtag ctctgaggga aggtgggaag    9660
gcttaacagg gtgtgtgtcg cctgacagtg attcctaacg ggggtgggc ggtggttacc    9720
atttaccagc actgcctggg gagatgcggc agccctcagg catcggggga gagggtggta    9780
ggatgctact gccactttgt tttccatggg agggtcccca ggtgatttct atgcaacttt    9840
agggtattca atatgccagt tttcagaatg aattaccact cggtgagaaa gttggcatct    9900
tagctagtca ctgtgacatc cctaaacagc aggggtgaat tacacagcaa agcccccca    9960
tcacagtcca ggaacctggt ggaattgata actggggcca tgttaacatc tgtacctttt   10020
attagattaa atgtgtgtat gattatacaa tcctatgtcc ttctcatagt ttcttgatcc   10080
taacctggat aagaaacacg accaatgaag gaattttgtc tgacacttta gggttattga   10140
atcgaaaaat cgttacaata ttctagcact tggttagaac gtgtgatttt ttttcctaaa   10200
tgctaaggtt tttccctctt attctgaatg tcgtatgagc ggtattatga catagtatag   10260
gatttgtgtt tgcttatgcc ttaaccatta tcacaaataa ggttttcttt tttaggaata   10320
attttactc tagccaagga atagtggatg acagcggatc caccagcttt atgaaactga   10380
acacaagtgc cggcaatgtc gatatctata aaaaactgta ccacaggtat gcagcaattt   10440
cttcttgaaa aattttggaa tgaaatcaac taggagacac catggggaat cgttgtcctg   10500
agtctgattt ctctgagctg caatactcgg tctggatggg ttttgcattg ggaggagatt   10560
```

```
agagtctgac caggcctggt tactctaagc agcccttggt ttattcatag gaagtggctg    10620
aggtttctct gctatttcat tttcagcctc taccgtctgc ccttgttggt agcggctcac    10680
acttgcaaca tcgacattca actctattta gttttctttc ctcttcagac atttagaggt    10740
gtacctattt tgtcagggcg tggttctagg aatccaagat aatgtctcag tgtcccagcc    10800
agggtgaccg gctcattcca gtttgccagg gacttcactg gcttgagcaa gggaagtcct    10860
gctccattcc aggcagctgg gctggctggt cccgttagcc ccaaccccgg acagcagtg    10920
ccagagggtg ctctgtgagg gatgggcagc attctggcgg cctgggaatg agttgtggtg    10980
tttccagggg gtagaagtgg gtacaagcca caggtcacat gatgagtggc tgacctggct    11040
gggagggcag aagaggggat ggacttaggc tcttcctttt gctttgcaca tatttaggat    11100
gtttgcagac ttgctatgat tgttgctgtt atgtgttttc tgatgtgaaa gatacacagt    11160
gtcctttgcc catgagctct ccttgcctcc caggtcccca gggcttatgc ctggtgtcta    11220
ggcatcacct ccctgcctgc caggtgccag gtgctgcatt tcggggagg atgaactaat    11280
caccccgcgc cacctttcct ctgagtggga gcctggggca ggtttgcatt cctggaggcc    11340
gctggtggag gggtctgggg gcctgacttc cactgcagcc tgctgtcctg gggaatgtgg    11400
cagggcaagc ccagtgggga gggctgtgca cggccaggtg cacccatcaa aacagcaggg    11460
ctgcggtttg tccctgtgga gaagctaaac acagctgcct gggcactttg taaatgctga    11520
gtggttcttt gtctttctgg gttacacacg gaatcaggga gccaagtcca gccgggcagg    11580
gacgggggga gggaggagg tgctgccgtc ccttggcaag agccttggga actcacaagg    11640
aggctggagg gcttggaaga aagaagagaa ggccattgtc tggtaggctc tattctatct    11700
cggtggtggt ggtgggggga ggcgcacttc ttttcctctt tctgtgcagc agttgccctt    11760
tgatgcctga gttcttggct tgttttctgt cgggcttctg tgaataacca catgtgccct    11820
ggcgctgtga ccacacaggg ctatccctac cgaccttagg attcttagga aatgtcttct    11880
cttaaagggg acatgtcttc acttggccgt gtcagtgccc cagagccaga gtccacctgg    11940
aatgcacctg tagtcactga gaacccgggg ggtgtgcctt agtaagaagg tgtcaggaag    12000
gacctattat tgtagggcct gggctcctgc aaggtggttt ggggtggtt ggaggaagca    12060
gagatttgct ctggattgga tgctgtcagg aagcaggggt aattctgtga ggctgcttta    12120
ttatttttt tctaggagga ggttggaatg aggctaggct aaagctgtga ttggtaaaga    12180
aacgtccgtc gctcaagtta gccaggacag gaggagacat cagatcgtga ttttgtggtt    12240
gtgagcacaa ggttcctgtt ctgtctgttc agacatcatt tcggaggagg ctccttgtgt    12300
cttgccccat ctcaggcatg gagggccta gtccgatatt gacgctcagt gaaataattc    12360
aggttccgca gagcacacgg cccagctatc agggcgggcc agctctgcat gccaggggcc    12420
gcgtcttccc ttctcagcat agcctgggaa attcactgca ggacaaaatg catcagttac    12480
ttcctcttca tccataacct gggatgtttg actcccaaat gagtaactct tacgtttctt    12540
ctaatcctag ggaaactatt ggttatattg ctttcaacac tacaaattta aagcagttat    12600
aggagcccag aggttccaa atggcttcct taaaaattag aagatgattt taaattccaa    12660
gaggaaaaac aaaactagca ttattgtata cttaccctca caaccgtcct aggagctggt    12720
acaattttaa gagaggttaa gtaacttgcc caaggtcaca ctgtggggat gtgagccgcg    12780
tacctttggct cagtgtctgg tctttgccac tgtccctata tggatttact taccttattg    12840
gagttgtaac tagcagaccc ttctatgtct cagaagacag gagagggaac atcggaagaa    12900
atgactgatt tctaagcatg tgagaggcag ggtgactccgc actatcgtga ccagaatttc    12960
```

```
ccctgttctt tttgcagtga tgcctgttct tcaaaagcag tggtttcttt acgctgtata    13020
ggtaagttca tctggagtcc cccttttgat acttctaact aggaaaagct ctctactttc    13080
agaacagtac tccctgtgtc tctggggcg tgggagggaa gaaggtgggg tcacggttg      13140 gaatgtgccc agcggcgtct cgctctttcc aaggagctcc tggtttagat ttccatggcc    13200
tgtagacacc ttcagccttg ggtccaaggg acaccccctg agatcaggca cgctcaagaa    13260
gctgacaaag ccctacactt tatgccaccc atgagctgga ggcccggcag gtctctttct    13320
ccagaaagca aagggggtg gcgttagtga gccctggcag ccacctaacg tggacttgga     13380
gcatctgcgg ggctgtggtc cagcaccacc gtgtggccac caggtgctca tcagccagtg    13440
ggacccggga ggagggacaa gaccagagaa caacagtgct cttgcctctt ctctcctgaa    13500
ttttggacgg tggcttagac ttgggtgtcc ccatctctgt gtttagagtg cttacagttt    13560
ccaaactgtt tgcaaatgtg gaagccaccg tccctctcct ctgggatggc ccagtgctgt    13620
cgtggggccg tggtcctgag ctcagctttt catttgaaga ggtggaagga gctgacaccg    13680
tcccatcccg gcagggctgg ctcaggtctt ctttaggtcc tgagtggggg tccagcacag    13740
ccccaagggt gcgtggcacc cgccctgccc tctgcccatg cactcatctc ctggtggaga    13800
agacactcac acacaggaag cagggaaggc agcagacctc actcaccct cacccctca     13860 ctcaccccct actcacccc tcaacctctc attcaccacc caccccctcg cccctcact      13920 caccccctca ctccctcaac cctcactcac ctcctcactc cctcaaccct cactcacctc    13980
ctcacctcct cactctcccc ctcatccctc cctcacccca cccgtcacc tcctcactca     14040 cctcctcacc ccctcactca cccttcaccc cctcactcac cacctcacct cctcactcac    14100
cccctactca cccctcatt caccccctcac cccctcactc accctgcac cccctcactc     14160 acccttcat ccactcaccc acctgctcac ctcctcactc aaccctcac cccctcacta     14220 atccctcact ccctcacccc ctcacgccct cactcacacc ttcacctcct cactcacccc    14280
ctcaccccct caacccctta cttacccct cactcatccc ttcacccctc actcaccccc     14340 tctctcacc attcaccccc tcactcatgc cttcacccc tcactcacct cctcactcac     14400
accttcaccc ctcagtcacc ccctcactca ccccttcacc ccctcaatca tgccttcact    14460
ccctcactca cccttcacc ctctgaatta ctccctcatc ccctcactca ccctcact      14520 cacccttca ccccctcacc caccacctca cccacccctc acccaccccc tcacctcctt    14580 accctcacc ccctcactc acccctcac ccctcactca ccactcacc caccctcac        14640 ccaccccctc actcactccc tcatcccctc actcacccc tcaccccctc actcacccc     14700 tcacccaccc ctcacccacc ccctcacccc ctcactcacc ccttcacccc ctcactcacc    14760
ccctcactca cccttcacc ccctcactca ccacctcacc caccccctca ccaccccctc    14820
actcactccc tcaccccctc actcaccccc tcaccccctc actcaccccc tcatctcctc    14880
actcaccccc tcacctcctc actcacccgc tcacctcctc actcaccccc tcgcccctc     14940 actcacccct cacccctca ccctcact caccctcac cctcgccc cctcactcac         15000 cccctcgccc cctcactcac ccctcacccc ctcaccccct cactcatccc ctcacctcct    15060
cactcacccc ctcacctcct cactcacccc ctcacctcct cactcacccc ctcacctcct    15120
cacccacccc ctcactcact ccctcacccc ctcacccccc tcactcacccc ctcacctcct    15180 cactcacccc ctcacctcct cacccacccc ctcactcact ccctcacccc ctcacccct     15240 cactcacccc ctcacctcct cactcacccc ctcacctcct cactcacccc ctcacctcct    15300
```

```
cactcatgcc ctcaccccct cactcaccct ttcacctcct tgctcatccc ctcacttacc    15360
ccctcacttc gtcaatcacc cccccacctc gtcaatcacc ccctcacctt ttcactcacc    15420
ccctcactca cccccttact tcctcactta cctcctcacc ccccactcac cccctcaccc    15480
cccactcacc ccctcacccc acactcaccc cctcaccccc cactcacccc ctcacccctc    15540
tcacctcctc actcaccccc tcacctcctc acttatcccc tcacccctc aattacccc    15600 tcacccctc aattactccc tcatcctttc aattacccac tcacccctc acctcctcac    15660 tcctcactca ctccctcact caccccttca ccttctcact cacctcctcg tctcctcacc    15720
ccctcactca cttccagccc tgcccctccc atcttccttt tctttgtgtg agaatctggg    15780
gtccctgagt ggtgtcagtc cctccaagac tcaaggagtc cccagggcct tgttatccag    15840
aacaccccca cctgggtccc gggagacccc atgggatcac aggagtgttc agggaagtgg    15900
tgcttcctgg gtctgggtgg gctggagggg catcctccct tccccaagag gagacccca    15960 ggagcccct aagtccatcc ccagcagtgg tgccctgcc ctgtccttgc agcctgggag    16020
acccttggga ggggcgggcg ctgggtggct ggcggcttc tgctggtctc accccactgg    16080
cctcctgttt gtcatcctca gcctgcgggg tcaacttgaa ctcaagccgc cagagcagga    16140
ttgtgggcgg cgagagcgcg ctcccggggg cctggccctg gcaggtcagc ctgcacgtcc    16200
agaacgtcca cgtgtgcgga ggctccatca tcaccccga gtggatcgtg acagccgccc    16260
actgcgtgga aaagtatgcc aggggcgcg cgggccgggt gggggctcag ggctggccta    16320
cagccaccct gtgaccttga gcaggtctca acccttgcag ccccggcatc cttgtgttta    16380
aatgggagag tattgcacc tgcttcctag ggctgtgaga catcaagtgc gctcatgcca    16440
ggcagtgcat ggctgtatgc actgagtgtc ccctgcacgc agggcacagg gtgcaggtgg    16500
aacattctcc acgatgtcgc cgtgaccagc gttccttcca gccactgtcc tctgagctct    16560
gtcctgccct tgagcaaagc ccctgccccc tgaggtatcc tgtctccggg acgctagtcc    16620
caggagaggg cacactcaga caggcttcag gctgccctgc tggaaggtcc ctgggttaa    16680 gcgttcttgg ccacagcatt gctcatgcag agggttaggt aggggtgagg ctagccgtga    16740
cagtattagc atttatggac gctaccaccc cctccccttt tccttaaaca catagtgctt    16800
ttggtcacat gctgctttgg aggaggcctc acttggcgga tgtattttc tgccttagag    16860 agaggctgaa ctgggtttga ctgttggccc agcctctct tgctgcgtgc ccttagacga    16920
ttcactcaac gtctctgatc catggcatgt acaactataa gatgggcatg cccttctcct    16980
ctcgggctgt tatgaaggtc aaggaagcaa gggctgttac ccaagggtgc tcccttctct    17040 cccctcttc acaccccag gtgctctggg ccctctagga actgggtttc tctcaagggc    17100
tgttacccaa gggtgctccc ttctctcccc ctcttcacac cactgggtgc tctgggccca    17160
ctaggagctg ggattctctt aagagggaaa ctcttggata aggaaatgg tttgattgat    17220 atcgacaag tctgttcatt agtatccatt tattaagcac ctaccatgtg ccaggaaatg    17280
ctttggcgta caaaggaaaa taagggccag tcctgctaga aatggccttg aaaccccagg    17340
gagggatgtc ggcccattgt gggtgctgca gattccttga aggtgatgca agagccagaa    17400
agaaggatga tgtggggggc tgaggcaggg agtcggggtt gggggagtgt ggggagaag    17460 gggagaccga gcacctcttc cactatctcc ctgtgtggtt tttggtgaac catcctgcct    17520
ctgggtgtct tgcctccagc ttctgacgtt ggaagttcat ccactgagag ctctgtgttt    17580
atggctctga gatactgagt ccttcttctc tcccagacct cttaacaatc catggcattg    17640
gacggcattt gcggggattt tgagacaatc tttcatgttc tatggagccg gataccaagt    17700
```

```
agaaaaagtg atttctcatc caaattatga ctccaagacc aagaacaatg acattgcgct   17760
gatgaagctg cagaagcctc tgactttcaa cggtacgtgt ggctcaggct tggcaagcag   17820
gttggcagaa tcttaaagag atgttgattg gaaatgacac ttgtgctatg ccaaatggaa   17880
gggaggcatt tgcgttgagc gagggtagcg tgcagcgggt ggccaatggg agaggctcac   17940
agaggctaag agcacctgcc gcattttggg ggaggcagca gccaccacat ctgttctgta   18000
ctgtactgag tggtggtgat tcaagccagg catggaaaag ctagaacag ggcttt ccca   18060 ctgcagcacc cttgacatct gggtggttct ctgttgtagg gctctcttgt gccttgtagg   18120
atgtttaaca gcgtccccag cctctaccca ctggaggcca gtagctacca agctgtgaca   18180
accagtgttg cctgctgaca ttgccaaaca tccgctttga ggcaaagtca cttccagttg   18240
agaactactg gcctaaaatg tgtaaagatc cttgattttt aaagatacat tctaaaacca   18300
agttgcttaa ttcaggacaa acatgctttc tcttagcctc ttattcggtc ccactctggt   18360
ccatccaagg gtctggaatg ttctagcccc atgtggatac agaagaagca aaacctcagc   18420
cctccctaca gcatgtctgt attcacattg ggaaatggtt cacatataga agagcgaatg   18480
cctgagcaat ggcgtggtgc ctctggggcg aaagctgact ccattgactc catcggcttt   18540
ttggctgttg cctcctgtgt gtctttcccg tcttgatcac ctggagatat gtaattttgg   18600
aagcagagct agcaaataat tcctcttata agcagagcta gcaaataatt ctacttataa   18660
gtagcataac gtcttgcctg ccagaaggag aggtctggca gggggagaaa gtgagaatgt   18720
gggacttgtt gggatgcagg gtcctctggg cagggtggcc agggtgccag gcccagcagc   18780
ctgcatgtgg gaaggccagg tggagacata ggtgataccc gcctggctca ctgtgttttc   18840
tcttcttgaa acagacctag tgaaaccagt gtgtctgccc aacccaggca tgatgctgca   18900
gccagaacag ctctgctgga tttccgggtg ggggccacc gaggagaaag gtgaggctgc   18960
tcctgggcac acaggactgc agggcccaca gatggagcat tgggttcgga agtgggaggt   19020
ccaggtttta atcccagttc tactactcaa tgactggatg actttggttg attcccccag   19080
tccttgtgcc tcagtttctc catctgctaa gtgggagaaa tcctgcccag cctacctaat   19140
acactgtgtt cttatcgtga tcacacagag cagcatgtgg aatggctttt gaagtatctg   19200
ggccatacga gtttagaggt gcaggatctc ctgtgttgca ctcattgtga gtttagagct   19260
gccctggaga tcccaccaag gcctgcgtgg ctgagtgaca gggggcttgg tgaggacggg   19320
catcctggac ccatggtggc cacatctaag cctgtcctct gccctgataa ccacagagag   19380
aggctctctc cacccacttc ctttgcaatc tgcatttctc tctgacagtc tttcaaatga   19440
agggagcctg gctgcttcat ttttatggag ggttggaagt gcttagtggc aggcacaaag   19500 gttcattttta catattgttt atatccttct caaaagcgtc taggccatac agacaacaaa   19560 tccttt caaa caagggaaa agtacaaagg ttgggtgatt tctgggagc gtcagggaag   19620 gtagtggggg gcatcctggc tcctcatcag cagaaactta ctacagtaga gccacaggct   19680
gggcaaaaga cctcatggaa tccaagatga agggaatatc gacaaatatt tgtgcgcacc   19740
tgcacctagt acaggctggg tgctactcag gtgctgggaa tgcagaagtg aacagagtaa   19800
gacaaatgtc tctgctgtca ggagctttac ctctcttctg gatgtcggtg gtggggacgg   19860
ggcaggtgtg gtcagacaga tgggagacaa acaactgagc gaggtacttc caaacatctg   19920
agggtgggga tcacaaggtc ccggctattt tgaaggggtg gtcaggaaag gcttctcgga   19980
agaggtggca tttgagctga gactcaaatg gcaaaaatgt gtacacatca aaaaggctag   20040
```

-continued

```
tgcatgtatc ttcaggtgtg gtcaaggggc caaggaggtg ggctggggcc agattgcata    20100
ggtccttgtg gattatggtg aagacaccag cttctcatct gcttgaggtg gggagatcgt    20160
gagccggga gtgccatgat ctggcagctg cgtggggagt ggggatgaat ggatggagac    20220
gaggatgatg gtgacaagtc cattgctgtg gttccttgag acaggaagcc agctcatagc    20280
agagtgcggg cgtggatgtg aagagatgag ggtacactag ggctagagcc accagactta    20340
ctgatgggtt gcatgtctgt gggagagaga gtgagaagtc agggacgatg gctttccact    20400
ctgtggctga agccccaggg tggcgggtgg tgccattttt caagccagga aatattggtt    20460
ggtgagaatt tggggtggga gaaggtgtga cggagggttc tggttttgca cactaagccc    20520
acggtgccca gaagatgccc gaggggaggc agcaaagcga gagtgggaaa tgcagaggtg    20580
gcaagtgcag gccgtgtctt gagaagctct aatgtgcagg ggagccgaga agcaggcggc    20640
ctagggaggg tcacgtgtgc tccagaagag tgtgtgcatg ccagagggga aacaggcgcc    20700
tgtgtgtcct gggtgggtt cagtgaggag tgggaaattg gttcagcaga accaagccgt    20760
tgggtgaata agagggggat tccatggcac tgatagagcc ctatagtttc agagctggga    20820
atttctttcc ctgaagctga actccagagc tgcattcagc acaggcaccg ccagttgtaa    20880
ggagaatcca ggtttcccag gagagggtt ggtgctggga tgagctgacc ggggcagggc    20940
tggaaaatag ggctgtgacc atctgtgtag tgcgtgtgga ggtctcaggg agggaagtgt    21000
gctctccctg cgagagctgc aggcaacact gggagctcaa caagtctccc tgtccttagg    21060
gaagacctca gaagtgctga acgctgccaa ggtgcttctc attgagacac agagatgcaa    21120
cagcagatat gtctatgaca acctgatcac accagccatg atctgtgccg gcttcctgca    21180
ggggaacgtc gattcttgcc aggtaattca acatttttat tctacctttg gtccttacca    21240
gatcctactg aacccccat gagagagagg gcattcttgg ggtcagcaga gcctcctcag    21300
tgacacggag ccagctcggg gcagtcatgg gaagtgacgg ccacaaacag tgcgaacgct    21360
tctggtggca gaaggaagta cagtcaacaa atcacacaca ccctctgaaa aaccggtatt    21420
tggtaaaagt gccagtggaa cagaaacaag tatttagact attttaaatt atgaacggca    21480
atttatttag taacttttag cttgaacaga ttaaaattca ggatggggc tatctctttg    21540
ggggttacat ctctgttacc atcaccccctt gatggtggag attcgaagcc cacacagtca    21600
ctcgtaactc acactgcgac ccccgccccc caactcctct aggcctggtc agtggtgtgc    21660
ggcagattgt gacttgattt tctgctctct gtaccttgct gtgtcccaca gggtgacagt    21720
ggagggcctc tggtcacttc gaagaacaat atctggtggc tgataggga tacaagctgg    21780
ggttctggct gtgccaaagc ttacagacca ggagtgtacg ggaatgtgat ggtattcacg    21840
gactggattt atcgacaaat gagggtaact atcctgtcct ccttctgact gtgttctccg    21900
attcctcgag ccaaagccag acatctgtta ggcgtggttc tgctgctgga agctgactgg    21960
tgaccactgg tcagcatgaa gcaaactctg cttcctccag ccacagcccc atcccccag    22020
tgtccaccca ttgccattg cctctcactg gcttcacttg catatttccc ctggtgtttg    22080
gatgaaaagc gctggggctc agcttgtgtg aaattccttg gtgctctgcc aaccacactt    22140
cgttctggct cagctgactc agctgttcca cccaggccac ctcacatcaa acttttttt    22200
ttttttttg agatggagtc tcactgtgtc gcccaggctg gagtgcagtg cacaatctc    22260
gactcactgc aacctttgcc tcctgggttc aagtgattct cctgcctcag cctcccaagt    22320
agctgggact acaggcatgc gccaccacgc ccagctactt tttgtatttt tagtagagat    22380
ggggtttctc catgttggcc aggctggtct cgaagccctg acctcaggtg attcacccac    22440
```

```
ctcagcctcc cacagtgctg ggattacaag tgtgaaccac ggtgcccggc ctcacatgaa    22500
acttttgatt tatagagagc agagggaaga gccggctgtg cccatccttt tctggggcca    22560
tcgagtggct cctgggcagc ccccaaggtt aggaagggca ggagcagcca gggttctctg    22620
atgccccaga ctcaagcacg agggaaggtc tcaggggttc catgtgagcc tcatggatgt    22680
ctctgcttag cagagccctg gctttgggca ttgtccagat aggggtgag  aaccagatct    22740 tctcatctcc aggacctcag acgtatagtt ttctcagatt tctgtgcttt ctggggctgg    22800
gctactagtg gaagaaagca gtctattctg tcttctccca aatctcccag atgcccagtc    22860
tgttgaagga ggagcagaac cagggggcct ttcccgctga ggcccgacct gtgtctcctt    22920
caaatgacac gcgggactca gggccttccc atgaccatgg ggcccagggg gcgtcacctg    22980
gcccagggcc cagtgctaga aacagatgac cccaggagga ggaggcaggg caggagggaa    23040
gctggcaggg ctgggatggt cagccaggct gaggggcgga ctcgcaccag gatggagcta    23100
ggaaatgatc caggtgtgtt tggcggctgc aggtgggtcc gcatggctgt gcagggaggg    23160
aagggctgcg tggcaggaga gcagccgggg gaggcccaga ctctgctgaa gagatgcctg    23220
ttgtgccggc ctccacatcc gctgcccgct ccttccggag ctcctgcccc gccatgctca    23280
gcctgactct gaccaacacg ttggagagaa gaatgatccc tttgtgctat taagcttgct    23340
tatttggttt ctaagtgctt catgcgaacc tagaggaaaa aattattttc cacctttgtt    23400
tgtcttaaga aaataacaca cttttttttt tcctatttga acaggcagac ggctaatcca    23460
catggtcttc gtccttgacg tcgtttttaca agaaaacaat ggggctggtt ttgcttcccc    23520
gtgcatgatt tactcttaga gatgattcag aggtcacttc atttttatta aacagtgaac    23580
ttgtctggct ttggcactct ctgccattct gtgcaggctg cagtggctcc cctgcccagc    23640
ctgctctccc taacccttg tccgcaaggg gtgatggccg gctggttgtg ggcactggcg    23700
gtcaagtgtg gaggagaggg gtggaggctg ccccattgag atcttcctgc tgagtccttt    23760
ccagggccca attttggatg agcatggagc tgtcacctct cagctgctgg atgacttgag    23820
atgaaaaagg agagacatgg aaagggagac agccaggtgg cacctgcagc ggctgccctc    23880
tggggccact tggtagtgtc cccagcctac ctctccacaa ggggattttg ctgatgggtt    23940
cttagagcct tagcagccct ggatggtggc cagaaataaa gggaccagcc cttcatgggt    24000
ggtgacgtgg tagtcacttg taaggggaac agaaacattt ttgttcttat ggggtgagaa    24060
tatagacagt gcccttggtg cgagggaagc aattgaaaag gaacttgccc tgagcactcc    24120
tggtgcaggt ctccacctgc acattgggtg gggctcctgg gagggagact cagccttcct    24180
cctcatcctc cctgaccctg ctcctagcac cctggagagt gcacatgccc cttggtcctg    24240
gcagggcgcc aagtctggca ccatgttggc tccttcaggc ctgctagtca ctggaaattg    24300
aggtccatgg gggaaatcaa ggatgctcag tttaaggtac actgtttcca tgttatgttt    24360
ctacacattg ctacctcagt gctcctggaa acttagcttt tgatgtctcc aagtagtcca    24420
ccttcattta actctttgaa actgtatcat ctttgccaag taagagtggt ggcctatttc    24480
agctgctttg acaaaatgac tggctcctga cttaacgttc tataaatgaa tgtgctgaag    24540
caaagtgccc atggtggcgg cgaagaagag aaagatgtgt tttgttttgg actctctgtg    24600
gtcccttcca atgctgtggg tttccaacca ggggaagggt cccttttgca ttgccaagtg    24660
ccataaccat gagcactact ctaccatggt tctgcctcct ggccaagcag ctggtttgc     24720 aagaatgaaa tgaatgattc tacagctagg acttaacctt gaaatggaaa gtcatgcaat    24780
```

-continued

```
cccatttgca ggatctgtct gtgcacatgc ctctgtagag agcagcattc ccagggacct    24840
tggaaacagt tggcactgta aggtgcttgc tccccaagac acatcctaaa aggtgttgta    24900
atggtgaaaa cgtcttcctt ctttattgcc ccttcttatt tatgtgaaca actgtttgtc    24960 ttttttgta tctttttaa actgtaaagt tcaattgtga aaatgaatat catgcaaata     25020
aattatgcaa ttttttttc aaagtaacta ctgcatcttt gaagttctgc ctggtgagta    25080
ggaccagcct ccatttcctt ataagggggt gatgttgagg ctgctggtca gaggaccaaa    25140
ggtgaggcaa ggccagactt ggtgctcctg tggttctcga gataacttcg tataatgtat    25200
gctatacgaa gttatgctag taactataac ggtcctaagg tagcgagcta gctccacgtg    25260
gctttgtccc agacttcctt tgtcttcaac aaccttctgc aagaaaacca agggcctgaa    25320
ttttaacttc ctg                                                       25333
```

<210> SEQ ID NO 7
<211> LENGTH: 491
<212> TYPE: PRT
<213> ORGANISM: Artificial Sequence
<220> FEATURE:
<223> OTHER INFORMATION: Recombinant protein

<400> SEQUENCE: 7

```
Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Arg Pro Val
                20                  25                  30

Ala Pro Asn Gly Tyr Asn Leu Tyr Pro Ala Gln Tyr Tyr Pro Ser Pro
                35                  40                  45

Val Pro Gln Tyr Ala Pro Arg Ile Thr Thr Gln Ala Ser Thr Ser Val
        50                  55                  60

Ile His Thr His Pro Lys Ser Gly Ala Leu Cys Thr Ser Lys Ser
65              70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Lys Phe Met Gly Ser Lys Cys
                100                 105                 110

Ser Asn Ser Gly Ile Glu Cys Asp Ser Ser Gly Thr Cys Ile Asn Pro
                115                 120                 125

Ser Asn Trp Cys Asp Gly Val Ser His Cys Pro Gly Gly Glu Asp Glu
            130                 135                 140

Asn Arg Cys Val Arg Leu Tyr Gly Pro Asn Phe Ile Leu Gln Val Tyr
145                 150                 155                 160

Ser Ser Gln Arg Lys Ser Trp His Pro Val Cys Gln Asp Asp Trp Asn
                165                 170                 175

Glu Asn Tyr Gly Arg Ala Ala Cys Arg Asp Met Gly Tyr Lys Asn Asn
                180                 185                 190

Phe Tyr Ser Ser Gln Gly Ile Val Asp Asp Ser Gly Ser Thr Ser Phe
                195                 200                 205

Met Lys Leu Asn Thr Ser Ala Gly Asn Val Asp Ile Tyr Lys Lys Leu
            210                 215                 220

Tyr His Ser Asp Ala Cys Ser Ser Lys Ala Val Val Ser Leu Arg Cys
225                 230                 235                 240

Ile Ala Cys Gly Val Asn Leu Asn Ser Ser Arg Gln Ser Arg Ile Val
                245                 250                 255

Gly Gly Glu Ser Ala Leu Pro Gly Ala Trp Pro Trp Gln Val Ser Leu
```

|   |   |   | 260 |   |   |   | 265 |   |   |   | 270 |   |
|---|---|---|---|---|---|---|---|---|---|---|---|---|
| His | Val | Gln | Asn | Val | His | Val | Cys | Gly | Gly | Ser | Ile | Ile | Thr | Pro | Glu |
|   |   |   | 275 |   |   |   | 280 |   |   |   | 285 |   |

```
            275                 280                 285

Trp Ile Val Thr Ala Ala His Cys Val Glu Lys Pro Leu Asn Asn Pro
        290                 295                 300

Trp His Trp Thr Ala Phe Ala Gly Ile Leu Arg Gln Ser Phe Met Phe
305                 310                 315                 320

Tyr Gly Ala Gly Tyr Gln Val Glu Lys Val Ile Ser His Pro Asn Tyr
            325                 330                 335

Asp Ser Lys Thr Lys Asn Asn Asp Ile Ala Leu Met Lys Leu Gln Lys
            340                 345                 350

Pro Leu Thr Phe Asn Asp Leu Val Lys Pro Val Cys Leu Pro Asn Pro
            355                 360                 365

Gly Met Met Leu Gln Pro Glu Gln Leu Cys Trp Ile Ser Gly Trp Gly
            370                 375                 380

Ala Thr Glu Glu Lys Gly Lys Thr Ser Glu Val Leu Asn Ala Ala Lys
385                 390                 395                 400

Val Leu Leu Ile Glu Thr Gln Arg Cys Asn Ser Arg Tyr Val Tyr Asp
            405                 410                 415

Asn Leu Ile Thr Pro Ala Met Ile Cys Ala Gly Phe Leu Gln Gly Asn
            420                 425                 430

Val Asp Ser Cys Gln Gly Asp Ser Gly Gly Pro Leu Val Thr Ser Lys
            435                 440                 445

Asn Asn Ile Trp Trp Leu Ile Gly Asp Thr Ser Trp Gly Ser Gly Cys
            450                 455                 460

Ala Lys Ala Tyr Arg Pro Gly Val Tyr Gly Asn Val Met Val Phe Thr
465                 470                 475                 480

Asp Trp Ile Tyr Arg Gln Met Arg Ala Asp Gly
            485                 490

<210> SEQ ID NO 8
<211> LENGTH: 2267
<212> TYPE: DNA
<213> ORGANISM: Mus musculus

<400> SEQUENCE: 8
ccggttgtgt tataggactt gaccagcccc aatagtcctc aagtcactcc tagatacagt      60
ggcaggtggt agctggcttg cggaaggaag aggaagaaga gaatgtgggc catcaaggag     120
caaggccagc cttgcacttg gccccctct gctcagtgct gaccagggct ttctgagccg      180
cttcctaatg aggctcattt gaagaccccc cccacccccc ctcctgctgt cttgggtggc     240
agagctagct ccaggctgta agaaaattag gaggattacc aaagcagtat ggagtcagac     300
agtggccaac ccctcaacaa ccgtgatatt gttccctttc gcaaaccccg aaggccccag     360
gagaccttca aaaggtggg gatccccatc attgcagtgc tgctgagcct gatagccctc      420
gtgattgtgg ccttctcat caaggtgatt ctggataaat actacttcat ctgcggcagt     480 ccctgacct tcattcagag gggccagttg tgtgacggcc accttgactg cgcctcaggg      540
gaggatgagg aacactgtgt caaggacttc cctgaaaagc ccggagtggc agtccggctc     600
tccaaggaca gatccaccct gcaggtgctg gatgcagcca cagggacctg gcctcagtc     660 tgtttcgaca acttcacaga agcactggcc aagacagcct gcagacagat gggctatgac     720
agccagcccg ctttcagagc agtggagatc cgtccagatc agaacctccc tgttgctcaa     780
gtcacaggaa acagccagga acttcaggtg cagaatggaa gcagatcctg cctctcaggc     840
```

```
tccctggttt ccttgcgctg ccttgactgt ggaaagagcc tgaagactcc tcgtgtggtg      900
ggtggggtgg aggcccctgt ggattcttgg ccgtggcagg tcagcatcca gtacaacaag      960
cagcatgtct gtggtgggag catcctggat ccccactgga tcctcacagc agcccactgc     1020
ttcaggaagt atcttgatgt gtcaagctgg aaggtcaggg caggctcaaa catactgggt     1080
aactctccat ccttgcctgt ggccaagatc ttcatcgctg aacccaatcc tctgtacccc     1140
aaagagaagg acattgccct tgttaagctg cagatgccac tcacattctc aggctcagtc     1200
aggcccatct gcctgccctt ctctgatgag gtgcttgtcc cagccacacc agtctgggtc     1260
attggatggg gctttacaga agaaaacgga ggaaagatgt ctgacatgct actgcaggca     1320
tcagtccagg tcattgacag cacacggtgc aatgcagagg atgcctacga aggggaagtg     1380
accgctgaga tgctgtgtgc aggtacccca cagggtggca aggacacctg ccagggtgac     1440
agtggtgggc ctttgatgta ccattctgac aagtggcagg tagtaggcat cgtgagctgg     1500
ggccatggat gcggcggccc aagtactcct ggagtgtata ccaaggtcac tgcctatctc     1560
aactggatct acaatgttcg gaagtctgag atgtaacgct gccgtccccc acatccagaa     1620
gctgcttccc ttcagaccta cctacggcat gaccccctcaa agtcagatat gggacaagag     1680
cctccttgaa caaactctgg tatccctgca gcaagcaagg atacattgca gaggtgcccg     1740
gagtggagtc agatgggcta gctcagccac ccctgcatct cccaaaccct gggagacatg     1800
tggcccatgg gagtaaatcc aggacattga ctcaactctc agaagtgtta ttcagtcaag     1860
gaggctctcc cttccactga aggaaggaaa gtcagctctc tcctgaaagg ccagatcact     1920
ggctgagtag atgagacaag ggtatgaaag gcctttgcca tcttctttgc ccagtcctga     1980
aagcactgac gtaagagacc agtcagttct aatgtaaggt gtatatttta gtgtcagggt     2040
attgcaattg tcacctctgt ggtcaatatc attaaacagg tatgagaatt cgctggcata     2100
gacttcctgg tctgcttaat aagaatccaa ctaaggatgt cacatgacag tttcccagaa     2160
aatgtgaaca gtgtccatc tgacacacgg caccaatgac aaaccaaaga agttattctg      2220
cctgagtctc agttgctgaa ctaataaatt agctgcggtt tcttgca                    2267
```

<210> SEQ ID NO 9  
<211> LENGTH: 435  
<212> TYPE: PRT  
<213> ORGANISM: Mus musculus

<400> SEQUENCE: 9

```
Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Ile Cys Gly Ser
    50                  55                  60

Pro Leu Thr Phe Ile Gln Arg Gly Gln Leu Cys Asp Gly His Leu Asp
65                  70                  75                  80

Cys Ala Ser Gly Glu Asp Glu His Cys Val Lys Asp Phe Pro Glu
                85                  90                  95

Lys Pro Gly Val Ala Val Arg Leu Ser Lys Asp Arg Ser Thr Leu Gln
            100                 105                 110

Val Leu Asp Ala Ala Thr Gly Thr Trp Ala Ser Val Cys Phe Asp Asn
```

```
              115                 120                 125
Phe Thr Glu Ala Leu Ala Lys Thr Ala Cys Arg Gln Met Gly Tyr Asp
        130                 135                 140

Ser Gln Pro Ala Phe Arg Ala Val Glu Ile Arg Pro Asp Gln Asn Leu
145                 150                 155                 160

Pro Val Ala Gln Val Thr Gly Asn Ser Gln Glu Leu Gln Val Gln Asn
                165                 170                 175

Gly Ser Arg Ser Cys Leu Ser Gly Ser Leu Val Ser Leu Arg Cys Leu
            180                 185                 190

Asp Cys Gly Lys Ser Leu Lys Thr Pro Arg Val Val Gly Gly Val Glu
        195                 200                 205

Ala Pro Val Asp Ser Trp Pro Trp Gln Val Ser Ile Gln Tyr Asn Lys
210                 215                 220

Gln His Val Cys Gly Gly Ser Ile Leu Asp Pro His Trp Ile Leu Thr
225                 230                 235                 240

Ala Ala His Cys Phe Arg Lys Tyr Leu Asp Val Ser Ser Trp Lys Val
                245                 250                 255

Arg Ala Gly Ser Asn Ile Leu Gly Asn Ser Pro Ser Leu Pro Val Ala
            260                 265                 270

Lys Ile Phe Ile Ala Glu Pro Asn Pro Leu Tyr Pro Lys Glu Lys Asp
        275                 280                 285

Ile Ala Leu Val Lys Leu Gln Met Pro Leu Thr Phe Ser Gly Ser Val
290                 295                 300

Arg Pro Ile Cys Leu Pro Phe Ser Asp Glu Val Leu Val Pro Ala Thr
305                 310                 315                 320

Pro Val Trp Val Ile Gly Trp Gly Phe Thr Glu Asn Gly Lys
                325                 330                 335

Met Ser Asp Met Leu Leu Gln Ala Ser Val Gln Val Ile Asp Ser Thr
            340                 345                 350

Arg Cys Asn Ala Glu Asp Ala Tyr Glu Gly Glu Val Thr Ala Glu Met
        355                 360                 365

Leu Cys Ala Gly Thr Pro Gln Gly Gly Lys Asp Thr Cys Gln Gly Asp
370                 375                 380

Ser Gly Gly Pro Leu Met Tyr His Ser Asp Lys Trp Gln Val Val Gly
385                 390                 395                 400

Ile Val Ser Trp Gly His Gly Cys Gly Gly Pro Ser Thr Pro Gly Val
                405                 410                 415

Tyr Thr Lys Val Thr Ala Tyr Leu Asn Trp Ile Tyr Asn Val Arg Lys
            420                 425                 430

Ser Glu Met
        435

<210> SEQ ID NO 10
<211> LENGTH: 3543
<212> TYPE: DNA
<213> ORGANISM: Homo sapiens

<400> SEQUENCE: 10
atcattccag tttggcaact tcacttgtag ggctgtttta atcaagctgc ccaaagtccc      60
ccaatcactc ctggaataca cagagagagg cagcagcttg ctcagcggac aaggatgctg     120
ggcgtgaggg accaaggcct gccctgcact cgggcctcct ccagccagtg ctgaccaggg     180
acttctgacc tgctggccag ccaggacctg tgtggggagg ccctcctgct gccttggggt     240
gacaatctca gctccaggct acagggagac cggaggatc acagagccag catggatcct     300
```

```
gacagtgatc aacctctgaa cagcctcgat gtcaaacccc tgcgcaaacc ccgtatcccc      360
atggagacct tcagaaaggt ggggatcccc atcatcatag cactactgag cctggcgagt      420
atcatcattg tggttgtcct catcaaggtg attctggata aatactactt cctctgcggg      480
cagcctctcc acttcatccc gaggaagcag ctgtgtgacg gagagctgga ctgtcccttg      540
ggggaggacg aggagcactg tgtcaagagc ttccccgaag ggcctgcagt ggcagtccgc      600
ctctccaagg accgatccac actgcaggtg ctggactcgg ccacagggaa ctggttctct      660
gcctgtttcg acaacttcac agaagctctc gctgagacag cctgtaggca gatgggctac      720
agcagcaaac ccactttcag agctgtggag attggcccag accaggatct ggatgttgtt      780
gaaatcacag aaaacagcca ggagcttcgc atgcggaact caagtgggcc ctgtctctca      840
ggctccctgg tctccctgca ctgtcttgcc tgtgggaaga gcctgaagac cccccgtgtg      900
gtgggtgggg aggaggcctc tgtggattct tggccttggc aggtcagcat ccagtacgac      960
aaacagcacg tctgtggagg gagcatcctg gaccccact  gggtcctcac ggcagcccac     1020
tgcttcagga acataccga tgtgttcaac tggaaggtgc gggcaggctc agacaaactg     1080
ggcagcttcc catccctggc tgtggccaag atcatcatca ttgaattcaa ccccatgtac     1140
cccaaagaca atgacatcgc cctcatgaag ctgcagttcc cactcacttt ctcaggcaca     1200
gtcaggccca tctgtctgcc cttctttgat gaggagctca ctccagccac cccactctgg     1260
atcattggat ggggctttac gaagcagaat ggagggaaga tgtctgacat actgctgcag     1320
gcgtcagtcc aggtcattga cagcacacgg tgcaatgcag acgatgcgta ccaggggggaa     1380 gtcaccgaga agatgatgtg tgcaggcatc ccggaagggg gtgtggacac ctgccagggt     1440
gacagtggtg gccccctgat gtaccaatct gaccagtggc atgtggtggg catcgttagt     1500
tggggctatg gctgcgggg  cccgagcacc ccaggagtat acaccaaggt ctcagcctat     1560
ctcaactgga tctacaatgt ctggaaggct gagctgtaat gctgctgccc ctttgcagtg     1620
ctgggagccg cttccttcct gccctgccca cctggggatc ccccaaagtc agacacagag     1680
caagagtccc cttgggtaca cccctctgcc cacagcctca gcatttcttg gagcagcaaa     1740
gggcctcaat tcctataaga gaccctcgca gcccagaggc gcccagagga agtcagcagc     1800
cctagctcgg ccacacttgg tgctcccagc atcccaggga gagacacagc ccactgaaca     1860
aggtctcagg ggtattgcta agccaagaag gaactttccc acactactga atggaagcag     1920
gctgtcttgt aaaagcccag atcactgtgg gctggagagg agaaggaaag ggtctgcgcc     1980
agccctgtcc gtcttcaccc atccccaagc ctactagaga agaaaccag  ttgtaatata     2040 aaatgcactg ccctactgtt ggtatgacta ccgttaccta ctgttgtcat tgttattaca     2100
gctatggcca ctattattaa agagctgtgt aacatctctg gcataggcta gctggaatgc     2160
ttgataagaa ctgagctggg atgattgaac tttcattctt tggcttgggg agaaaagaag     2220
tcctggggaa gcaattgagt ctcaaagtag aggcagggga aaaagagtt  agggagacca     2280 gatctgctga gtggcagcaa gagtgagctg cagattacag aaaccagggt gagcaagttt     2340
gagtcccaca cagggccttc tcccttgcc  tctttccctc cctccctgcc tgtgataatc     2400
agccaggagc cagggataac ctatgacttg ggaaagagat gagttaggca gtcaagggtg     2460
acattcaatc agggatccac aagtggctgg aaagaaatgc tggtcctgtg tcctaacttt     2520
ttccgcctgg agaccctca  gtgtggcttc ttacatttaa aaaacaaaaa ggatcagctg     2580
ccaggtgtga ggcagtcccc aagctgagtt gtgaggatgt aagcatgaat aagtccctgc     2640
```

```
actcaaaatg gtcaaagaat taaaccccat ggacttttt ggcatctgta tgaaagcttg   2700
ggttttctga ggactgtctt gctatagtta agtcagatcc tagatgaaat atacttgttc   2760
atactgtact aggttcttag gaaacaacag aattcctcaa atgccaaaaa caagaaaat    2820 agaaacccag aaaacaaaac aaaataaaac aaaaccatca gaactgtgag tggaaactaa   2880
ggtgatgatc tgggagcaat acactaaaat cttgggtcga gacctatatg aaggctggca   2940
gtggagctaa acctggacac actgaagaca agggagctga accagggctc ctacatgaag   3000
cagggataac tgatggcagt aaatgtggtc tcaaattgca gatggtctgg aggaaaattt   3060
cccaaattta gagcctcagg attcccaaag atcctccaaa tatgagctca caatcaaaga   3120
tcagagacgt tgaaaataa aaaacacctt aagtgggcag cataaaaaac agctaattta    3180 gaacccaaa ggcttcagat gtcagaatat tagagactta tgataataag caatatttgc     3240
agagtatttg tatgtgccag acactattgt aagtgcttca tcatgtactg attcatttaa   3300
tactcacaga aatctgtgag atgggtatta ttcttatcct cactctatgg attaaaaaaa   3360
ctaaggcaca aagtggttaa gctccttgcc tgagattata gactgtaagt tgaacgtgag   3420
cacttggaat acagagttca tgctgtaaac taccacacta tagggcctcc aatatgataa   3480
tttataaaat atttgaataa aaaatgaata ctagttccac attttaaaaa aaaaaaaaaa   3540
aaa                                                                  3543

<210> SEQ ID NO 11
<211> LENGTH: 437
<212> TYPE: PRT
<213> ORGANISM: Homo sapiens

<400> SEQUENCE: 11

Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
                20                  25                  30

Gly Ile Pro Ile Ile Ile Ala Leu Leu Ser Leu Ala Ser Ile Ile Ile
            35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205
```

```
Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
            420                 425                 430

Trp Lys Ala Glu Leu
            435

<210> SEQ ID NO 12
<211> LENGTH: 20078
<212> TYPE: DNA
<213> ORGANISM: Artificial Sequence
<220> FEATURE:
<223> OTHER INFORMATION: Recombinant polynucleotide

<400> SEQUENCE: 12
ccacccgcac acactacagt cgagataact tcgtataatg tatgctatac gaagttatat      60
gcatggcctc cgcgccgggt tttgcgcct cccgcgggcg cccccctcct cacggcgagc     120
gctgccacgt cagacgaagg gcgcagcgag cgtcctgatc cttccgcccg gacgctcagg     180
acagcggccc gctgctcata agactcggcc ttagaacccc agtatcagca gaaggacatt     240
ttaggacggg acttgggtga ctctagggca ctggttttct ttccagagag cggaacaggc     300
gaggaaaagt agtcccttct cggcgattct gcggagggat ctccgtgggg cggtgaacgc     360
cgatgattat ataaggacgc gccgggtgtg gcacagctag ttccgtcgca gccgggattt     420
gggtcgcggt tcttgtttgt ggatcgctgt gatcgtcact tggtgagtag cgggctgctg     480
ggctggccgg ggctttcgtg gccgccgggc cgctcgtgg gacggaagcg tgtgagaga     540 ccgccaaggg ctgtagtctg ggtccgcgag caaggttgcc ctgaactggg ggttgggggg     600
agcgcagcaa aatggcggct gttcccgagt cttgaatgga agacgcttgt gaggcgggct     660
gtgaggtcgt tgaaacaagg tgggggcat ggtgggcggc aagaacccaa ggtcttgagg     720
```

-continued

```
ccttcgctaa tgcgggaaag ctcttattcg ggtgagatgg gctggggcac catctgggga    780
ccctgacgtg aagtttgtca ctgactggag aactcggttt gtcgtctgtt gcggggggcgg   840
cagttatggc ggtgccgttg ggcagtgcac ccgtacccttt gggagcgcgc gccctcgtcg   900
tgtcgtgacg tcacccgttc tgttggctta taatgcaggg tggggccacc tgccggtagg    960
tgtgcggtag gcttttctcc gtcgcaggac gcagggttcg ggcctagggt aggctctcct   1020
gaatcgacag gcgccggacc tctggtgagg ggagggataa gtgaggcgtc agtttctttg   1080
gtcggtttta tgtacctatc ttcttaagta gctgaagctc cggttttgaa ctatgcgctc   1140
ggggttggcg agtgtgtttt gtgaagtttt ttaggcacct tttgaaatgt aatcatttgg   1200
gtcaatatgt aattttcagt gttagactag taaattgtcc gctaaattct ggccgttttt   1260
ggcttttttg ttagacgtgt tgacaattaa tcatcggcat agtatatcgg catagtataa   1320
tacgacaagg tgaggaacta aaccatggga tcggccattg aacaagatgg attgcacgca   1380
ggttctccgg ccgcttgggt ggagaggcta ttcggctatg actgggcaca acagacaatc   1440
ggctgctctg atgccgccgt gttccggctg tcagcgcagg ggcgcccggt tctttttgtc   1500
aagaccgacc tgtccggtgc cctgaatgaa ctgcaggacg aggcagcgcg gctatcgtgg   1560
ctggccacga cgggcgttcc ttgcgcagct gtgctcgacg ttgtcactga agcgggaagg   1620
gactggctgc tattgggcga agtgccgggg caggatctcc tgtcatctca ccttgctcct   1680
gccgagaaag tatccatcat ggctgatgca atgcggcggc tgcatacgct tgatccggct   1740
acctgcccat cgaccacca agcgaaacat cgcatcgagc gagcacgtac tcggatggaa   1800
gccggtcttg tcgatcagga tgatctggac gaagagcatc aggggctcgc gccagccgaa   1860
ctgttcgcca ggctcaaggc gcgcatgccc gacggcgatg atctcgtcgt gacccatggc   1920
gatgcctgct tgccgaatat catggtggaa aatggccgct tttctggatt catcgactgt   1980
ggccggctgg gtgtggcgga ccgctatcag gacatagcgt tggctacccg tgatattgct   2040
gaagagcttg gcggcgaatg ggctgaccgc ttcctcgtgc tttacggtat cgccgctccc   2100
gattcgcagc gcatcgcctt ctatcgcctt cttgacgagt tcttctgagg ggatccgctg   2160
taagtctgca gaaattgatg atctattaaa caataaagat gtccactaaa atggaagttt   2220
ttcctgtcat actttgttaa gaagggtgag aacagagtac ctacattttg aatggaagga   2280
ttggagctac gggggtgggg gtgggtggg attagataaa tgcctgctct ttactgaagg   2340
ctctttacta ttgctttatg ataatgtttc atagttggat atcataattt aaacaagcaa   2400
aaccaaatta agggccagct cattcctccc actcatgatc tatagatcta tagatctctc   2460
gtgggatcat tgttttttctc ttgattccca ctttgtggtt ctaagtactg tggtttccaa   2520
atgtgtcagt ttcatagcct gaagaacgag atcagcagcc tctgttccac atacacttca   2580
ttctcagtat tgttttgcca agttctaatt ccatcagacc tcgacctgca gccctagcc    2640
cgggcgccag tagcagcacc cacgtccacc ttctgtctag taatgtccaa cacctccctc   2700
agtccaaaca ctgctctgca tccatgtggc tcccattat acctgaagca cttgatgggg    2760
cctcaatgtt ttactagagc ccaccccct gcaactctga daccctctgg atttgtctgt    2820
cagtgcctca ctgggcgtt ggataatttc ttaaaaggtc aagttccctc agcagcattc    2880
tctgagcagt ctgaagatgt gtgcttttca cagttcaaat ccatgtggct gtttcaccca   2940
cctgcctggc cttgggttat ctatcaggac ctagcctaga agcaggtgtg tggcacttaa   3000
cacctaagct gagtgactaa ctgaacactc aagtggatgc catctttgtc acttcttgac   3060
tgtgacacaa gcaactcctg atgccaaagc cctgcccacc cctctcatgc ccatatttgg   3120
```

```
acatggtaca ggtcctcact ggccatggtc tgtgaggtcc tggtcctctt tgacttcata    3180
attcctaggg gccactagta tctataagag gaagagggtg ctggctccca ggccacagcc    3240
cacaaaattc cacctgctca caggttggct ggctcgaccc aggtggtgtc ccctgctctg    3300
agccagctcc cggccaagcc agcaccatgg gtacccccaa gaagaagagg aaggtgcgta    3360
ccgatttaaa ttccaattta ctgaccgtac accaaaattt gcctgcatta ccggtcgatg    3420
caacgagtga tgaggttcgc aagaacctga tggacatgtt cagggatcgc caggcgtttt    3480
ctgagcatac ctggaaaatg cttctgtccg tttgccggtc gtgggcggca tggtgcaagt    3540
tgaataaccg gaaatggttt cccgcagaac ctgaagatgt tcgcgattat cttctatatc    3600
ttcaggcgcg cggtctggca gtaaaaacta ccagcaaca tttgggccag ctaaacatgc    3660
ttcatcgtcg gtccgggctg ccacgaccaa gtgacagcaa tgctgtttca ctggttatgc    3720
ggcggatccg aaaagaaaac gttgatgccg gtgaacgtgc aaaacaggct ctagcgttcg    3780
aacgcactga tttcgaccag gttcgttcac tcatggaaaa tagtgatcgc tgccaggata    3840
tacgtaatct ggcatttctg gggattgctt ataacaccct gttacgtata gccgaaattg    3900
ccaggatcag ggttaaagat atctcacgta ctgacggtgg gagaatgtta atccatattg    3960
gcagaacgaa aacgctggtt agcaccgcag gtgtagagaa ggcacttagc ctggggggtaa   4020
ctaaactggt cgagcgatgg atttccgtct ctggtgtagc tgatgatccg aataactacc    4080
tgttttgccg ggtcagaaaa aatggtgttg ccgcgccatc tgccaccagc cagctatcaa    4140
ctcgcgccct ggaagggatt tttgaagcaa ctcatcgatt gatttacggc gctaaggtaa    4200
atataaaatt tttaagtgta taatgtgtta aactactgat tctaattgtt tgtgtatttt    4260
aggatgactc tggtcagaga tacctggcct ggtctggaca cagtgcccgt gtcggagccg    4320
cgcgagatat ggcccgcgct ggagtttcaa taccggagat catgcaagct ggtggctgga    4380
ccaatgtaaa tattgtcatg aactatatcc gtaacctgga tagtgaaaca ggggcaatgg    4440
tgcgcctgct ggaagatggc gattgatcta gataagtaat gatcataatc agccatatca    4500
catctgtaga ggttttactt gctttaaaaa acctcccaca cctcccctg aacctgaaac     4560
ataaaatgaa tgcaattgtt gttgttaaac ctgcccagt tgcggccaat tccagctgag     4620
cgtgcctccg caccattacc agttggtctg gtgtcaaaaa taataataac cgggcagggg    4680
ggatctaagc tctagataag taatgatcat aatcagccat atcacatctg tagaggtttt    4740
acttgcttta aaaaacctcc cacacctccc cctgaacctg aaacataaaa tgaatgcaat    4800
tgttgttgtt aacttgttta ttgcagctta taatggttac aaataaagca atagcatcac    4860
aaatttcaca ataaagcatt ttttcact gcattctagt tgtggtttgt ccaaactcat      4920
caatgtatct tatcatgtct ggaataactt cgtataatgt atgctatacg aagttatgct    4980
agtaactata acggtcctaa ggtagcgagc tagccaagtc tgtgtgctac caagtagcaa    5040
aactgagcct ggaactcaca catgcgtgtc tgagagccca gcactatcgc caggaaaacc    5100
cagcgtctcc ctgctcaagc ctgaccctca gccctctctg cctctccctg cacttgcctt    5160
ccagtcaagg tgattctgga taaatactac ttcctctgcg ggcagcctct ccacttcatc    5220
ccgaggaagc agctgtgtga cggagagctg actgtccct tggggagga cgaggagcac      5280
tgtgtcaaga gcttcccga agggcctgca gtggcaggtg agtgcagggt ctgaggcaca     5340
agagaagtgg gccagcagg aggtctgctc aggcccccac ggcccactgc atagtatctg     5400
ccccctactt gtcacttttc atccttgttg tataaggttc tttgtttgtt tgtttgttgt    5460
```

```
tgttttgagg cagagtgctc tgtggcccaa gatggagtgc agtgtcttgg tctcggctca    5520
ctgcaacctc tgcctcccag tttcaagtga ttcttctgcc tcagcctcat gagtagctgg    5580
gattacaggt gccagccacc acgcctggct aattttttata ttttttagtag agacggggtt  5640 ttgccacatt ggtcaggctg atcttgaact cctgacctca ggtgatctgc ccgcctcagc    5700
ctcccaaagt gctgggatta caggcgtgag ccaccgtgcc cagctgtgta agtttcttga    5760
gagcaggacc ctgtcttgtc tacctttaaa tcctagtact taacacacag caaacagtaa    5820
ctatttgatg accaaatgtg agccagaaag gacaggaaat tgtaactgag gctgccccat    5880
gcgtgctgcg cctggtggat ttcaggcaga gggctagact gggtgacctt ggggcattcc    5940
tcctttctat gaaatttgtt atttcaagga gactagaaaa gagacttctc agccacttcg    6000
ccagctattg gtccttctat tcattagtgt ttgctgagac atgctatgtg acaggactga    6060
gccaggtcct ttcaatggat aggagatgtt ttgagcataa aatccacgtt ctctcttggg    6120
ctgggctctt ctaccttctt cccctggtg cttgggctct gaagaaaaaa agataggtag     6180
gagatgagtg atggggcttc tgagggcagg gctgagtgac tttctgtgta tttgctcttt    6240
ctttatcaga agtcaaatgc ccacaggcac ctgtcatcct actgccagta ggacttctca    6300
ctcaaccttc ccctctgacc ttacttggag aaggacttag gtccctctct cagacatttc    6360
cccaggctgg gcaagttgtg tggaccatgg atgggtatgt ggtccataca atttaaacaa    6420
gctgtatatg gtcgctgggt agagtgacca cataattgat catcaaaact gatacctgta    6480
agagcaaaag ggggcactat taaccattgg gtcagggcaa caggtcaaaa tggagaccta    6540
ccctgggact tctggtcaca ctagctactg tcaaatggg gcccaaatag acaaagccaa     6600
atggaagaaa ttcccttgac attgaaagtg ttggggctct gtggcacccc cagttctagg    6660
ttgggggagc ttgggctggt ctcatgatga gttctgaggg ggatgggcca gttgggcccc    6720
ccgttccatc taactcaggt tcctttcctc ccagtccgcc tctccaagga ccgatccaca    6780
ctgcaggtgc tggactcggc cacagggaac tggttctctg cctgtttcga caacttcaca    6840
gaagctctcg ctgagacagc ctgtaggcag atgggctaca gcaggtaacc aacctgggcc    6900
tctctccttt ttccctcctt cctccttcct cctcttcctc ctttcttcc tcccttcttc    6960 tctctttcct aaaaattacg ggcattggag ccaggcagaa tggcttttga atcccagcat    7020
ttcacttata agcaacatga agttaaattt cctaagcctc aggttcctca ggagttaatt    7080
gggggaacta atgccaacct cataggatag ttttgcaatg ccagtgagag aatgtgtgct    7140
gccctccaac acacacacac acacttctag cgtctatgca gtcctctcct ttccttact    7200 cctcaacctt cactcctttg tgctggcttt gcaagaaact gttcctgccc agtaatacaa    7260
aagctaagtt aacttattca aagtttcgtt agttaagatt tagcttaagt gagcctagtt    7320
tcagtggggc cccatcttca gcaatcccag ctctctctgc aaatttcaaa agcagttcca    7380
aatctggagt ggatgaaaag gtgtaagatg atagtaagag taatttgcat tctatatatt    7440
tatattcact tgattttggc agaaaaccaa aaagatagtt attatatctt atatatagat    7500
atatattata tctatttcat aaataggctc aaacaaagta agtaacttgc tagggtacta    7560
gctgggaggt agagggctag aatttgagcc caagaccect aattcttgcg cattaggagt    7620
tcccacattg tttctgtttc tagactgagt aattctttat tctcatgtag gacatcatct    7680
ctaagggaag gggctaatga gatggttgat cactcagaga gtttagctgg agaggatgga    7740
aaagaaccca tacattcagt tgcagattga gatagctat ctctggcagg cctcagattt     7800
cttcaggatt ctaacagact ggacccagag actaggccaa acaaacaaac aaacaaaaac   7860
```

```
tctactaggc agacatcacc aaccaatcac agaactctct cccatggatc cctaatacag    7920
cctcaaagtc cttttcagta aatgctccag gcagccatta caaatcaatc agaattattt    7980
gcctttctct tctctgctca acgggcttct gctgctctct actttccata gggggcaact    8040
tccattaccc tctagaaagc acacccccacc accttcattt caaggagagt gaggaactca   8100
tgcccagcac ctgctattct cccctcttcc tgcagccacg gagcccagcc tcgctgcagc    8160
cagccctgcc tccccactgt agtccagtca actgctgcat cagccgttcc tggcacagca    8220
ggctgagcct tgattatgaa acctgggtgt ctccaggggt tcttaagatg ataggctcct    8280
ggaatttctg tccttttgga gctcagtaag gcaccaaacc acctgagtct tgtgcttcac    8340
aaaatcaaag ttcatcagaa tcattcattg ggatggaatt ggtgaacaga agttaacttt    8400
cctgggaatg tccatttcca ccatattccg tccttctagg tctcagactt ctctactttc    8460
tttcctctct ctagatcgga ggcccttctt gtcctagaac cataggcatt tcaagatgtg    8520
ggagaccccta gggatcatct agtccacgca tcttttttttt tttttttttga cagagtctca  8580
ctctgtcacc caggctggag tgcaatggca ccatctctgc ttactgcaac ctccacctcc    8640
caggttcaag tgattctttc gcctcagcct cccaagtagc tgggattaca ggcacgcacc    8700
atcatgccca gctaattttt atattttttgt agagaccgag tttcaccatg ttggccaggc   8760
tggtcttgaa ctcctgacct caggtgatcc acccacctcg gcctcccaaa gtgctgggat    8820
tacaggcgtg agccactgca cccagccccg tgcatctttt tatagagggg gaaactgagg    8880
cttggagaga cccagaaaaa gaatatgacc tgcccaaggc cacacatcaa actagtgcca    8940
gagccaggga cagaacctag atcatgagga ctcttaaaat gcactctagt cctcccaggt    9000
ctgagacttg ggtccttcca ggaagtgcca gcattcctgc ctgagaatgt gccaatccac    9060
cagtattgcc aatgactcag ccctccatgg agagcttcta ctaacattac tagcatagtt    9120
agggatggaa ggaaaagatt tagaagaggc agattcagta aaggaacaat cagagagatg    9180
gaattaatca aggaaggctt cctggaggag gaaaaacttc aacccaaggt ttgaaagtag    9240
caagcatgga ttagcaggga gaaagaggga gagtggtcca gttgagagaa acgtttgtct    9300
ggattcatat gaagacagat ctagtcctgt tctattaaat atctctaagg gggccaaaaa    9360
cataccccccg ctatcaaagt cagaccagat gctttgtttg gagaacgaaa tatccacatt   9420
ccaactccct cccaggtgag aagggagcta acctgagccc ctatgcctct ttgtttccct    9480
gctgtgaacc agaagacatt gctgggatat ttgaaatagg acagagctg ggaatatgga     9540
aaggagaccc ctaacatttc tccagggctc tgggttctgg atttggattc cccacccaag    9600
aaagcaagtt acatcagcaa tgcactgagg gttgagtcct gggatgccaa gggtcggttc    9660
tttattgtat agcaaagcag gccccatctt cactgactaa gaccatctcc actccctggc    9720
cactccccac caagcattct ctgccactct ttctcctgaa agtgggggcc aactctacca    9780
tcttgttcta accccctgcc ccagctcaca actctctctc cctcttgatg tgagcagcaa    9840
acccactttc agagctgtgg agattggccc agaccaggat ctggatgttg ttgaaatcac    9900
agaaaacagc caggagcttc gcatgcggaa ctcaagtggg taagtgaggg gacaccttct    9960
ggcctacaga aggcccccac atggacgctg ctcttcaggt tgcaaccagc tcacctgaaa   10020
ccccaagcag ccaggggaat gtaagcagac atcaggaaga actcctagcc agatggatca   10080
ttcaatgcca agagctatag actcacattt tggagaggtt ttctgtgttg acttgttttt   10140
aatacaatgg acagctggac aaagtgtgtt gtcctactca gagccagagg gatggataat   10200
```

```
gtgacctttc catcaatctg gatagtaaat agttttttgct actgctgtag gttttctaat    10260
aaattgccca ataggcaaga ttccaaagtc actttgtcct tccctaccac ttacccagcc    10320
agagctcccc accttcttga tgctccaggg aagaggctcc atggcccttg tgggtggcct    10380
gttcctgagc ctcgccaccc tgtgttagag cagagcatcc agatgaaatc tgtcacactg    10440
tggcaaagtg gctcagagag gaggctggct tcctagcatt cagggacgtt gctgagggcc    10500
gcttattcac cgaaaataaa tcttgaaaag gacagggctg gtagcagaat gatcctttac    10560
ctaaaattct atcaaaatcc cattcttcca tttggaaagc ccacagtgtc acagactctg    10620
ttccgggctc tgtcctcttc cctcttgggt cccaggagcc caggctgggc tttgaagcag    10680
gcagggccca gcacacagta ggtactcagc agtgggggtg ttgaatccaa tcaaacggaa    10740
gtgtcaatgc aggaaatgca atggatgtca atgcagtctc caaatgttcc ccactgtgca    10800
gcttccacat tcccgaggta ttgggagggg acttgaatta acagcttcgg gaggcctgag    10860
tccctgcctc ccagctgagg aagaagctta aatcacaggg cgctgtgtct gtcttccagg    10920
ccctgtctct caggctccct ggtctccctg cactgtcttg gtgagtaccc ccaatctctg    10980 aggggtttggg gcctgggcca gcaatgagca gggaggaaga ccttcatctt cactcctaaa    11040
tttctgggac tccaagtttc attctgcctt ggtctacagc ccttgggctt gtcggtcaat    11100 gcccctcga gttgttggtg gccttgggca ggtcacattc ttttttctggg tctttccaag    11160 ccccagtttc ccccttctac catctgtgca tggctccatg acctaagtgg agacctggga    11220
gagagtgtta ggaagaccga aaagggcagg acggggcctc cactgcctcc catccctggt    11280
ccgggcccac atagccttct tgtcacaat cagctcaggt atccaagatc agattaccca    11340
cattcattat ttgagcaact attcattgaa cagttagaat atgtctcact ctgtcagttg    11400
ctggctagaa gtagaaagta ccagatgagt gaaataattg gccactatcc ttggtagctg    11460
atgactaagt aagagagaga tgcaagacaa catgtggaaa atgccaaact gagtagcagt    11520
cacagttgac atgctgcaga gagagctggc cggggggtcag aagacctggg caccagtcct    11580
gttcatttcc agtgtggcct cgagtcattc acctgacctc cctgaagttc attttcccaa    11640
gaagttgttt agtccaactg cccatcaagg atctttaggg acccttctag ctctaacaga    11700
ggagatcaga aaagaaaaca agcaatgtgg ctcagctcat cctacaagct tcatagagaa    11760
ctgagactgg cctggaagca tagccagaaa ttagaacgcc taaggaaga aggtcacaac    11820 gctgcctctg caatttagga gtgtatatgc tttcctgcag gatgttgaga gtttcattca    11880
ttatcgtatg cccctaccc cggccccaca atacctagtg cgtgggatct gacacgtggt    11940
ggctggtcaa tgaatgaatg aatgaatggt cacaccatct gaggttctgc actgagtagc    12000
cctgaaggct tgaagcagca taagtgacag gtcctccctt gaggggcctc tgttttacca    12060
ataagccaag acctaagctc aacaacactg aaagggtggc caatacccag acagcctgt    12120 gggaattcca gagaaaggga gattcccagg gactgggggc ccaggctaaa cactgaaaaa    12180
tgcatctgta ggctcaagga ggaaaagccc atgtctgtct gtcttgccca ccactctctc    12240
ccagcaccca gcactgcccc aggacagaga gcacttgaca caagttggtt agattaatga    12300
atgatttaga gttcagtggt ccccaacctt tttggcacaa gagactggtt gcatggaaga    12360
caatttttcc gcaaaccaag agggggatag agagcattag attctctctt ttttttttt    12420 ttgagaccaa gtctggctct tgtcactcag cctggagtaa agtgttgcga tctcggctca    12480
ctgcaacctc cgcctcctgg attcaagcga ttctcctgcc tcagcccct aaatagctgg    12540 gattacaggc acccgtcacc agcccagctg ggactatagg catgtgccac catgcccggc    12600
```

```
taattttttgt attttttagta gagacggcgt ttcaccatgt tggccaggct agtctcgaac    12660
tcctgacctc aggtgatctg cccgcctgag cctcccaaag tgctgggatt acaggcatga    12720
gctgcctcac ccagcctaaa gtctcataag gaacgtacag catagatccc tcacatgtgc    12780
agttcacaat aaggttgtgc tcctacaaga atctaacgcc acctctgatc tgacaggagg    12840
tgaagctcag gtggtcatgc tcgcttgtcc ctgccactca cttcctaatg tacagccagg    12900
ttcctaacag gccacgaacc agtgggaagg gcatctttt ggatcaaaaa cagaattact    12960
ttttagagaa ctacaagcag atcaatttgg ctagacagag actttatatg aaacagcagg    13020
aggctgctag gaggagtgga aactctactt tgccctcaag ggagatcccg aagggctttg    13080
caggagcggg caaggtggca tgaagaaagc agtgtttgaa atcaggtggt atttgaaaag    13140
cccagccctt cccttagaa tggcccttct accatctgtg catggctcca caaccgtggt    13200
ggtggctgcc agaagaattg gaaaggcaga gcatgggtgg agaggggga cctgagggct    13260 ttacaggagt tccggggtg gtgagggtgt gaaagccagg tcagtcagta ggaagacagg    13320
atgtcagatt gagagactcc cctggccggg gaaacagact tggagaaggg ggagttttgg    13380
atgagacagt ccacttccga gtcacaaaat agcttgtggg tgtctgttta ctgttactca    13440
gtgggagtgg ctggggacac gccacctggg cagggctttc gtaattctgc atcacttgtg    13500
aaggtcacag attcccagca caacggacac acccatgttc atagtctgaa ctcctaaaca    13560
catcttaaac caaaataaaa aaaaagaaa gaaagaaaga aaaggagag ggaggtttga    13620 ggaaagccta tggtctggga cactcaatac ctcccatgaa tatctcatat tgggctggtc    13680
ctctctccac tctggcccca gccataaggg ccctgcttag agcagatttt gggtgctgag    13740
tggaggcagc ctcatcccca acagcctgac ttcctgcctc ctccctgcct ctgcctgtgt    13800
ccagcctgtg gaagagcct gaagaccccc cgtgtggtgg gtgtggagga ggcctctgtg    13860
gattcttggc cttggcaggt cagcatccag tacgacaaac agcacgtctg tggagggagc    13920
atcctggacc cccactgggt cctcacggca gcccactgct tcaggtaaga ccccagctgt    13980
aaggaggtct ctggggacca aggccagtca gggaccagag agcttggggt cctgtctcct    14040
ggcaccgtcc ttctcttcac tctcccacta gagacgtttt ccaggttgtg gtggcccaa    14100 tgagacaatg gccatgatgc cctttgttag gcttttgggt gtctgagcag agggtgctgg    14160
tcaccaagca tggcctcttc ctggtgggac accagcagat acccagagtc ctcacccac    14220 ccccatatcg ttcaagctac aaaagctctt cccacctgcc tcaacttcca agaactcact    14280 ctcttttgc ttgtttccag gaagttgttc cagggtctag agtcatagcc acgtcctcat    14340
tatgtctgga aactttaaa aaattaaaga gcataggttc ctttcagtcc acagagaagc    14400
ctggccttac ctcagggaag ggctactccc agaccccctt cactttttt ttttttttt    14460 tttttttttt tttgagaca gagtcttgct ctgttgctta ggctggagcg cagcagcatg    14520
atcttggctc actgcaacct ccgcctcctg agttcaagca attctcctgc ctcagcttcc    14580
caagtagctg ggactatagg catgggccac catgcccggc taattttgt attttggta    14640 gagacagggt ttcaccatgt tggccaggct gatctctaac tcctgacctc aagtgatctg    14700
cccacctcag cctcccaaac tgctgggatt acaggcatga gccagggcat ccggctttta    14760
tttattcatt cattcaatat ctaatgagca cctaccaggt accaaacacc agatgatgcg    14820
cccaagttca ttagacccca ccgctgtctt caaggcactc atgatctagg ccagcgtttt    14880
ttaaccactt tttttttt tttttttgag attctggtga gagctataaa ttctttcctg    14940
```

```
gaaaaacatc tctgcacact aagctgtgcc tggcattggg aaaaagaaag cacgtaatgt   15000
aactgacagc atgagtaaca cagtgagaaa ggttggagga gagagcgcca ggacctcaga   15060
actcaggcat tagaggagcc ccttccccag ccctccttga ggtttcgttg gcaggtttc    15120 actgaggaaa aagggtcaaa tcccttttc gaatttgact tcttgtaagt gccagaagac   15180
tgccccttct ccaccatccc tgcctcacca tcatctttcc tcccaaggca gtgacatcca   15240
gcaccccgat ccctagggcc ctggggaccc agcctttggc aaagtctcct caggcttgga   15300
tcaggcctga acccagctgt ctctaccccc aggaaacata ccgatgtgtt caactggaag   15360
gtgcgggcag gctcagacaa actgggcagc ttcccatccc tggctgtggc caagatcatc   15420
atcattgaat caaccccat gtaccccaaa gacaatgaca tcgccctcat gaagctgcag    15480
ttcccactca ctttctcagg tgagaagcag ggcccaaggc cactcaagcc tcttacatca   15540
gttttcacgc ccactctgct attagctcac tgaccgccct tggcacataa tgtctcctct   15600
caagtcctca gcttgcccat ttgtctctaa tacgtcagcc taacatcact gatgccatga   15660
ggcctcctca agctgtcagc taacacctcc actccattcc ctgccagaga ttcttccaag   15720
gcctgtcttc cctatgtgga gcccctcgag tgagaactgg agtttcatcc aatcttggag   15780
ttttaggaga ccttttaaaa agattatcga gctaattccc caccactgac caacacgcaa   15840
gagcctgctc agtatccctg ccaaggagtc attgtgcccc tgtttgctct cctccagggg   15900
cagggaaccc attcctgtg aggcagccca cagagtcttt gaacagctct gttggatgcc    15960
ttgtgcttat actgaaatgt atttagatca ggattcccaa ctgtgggggtc cacaagacac  16020 tggccccttg gagaagagag gattccattg tcaaataagt ttggggaaca ttttcatact   16080
acagctccct tcttggaaca cattagttta ttaaaggtag gagaagtttt taaaataatc   16140
tgttttattg cgtttaacct acattttta aatttattg accacagaat cctttttca     16200 tgctacttct attagcatcc catagaacaa gtgttctaga gaccctggtg tgaccccttt   16260
cagagagctt aactgccagg ctctcctgag ccctggtgtg tgtttcaaga tttgtgcctg   16320
ggaattgttt taatcaggta tggcaaggtg acagatacag acacagctat ctttgaaaga   16380
agagtttatt atttataatt cctgagagaa agggacatac cccaccccc aacacaggga    16440 caccgggga agcagctggg tccaccagga ggcaggagtg aggggaaggc atggcccaga    16500
gccacctgtg gcttccatgg gcaggtctgg ccaaggtagg gtaggcaaga ttgagcatgc   16560
tcaggattgg atagtgtgga caattctcta ggctatagat gtcagcctct ggttgtctag   16620
tatctgtccc tggggtgatt tagggcaggg aaaatattgg cttggtgtct gagagtcaga   16680
taaaggaagt ggttggggat atgggctttg ggttggctgg tttgcctatt aaaggcgtgc   16740
ccaaagccaa gttgtttact atctgcagga attagctaac ccagtctctc ccagaccagc   16800
aagatcccca taatcataaa gcatcataat ttacagaaaa ttaacactta tgatgaataa   16860
aagatctcct tcttcctctg tgctcctggc aggcacagtc aggcccatct gtctgccctt   16920
ctttgatgag gagctcactc cagccacccc actctggatc attggatggg gctttacgaa   16980
gcagaatgga ggtaagtcct gggtgcagga ccacagggca ggagatgccc ttgtatgagg   17040
gagcagcttc cagaagtaat gggaaggagg accacccttc agagaaaccc atcctggagg   17100
accaagcacc aaggcgccag gcagaaagca aagtggtttg gcaatccagg gctgggggat   17160
agaaggcaag gatgggaatg tgagtgtttt taccctccca gggaagatgt ctgacatact   17220
gctgcaggcg tcagtccagg tcattgacag cacacggtgc aatgcagacg atgcgtacca   17280 ggggggaagtc accgagaaga tgatgtgtgc aggcatcccg gaagggggtg tggacacctg  17340
```

```
ccaggtgggg cctccaagaa tcatggggag ttctaagaat agggtttagg tcctagagag   17400
atgagaaaac ccagaggctg catgccctac aggaagcctt gcatatcatg ggcactcaat   17460
gtgtgatgat gggaggaaga gagggaggga aggaaaggat agtcagataa aagtgtacca   17520
atagatgagt gggtggatgg atggatgcag acaagcagag agatttcaaa tgtctctttc   17580
acattcgaag atgatgttac tggcctggca tggtggctca cgcttgtaat cccagcactt   17640
tgggaggctg aggcgggcag gtgatttgag gtcaggaatt caagaccagc ctggccaaca   17700
tggtgaaatc ccatctctac taaaaagaat acaaaaatta gctgggcgtg gtggcacgtg   17760
cctgtaatcc cagctacttg ggaggctgag gcaggagaat tgcttgaacc caggaggcag   17820
aggttgcagt aagctgagat tgcgccactg cactccagcc tgggtgaccc agcaagactc   17880
catctgaaaa caacaacaac aacaaagatg acattactca tccacccccac ccacccttct   17940 cactagctac agaatgatta gcccccttgag gtcaggaatc ccaggtctat tttctctgtg   18000
actctcccca agctgctgaa ctacactagg aaagaattac cgcctgcaga atgctggaag   18060
cacatctgtg tgtgccctca ccccggcctc attggccatc aggactgctt agcaatccct   18120
gtagaccttc ttcctccccc atacttccag aggatcttct gaactatttt ctttttttat   18180 tttttcttt atgttttta acagagacag ggtcactatg ttgcccagtc tggtctcaaa   18240
ctcctgggtt caaggggattc tcccacctca gctttccaaa atgctgggat tacaggcatg   18300
agccatcgtg cttggcctga accattttca ttaaaacccc taccctactc tcacctccat   18360
ttccagtcat taaattcctt catttaagag gcatctctta gtcatcgcat gtgtgccatg   18420
aacatggtag tctttggaga cccctcaggg agctcacagt ggttggggga aagggggca   18480 ttaaacagac atttaagcta tagtttggg ttcagaggga ggaagcccca ggggctaaaa   18540
cagctgataa ggactcccag ataagtgcac ttttcactat ctggcatttt cttgttttgt   18600
tatttgcttg ttcactgtct ctcacccccat ttgatcctaa gctttctgag ggcagggatc   18660 tttgttttt ttcatcagtt ggatcccaat tgcttagaac actacctggc acaaaatagg   18720
cactctataa gtgattacac aaattttgga acgactaggt taaacaatga taaccaggct   18780
tttttttttt ttttgagac tgagtctcac tctgttgccc aggctagagt gaagtggttt   18840
gatctcggct cactgcagcc tccgcctctg ggttcgaatg attctccacc tcagcctcct   18900
gagtagctgg gattacaggt gcctgccact atgcccagct aattttttgta tttgtagtag   18960 agacgggttt caccatgttg gccaggctgg tcttgaactc ctgacctcaa gtgattcacc   19020
cgcctcagcc tcccaaggtg ctgggattac aggtgtgagc caccgctcct ggccaacaac   19080
caggcttttt taagacatca ctcagagcct ttaatttgct aatgtgagtt gtgaatctct   19140
gagagaaggc taacggcatg cttgcaactt acttgtccac agacaagcct ttctgcccca   19200
gaagagaaga ccattctagg gtgctaatga gcaaagaggg tgagggtgga atatcggaga   19260
gcagcaggga gtgcagggga acagataggc cagttcaggg agcagagaag gagaagcccc   19320
cccacctcac ctgccctccc cagcagtctc tgttctggtc tctcacaggg tgacagtggt   19380
gggcccctga tgtaccaatc tgaccagtgg catgtggtgg gcatcgttag ttggggctat   19440
ggctgcgggg gcccgagcac cccaggagta tacaccaagg tctcagccta tctcaactgg   19500
atctacaatg tctggaaggt aaggtacctt tgccctaccc actgtgcctt ccctccagtc   19560
ctctacctgg ggggtgccaa tccatcctca ggtttgattt aaatggttct gacaactctt   19620
tacatcccaa ataactttcc ctccaagcaa gggacagcct gagattgcac tattaaggct   19680
```

```
gaaattcctt aggtcagaga tttctgataa atgcaaatac cttagggaat agaacacacc    19740
aagcctttct ttctcttttc tgacagaatg agactatcag atcctttcta gagagaagat    19800
tctgataagg aagagagtgg aaaggctcat gagacctcct ggccctctgc agggtaggga    19860
gagaagcaaa gtgtttcaga aaaggaagac tcacgttaca catgtcacca ctttgtccag    19920
tttcagataa tctgactttc tcttcatcgg tctctcttat tctaggctga gctgtaacgc    19980
tgccgtcccc cacatccaga agctgcttcc cttcagacct acctacggca tgaccectca    20040 aagtcagata tgggacaaga gcctccttga acaaactc                            20078
```

<210> SEQ ID NO 13
<211> LENGTH: 15159
<212> TYPE: DNA
<213> ORGANISM: Artificial Sequence
<220> FEATURE:
<223> OTHER INFORMATION: Recombinant polynucleotide

<400> SEQUENCE: 13

```
ccacccgcac acactacagt cgagataact tcgtataatg tatgctatac gaagttatgc      60
tagtaactat aacggtccta aggtagcgag ctagccaagt ctgtgtgcta ccaagtagca     120
aaactgagcc tggaactcac acatgcgtgt ctgagagccc agcactatcg ccaggaaaac     180
ccagcgtctc cctgctcaag cctgaccctc agccctctct gcctctccct gcacttgcct     240
tccagtcaag gtgattctgg ataaatacta cttcctctgc gggcagcctc tccacttcat     300
cccgaggaag cagctgtgtg acggagagct ggactgtccc ttgggggagg acgaggagca     360
ctgtgtcaag agcttccccg aagggcctgc agtggcaggt gagtgcaggg tctgaggcac     420
aagagaagtg ggcccagcag gaggtctgct caggcccca cggcccactg catagtatct     480 gcccctact tgtcactttt catccttgtt gtataaggtt ctttgtttgt ttgtttgttg     540 ttgtttgag gcagagtgct ctgtggccca agatggagtg cagtgtcttg gtctcggctc     600
actgcaacct ctgcctccca gtttcaagtg attcttctgc ctcagcctca tgagtagctg     660
ggattacagg tgccagccac cacgcctggc taatttttat attttagta gagacggggt     720 tttgccacat tggtcaggct gatcttgaac tcctgacctc aggtgatctg cccgcctcag     780
cctcccaaag tgctgggatt acaggcgtga gccaccgtgc ccagctgtgt aagtttcttg     840
agagcaggac cctgtcttgt ctacctttaa atcctagtac ttaacacaca gcaaacagta     900
actatttgat gaccaaatgt gagccagaaa ggacaggaaa ttgtaactga gctgccccca     960
tgcgtgctgc gcctggtgga tttcaggcag agggctagac tgggtgacct tgggcattc    1020 ctcctttcta tgaaatttgt tatttcaagg agactagaaa agagacttct cagccacttc    1080
gccagctatt ggtccttcta ttcattagtg tttgctgaga catgctatgt gacaggactg    1140
agccaggtcc tttcaatgga taggagatgt tttgagcata aaatccacgt tctctcttgg    1200
gctgggctct tctaccttct tcccctggt gcttgggctc tgaagaaaaa agataggta    1260 ggagatgagt gatgggcctt ctgagggcag ggctgagtga cttctgtgt atttgctctt    1320 tctttatcag aagtcaaatg cccacaggca cctgtcatcc tactgccagt aggacttctc    1380
actcaacctt cccctctgac cttacttgga gaaggactta ggtccctctc tcagacattt    1440
ccccaggctg ggcaagttgt gtggaccatg gatgggtatg tggtccatac aatttaaaca    1500
agctgtatat ggtcgctggg tagagtgacc acataattga tcatcaaaac tgatacctgt    1560
aagagcaaaa gggggcacta ttaaccattg ggtcagggca acaggtcaaa atggagacct    1620
accctgggac ttctggtcac actagctact gtcaaaatgg ggcccaaata gacaaagcca    1680
```

```
aatggaagaa attcccttga cattgaaagt gttggggctc tgtggcaccc ccagttctag    1740
gttgggggag cttgggctgg tctcatgatg agttctgagg gggatgggcc agttgggccc    1800
cccgttccat ctaactcagg ttcctttcct cccagtccgc ctctccaagg accgatccac    1860
actgcaggtg ctggactcgg ccacagggaa ctggttctct gcctgtttcg acaacttcac    1920
agaagctctc gctgagacag cctgtaggca gatgggctac agcaggtaac caacctgggc    1980
ctctctcctt tttccctcct tcctccttcc tcctcttcct cctttccttc ctcccttctt    2040
ctctctttcc taaaaattac gggcattgga gccaggcaga atggcttttg aatcccagca    2100
tttcacttat aagcaacatg aagttaaatt tcctaagcct caggttcctc aggagttaat    2160
tgggggaact aatgccaacc tcataggata gttttgcaat gccagtgaga gaatgtgtgc    2220
tgccctccaa cacacacaca cacacttcta gcgtctatgc agtcctctcc tttccttttac   2280 tcctcaacct tcactccttt gtgctggctt tgcaagaaac tgttcctgcc cagtaataca    2340
aaagctaagt taacttattc aaagtttcgt tagttaagat ttagcttaag tgagcctagt    2400
ttcagtgggg ccccatcttc agcaatccca gctctctctg caaatttcaa aagcagttcc    2460
aaatctggag tggatgaaaa ggtgtaagat gatagtaaga gtaatttgca ttctatatat    2520
ttatattcac ttgattttgg cagaaaacca aaaagatagt tattatatct tatatataga    2580
tatatattat atctatttca taaataggct caaacaaagt aagtaacttg ctagggtact    2640
agctgggagg tagagggcta gaatttgagc ccaagacccc taattcttgc gcattaggag    2700
ttcccacatt gtttctgttt ctagactgag taattcttta ttctcatgta ggacatcatc    2760
tctaagggaa ggggctaatg agatggttga tcactcagag agtttagctg gagaggatgg    2820
aaaagaaccc atacattcag ttgcagattg agatagccta tctctggcag gcctcagatt    2880
tcttcaggat tctaacagac tggacccaga gactaggcca aacaaacaaa caaacaaaaa    2940
ctctactagg cagacatcac caaccaatca cagaactctc tcccatggat ccctaataca    3000
gcctcaaagt ccttttcagt aaatgctcca ggcagccatt acaaatcaat cagaattatt    3060
tgcctttctc ttctctgctc aacgggcttc tgctgctctc tactttccat agggggcaac    3120
ttccattacc ctctagaaag cacacccac caccttcatt tcaaggagag tgaggaactc      3180
atgcccagca cctgctattc tcccctcttc ctgcagccac ggagcccagc ctcgctgcag    3240
ccagccctgc ctccccactg tagtccagtc aactgctgca tcagccgttc ctggcacagc    3300
aggctgagcc ttgattatga aacctgggtg tctccagggg ttcttaagat gataggctcc    3360
tggaatttct gtccttttgg agctcagtaa ggcaccaaac cacctgagtc ttgtgcttca    3420
caaaatcaaa gttcatcaga atcattcatt gggatggaat tggtgaacag aagttaactt    3480
tcctgggaat gtccatttcc accatattcc gtccttctag gtctcagact tctctacttt    3540
ctttcctctc tctagatcgg aggcccttct tgtcctagaa ccataggcat ttcaagatgt    3600
gggagaccct agggatcatc tagtccacgc atcttttttt tttttttttg acagagtctc    3660
actctgtcac ccaggctgga gtgcaatggc accatctctg cttactgcaa cctccacctc    3720
ccaggttcaa gtgattcttt cgcctcagcc tcccaagtag ctgggattac aggcacgcac    3780
catcatgccc agctaatttt tatatttttg tagagaccga gtttcaccat gttggccagg    3840
ctggtcttga actcctgacc tcaggtgatc cacccacctc ggcctcccaa agtgctggga    3900
ttacaggcgt gagccactgc acccagcccc gtgcatcttt ttatagaggg ggaaactgag    3960
gcttggagag acccagaaaa agaatatgac ctgcccaagg ccacacatca aactagtgcc    4020
```

```
agagccaggg acagaaccta gatcatgagg actcttaaaa tgcactctag tcctcccagg    4080
tctgagactt gggtccttcc aggaagtgcc agcattcctg cctgagaatg tgccaatcca    4140
ccagtattgc caatgactca gccctccatg gagagcttct actaacatta ctagcatagt    4200
tagggatgga aggaaaagat ttagaagagg cagattcagt aaaggaacaa tcagagagat    4260
ggaattaatc aaggaaggct tcctggagga ggaaaaactt caacccaagg tttgaaagta    4320
gcaagcatgg attagcaggg agaaagaggg agagtggtcc agttgagaga aacgtttgtc    4380
tggattcata tgaagacaga tctagtcctg ttctattaaa tatctctaag ggggccaaaa    4440
acataccccc gctatcaaag tcagaccaga tgctttgttt ggagaacgaa atatccacat    4500
tccaactccc tcccaggtga aagggagct aacctgagcc cctatgcctc tttgtttccc     4560
tgctgtgaac cagaagacat tgctgggata tttgaaatag gacagagct gggaatatgg     4620 aaaggagacc cctaacattt ctccagggct ctgggttctg gatttggatt ccccacccaa    4680
gaaagcaagt tacatcagca atgcactgag ggttgagtcc tgggatgcca agggtcggtt    4740
ctttattgta tagcaaagca ggcccatct tcactgacta agaccatctc cactccctgg     4800
ccactcccca ccaagcattc tctgccactc tttctcctga aagtgggggc caactctacc    4860
atcttgttct aaccccctgc cccagctcac aactctctct ccctcttgat gtgagcagca    4920
aacccacttt cagagctgtg gagattggcc cagaccagga tctggatgtt gttgaaatca    4980
cagaaaacag ccaggagctt cgcatgcgga actcaagtgg gtaagtgagg ggacaccttc    5040
tggcctacag aaggccccca catggacgct gctcttcagg ttgcaaccag ctcacctgga    5100
accccaagca gccaggggaa tgtaagcaga catcaggaag aactcctagc cagatggatc    5160
attcaatgcc aagagctata gactcacatt ttggagaggt tttctgtgtt gacttgtttt    5220
taatacaatg gacagctgga caaagtgtgt tgtcctactc agagccagag ggatggataa    5280
tgtgaccttt ccatcaatct ggatagtaaa tagttttgc tactgctgta ggttttctaa     5340
taaattgccc aataggcaag attccaaagt cactttgtcc ttccctacca cttacccagc    5400
cagagctccc caccttcttg atgctccagg gaagaggctc catggcccctt gtgggtggcc    5460 tgttcctgag cctcgccacc ctgtgttaga gcagagcatc cagatgaaat ctgtcacact    5520
gtggcaaagt ggctcagaga ggaggctggc ttcctagcat tcagggacgt tgctgagggc    5580
cgcttattca ccgaaaataa atcttgaaaa ggacagggct ggtagcagaa tgatccttta    5640
cctaaaattc tatcaaaatc ccattcttcc atttggaaag cccacagtgt cacagactct    5700
gttccgggct ctgtcctctt ccctcttggg tcccaggagc ccaggctggg ctttgaagca    5760
ggcagggccc agcacacagt aggtactcag cagtgggggt gttgaatcca atcaaacgga    5820
agtgtcaatg caggaaatgc aatggatgtc aatgcagtct ccaaatgttc cccactgtgc    5880
agcttccaca ttcccgaggt attgggaggg gacttgaatt aacagcttcg ggaggcctga    5940
gtccctgcct cccagctgag gaagaagctt aaatcacagg gcgctgtgtc tgtcttccag    6000
gccctgtctc tcaggctccc tggtctccct gcactgtctt ggtgagtacc cccaatctct    6060
gagggtttgg ggcctgggcc agcaatgagc agggaggaag accttcatct tcactcctaa    6120
atttctggga ctccaagttt cattctgcct tggtctacag cccttgggct tgtcggtcaa    6180 tgcccctcg agttgttggt ggccttgggc aggtcacatt cttttctgg gtctttccaa      6240 gccccagttt cccccttcta ccatctgtgc atggctccat gacctaagtg gagacctggg    6300
agagagtgtt aggaagaccg aaaagggcag gacggggcct ccactgcctc ccatccctgg    6360
tccgggccca catagccttc tttgtcacaa tcagctcagg tatccaagat cagattaccc    6420
```

```
acattcatta tttgagcaac tattcattga acagttagaa tatgtctcac tctgtcagtt    6480
gctggctaga agtagaaagt accagatgag tgaaataatt ggccactatc cttggtagct    6540
gatgactaag taagagagag atgcaagaca acatgtggaa aatgccaaac tgagtagcag    6600
tcacagttga catgctgcag agagagctgg ccggggtca gaagacctgg gcaccagtcc    6660
tgttcatttc cagtgtggcc tcgagtcatt cacctgacct ccctgaagtt cattttccca    6720
agaagttgtt tagtccaact gcccatcaag gatctttagg gacccttcta gctctaacag    6780
aggagatcag aaaagaaaac aagcaatgtg gctcagctca tcctacaagc ttcatagaga    6840
actgagactg gcctggaagc atagccagaa attagaacgc ctaagggaag aaggtcacaa    6900
cgctgcctct gcaatttagg agtgtatatg ctttcctgca ggatgttgag agtttcattc    6960
attatcgtat gcccctacc ccggcccac aatacctagt gcgtgggatc tgacacgtgg    7020
tggctggtca atgaatgaat gaatgaatgg tcacaccatc tgaggttctg cactgagtag    7080
ccctgaaggc ttgaagcagc ataagtgaca ggtcctccct tgaggggcct ctgttttacc    7140
aataagccaa gacctaagct caacaacact gaaagggtgg ccaatacccca ggacagcctg    7200 tgggaattcc agagaaaggg agattcccag ggactggggg cccaggctaa acactgaaaa    7260
atgcatctgt aggctcaagg aggaaaagcc catgtctgtc tgtcttgccc accactctct    7320
cccagcaccc agcactgccc caggacagag agcacttgac acaagttggt tagattaatg    7380
aatgatttag agttcagtgg tccccaacct ttttggcaca agagactggt tgcatggaag    7440 acaattttc cgcaaaccaa gagggggata gagagcatta gattctctct tttttttttt    7500
tttgagacca agtctggctc ttgtcactca gcctggagta aagtgttgcg atctcggctc    7560
actgcaacct ccgcctcctg gattcaagcg attctcctgc ctcagccccc taaatagctg    7620
ggattacagg cacccgtcac cagcccagct gggactatag gcatgtgcca ccatgcccgg    7680 ctaattttg tatttttagt agagacggcg tttcaccatg ttggccaggc tagtctcgaa    7740
ctcctgacct caggtgatct gcccgcctga gcctcccaaa gtgctgggat tacaggcatg    7800
agctgcctca cccagcctaa agtctcataa ggaacgtaca gcatagatcc ctcacatgtg    7860
cagttcacaa taaggttgtg ctcctacaag aatctaacgc cacctctgat ctgacaggag    7920
gtgaagctca ggtggtcatg ctcgcttgtc cctgccactc acttcctaat gtacagccag    7980
gttcctaaca ggccacgaac cagtgggaag ggcatctttt tggatcaaaa acagaattac    8040
tttttagaga actacaagca gatcaatttg gctagacaga gactttatat gaaacagcag    8100
gaggctgcta ggaggagtgg aaactctact ttgccctcaa gggagatccc gaagggcttt    8160
gcaggagcgg gcaaggtggc atgaagaaag cagtgtttga aatcaggtgg tatttgaaaa    8220
gcccagccct tccccttaga atggcccttc taccatctgt gcatggctcc acaaccgtgg    8280
tggtggctgc cagaagaatt ggaaaggcag agcatgggtg gagaggggggg acctgagggc    8340 tttacaggag ttccgggggt ggtgagggtg tgaaagccag gtcagtcagt aggaagacag    8400
gatgtcagat tgagagactc ccctggccgg ggaaacagac ttggagaagg gggagttttg    8460
gatgagacag tccacttccg agtcacaaaa tagcttgtgg gtgtctgttt actgttactc    8520
agtgggagtg gctggggaca cgccacctgg gcagggcttt cgtaattctg catcacttgt    8580
gaaggtcaca gattcccagc aacggaca cacccatgtt catagtctga actcctaaac    8640
acatcttaaa ccaaaataaa aaaaaagaa agaaagaaag aaaaaggaga gggaggtttg    8700
aggaaagcct atggtctggg acactcaata cctcccatga atatctcata ttgggctggt    8760
```

```
cctctctcca ctctggcccc agccataagg gccctgctta gagcagattt tgggtgctga    8820
gtggaggcag cctcatcccc aacagcctga cttcctgcct cctccctgcc tctgcctgtg    8880
tccagcctgt gggaagagcc tgaagacccc ccgtgtggtg ggtgtggagg aggcctctgt    8940
ggattcttgg cctttggcagg tcagcatcca gtacgacaaa cagcacgtct gtggagggag    9000
catcctggac ccccactggg tcctcacggc agcccactgc ttcaggtaag accccagctg    9060
taaggaggtc tctggggacc aaggccagtc agggaccaga gagcttgggg tcctgtctcc    9120
tggcaccgtc cttctcttca ctctcccact agagacgttt tccaggttgt ggtggcccca    9180
atgagacaat ggccatgatg ccctttgtta ggcttttggg tgtctgagca gagggtgctg    9240
gtcaccaagc atggcctctt cctggtggga caccagcaga tacccagagt cctcacccca    9300
cccccatatc gttcaagcta caaaagctct tcccacctgc ctcaacttcc aagaactcac    9360
tctcttttg cttgtttcca ggaagttgtt ccagggtcta gagtcatagc cacgtcctca    9420
ttatgtctgg aaactttaaa aaaattaaag agcataggtt cctttcagtc cacagagaag    9480
cctggcctta cctcagggaa gggctactcc cagaccccct tcactttttt ttttttttt    9540
tttttttttt tttttgagac agagtcttgc tctgttgctt aggctggagc gcagcagcat    9600
gatcttggct cactgcaacc tccgcctcct gagttcaagc aattctcctg cctcagcttc    9660
ccaagtagct gggactatag gcatgggcca ccatgcccgg ctaattttg tattttggt    9720
agagacaggg tttcaccatg ttggccaggc tgatctctaa ctcctgacct caagtgatct    9780
gcccacctca gcctcccaaa ctgctgggat tacaggcatg agccagggca tccggctttt    9840
atttattcat tcattcaata tctaatgagc acctaccagg taccaaacac cagatgatgc    9900
gcccaagttc attagacccc accgctgtct tcaaggcact catgatctag ccagcgttt    9960
tttaaccact ttttttttt ttttttga gattctggtg agagctataa attctttcct    10020
ggaaaaacat ctctgcacac taagctgtgc ctggcattgg gaaaagaaa gcacgtaatg    10080
taactgacag catgagtaac acagtgagaa aggttggagg agagagcgcc aggacctcag    10140
aactcaggca ttagaggagc cccttcccca gccctccttg aggtttcgtt gggcaggttt    10200
cactgaggaa aaagggtcaa atccctttt cgaatttgac ttcttgtaag tgccagaaga    10260
ctgccccttc tccaccatcc ctgcctcacc atcatctttc ctcccaaggc agtgacatcc    10320
agcaccccga tccctagggc cctggggacc cagccttgg caaagtctcc tcaggcttgg    10380
atcaggcctg aacccagctg tctctacccc caggaaacat accgatgtgt tcaactggaa    10440
ggtgcgggca ggctcagaca aactgggcag cttcccatcc ctggctgtgg ccaagatcat    10500
catcattgaa ttcaaccca tgtaccccaa agacaatgac atcgccctca tgaagctgca    10560
gttcccactc actttctcag gtgagaagca gggcccaagg ccactcaagc ctcttacatc    10620
agttttcacg cccactctgc tattagctca ctgaccgccc ttggcacata atgtctcctc    10680
tcaagtcctc agcttgccca tttgtctcta atacgtcagc ctaacatcac tgatgccatg    10740
aggcctcctc aagctgtcag ctaacacctc cactccattc cctgccagag attcttccaa    10800
ggcctgtctt ccctatgtgg agccctcga gtgagaactg gagtttcatc caatcttgga    10860
gtttaggag acctttaaa aagattatcg agctaattcc ccaccactga ccaacacgca    10920
agagcctgct cagtatccct gccaaggagt cattgtgccc ctgtttgctc tcctccaggg    10980
gcagggaacc cattacctgt gaggcagccc acagagtctt tgaacagctc tgttggatgc    11040
cttgtgctta tactgaaatg tatttagatc aggattccca actgtggggt ccacaagaca    11100
ctggccccctt ggagaagaga ggattccatt gtcaaataag tttggggaac attttcatac    11160
```

```
tacagctccc ttcttggaac acattagttt attaaaggta ggagaagttt ttaaaataat    11220
ctgttttatt gcgtttaacc tacatttttt aaatttattt gaccacagaa tccttttttc    11280
atgctacttc tattagcatc ccatagaaca agtgttctag agaccctggt gtgacccctt    11340
tcagagagct taactgccag gctctcctga gccctggtgt gtgtttcaag atttgtgcct    11400
gggaattgtt ttaatcaggt atggcaaggt gacagataca gacacagcta tctttgaaag    11460
aagagtttat tatttataat tcctgagaga aagggacata ccccaccccc caacacaggg    11520
acacccgggg aagcagctgg gtccaccagg aggcaggagt gagggaagg catggcccag     11580 agccacctgt ggcttccatg ggcaggtctg gccaaggtag ggtaggcaag attgagcatg    11640
ctcaggattg gatagtgtgg acaattctct aggctataga tgtcagcctc tggttgtcta    11700
gtatctgtcc ctggggtgat ttagggcagg gaaaatattg gcttggtgtc tgagagtcag    11760
ataaaggaag tggttgggga tatgggcttt gggttggctg gtttgcctat taaaggcgtg    11820
cccaaagcca agttgtttac tatctgcagg aattagctaa cccagtctct cccagaccag    11880
caagatcccc ataatcataa agcatcataa tttacagaaa attaacactt atgatgaata    11940
aaagatctcc ttcttcctct gtgctcctgg caggcacagt caggcccatc tgtctgccct    12000
tctttgatga ggagctcact ccagccaccc cactctggat cattggatgg ggctttacga    12060
agcagaatgg aggtaagtcc tgggtgcagg accacagggc aggagatgcc cttgtatgag    12120
ggagcagctt ccagaagtaa tgggaaggag gaccacccct cagagaaacc catcctggag    12180
gaccaagcac caaggcgcca ggcagaaagc aaagtggttt ggcaatccag ggctggggga    12240
tagaaggcaa ggatgggaat gtgagtgttt ttaccctccc agggaagatg tctgacatac    12300
tgctgcaggc gtcagtccag gtcattgaca gcacacggtg caatgcagac gatgcgtacc    12360 aggggggaagt caccgagaag atgatgtgtg caggcatccc ggaagggggt gtggacacct   12420
gccaggtggg gcctccaaga atcatgggga gttctaagaa tagggtttag gtcctagaga    12480
gatgagaaaa cccagaggct gcatgcccta caggaagcct tgcatatcat gggcactcaa    12540
tgtgtgatga tgggaggaag agagggaggg aaggaaagga tagtcagata aaagtgtacc    12600
aatagatgag tgggtggatg gatggatgca gacaagcaga gagatttcaa atgtctcttt    12660
cacattcgaa gatgatgtta ctggcctggc atggtggctc acgcttgtaa tcccagcact    12720
ttgggaggct gaggcgggca ggtgatttga ggtcaggaat tcaagaccag cctggccaac    12780
atggtgaaat cccatctcta ctaaaaagaa tacaaaaatt agctgggcgt ggtggcacgt    12840
gcctgtaatc ccagctactt gggaggctga ggcaggagaa ttgcttgaac ccaggaggca    12900
gaggttgcag taagctgaga ttgcgccact gcactccagc ctgggtgacc cagcaagact    12960
ccatctgaaa acaacaacaa caacaaagat gacattactc atccaccca cccacccttc      13020 tcactagcta cagaatgatt agccccttga ggtcaggaat cccaggtcta ttttctctgt    13080
gactctcccc aagctgctga actacactag gaaagaatta ccgcctgcag aatgctggaa    13140
gcacatctgt gtgtgccctc accccggcct cattggccat caggactgct tagcaatccc    13200
tgtagacctt cttcctcccc catacttcca gaggatcttc tgaactatt tcttttttta      13260 tttttcttt tatgtttttt aacagagaca gggtcactat gttgcccagt ctggtctcaa     13320
actcctgggt tcaagggatt ctcccacctc agctttccaa aatgctggga ttacaggcat    13380
gagccatcgt gcttggcctg aaccattttc attaaaaccc ctaccctact ctcacctcca    13440
tttccagtca ttaaattcct tcatttaaga ggcatctctt agtcatcgca tgtgtgccat    13500
```

```
gaacatggta gtctttggag acccctcagg gagctcacag tggttggggg aaaggggggc    13560
attaaacaga catttaagct atagttttgg gttcagaggg aggaagcccc aggggctaaa    13620
acagctgata aggactccca gataagtgca cttttcacta tctggcattt tcttgttttg    13680
ttatttgctt gttcactgtc tctcacccca tttgatccta agctttctga gggcagggat    13740
ctttgttttt tttcatcagt tggatcccaa ttgcttagaa cactacctgg cacaaaatag    13800
gcactctata agtgattaca caaattttgg aacgactagg ttaaacaatg ataaccaggc    13860
tttttttttt ttttttgaga ctgagtctca ctctgttgcc caggctagag tgaagtggtt    13920
tgatctcggc tcactgcagc ctccgcctct gggttcgaat gattctccac ctcagcctcc    13980
tgagtagctg ggattacagg tgcctgccac tatgcccagc taattttgt atttgtagta    14040 gagacgggtt tcaccatgtt ggccaggctg gtcttgaact cctgacctca agtgattcac    14100
ccgcctcagc ctcccaaggt gctgggatta caggtgtgag ccaccgctcc tggccaacaa    14160
ccaggctttt ttaagacatc actcagagcc tttaatttgc taatgtgagt tgtgaatctc    14220
tgagagaagg ctaacggcat gcttgcaact tacttgtcca cagacaagcc tttctgcccc    14280
agaagagaag accattctag ggtgctaatg agcaaagagg gtgagggtgg aatatcggag    14340
agcagcaggg agtgcagggg aacagatagg ccagttcagg gagcagagaa ggagaagccc    14400
ccccacctca cctgccctcc ccagcagtct ctgttctggt ctctcacagg gtgacagtgg    14460
tgggcccctg atgtaccaat ctgaccagtg gcatgtggtg ggcatcgtta gttgggggcta   14520 tggctgcggg ggcccgagca ccccaggagt atacaccaag gtctcagcct atctcaactg    14580
gatctacaat gtctggaagg taaggtacct ttgccctacc cactgtgcct tccctccagt    14640
cctctacctg gggggtgcca atccatcctc aggtttgatt taaatggttc tgacaactct    14700
ttacatccca aataactttc cctccaagca agggacagcc tgagattgca ctattaaggc    14760
tgaaattcct taggtcagag atttctgata aatgcaaata ccttagggaa tagaacacac    14820
caagcctttc tttctctttt ctgacagaat gagactatca gatcctttct agagagaaga    14880
ttctgataag gaagagagtg gaaaggctca tgagacctcc tggccctctg cagggtaggg    14940
agagaagcaa agtgtttcag aaaaggaaga ctcacgttac acatgtcacc actttgtcca    15000
gtttcagata atctgacttt ctcttcatcg gtctctctta ttctaggctg agctgtaacg    15060
ctgccgtccc ccacatccag aagctgcttc ccttcagacc tacctacggc atgacccctc    15120
aaagtcagat atgggacaag agcctccttg aacaaactc                           15159
```

<210> SEQ ID NO 14
<211> LENGTH: 435
<212> TYPE: PRT
<213> ORGANISM: Artificial Sequence
<220> FEATURE:
<223> OTHER INFORMATION: Recombinant protein

<400> SEQUENCE: 14

```
Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Val Ala
        35                  40                  45

Leu Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
```

```
                65                  70                  75                  80
        Cys Pro Leu Gly Glu Asp Glu His Cys Val Lys Ser Phe Pro Glu
                         85                  90                  95
        Gly Pro Ala Val Ala Val Arg Leu Ser Lys Asp Arg Ser Thr Leu Gln
                        100                 105                 110
        Val Leu Asp Ser Ala Thr Gly Asn Trp Phe Ser Ala Cys Phe Asp Asn
                        115                 120                 125
        Phe Thr Glu Ala Leu Ala Glu Thr Ala Cys Arg Gln Met Gly Tyr Ser
                    130                 135                 140
        Ser Lys Pro Thr Phe Arg Ala Val Glu Ile Gly Pro Asp Gln Asp Leu
        145                 150                 155                 160
        Asp Val Val Glu Ile Thr Glu Asn Ser Gln Glu Leu Arg Met Arg Asn
                            165                 170                 175
        Ser Ser Gly Pro Cys Leu Ser Gly Ser Leu Val Ser Leu His Cys Leu
                        180                 185                 190
        Ala Cys Gly Lys Ser Leu Lys Thr Pro Arg Val Gly Val Glu Glu
                        195                 200                 205
        Ala Ser Val Asp Ser Trp Pro Trp Gln Val Ser Ile Gln Tyr Asp Lys
                    210                 215                 220
        Gln His Val Cys Gly Gly Ser Ile Leu Asp Pro His Trp Val Leu Thr
        225                 230                 235                 240
        Ala Ala His Cys Phe Arg Lys His Thr Asp Val Phe Asn Trp Lys Val
                            245                 250                 255
        Arg Ala Gly Ser Asp Lys Leu Gly Ser Phe Pro Ser Leu Ala Val Ala
                        260                 265                 270
        Lys Ile Ile Ile Glu Phe Asn Pro Met Tyr Pro Lys Asp Asn Asp
                    275                 280                 285
        Ile Ala Leu Met Lys Leu Gln Phe Pro Leu Thr Phe Ser Gly Thr Val
                    290                 295                 300
        Arg Pro Ile Cys Leu Pro Phe Phe Asp Glu Glu Leu Thr Pro Ala Thr
        305                 310                 315                 320
        Pro Leu Trp Ile Ile Gly Trp Gly Phe Thr Lys Gln Asn Gly Gly Lys
                            325                 330                 335
        Met Ser Asp Ile Leu Leu Gln Ala Ser Val Gln Val Ile Asp Ser Thr
                        340                 345                 350
        Arg Cys Asn Ala Asp Asp Ala Tyr Gln Gly Glu Val Thr Glu Lys Met
                        355                 360                 365
        Met Cys Ala Gly Ile Pro Glu Gly Gly Val Asp Thr Cys Gln Gly Asp
                    370                 375                 380
        Ser Gly Gly Pro Leu Met Tyr Gln Ser Asp Gln Trp His Val Val Gly
        385                 390                 395                 400
        Ile Val Ser Trp Gly Tyr Gly Cys Gly Gly Pro Ser Thr Pro Gly Val
                            405                 410                 415
        Tyr Thr Lys Val Ser Ala Tyr Leu Asn Trp Ile Tyr Asn Val Trp Lys
                        420                 425                 430
        Ala Glu Leu
                435

<210> SEQ ID NO 15
<211> LENGTH: 2046
<212> TYPE: DNA
<213> ORGANISM: Mus musculus

<400> SEQUENCE: 15
```

```
cagaaacaag gacctcttca ttattcaaga gtaaaatgta taggccaaga ccaatgctat      60
caccgtcaag attcttcact cccttttgcag tagctttcgt tgtcataata acggtagggc    120
tcctggccat gatggcaggt ctacttattc acttttttagc ttttgacaag aaagcttact    180
tttatcatag cagctttcaa atcctaaacg ttgaatacac tgaggcttta aactcaccag    240
ctacacacga atacagaacc ttgagtgaaa gaattgaggc tatgattact gatgaatttc    300
gaggatcaag tctaaaaagt gagtttatca ggacacatgt tgtcaaacta agaaaagaag    360
ggactggtgt ggttgcggat gttgtcatga aatttcgatc tagtaaacgt aacaacagaa    420
aggtaatgaa aaccagaatt caatctgtgc tacgaagact cagcagctct ggaaacttgg    480
aaatagcccc ttcgaatgag ataacatcac tcactgacca ggatacagaa atgttttga    540
ctcaagaatg tggagcacgt ccagaccta taacactgtc agaagagaga atcattggag    600
gcatgcaagc tgagcccggt gactggccct ggcaagtcag tctacagctc aataatgtcc    660
accactgtgg aggtgccctg atcagtaaca tgtgggtcct gacagcagct cattgcttca    720
aaagctatcc taatcctcaa tattggacag ccacctttgg ggtttctaca atgagcccta    780
ggctgagagt gagagtaagg ctatttttag cccacgacgg gtacagctcc gtaactcgtg    840
acaatgacat cgcagttgta caacttgaca gatctgtcgc cttttccaga aatatccata    900
gggtatgtct cccagcagca acccaaaata tcatccctgg ttctgtcgca tatgttacag    960
gatgggggatc tctcacatat ggaggcaacg cagtcacaaa tctacggcaa ggagaggtca   1020
gaataataag ttcagaggaa tgcaatacgc cagctggtta cagtggaagt gtcttgccag   1080
gaatgctgtg tgctggaatg cgttcagggg ccgtggatgc atgccagggt gattcaggtg   1140
gcccgctagt acaagaagac tcaaggcggc tttggtttgt tgtgggcatt gtgagctggg   1200
gatatcagtg tggcctccca aataagccag gcgtgtatac tcgagtgaca gcctaccgca   1260
actggatcag acagcagacg ggaatctagt gcaaccgagg aaaaaacgtg ccatgaggtc   1320
tctgtatcca agtgtgactg actcggatgc catggcttca catttcaact gcaaaggaga   1380
ctggaaatgc cccttctgaa cgtcccatta cataaatatg gtttaactgt ttagtatttc   1440
tttgtcggta cagatttta ctttcttgag gaaaaaaaaa acatgaacat ggctaagtaa   1500
gaattatgtt aggctagtaa caggaagaca tttattacat gggtggtcag gtgtagtagt   1560
gagaagtcag gtaagttaag tcaataattt acagaaaata atgtcaggta gtcctaacgt   1620
taaatatgtg aggccacaga acaaatagtg ttagaactga agccatccca agtatttaac   1680
atttgttttc aagtgaaact aagaaacaga cttacatata gttttaatgg tgaattttca   1740
ttttaaatat tttatctaca tagaaaagac atatctcctt catgaagaag ctgaggtgat   1800
gaatcaacac agcctcttca gctatgtttg caaccacaag atttgtggga agaaatccc   1860
tactaccaac ttcctactgt tggcattatt ttttagagta acacgacgca caatagcaaa   1920
atttaagtaa caaattaaaa gttaatgatg aagaagaagt aaagagtttg tttgcaaaga   1980
caaaaattaa acagattaat atcaataaat ctggagacag aagggtctca gattcatatt   2040
ctctct                                                              2046
```

<210> SEQ ID NO 16
<211> LENGTH: 417
<212> TYPE: PRT
<213> ORGANISM: Mus musculus

<400> SEQUENCE: 16

Met Tyr Arg Pro Arg Pro Met Leu Ser Pro Ser Arg Phe Phe Thr Pro

-continued

```
1               5                   10                  15
  Phe Ala Val Ala Phe Val Val Ile Ile Thr Val Gly Leu Leu Ala Met
                   20                  25                  30
  Met Ala Gly Leu Leu Ile His Phe Leu Ala Phe Asp Lys Lys Ala Tyr
                   35                  40                  45
  Phe Tyr His Ser Ser Phe Gln Ile Leu Asn Val Glu Tyr Thr Glu Ala
                   50                  55                  60
  Leu Asn Ser Pro Ala Thr His Glu Tyr Arg Thr Leu Ser Glu Arg Ile
 65                  70                  75                  80
  Glu Ala Met Ile Thr Asp Glu Phe Arg Gly Ser Ser Leu Lys Ser Glu
                   85                  90                  95
  Phe Ile Arg Thr His Val Val Lys Leu Arg Lys Glu Gly Thr Gly Val
                  100                 105                 110
  Val Ala Asp Val Val Met Lys Phe Arg Ser Ser Lys Arg Asn Asn Arg
                  115                 120                 125
  Lys Val Met Lys Thr Arg Ile Gln Ser Val Leu Arg Arg Leu Ser Ser
                  130                 135                 140
  Ser Gly Asn Leu Glu Ile Ala Pro Ser Asn Glu Ile Thr Ser Leu Thr
 145                 150                 155                 160
  Asp Gln Asp Thr Glu Asn Val Leu Thr Gln Glu Cys Gly Ala Arg Pro
                  165                 170                 175
  Asp Leu Ile Thr Leu Ser Glu Gly Arg Ile Ile Gly Gly Met Gln Ala
                  180                 185                 190
  Glu Pro Gly Asp Trp Pro Trp Gln Val Ser Leu Gln Leu Asn Asn Val
                  195                 200                 205
  His His Cys Gly Gly Ala Leu Ile Ser Asn Met Trp Val Leu Thr Ala
                  210                 215                 220
  Ala His Cys Phe Lys Ser Tyr Pro Asn Pro Gln Tyr Trp Thr Ala Thr
 225                 230                 235                 240
  Phe Gly Val Ser Thr Met Ser Pro Arg Leu Arg Val Arg Val Arg Ala
                  245                 250                 255
  Ile Leu Ala His Asp Gly Tyr Ser Ser Val Thr Arg Asp Asn Asp Ile
                  260                 265                 270
  Ala Val Val Gln Leu Asp Arg Ser Val Ala Phe Ser Arg Asn Ile His
                  275                 280                 285
  Arg Val Cys Leu Pro Ala Ala Thr Gln Asn Ile Ile Pro Gly Ser Val
                  290                 295                 300
  Ala Tyr Val Thr Gly Trp Gly Ser Leu Thr Tyr Gly Gly Asn Ala Val
 305                 310                 315                 320
  Thr Asn Leu Arg Gln Gly Glu Val Arg Ile Ile Ser Ser Glu Glu Cys
                  325                 330                 335
  Asn Thr Pro Ala Gly Tyr Ser Gly Ser Val Leu Pro Gly Met Leu Cys
                  340                 345                 350
  Ala Gly Met Arg Ser Gly Ala Val Asp Ala Cys Gln Gly Asp Ser Gly
                  355                 360                 365
  Gly Pro Leu Val Gln Glu Asp Ser Arg Arg Leu Trp Phe Val Val Gly
                  370                 375                 380
  Ile Val Ser Trp Gly Tyr Gln Cys Gly Leu Pro Asn Lys Pro Gly Val
 385                 390                 395                 400
  Tyr Thr Arg Val Thr Ala Tyr Arg Asn Trp Ile Arg Gln Gln Thr Gly
                  405                 410                 415
  Ile
```

<210> SEQ ID NO 17
<211> LENGTH: 2800
<212> TYPE: DNA
<213> ORGANISM: Homo sapiens

<400> SEQUENCE: 17

| | | | | | |
|---|---|---|---|---|---|
| atttgagtgg | gaatctcaaa | gcagttgagt | aggcagaaaa | agaacctct tcattaagga | 60 |
| ttaaaatgta | taggccagca | cgtgtaactt | cgacttcaag | atttctgaat ccatatgtag | 120 |
| tatgtttcat | tgtcgtcgca | ggggtagtga | tcctggcagt | caccatagct ctacttgttt | 180 |
| acttttttagc | ttttgatcaa | aaatcttact | tttataggag | cagttttcaa ctcctaaatg | 240 |
| ttgaatataa | tagtcagtta | aattcaccag | ctacacagga | atacaggact ttgagtggaa | 300 |
| gaattgaatc | tctgattact | aaaacattca | aagaatcaaa | tttaagaaat cagttcatca | 360 |
| gagctcatgt | tgccaaactg | aggcaagatg | gtagtggtgt | gagagcggat gttgtcatga | 420 |
| aatttcaatt | cactagaaat | aacaatggag | catcaatgaa | aagcagaatt gagtctgttt | 480 |
| tacgacaaat | gctgaataac | tctggaaacc | tggaaataaa | cccttcaact gagataacat | 540 |
| cacttactga | ccaggctgca | gcaaattggc | ttattaatga | atgtggggcc ggtccagacc | 600 |
| taataacatt | gtctgagcag | agaatccttg | gaggcactga | ggctgaggag ggaagctggc | 660 |
| cgtggcaagt | cagtctgcgg | ctcaataatg | cccaccactg | tggaggcagc ctgatcaata | 720 |
| acatgtggat | cctgacagca | gctcactgct | tcagaagcaa | ctctaatcct cgtgactgga | 780 |
| ttgccacgtc | tggtatttcc | acaacatttc | ctaaactaag | aatgagagta agaaatattt | 840 |
| taattcataa | caattataaa | tctgcaactc | atgaaaatga | cattgcactt gtgagacttg | 900 |
| agaacagtgt | cacctttacc | aaagatatcc | atagtgtgtg | tctcccagct gctacccaga | 960 |
| atattccacc | tggctctact | gcttatgtaa | caggatgggg | cgctcaagaa tatgctggcc | 1020 |
| acacagttcc | agagctaagg | caaggacagg | tcagaataat | aagtaatgat gtatgtaatg | 1080 |
| caccacatag | ttataatgga | gccatcttgt | ctggaatgct | gtgtgctgga gtacctcaag | 1140 |
| gtggagtgga | cgcatgtcag | ggtgactctg | gtggcccact | agtacaagaa gactcacggc | 1200 |
| ggctttggtt | tattgtgggg | atagtaagct | ggggagatca | gtgtggcctg ccggataagc | 1260 |
| caggagtgta | tactcgagtg | acagcctacc | ttgactggat | taggcaacaa actgggatct | 1320 |
| agtgcaacaa | gtgcatccct | gttgcaaagt | ctgtatgcag | gtgtgcctgt cttaaattcc | 1380 |
| aaagctttac | atttcaactg | aaaaagaaac | tagaaatgtc | ctaatttaac atcttgttac | 1440 |
| ataaatatgg | tttaacaaac | actgtttaac | cttctcttat | tattaaaggt tttctatttt | 1500 |
| ctccagagaa | ctatatgaat | gttgcatagt | actgtggctg | tgtaacagaa gaaacacact | 1560 |
| aaactaatta | caaagttaac | aatttcatta | cagttgtgct | aaatgcccgt agtgagaaga | 1620 |
| acaggaacct | tgagcatgta | tagtagagga | acctgcacag | gtctgatggg tcagaggggt | 1680 |
| cttctctggg | tttcactgag | gatgagaagt | aagcaaactg | tggaaacatg caaaggaaaa | 1740 |
| agtgatagaa | taatattcaa | gacaaaaaga | acagtatgag | gcaagagaaa taatatgtat | 1800 |
| ttaaaatttt | tggttactca | atatcttata | cttagtatga | gtcctaaaat taaaaatgtg | 1860 |
| aaactgttgt | actatacgta | taacctaacc | ttaattattc | tgtaagaaca tgcttccata | 1920 |
| ggaaatagtg | gataattttc | agctatttaa | ggcaaaagct | aaaatagttc actcctcaac | 1980 |
| tgagacccaa | agaattatag | atattttca | tgatgaccca | tgaaaaatat cactcatcta | 2040 |
| cataaaggag | agactatatc | tattttatag | agaagctaag | aaatatacct acacaaactt | 2100 |
| gtcaggtgct | ttacaactac | atagtacttt | ttaacaacaa | aataataatt ttaagaatga | 2160 |

```
aaaatttaat catcgggaag aacgtcccac tacagacttc ctatcactgg cagttatatt    2220
tttgagcgta aaagggtcgt caaacgctaa atctaagtaa cgaattgaaa gtttaaagag    2280
ggggaagagt tggtttgcaa aggaaaagtt taaatagctt aatatcaata gaatgatcct    2340
gaagacagaa aaaactttgt cactcttcct ctctcatttt ctttctctct ctctcccctt    2400
ctcatacaca tgcctccccc accaagaat ataatgtaaa ttaaatccac taaaatgtaa     2460
tggcatgaaa atctctgtag tctgaatcac taatattcct gagtttttat gagctcctag    2520
tacagctaaa gtttgcctat gcatgatcat ctatgcgtca gagcttcctc cttctacaag    2580
ctaactccct gcatctgggc atcaggactg ctccatacat ttgctgaaaa cttcttgtat    2640
ttcctgatgt aaaattgtgc aaacacctac aataaagcca tctactttta gggaaaggga    2700
gttgaaaatg caaccaactc ttggcgaact gtacaaacaa atctttgcta tactttattt    2760
caaataaatt cttttaaaa taaaaaaaaa aaaaaaaaa                            2800
```

<210> SEQ ID NO 18
<211> LENGTH: 418
<212> TYPE: PRT
<213> ORGANISM: Homo sapiens

<400> SEQUENCE: 18

```
Met Tyr Arg Pro Ala Arg Val Thr Ser Thr Ser Arg Phe Leu Asn Pro
1               5                   10                  15

Tyr Val Val Cys Phe Ile Val Ala Gly Val Val Ile Leu Ala Val
                20                  25                  30

Thr Ile Ala Leu Leu Val Tyr Phe Leu Ala Phe Asp Gln Lys Ser Tyr
            35                  40                  45

Phe Tyr Arg Ser Ser Phe Gln Leu Leu Asn Val Glu Tyr Asn Ser Gln
        50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255
```

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile

<210> SEQ ID NO 19
<211> LENGTH: 38992
<212> TYPE: DNA
<213> ORGANISM: Artificial Sequence
<220> FEATURE:
<223> OTHER INFORMATION: Recombinant polynucleotide

<400> SEQUENCE: 19

```
gagggagggt ggtgctttgc taatggtgaa ttactaactc ctcaataaag aatattattt      60
gaaataattt ttgaaatttc ataattactt tgggttcttt cttaatgata aataaataat     120
agtatattac aaacatacat taatatttcc tgaatgaata caccacaaat ctcccttaaa     180
atatagcaag aataaaaatt atactatttc tgacaatttt taatttctca ataataata      240
ccactctgat ttttaaacat ctacaccact ctggctttgc caatcttttt aaaaattgaa     300
aagataataa ttttatcata attacactga agcatagaac ttttttcttc aaggaaagca     360
aattttgaa attctataat ataacctccc ataatcctga ataaattaaa ggttcaacaa      420
cttagtaaag taagactgac cttccctttt atttcttttt cagatcaaaa atcttacttt     480
tataggagca gttttcaact cctaaatgtt gaatataata gtcagttaaa ttcaccagct     540
acacaggaat acaggacttt gagtggaaga attgaatctc tggtaagtta atatttgtct     600
ttgctcttta ttccattata aaatgaatat gataataaac ctaatgtttt gtaatatatt     660
ttcagttgct aagtgctcta catatttttcc ttccttgaat ggtgaaacat gtgtttctct     720
ctgctttat ccagttagtt tactcatata ctggttctta ttcacatctt tgtcatgagt      780
aaaaagtgtt agaaaggcca cgagtaaata tgcatttat ttgtttatga attcaaatac      840
taaaagtttt ttatttgttt aattaagcat tgacattgtc tttttaaatt cttttcattt     900
taccttcttc cctcttcctt atccaactaa agacgcaaag caggaggtgt taaaaaacag     960
gtttaccata tcagcagtaa catagtttgg acaacattac actttggttc aatgatagac    1020
atagaagttt gaacagaaat atgcaaagca agtttgagct ctaacttgaa gagagcctct    1080
gggtgcctgc caggaaaccct cacgagtgga cccttaacat tcatgtgtca ccacaaacta    1140
```

```
ggggctgccc tttagttttg accagtctca gtgtcactca cttacccctta ccttttcaaa    1200
aaaaagtcct aagaatataa agtaattcaa tggttctaca attttagcat gtaactgagt    1260
cacctggcag ggttgctttg gtgagctcaa gataaaattt tatcagcatt tctacatttt    1320
ctggaatatt ccttaatcca ggcttttaat cccttggtgc ttttctgaac cactgcaatg    1380
agcttctaac tgttctcact gtgtgcaggc tcttttcctt ctaatctaat ttacacactt    1440
ctgaacacaa atctctcaca gcctgtttcc ttcatgttac ctccagctca agacttttg    1500
cctacaaaat aaaattcaaa cttgttagct aagcaccttc tcatgtctat gctttggctc    1560
atatttcagc catcgtgtgc cccacttatt cttatagcca acctgaaaag ccatctttta    1620
taagaaacta cctctgctct ccatgattgg atataattaa tcctccttcc acatcacctc    1680
gccacaaaat tgtatctgtg ttgatctcat gccacatacc tgtatgtatt ttatattata    1740
aatatttgca gacttgttta atttgccatg ttagactaag ttccatgaag acagctccat    1800
atccattcca tttttatata tccacaacat ttggtcgggt tgatgcttaa taaatgttta    1860
ttgaaggaac aggagtctcc cacttctgac ataatgaact tatttccccc agtgttaacc    1920
ctacatctgg ttcctgtcca agagtctctt cccaaatcat tctgattcaa ctgttcattc    1980
tgatctcatt aaacatttaa atgatatatc taacttcgct tgctttattc tatgctcatc    2040
ctgcagtctc ctcataactt ggtttcaatg atgcttgctt ctagagaaaa aaatgtatta    2100
aataagctta tgattcagtc ctccagctgt gatggttctc actgaacatt agctcagtgg    2160
ttttcgaagt atggtctcta gcataaccta gaaacttgtt agaaatgcaa attcttgggc    2220
tcaccaagac atactaaatc aaaaattctg acattggggc ctagaaatct gtgttttaac    2280
aagcctgcca gtgcagcctg gtccctttc ttctcggagc cccactcaaa gctttcagtg    2340
ctcatctccc accaatgaca gggtcctcta tggaaaccgg caggacggtt tccaactcta    2400
actacgtttt agagtttgct tcctagggct atccaggcac caagtatcac aggttagttt    2460
cccagggaag cagactctga gacttgcatg cagggagtgt ctctggggtg ctctcaacca    2520
acaccttcag gaagagaagg aagcagcatt gggcagaggc atagtcaaac tacagtgctg    2580
ttggcacaga agactgaagg gagtcagagc caggggggtag aggtgggccc ttagcatcca    2640
tccttcacca ttaggtgtga gttgccccac ctccttgatg gtgtaacctc agtcccaagg    2700
tgggtgggag tgcagcagag cagccccctac aagggccaaa ccagagatac accaggcgcc    2760
agaagtgctg ccagggaata gagaggaaag gatgggctta aggtaggatc cacagaactt    2820
ggcaatggat tagaagacag gatgagaagt gacaggttaa cactaacaca gaaatgtcta    2880
acttcggtag ataatggtgc cattggctag aagaggaaac cgaaatgaaa gcaggttgtt    2940
cagggagaca aaagttcact gtggacatct cagcagagtg attcagtggg gaaggaatg    3000
gatgcccaga ccacctcaga ggaagatcta agctggagcc agcaataaag atacaagatg    3060
aacaatccct aacgaactgc tcctcagcca tgctccccag acacgctgct tcagatttat    3120
agtccgggtg aggctaggag gtgcgcctcc ctcagtggag gacagcaaag caccagtggc    3180
tccagggagt taaatctttt tgataatttt tgttctagca tctgtctgca gagctgtctc    3240
tcagccattg cctgccttta cacaggagtg cagtccgaaa ttgggagatg agtgaaattt    3300
attatgccta gagatctgga tccccagttg tttgggagta tattttctga accacttgtt    3360
ggtttaagta atgcagattt attgatgcca cttctcttga atctgtgact ctggaccccac    3420
catctaagtg aatgtgcaga gggaacggaa tggctgcaat agatctccat taaaaccagt    3480
```

```
gcatcctccc agacacatac agtagtaggg aggtgagtca atgtcaggac agcaccagct    3540
cccgcttcgg tacatttcca aagttctcag tctgtgtaca aaggtttgct ctggggcagc    3600
agaaatagcc ctgggcaggt agtcaaaggc ctggtttgat ttcctccact tccaggcaag    3660
tcactcgaag gctcacaggc ttttcctca cctgccacat gggtccagtg agatctactg      3720
agctgtaaat aatgaaatga gtgtgtgtgc agtcatctat aagttgtaaa gtactagaaa    3780
atggtgaaac tttgggattt gggctattta aggctgaatg ctaaaaatgt caggcattgt    3840
ggagaaagga atttaaatat aagattgatt gactgggatt taaagacaaa tgaaggcaca    3900
cacgcaagtg cacacccaca ctgacactgc acagctcccg ttggaggcat atcctgacca    3960
tgcagacctg gggctctgcc tgtccaagtg cactcctta ctacataaac cctccttctc      4020
ttttggggct gtcaccccac cagagctggc accgagccct tgctgctgcg cttccctggg    4080
gtgtcagctt ttgacagggt gtttcctccc tctgcaggag ccttaacatc ccttggactt    4140 ccttccccc acccaccccc agcagttta tctcttccta actcgggacc cttttttcc        4200 cacacaaagt ttattgtcag ttgctggttt catctgtttg agcggctgca acaaaatacc    4260
atagactggg tggcatatgc acgacaaaaa tttatttctc acaggagaag tcaaagatta    4320
atgcaccagc agatctggtg tctgagggc caccttctgg tttgtagatg atgctttcta     4380
gttaaaacac ctatttaaca cactattaaa cactaagtgt gttaaatagt gcagttgatg    4440
tatttgtcat gtcacccttta tcatacacta aatccttctt tgtctttttt tctgtactct    4500
aatctctttc tgtaagtaat ctttgcttgc agcagtagga tatttagagt actgtggctt    4560
gacaatatat ttagtatttc aagatttcca tgaaattctt ctgatgtatg agttccctag    4620
ttaatcttac atatgtatcc ctttgtaaaa acactttgaa cattaaaat gatacatgaa     4680 tagtactcta atacaatgcc ataaaaatta taaatcattt gtatagactg gtaagtaaag    4740
attgtgagat taagaaacgc atcaaaggcc attgagctgg aaagtggtat aatgagaatt    4800
caaaccaggg tctcttgact caaaatctaa ggatcatacc atttctcatg ataatatgag    4860
tattattgtt atctctatcc catagacaaa gtgttaacac tgaatgagca gtgaaatagt    4920
ctcagaattt tttatttat ttagcaattc acttgtcatt tctggtcctc agtttattca     4980
cgagtaaaat aaaatagttg gactagataa tttctatagt acattcttac acaaaaaatc    5040
tatgattttg ttattttaaa tgtgatatac tcatggcact cattcacctc attttcccag    5100
cctgcctcac tggtcattac ttctctgtgt tctttacagg ctccccctcc tctacactgc    5160
cattaaatat tgaaacacct caaagcttta cttatgtcca cctctcctct gacactatca    5220
ttctgtctag atgatcccat acatacatgc ccattacttc aacctgtatt tatacgccaa    5280
tgattcacta tatttccagc ctagacattc ttttgtactc tagttaccag cttgatatcc    5340
ttacatggct gtttcaaaac aactcaaata tattatctct caaaatcaaa ctcatgatgt    5400
ccccacacca tcctagcttt ccaccaacaa tacctatccc tattaatagc ataccatttt    5460
attcagttat ccaaatcaaa aacctagaat tcatccttaa aattctacta tcattccaaa    5520
tatcctatcc atcagcagcc actgtattct taatcccctg tatttccttc aaatccattc    5580
acctctctcc atatccattg ctgcatgact atccaagcca tcgcctctac cctagggtac    5640
caaaatagca acaaacctaa tctgttcatt tgcattattt tttctccaaa actgattatc    5700
tatatgtagc aagacagatt gttctcaaat tgcaaatccc actatattat cctcttgctt    5760
caaacacttc catggtttcc cattgtttat gataaaacca aatgcttcaa gttcgaagac    5820
cggcatgatt gggaatttcc tgtcacccta gcctacttgc tctccatggt acagttgcac    5880
```

```
tggctttctt tcattcctta agtacaacct gtttcctccc acctcaggac tgtgcatgtg    5940
ccattcattc tgctgaggag ccttttcct tccacttcaa tcagctaagt ctgattcttc     6000
ctgacaatct cagctcaata agcatttcct ctaagaaatg tctctaatat cattaattgg    6060
ctcaggtccc tctactgtat tgctgcactt ttcacagtta taattttact taattatgaa    6120
tgattatttg attaggtcta tttccatcca ttagacataa gcttcatgat ggccagatta    6180
ctgttttcta tccatcgttg tattccaata cctgacagaa ggagggcggg aggtggtggc    6240
acacaagaga tgctcaaaaa caattgttga ataagtaaat gaatgaggcc atttagaaat    6300
aacgaaagta cctgtttaca aagtacatgt atcaaaacta tgaatgcatt ctacttacat    6360
ggttttctcc aaataaaaca aaagacttca atcaggatta atacctggga taaactgagt    6420
cattaaatct ctcctttgcc atcaggagtg acattgaaac aaatgtctgc aaacaacaaa    6480
tacttttttc ccaaaatata ttgaatggca tttccataaa caaactagaa catgggagga    6540
gaaagaaagc aatattaatt taaaattaat cttatcacat aacttatacc atcagggatt    6600
tcgggtaaaa ttcctttcag gcacatccat ttaacaagaa ttgattgtta ctgaaagcct    6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
aaaatactca aaggtcattt tacatgtatt ttttctctaa attactttc ttaagacaca     6900 gaaaacaaaa aaagaaactt agctttgtta ctttctaaca aatagttaaa tcattaaaca    6960
ggattgacac tagcatcctt gtttggtctt atgccttagg ggaacatgaa atgtgtgaag    7020
acattctgag atctgaggga agggtagaca gtaatacagt gggactgacc aggcttcagc    7080
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaaccccatc    7560
tctacaaaaa tacaaaaatt agccagggat gatggtggat gcttgtagtc ccagctactc    7620
aagaggcaga ggcaggagaa tcacttgaac ctgggaggca gaggttgcag tgagccaaga    7680
tcacccattg cactccagcc tgggcaacag agtgagactc tgtctcaaaa aaaaaaaat    7740 cacttttag ataaaattca tgctatagag agaagactat gaaaatatgt ttagcaatgt    7800
gtccatcatt aggtgattga gttccttttt gttttgtttt actgaaaatc atataaagta    7860
tgttatctgt aaaagttctc tgacatgcac acataaaaat ttgggagaaa agattaacta    7920
taatgtttaa tagattttgt acacatttct ttaaaaatat ataaaacaca acacctttca    7980
attggtttgc aagaataacc aattgacatc atggaaaatg gaaattcact tgctgaattt    8040
taacaaaaat ttgcatgatg agtgagactg acaacttagt gtcatgattt aatgaattat    8100
gccaatggta aacttcatgc acatggggcc aggtaattat gtggaaactt tttcaatgct    8160
taaagccaag tattgaaatt aaacttagaa tcagaccttt gaaccatttt atgacaatgt    8220
```

-continued

```
tcaaaaatta taaattctat ccacttatat tataatatta aaaatatcat tacaaaaaaa      8280
acctgtgttt attttataac tcagcctttt taatttctaa tttcataaat atattataat      8340
ggatattgtt agtaatgtag tattattaca tgtatataat ttataagtaa atatacatgt      8400
tttggctact catgcataaa atgtttcacc cataggagca cataatcaga aatgtctgga      8460
gaccattata gtaatagata gatcatattg ccacatattt tatctcctcc ttgacaactg      8520
agctttccag atcttctggt gaaacgaaag agaaagttgt aacagaagag tgattaaaat      8580
gacaaaagca ttacttctat tacttctatt ctaataatat gagcaaagct ataactatca      8640
agtaataatg cactaaagaa ggtgattaat ctgatatatt cacaggcaac taataagacc      8700
tttctattgc agccatgaaa aatatgtgac aattatagat atcctgtgtg cagtgtttca      8760
acctttatgt gacctgttct actaacagat ttagtgatgt tcactttgtt agaattttct      8820
tacacatgcc ataacttgct tcagtctttt gattatgaat attatggata ttaaggattc      8880
tagactattc tagattttaaa aaataatatt gtcacctcaa tcagaaggga aatattaaat     8940
agttctcatt ttttcaatgt ttactcagtt tttgtccaat gtaatgaaag tgtcagcagt      9000
acaggttaca aaataaaatg tgtattaaag taaactcatt tgaacaggtt aataattgta      9060
gagggaggga aaaggctaaa agattgaatg taaaacttat gaaaagtaga tacatcgtct      9120
ctatgatttg cagtagtcaa ctgcatacag atgaatcatt ttaatacacg ttaactactt      9180
tcctttaca gatggagaaa ctgagaggaa gaaagtttat atggttcatt aaactttgtg       9240
atgcaagcta aactaacctg tctctgtatt ttccatctac tgcccttatc actatctcat      9300
tagaatactc ttcaagcatc tccttactga ttttcttacc aagcatttgt taagttctaa      9360
tgagagttgg tagtaacatt ttcacccact ctgtgaaata tgaaatctta ttcataggcc      9420
tcttctttta ttcttgtatt tgcatatcaa ccaattaatc aacttgcttt ctttatgttg      9480
cttattatct tagtccttac taaattgcct cttaatgttg tccacataac agaaatgtta     9540
aggtggatac ttaacatttt agtccagtct agccggtgcc agtgcaatgc caaatcatga     9600
attaaaatat aattacaaga accacttatc aaattttaac aattccttca gctttgtgac     9660
agttttttct acttcgatta aagtcaagta aaattaaagt taaatatttt tattaaaata    9720
tctcctttaa cattccatat taataaacat attaaagctc atgcttctaa gtagattact     9780
agaagttact ttatcgaatt acagcaatgg ttaattctag atcatagaat ttagaatgac    9840
ttttttgcctt cttctttttt ttcctttttt ttaaacagag tcttgctctg ttgtccaggc   9900
tggagtgtac tggcgcgatc ttgactcact gcgacctctg ccctgcaggt tcaagtgatt   9960
ctcctgcccc agcctcttaa gtagttggga ttacaggtgc ctgccaccac acctggctaa  10020
tttttttttt gtattttttag gagagacagg gtttcaccat gttggccaga ctggtctcga  10080
actcctgacc tcaagtgatc cacttgcctc agcctcccaa agtgctggga ttacaggtgt  10140
gagccactgt gcctggcctg acttttttgct ttcttcttaa tacttactag tatttcttga  10200
attttttaaaa aagaaacata aagtactttg ataaaaccaa cagtctcatt gttcttaaaa  10260
ttgttcaaag gttctctgga aaaaaaaaag aaaattatca tttggttaag aatcatgttg   10320
gtctgacatc aatcatccta taggagtgaa tattgaaaaa gtaagatata ttgtggtata    10380
atcgagattg cataaatttt accatttttg agaagaatct gctccaaatc ctggcttaat    10440
gtaatatcca gcatgctact taattttctt gtcttcacct tttcatatcc acatccacct    10500
aggtgccacc tcacagtata agccagcata atccattctt ctcaatgaaa ccacaataca   10560
tctgacccctg catctcagga gaactgtatc agccacagca cttccagttg actatgaatc  10620
```

```
tgaatgttat gcctcaggag aaacatcctt gctgggactg agtagtgatt caaggagata  10680
gttatgattc agtcaagaaa ttaataatta gtgttatttt tattattgag acagagtctc  10740
gttctgtagc ccaggctgga gtacagtggc atgatctcgg ctcactgcaa cctctacctc  10800
cccggttcaa gtgattctcc tgcctcagcc tcccaaataa ctgggacagc aggcacttgc  10860
caccacgcct agctaatttt ttgtattttt agtagagacg gagtttcacc gtgttagcca  10920
ggatggtctc gatctcctga cctcaaggtc cacctgcctc agcctcccaa agtgctggga  10980
ttacaggcgt gagccactgc gcccggccat aaattattaa ctgagccagg cacagtggta  11040
cacacttata gtcccagata ctcaggagac tgaggttgga gtatcctttt ttatgttatt  11100
ttatttttaa ttattatggg tacataatag gtgtacatac ccatggagta caagtcatgt  11160
tctgatacag acataatg tttaataatc acatcagggt aattgggata tccatccact  11220
caagcattta tctttctttg tgttaggaac attccacctc cactcttgga ataggcaccc  11280
tgttgtgcta ttaaatacga ggtcttattc atttcatcta actatatttt tctacccatt  11340
aaccatcacc tcttttcccc tcttccccac tacctttcct gtgaggctgc aggattctta  11400
agcacaacag ttagaggcca gcctggacaa catagtgaga ctcaatttct aaaaaataaa  11460
aaagaaatta ccaactaatg ctaaaaaaat agtctctgat gcttaggtat gaattagaaa  11520
tgaccaaaaa aaaaaaaaaa aaaaagactg ccctttgctt ccttctcccc ttctcttcaa  11580
gttttccatt gctactcatt ttagtctggt ttaatcaggt ttcatccatt aaaagcaatt  11640
gttgggatca cacattttga gttgtgtcag tggacttccc tcatgctggc atgattcctg  11700
ccccaagccc ttagtaaaag ccaccaagcc atataacata atctctcatt gagtaaaaca  11760
tctgatgtgt ttagaatgac ttctagcaaa aaaccagcct gtccagcatc atctctgtat  11820
aacagataaa ggaataggta ctgcatcaaa aggttataga acctgcccaa atcaatccca  11880
tgtgttttgc aatggaatta ggttgaacta aagtgaaaat tcagttttct actcctcatt  11940
aacatgtctc atgttgcaag gttgagagga aggagaagaa gaactgtatt tacagagaga  12000 ttcccctct ctttctttct acagattact aaaacattca aagaatcaaa tttaagaaat  12060
cagttcatca gagctcatgt tgccaaactg aggtgagtgg aactgtagaa aaaatattta  12120
agtatagata caatgtggca tacttgactt tttgtcacag aatgaatagt aaatgacatg  12180
ttcagataag ttgttgtaat attatgaaaa tagtatttta gtcagcttaa aaaccaatgc  12240
caaaaaagcc aaacatatga tctatttagc tactaatgta aataaccata ttatatctat  12300
tcttattggg aagaggaaga aggggtggag agagagttgg ggtgaaggta cagtaacaag  12360
gccatcctat tgtaaaactc cagtggatat cattcacagt gcagcctatg taaacagtcc  12420
ctcctggagt tgtacaatgc tgtggtttgg gtgtatccat ccaagatcaa gacactatga  12480
ccaacatcaa aagtggcttt ttggttttat ctgcctgatg tgctataata aaagggtatt  12540
atggccaaat ccaaggcatg tctatcatga attaataata ggaggagtag cagcatgcat  12600
gctagttatt tgccattcct gccttagtta aatatgatgt gataaaacca gcctttccaa  12660
ctgaaatagt caccttact gactctcccg caaatgtctc aaatgaccac attgctctag  12720
tctttaaata atatgcaata gttctttggt agaagaggaa ttatactaat tctttctcaa  12780
atactagcat cacaagaaaa ttaattcttg ttctctggag agtcacctag taagtatctg  12840
gagcacagat gtctggtcag gtaagttttg atgaggagtt aaagggataa gaagagtcca  12900
tgagaagggt attttccaaa acacctttcg gtcaattcag tgcacattca cttagtactt  12960
```

```
tcttgtcagt atctgtatca gccactaatg ttcaaaagtg agtaagccct gaaaacctgt   13020
aggactacat gagccttctg cctttctct cctttgttc acttcccact tatcactcaa    13080
tcctctgcaa cctggcttca ataccaccat aaaatatcaa ctgctcttgc cgattcaaca   13140
atgacatcca gataacaaaa tccaaagaaa ccacatcagt cctattcttg gccttttcaa   13200
cagtatttgg tcctgttggc ctgtcactcc ttgaaatagg actatcccttt ggtttgcatg   13260 gccttgtata ccctgatttt ccccttacct ccctagctat tccttcttag tttcctttac   13320
taggtcttac ttctttgtat attccttaaa tgttgctgaa catcaggctg tgctctaggc   13380
ctctcatctt ctcaggtcac actctctcct ttccttggcc ttcactgcca cccatatgct   13440
gagtgctctc aaagttgtat ctctaggcca gtcctctttt gcctccaaac atgaatatat   13500
gcagccatct acttggtacc atcacatgga taattctcat gatctcttcc agtatgactg   13560
cttctttatt tttttctggg ctctttttta gcattgcttt acatggaact ttatcatgtc   13620
tctcaacctc tattttatct tttatctatg tatgtagagt ctgtgtaatt tcttcatctc   13680
ttttagataa ctaatatctc ttcagcttg acttgtattc tgtgtaaccc atttattgcg    13740
ttttcaattt caatgagtat gttttcctat ctgcaagttc tatttgtttc ttttgagaat   13800
cttcctggtc ttttaaacac atttcttatt ttaattttg ggggtaccta gtagttgtat    13860 gtattttgg agtacatgag atgttttgat acaagcaaac aatgcataat aatcacattg    13920
tgtaaaatgg ggtatccatc ccctcaagca tttatccttt gtgttacaaa caatccaatt   13980 atattcttt agttattttt aaatgtacaa ttaaattatt attgaccata gtgactctgt    14040
tgtgctatca gatactaggt gatcttttaa aaataatgtt ttctacttaa tctcatttt    14100 atgattccct cttttacgtc atttgtcatt tcaaatacag tcacttgtct gttgattcta   14160
ttatgtgaag tttttgagga taatcttttt gttactttga ttccaccttg gtatggtttg   14220
gctgtgcccc cactaaaatc tcatcttgaa ctctggttcc cataatacccc acatgttgtg   14280 ggagggacct tgtgggaggt gattagatta tagggacgtt tccccccttt gctctgttct   14340
ttttcctgcc accatgtaag aaagatgtgt ttgcttcccc ttctgccatg attgtaaatt   14400
tcctgaggcc tccgcagcca tgcaggacct ctttcttg taaattaccc agtctccggc    14460
ggttctttat agctccgtga gaaaaaacta atacacacct catgatgtat tgtttaccac   14520
tgaaattgta tgcttaaatt taatctcact tgggaccctg tacaacctag acttaacata   14580
tctacctcca gagcagttac atctgtcaga cattctagag gaatcagcag cacatggact   14640
ttgttgttgt taatttgttg tcggggggagg ggggagggat agcattagga gatacaccta   14700
atgctaaatg acgagttaat gggtgcagca caccaacatg gcacatgtat acatatgtaa   14760
caaacctgca cgttgtgcac atatacccta aaacttaaag tataataata ataaaattaa   14820
aaaaaaaaag gttctgggag tattcaggta gtattaatga agattcagac atcgtgcagc   14880
caggcccatg cttatgaatt ttcaggtgat acttcttttt cttttttcttt aatttaaagc   14940 tggatctcgg aaacagataa atttattttt ttatgacatg acgagcattt ttttcattct   15000
agttcatgct gttattgggt gtttagttct ttgagactcc tggcctttt ctaaaacctc    15060 aagttcaact tccatttttg cactggccca aggtcccatc tccagtctct atgtaaatgc   15120
taaacataag cctgtggaat attctagtct caccacatac tattcacatt cttctttgtt   15180
tttggtcttc caggattttc cttactttc tatgaaccca gtcttgcatt tgaaatggaa    15240
tttattatat attatctatc ctttctattt gttttatgca gaaagtgttt tctaaaatta   15300
tttaggcttc catattgcta gacatggaag ttgtaattat ttgttcagtg cctgttctta   15360
```

```
catctaaact gcaagaccca tatggcaact gtgaatctta gtcccagcta atttctgaag    15420
cttagaatag tgcctagcac aagaagttgt ttatctaaca ttttaaaaa taaatattaa     15480 attcatatct ggaatgaata ttaagttaga gctggtcatt gaggtgagag gaggaagcca    15540
agagagaata tgagagcctc aaagccaaat atctttaatg tacttttca gaaaagaaga     15600 cagccaatgt caggtggagg aactggttta tgaggtaact ttcctggaag aaaatagaaa    15660
ttactgaggt tttagataat ccaaatattt aatcaagtca ccaaggttta ttgtggggaa    15720
tctttattat taattaaaat gagtgatgaa atcttaatat acgacaaaag ttaaaatttg    15780
cttttgcagg cagatgaatg gtctaggtat caaaaaatta agttgagtct ctaactcaca    15840
caaatttaca accctatcac tttatgaatt tgtttaggag attatttta ataacactgg     15900 tgaagtctaa gaatagctaa aatttatagt acacttattg tgtgctattg actcttcttt    15960
gaagttttgc atatagtgat tcatctaatc ttcataaccc attttacatg tgaagaaact    16020
tagatataga aagattaaga aacttacata acttatccaa agttacacag taaaactctg    16080
gcattataac ttcaaaatca gctatcctac agtgagtaca gtgttctgtg cattgaaatc    16140
aaataagtga gatagcatcg tgatatagta ttacgtatgc aaacactgtt acagagatct    16200
gtctaaagtt aaattccaca aatgaattct ttaaagggt ttaatcaaga agaatatata     16260
aacaggatgg tgaaaaattg tcatattatt tgtttttaa aatatcttta tgatttacag     16320
gcaagatggt agtggtgtga gagcggatgt tgtcatgaaa tttcaattca ctagaaataa    16380
caatggagca tcaatgaaaa gcagaattga gtctgtttta cgacaaatgc tgaataactc    16440
tggaaacctg gaaataaacc cttcaactga gataacatgt aagtataatt tttcataaac    16500
aattttattt caatatatcc ctcaagttta ccaattcaaa ttcatatttt aattgagagg    16560 ctgactttc tttctttgaa actaaactgt gaaaacaatc cattaaaaag ctaaatatac     16620
catatagctc cctaacgtaa atcattctaa gacttaaaga atcatttggc atttatatag    16680
taaattttat ttgctaaaaa ttctcattaa ttatccctgc aacattcctt atgagtgatg    16740
ttactgtcag atgtcattag tggataggcc ataggagggg tacatagatg ctcaaggtca    16800
gagaactatt taattaatga tccacctcag aggcttcttc atttttcttt gtaacattta    16860
tcacaattga aattacaaag ttatctgtgt aaattttgta ttgtttggct tcatcctaca    16920
ctgtaatcat cctaaaagaa agaaccagtc aaccttcttc atcctactac cctcctacca    16980
cccagtctcc atcatataac acatattcaa taaataattc ttgcatgact gaaagaaaag    17040
aaataatata tgcatagaat ttaaggacat tcctccaagt tggttacatt ctgctagttt    17100
aataagccat tatttcttct cgatgagctc aagattaaaa ggattttgat gattcccata    17160
ctagactggt aggtaccagt tacagatgta ctaactgtta aatattgaaa tgctttccta    17220
tttgttggta aacaattact gcatcaggcc cacaaagttg tcttccgaga tgtttcaaat    17280
ccactgcccc tgctgctaaa gagttatgct tagcaaagca aagcactcta agacactgct    17340
ccaactccat ggcctgattg catctttat gactggccaa tgctcacgca ctgcagtttg     17400
ttaggtagtt gaatattacc tctgcttcca cacattaagg aatgctcccg aacgcacttc    17460
ccaagtgttt atttatttat cattatacta gacaatatgt tgatacgatg gtcacagaat    17520
agcggtttcc acctccagag cccataatct agttgaaggg aaagatattc caacacaaga    17580
gtgttgacaa tcaagataga atatgatcaa gggcccagtg tgaggccag gcaatgatca     17640 ctgcaggaat ctggggaaga aagagaccag cgtgcttggg atatctagca aaagtttcat    17700
```

```
gaaggagaat ggactttgac tttgaaatat gggtaggatt tacatatttt gagatgagaa    17760
aaagaaagtt cccagagaag gaaagcatga aaaggcaaac agtctgtact gaacgcgatg    17820
ctttgacaga ataatgaaga aagggacctg ctggaatgat tgatcagtgt tcatcattca    17880
caccatcatc atcaaaacac ttatttaatg agaacttact gttttttagg catggcttta    17940
atgccctata tgaattttt tcttgattaa tccttacaac aaacatatcc catagatagt    18000
tttattgtcc cccttagaaa agataaattg cctaggctga cacagtcagt atatgaggca    18060
gtcaggattc aaactaagtc tgtttgttca aaaaattaag aatggccagc ttttaaaat     18120 tttctgtctc cagaagtatg atttggctcc actgaagttt gcaaacaaa tgtgataccc     18180 aaaccttgtg aaacttttag tgggaaataa ctttgcataa gtcggtttga gagagcgtgg    18240
aaacctgtct tgaaaagttt taatttaact tgcaggaaat aaaaatgatg ggtttctcaa    18300
ttaaaatttt caatcaagga aggatatgag ctaacataac attttttaa aaagatcagt     18360 ctggtaaggt agaggtgcat aaactgaaaa ggagcaaaag tggtggaatt cagttagaaa    18420
attattgtaa ctgtactgat gtcaaatgat gaaaccatga actaaagtag taccaaaagg    18480
agtgaggagg atggaataat tcaaaagata gaggacagat gtgcagaacc tggagattat    18540
aagatgtgaa aggaggagtt tgagaaaatt tcagattttg gaagtggtgt cattttacta    18600
aaaggatata ataagtagca aattttggat aaagttgggt cccactgagt ttgagatggc    18660
tgttggacat gcagagaaaa ctgtcttgta tgctgttctt aaattgaaat agacagacct    18720
ttaccctctg atactgacat attttccttt ccaggctcac cctccatttc cctaaacaca    18780
acacatgcac tagctctcct tactttattg ctccacaaac atcttacacc tccaagcatt    18840
tgtgcccact gtaccttcta tctggaatct cttttgtcct cttgtgtgcc tgaaaaattc    18900
ctttcagatc ttcaaaatac agtgcagatg ctatttcttc tagctcaaat attatctcct    18960
ccatataatt taattactct ctttttttctt ttctctactt tgcacttaca tttatttgaa    19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaaagagata tctattaagt    19260
atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcattttt aatactagca cttactgacc aggctgcagc aaattggctt    19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg tttccccttt cctttttagaa aaaggaagaa gttgtagtgg aggactaccc    19800
actctgcact caaaattgcc ctcatgaaaa tttctttggc agctttgaga accttttact    19860
gccctggttc taaggtggca tttctgtaga cttacaaatt atgtttgatg acaccgttta    19920
tgtagcttct cctaaccacc agagtagctt gctttgttgt gaattcaggt taatcacaaa    19980
gtataataaa aaagaattgt cagaagtctt cccagctttg ggtctataac ctgaaggaaa    20040
agtcactact cttcaacatc atcctatgta ctctcaggct aggatagcag aaatgcaatc    20100
```

```
cctagaaaac agcaacttac ttctctgacc aaaaaaatgc agttaaaaat tagttcaatg    20160
tacctggtag ctggcctatc ttaggtactt cagtgatttt acaaagtgat ggtagtccta    20220
tgggtgtttt tcagcttcac tacgtattta attcatgctt attgttaatg aaactgtgat    20280
aagcaattta ctagggtatt tgtttgggag atgccacaaa ggaacacatg tatctcttaa    20340
tggaagcctg gtcctccttt atccaggaaa tttgctagga aaaaaagcc tttaggtggt     20400 tgtgctatta aaccagggca ctacttaaaa gccagcccag caatagttgt gtgatttacc    20460
attaatttct tagtaataga ccacacaaaa gaagaaaatt atgggaatgc gagttgagag    20520
gaattgggtg atcagcctac cccagcccgt ttcagctctg gccagtagac tattcacgag    20580
ctctttgaaa acatttaaat aaaccttatt tagatactag aaaccctctg tcaccctcaa    20640
gaatattctg tggtatagcg actcctttat gagggcatgt ttggtaatac agcatcagtc    20700
ttggaggtgg actggattct acaaggtgaa ctgcagtcac taaggagtct tttggatgag    20760
accagttttc ctccaacttc aatgtgtgca tgaacctcac atcaaaatgt agctttagat    20820
ttgtcccatg atgtggttcc aagaatcagc acttctaata agtttccagg ggatgcccat    20880
gctgcaggcc cacaaaccac actgagcata gcaagactat tgagaaaaag gaaatttccc    20940
aggagtctgt ggcctgagct ggcacatcca ataatgacct atcttaacct caactcatga    21000
ggaattccag ggaactctga agctgctcaa aatttgaagc ctatatgcca actaaattca    21060
gaaatgttct ccaaaatgct atctataagc aacagtagtc acaaatgcat gtagaaaata    21120
tatcgatcat gcttttttgga aaatccagca tgtcctgagg aagaatgtat aagacataaa    21180
agtcataaat tatggaaaga ctcttcagct tcttccaaat gtaaaggaat catgatcttc    21240
ccagcacatt aatgcccttt ctcattagaa tgtggggccg gtccagacct aataacattg    21300
tctgagcaga gaatccttgg aggcactgag gctgaggagg aagctggcc gtggcaagtc     21360 agtctgcggc tcaataatgc ccaccactgt ggaggcagcc tgatcaataa catgtggatc    21420
ctgacagcag ctcactgctt cagaaggtga ggccaccact acctacccat ctgggaacaa    21480
ttagaataga caggtcatga agactgcacc ctctacccta ggattgaatt gagccagaaa    21540
taattcaatg caaaaaaatc agtaagaatt ttcttcctat tcatgaaagg aaaaggattt    21600 ttcccctta gcatgctaat ttagtgctat ttctctgttt caggtaataa tatattagca     21660
cagtaaagaa caaagattta tatgtcagaa tgttttttaa atcctagcta taaaagctta    21720
agaaatttac taaatctcca taagctttat ttttttttcca aattaaggga caacactgtt    21780
atctgtgact tagtgttact ggtagcattg agtacactaa tgtaaacata cgttaaatgt    21840
tagcgaaacg aattgctgtg gaagatttgc acattatatc atgggagctg atggctaacc    21900
tagagactgc cccatgccat taatttattc attcataaag attattgagt atctagtatg    21960
agcacagtgt tatatattgt agaagctact agtataaaca aagtattgcc tctgccttca    22020
aagagcttac actcgaatgt tggaatcaga atgcacaaaa ataatgatca attacaatga    22080
gtagcataaa taaaattaat gtaggcaact tacaagaatt cttaattgag gtgactaaac    22140
tattgccaac actagggtga tatgctacca gtggcgagta ggttgcataa acttaccta    22200 ttggtaaaaa gaaaagttca cattgctcat aaaagaagga ttttagattt cagcataact    22260
aaaatctgtt tcaaacctgc cttgttactg gggcatcgca gaccacaaca gttgttggga    22320
acttaactca aaaagttcac ccagaaaaat aatggagatt tgaactcgtg tgcccctgac    22380
catatcaatt ttcttctcag actcttactc taaactggac ctccttatca cacacacaaa    22440
```

```
gccttccata ggcagatcaa tccagtctta tttctcaaag catgtacctt gagcttcaga    22500
taaacagcat tgttctcttc ccctggactc ttcctacatt tccctaccta tgagtatctg    22560
atcaatctgc ttatccttga aatgttaata tatttaccac atctctattt gaattttatg    22620
aaatttttga taatttctaa gtagtttttt cagatttata ggcactactt catggtacag    22680
tgactgttac aaacgtattt gttaaattta aaggaataa agatttaaaa gactagggta     22740
gttactgaac taaagttta ggaaatccca aattatttca aattttctt atggtaattt      22800 tatgacttaa tattttata tgcagtgaac aaatttgaaa ctttaaaaga tactcccaga    22860
attatcagtt ttctgatgta gattggcaaa tttattacta tatcccaaat aacccaagag    22920
acaaaattca caaaaacatt tcaattttca ttgccacttg aaaggccaaa aagcagaaat    22980
ggcacgcatt gatttcaatc gtactcttga gtgtgggaac caggaattaa aatacctgga    23040
cttatcaggc acttagcata accaagaacg gaatagaaac ctccctggat tctaagccct    23100
attcagtccc aatcaccaaa aaccaagtaa acgatatcac tataatgaaa gccacagtta    23160
taaatatcga caacgattac caaaggaatc catggaactt tgaattttgc caccccacat    23220
ccttctattc attaccatga ttgatccact aaagctaaca gactctgtga accttgtatt    23280 ggaccctcc ctaaagacct gattgtcact gagaaccatc agtgaggatt tgtttggggc     23340
atgaccagcc ttacatcaaa gtacatagaa gtgatgaggt cttatcaaag aggattattg    23400
aattatcacc tcttctatgt agctttccct gatactctct ttcctctcca ttgagttcca    23460
cagaaatttt tttatctgcc tttaacagtt gtcctcatga tttgtgatat ttgacttacc    23520
tcttgtcagt ttccttcact agtgtagagt tcctcaaaga aagagaccat aattacttat    23580 attttattc ctggagactc atactattcc ttatacaaag tagacactta acaatggctt     23640
gttgaactat aattaatgaa ataatagct accttcatga aagttcactt tgtgccaaac     23700
actatagttg acataataca tttgtctcat taatacttaa caattgtgtg agaaggtatc    23760
accaatcaca tttatatgt aaataaaccc cagagctatt aattaacttg tcataaataa     23820 cactttcat atgtggcata gccaagattt aaatataaat gttactggtt ccaaaatgat     23880
gctctaattc acttgctgga aagaaggaaa ggaagaaaat aaacgagtgg aaggaagaga    23940
gggagggaag agagaaaagg aaggaaagaa aaaagagtct cttcagaacc ttcactgtaa    24000
agactccgag caaagaagt tgaatataaa acaacatag gtttgtttgt tttctaatat      24060 ttttcttca aaatttttaa ctcaggttca ctcttacaca aactactgtg tcttataaaa     24120
gtatttccgg tcatagaatt tttattttct gtattaactc cactatctaa tctccataaa    24180
actcctaaat tggtattatc ggtaacattt tgttttact caaccccttag gaacaatgtt    24240 aagttaatca gccctccaca tcacagatcc ttattttcat cagtctgtac aaggcatttc    24300
tctcatttta attttttttc ctcctgtcat ccctggattt cactttcact gccctccttc    24360
cacccatatg cctcatacta atatattcga aatatacatg tcttaaaggt acatgcacgc    24420
acctacaaaa cctatagtgt ttttttgtat gtatatgtct ttaatttaaa taagtagcat    24480
tgtgtaaaag tctaatattg tttcttactg ttttcactca attcttggaa ttttcatctg    24540
atgcactgct gcatagcacc ccatggtatg cagccaccat atttccttca tccaattagg    24600
ttgcatgacc taccttccca ttgccacaaa gagtacacac aaaatatttg tacttatctt    24660
tctgtaaacc ttcaggaatt tcagaagcac acatgcaggc tgctaaatat accagaatac    24720
tttccagcca cttaaatctt taccagtatt gcaaagagg ccccatttcc ctccacatca     24780
acatttagta ttattcttt gtttaagttt tatcaatctt ttaaatgtac acaagatgct     24840
```

```
catttttata attttaattt ctcagattac tagtttgagt atcttttcat atatctaaga    24900
gctgttttga tctcccctac catgaactgc cactaatatt ctttgcctat tttacaatgg    24960
tttttctgct tatttattac tggtttacag acttttaaaa tatattctac aaaaatttta    25020
gacattaaac attaccaata ttttcccatg gttcctcatc catctggtaa acttgtctat    25080
ggtatatcta atttgattt aatagaattc attctatttt taccttttag tttgtgtttt    25140
tgttgtttag ccaaaaagtc cccattccta ggtcataaag gtaatgtcct ttttttttt    25200
ttaacgctac tgttctctct ctgtctcccc ctatgtatat aggtgcacat atacttgtac    25260
acacatacat atacctatat atgagggggag ttcgataagt ttatggaaaa taaaattaaa    25320
agataaaata aaaaattata aactttattt ctcaacataa gctccttcaa gttcaagaca    25380
cttttgtaag caataatacc agccatatcg tccatcccta aagaactgag ggtcctgaga    25440
atttaactat gtcaatgcag tcttttttac attactttt tacagtactt attgatgaaa     25500
aatgggtgcc ttttaaagat tgttttaaga ttagggaaca aaaataagtc agaggaagtc    25560
aaatcaggac tgaaaggtgg atgcctagtg atttattgct gaaactttca taaaactaac    25620
cttatttgat gagaggaatg agcatgagca tggttgtgat ggagaagaac tctggtggag    25680
ctttcctgga cacttttttct actaaagctt tggctaactt tcttactctc ataagaagaa    25740
gatgttattt ttcactgacc ctttagaagg tcaacaagca aaatgccttc agcatcccaa    25800
atgtctgttg tcatgacttt tgttcttgac tagtctggtt ttgctttgac tggaccactt    25860
ctacctcttt atagccattg ctttgatggt gctttgtctt caagattgta ttagtaaagc    25920
catatttcat cttctgttac aattcttcaa agaaatactt cagaatcttg atctgacatg    25980
tttaaaattt ctattggaag ctctgacctt gggtgcagct gatctgggcg aaacagtttt    26040
ggcatccatc aagtagaaag tttgctcaac tttagttttt cagtcagaat tgtataagct    26100
gaaccagttg agatgtctat ggtgttgtct attgtttctc acagttaatt gttggtcctc    26160
tttgagacat gaacaagatg aaattttttcc tagcaaactg atgtggatga tctgttgctg    26220
cgggcttcac cctcaacaac atctctttct ttcttgaaac aaattatcca ttagtaaact    26280
gatgattggg ggagatgctg tccccataaa ctttttgtaa ggcataaata atttcaccat    26340
tcttccagtt tcaccataaa tttgacgttt ttttgcttca attttagcag cattcatgtt    26400
gctttgataa gagctctttt caaattcatg tcttattcct cttagtgcct caaactagat    26460
cttgttcagt atgacaagtt agtatgagtt tatctgcatg caaaaatctt tgaaatccat    26520
gcatagtttg tttataatat acattttcaa tgaacttttg aagaccccat acatacatat    26580
gtatatatat gcacacacac acacacacac acaccaaaat cttcaaccat tatcagactt    26640
agtgcagaaa aattattcat ccattaacaa gataagaatg cccctttatca tcactactat    26700
ttaaatggag ctcctggcta aaggaaaaga cagggattga aaaaaattag ttaaatctaa    26760
aatgtttatt atttcaggtt tcttagttgc ttaaatggga agggaggtat ggacaaaaga    26820
gaaatcaaag atatttgtgt tatgctactt atcattaaag tatcagaata acttcattgg    26880
aatagaaaaa caccaagatc accccacgat atgttttcta aaatcttctc catttctta    26940
gacaagtgac catgtattcg gccagtgaag aattaaactc acttgccagc ttataatgca    27000
ggaaaatata gcaaagagat gtggatccaa tagtttctag atagtggtac aggatggcta    27060
agatgaattt atatatctga aatgttcaca aattccctac tcatatagca tgttttcata    27120
atgttttagc aactctaatc ctcgtgactg gattgccacg tctggtattt ccacaacatt    27180
```

```
tcctaaacta agaatgagag taagaaatat tttaattcat aacaattata aatctgcaac    27240
tcatgaaaat gacattgcac ttgtgagact tgagaacagt gtcacccttta ccaaagatat   27300
ccatagtgtg tgtctcccag ctgctaccca gaatattcca cctggctcta ctgcttatgt    27360
aacaggatgg ggcgctcaag aatatgctgg taagtgtctc ggaaaaaaaa attaacaata    27420
gaaatgtctt atatttgcta ttaggtaatt ttttaaatta ggaaacatct ggaataggtg    27480
tttctattct tctacagaca gaaccattct atattctgct cagcccaagc tctggctacc    27540
cctgagtctc cttagcaaag caaagcaatg ctccagaaac tatgggaatt ctcaaatata    27600
gtaataggaa aatgtaaaag aaagttatga agacacgagt tctttaataa tccagagatt    27660
ctataagatt caaatagctt ccctataaac aataaaaaag attttgtttg tttgtttgtt    27720
tgcttgtttt ttagagacaa agactttctc agactggagt gcagtggtgc aatcatggct    27780
tactgcagcc tcaaactctg gtcttaagaa atcctcttgc ttcagcctcc caagtagcta    27840
gaattataaa taagtgtgta ccaccatacc cagcttttt tttttttttc tacagacagg     27900
ttcttgctct gttgcccagg ctggtctgga attcctgccc tcaagccatc ctcctgcctt    27960
gttggcctcc caaagcaatg ggaggattta gattagacat tgtatgaggg cttaataatc    28020
cttaaggtat taactgccct ttaaagtatt ctgggatatg gcaaaactc gatgtgtata     28080
taaacattgg tcatatttgt ttattgaatg aataaaatgg aaactaaaat gaggacaatg    28140
cacaagagct actagaacca gtaagagtat cagcgaagga gtggaagggt agcattgaca    28200
atttccctgg gcttttaccc atgttgtaga ttgtctctcc aaggaataat acaaagcctt    28260
aatagtccta gaacacattc tattgtgttc ttatggccca aagtaaattg gtgtagtaga    28320
taacatttgc accagtcatg aaaaactatt ggtgtcattc tgagagtaca tcaatataaa    28380
atagactagt tctttagcct tgaaactaga ctggtttctc ttttgctgct aggttaaagg    28440
ttattcaata tgtaatcttc caatccaaaa tctgtcagtg gataatttaa aagctttag     28500
tcaattttaa gatatttgtt ttcttaaaat tttaagggc actgtgtcac aaagctaaag     28560
aaaaaaaga aaaaaaaact gatctgtgaa agggggttatc ctcatctact tggggaattt   28620
tggctgcgaa gaaactccaa agtaaatctt tagaagcctt cattgttaaa tatgaaataa    28680
tgtttggagt acatttattt cttctcaaat ttattatagg gtcaataatg tacacatctt    28740
gaagtccatt tttttcctgc ttttataaca aacaggccac acagttccag agctaaggca    28800
aggacaggtc agaataataa gtaatgatgt atgtaatgca ccacatagtt ataatggagc    28860
catcttgtct ggaatgctgt gtgctggagt acctcaaggt ggagtggacg catgtcaggt    28920
aagctcaaga caatctcatc catgtcatca tccaagaagt gtataagcac ttcctagtat    28980
gtgataatgt gatagacata agtgtaacag ttacaataca cagccctgtt cctctaaaat    29040
ttataatcta gattttagaa ataaattttt ttatgaatga agtttatcta tcatgaaagc    29100
attaactctg agaggccaaa ttacagagta gttaaccatc caaagctcaa gaatcagaaa    29160
gacctcgatt tgaattcctt aacctctatt accagtctc taactaaaag ctgggggataa    29220
tcataatagc acctaacttt ttgggtacta agaaaagtta aatgaagact aaatatatca    29280
ggcacatggt aaacaacaaa gaaatctcat ctatttcact attattaatg tagaccatgg    29340
tcactcgtgt taataacttt aacctcaacc ttttaactgc tgtgaaggat taaataaaaa    29400
attaatcact atattataaa aattaattga tatataataa atgaattta agagatacgt     29460
aataattcat ggactccttg aagatagaaa atttatacaa aatcctagta atttgagtca    29520
caaaagctcc tacaataatg aaacagtatg aatgaaaaag aaaagaaata actattatat    29580
```

```
ttggatctag cccataattt ttaaccaaat gcacaaaaac aaacaacaaa tatgaaattc    29640
tcactgtaaa gtgattaaaa tcaaatttga attctaaaat tttaaattaa attatctaaa    29700
cataattgat gcagttatat gttttaatag gttttgttca catatctgaa atccaactcc    29760
acacagtagc aggaacagct ggtgtcagaa attaaatatt cttttagtct ggagttttaa    29820
aaaatcaatc tgtttacttg agtaatttgt tgctgttttc atgggtgaat tgtatacaga    29880
aggataagaa ttattcttcg catcaaaagg tcactgactt tcatatttag tgctcatggt    29940
ctttaaaaag tggataaaaa gtagttctca catttcatgg aaagccccca atccatgagc    30000
acatttccca aaatgaaaca tttttatcaa ctgcaagttg tgtgtaggtg gagatttgtt    30060
tttcaattgt caagatactg ttaattaccc agtcctttat ctccttttgg tggagatgtc    30120
tctgtgctag gaaacccttc ttgctctcct tcctgtttct cttttactac tggccctgaa    30180
acaacaaatt ctcaagtttc atgacagctt tccaaagaat ccatcaatca ataagcaac     30240 acaactcgac actgacaatt ccagacctac taagagcatt aattaagact taaaaataaa    30300
catgagtttt aaaagggtgt tattcattat tttcccattt ataacgtccc ttaccttctg    30360
tccttcagtg catacaaatt attatcttcc ttgaagccca gttcaagccg tacctcacca    30420
tgataccttc catgtatatt ccactctagg cctcactgat ttttaactga aatactataa    30480
tgcatagttc acacttaaaa aaaaaaaaaa aacacagcac tttacataag agcttacagg    30540
atcctatttg ttttatccat tcttttgttc atttttacaa tcattaattc aaaggaatta    30600
tattaattac tttctatgca cccgacgttg tgttaacaca acaatactat ccctgcattc    30660
agcaagtcta tggtctacaa gagaggacac aaattcaaat gtctgtagtc aagcagtgaa    30720
gctggctaga tatggaaaaa ttacaagtcc ctcttgcttt aacatttgct tgcccacatt    30780
tggtcagaca tcatgcaaaa taatttctca ctatagaaaa aaaacactaa caaaaacaat    30840
aatataaaga actgagaact ggttaactga agcatgcata tgtcatctaa aagaagcagg    30900
tgacgaccag cttcatgaag tacttgccat gcatattggc acttcacaca ctgacccttc    30960
tccccaccta gaccagtaat taaacaggta tggatgagct agctactaag agcagccaac    31020
tgaatagctg actaacttag aagcacactt ggtaataata gctgactttt attagtactg    31080
actatactat atgctaagct gtactcaaag tgctttgagt tttaaactga tacaaacatt    31140
atatgaggaa acagaggtac agagagctat tcaccagctt accaaaggtc acatagctgg    31200
taagtggagg acttaaaccc agactatcta gtttcagaac ccacagactt aatccatcgt    31260
gcagaacata agacatactc catctgtctc cccaactagg ttattatgtg cacaaatatt    31320
tattggttgg ttggttcatt attatgactg ggtggtaagt atgtcattag gagtgttttg    31380
cttatgacta tataaatttc ttcaccaaaa gaagactttc tgatgatata ctatgcatca    31440
gacaccacgc agggtgctaa ggttaggaag ataagtgaga cttctagaaa ctcattcatt    31500
caacaaatat ctcctaaggg ctagaagctt aggtttcagc agtgaacaga ataggtatgt    31560
tctctttcgt gttggacctt atagtatatc tgggaaaaca gacattgaat aaatatcaca    31620
aatgcaagtg agtgtttcag agacatgcag ctgctacatc aaaacaaaac agaacaaaac    31680
aaacaaacaa aaactgacca gtgggattaa gtgtaaatag gcacacaaat gcacaaatat    31740
gcttttataa aatagtgaag cagtgacaga gacacacaca agatataaag acacaatgaa    31800
gaacaattga gcccaaagct ggaaagggtg agagtgtgaa ggaaaaaggt tgatcagaga    31860
agttttcccg aaggagagaa agcctggatg attaggaggc aaccactcgg tgactgaggg    31920
```

```
aaatctgaaa aatgtatttg tcatcttctc agacttgctg aaggaatgac ttgggtactt   31980
tgaggatttc agtaattttt ccatgacttg gtataatatt tcaaaaggaa ataggctgac   32040
tttatttgta taatgaatgt gactccttcc tcgactgcca tagaaataaa ctccttaata   32100
ttttgggttt gtcttttgcac ttaagtaatc agtcattctg ttttttttaca gggtgactct   32160 ggtggcccac tagtacaaga agactcacgg cggctttggt ttattgtggg gatagtaagc   32220
tggggagatc agtgtggcct gccggataag ccaggagtgt atactcgagt gacagcctac   32280
cttgactgga ttaggcaaca aactgggatc tagtgcaaca agtgcatccc tgttgcaaag   32340
tctgtatgca ggtgtgcctg tcttaaattc caaagcttta catttcaact gaaaagaaa    32400 ctagaaatgt cctaatttaa catcttgtta cataaatatg gtttaacaaa cactgtttaa   32460 cctttctttta ttattaaagg ttttctatttt tctccagaga actatatgaa tgttgcatag  32520
tactgtggct gtgtaacaga agaaacacac taaactaatt acaaagttaa caatttcatt   32580
acagttgtgc taaatgcccg tagtgagaag aacaggaacc ttgagcatgt atagtagagg   32640
aacctgcaca ggtctgatgg gtcagagggg tcttctctgg gtttcactga ggatgagaag   32700
taagcaaact gtggaaacat gcaaaggaaa aagtgataga ataatattca agacaaaaag   32760
aacagtatga ggcaagagaa ataatatgta tttaaaattt ttggttactc aatatcttat   32820
acttagtatg agtcctaaaa ttaaaaatgt gaaactgttg tactatacgt ataacctaac   32880
cttaattatt ctgtaagaac atgcttccat aggaaatagt ggataatttt cagctattta   32940
aggcaaaagc taaaatagtt cactcctcaa ctgagaccca agaattata gatattttc    33000 atgatgaccc atgaaaaata tcactcatct acataaagga gagactatat ctattttata   33060
gagaagctaa gaaatatacc tacacaaact tgtcaggtgc tttacaacta catagtactt   33120
tttaacaaca aaataataat tttaagaatg aaaaatttaa tcatcgggaa gaacgtccca   33180
ctacagactt cctatcactg gcagttatat ttttgagcgt aaaagggtcg tcaaacgcta   33240
aatctaagta acgaattgaa agtttaaaga ggggaagag ttggtttgca aaggaaaagt    33300
ttaaatagct taatatcaat agaatgatcc tgaagacaga aaaaactttg tcactcttcc   33360
tctctcattt tctttctctc tctctcccct tctcatacac atgcctcccc caccaaagaa   33420
tataatgtaa attaaatcca ctaaaatgta atggcatgaa aatctctgta gtctgaatca   33480
ctaatattcc tgagttttta tgagctccta gtacagctaa agtttgccta tgcatgatca   33540
tctatgcgtc agagcttcct ccttctacaa gctaactccc tgcatctggg catcaggact   33600
gctccataca tttgctgaaa acttcttgta tttcctgatg taaaattgtg caaacaccta   33660
caataaagcc atctactttt agggaaaggg agttgaaaat gcaaccaact cttggcgaac   33720
tgtacaaaca aatctttgct atactttatt tcaaataaat tcttttttaaa ataatttccc  33780 tgcctaatta tttatggaag ttatgacttt tgaaggacaa ttcaaaacca tttatttaat   33840
tggttctgca atgaaagaac tgccccatat actctactaa aggcttggca cttctgctg   33900 cctttttaatc cagcgctata attgaggcaa gcgtccagct tgacacctcg agataacttc   33960
gtataatgta tgctatacga agttatatgc atggcctccg cgccgggttt tggcgcctcc   34020
cgcgggcgcc cccctcctca cggcgagcgc tgccacgtca gacgaagggc gcagcgagcg   34080
tcctgatcct tccgcccgga cgctcaggac agcggcccgc tgctcataag actcggcctt   34140
agaaccccag tatcagcaga aggacatttt aggacgggac ttgggtgact ctagggcact   34200
ggttttcttt ccagagagcg gaacaggcga ggaaaagtag tcccttctcg gcgattctgc   34260
ggagggatct ccgtggggcg gtgaacgccg atgattatat aaggacgcgc cgggtgtggc   34320
```

```
acagctagtt ccgtcgcagc cgggatttgg gtcgcggttc ttgtttgtgg atcgctgtga    34380
tcgtcacttg gtgagtagcg ggctgctggg ctggccgggg ctttcgtggc cgccgggccg    34440
ctcggtggga cggaagcgtg tggagagacc gccaagggct gtagtctggg tccgcgagca    34500
aggttgccct gaactggggg ttggggggag cgcagcaaaa tggcggctgt tcccgagtct    34560
tgaatggaag acgcttgtga ggcgggctgt gaggtcgttg aaacaaggtg ggggcatgg     34620 tgggcggcaa gaacccaagg tcttgaggcc ttcgctaatg cgggaaagct cttattcggg    34680
tgagatgggc tggggcacca tctggggacc ctgacgtgaa gtttgtcact gactggagaa    34740 ctcggttttgt cgtctgttgc gggggcggca gttatggcgg tgccgttggg cagtgcaccc    34800
gtacctttgg gagcgcgcgc cctcgtcgtg tcgtgacgtc acccgttctg ttggcttata    34860
atgcaggtgt gggccacctg ccggtaggtg tgcggtaggc ttttctccgt cgcaggacgc    34920
agggttcggg cctagggtag gctctcctga atcgacaggc gccggacctc tggtgagggg    34980
agggataagt gaggcgtcag tttctttggt cggttttatg tacctatctt cttaagtagc    35040
tgaagctccg gttttgaact atgcgctcgg ggttggcgag tgtgttttgt gaagtttttt     35100 aggcacctttt tgaaatgtaa tcatttgggt caatatgtaa ttttcagtgt tagactagta    35160
aattgtccgc taaattctgg ccgttttttgg cttttttgtt agacgtgttg acaattaatc    35220
atcggcatag tatatcggca tagtataata cgacaaggtg aggaactaaa ccatgggatc    35280
ggccattgaa caagatggat tgcacgcagg ttctccggcc gcttgggtgg agaggctatt    35340
cggctatgac tgggcacaac agacaatcgg ctgctctgat gccgccgtgt tccggctgtc    35400
agcgcagggg cgcccggttc ttttttgtcaa gaccgacctg tccggtgccc tgaatgaact    35460
gcaggacgag gcagcgcggc tatcgtggct ggccacgacg ggcgttcctt gcgcagctgt    35520
gctcgacgtt gtcactgaag cgggaaggga ctggctgcta ttgggcgaag tgccggggca    35580
ggatctcctg tcatctcacc ttgctcctgc cgagaaagta tccatcatgg ctgatgcaat    35640
gcggcggctg catacgcttg atccggctac ctgcccattc gaccaccaag cgaaacatcg    35700
catcgagcga gcacgtactc ggatggaagc cggtcttgtc gatcaggatg atctggacga    35760
agagcatcag gggctcgcgc cagccgaact gttcgccagg ctcaaggcgc gcatgcccga    35820
cggcgatgat ctcgtcgtga cccatggcga tgcctgcttg ccgaatatca tggtggaaaa    35880
tggccgcttt tctggattca tcgactgtgg ccggctgggt gtggcggacc gctatcagga    35940
catagcgttg gctacccgtg atattgctga agagcttggc ggcgaatggg ctgaccgctt    36000
cctcgtgctt tacggtatcg ccgctcccga ttcgcagcgc atcgccttct atcgccttct    36060
tgacgagttc ttctgagggg atccgctgta agtctgcaga aattgatgat ctattaaaca    36120
ataaagatgt ccactaaaat ggaagttttt cctgtcatac tttgttaaga agggtgagaa    36180
cagagtacct acattttgaa tggaaggatt ggagctacgg gggtgggggt gggtgggat    36240 tagataaatg cctgctcttt actgaaggct ctttactatt gctttatgat aatgtttcat    36300
agttggatat cataatttaa acaagcaaaa ccaaattaag gccagctca ttcctcccac     36360 tcatgatcta tagatctata gatctctcgt gggatcattg ttttttctctt gattcccact    36420 ttgtggttct aagtactgtg gtttccaaat gtgtcagttt catagcctga gaacgagat     36480 cagcagcctc tgttccacat acacttcatt ctcagtattg ttttgccaag ttctaattcc    36540
atcagacctc gacctgcagc ccctagcccg ggcgccagta gcagcaccca cgtccacctt    36600
ctgtctagta atgtccaaca cctccctcag tccaaacact gctctgcatc catgtggctc    36660
```

```
ccatttatac ctgaagcact tgatggggcc tcaatgtttt actagagccc accccctgc    36720
aactctgaga ccctctggat ttgtctgtca gtgcctcact ggggcgttgg ataatttctt    36780
aaaaggtcaa gttccctcag cagcattctc tgagcagtct gaagatgtgt gcttttcaca    36840
gttcaaatcc atgtggctgt ttcacccacc tgcctggcct tgggttatct atcaggacct    36900
agcctagaag caggtgtgtg gcacttaaca cctaagctga gtgactaact gaacactcaa    36960
gtggatgcca tctttgtcac ttcttgactg tgacacaagc aactcctgat gccaaagccc    37020
tgcccacccc tctcatgccc atatttggac atggtacagg tcctcactgg ccatggtctg    37080
tgaggtcctg gtcctctttg acttcataat tcctaggggc cactagtatc tataagagga    37140
agagggtgct ggctcccagg ccacagccca caaaattcca cctgctcaca ggttggctgg    37200
ctcgacccag gtggtgtccc ctgctctgag ccagctcccg gccaagccag caccatgggt    37260
acccccaaga agaagaggaa ggtgcgtacc gatttaaatt ccaatttact gaccgtacac    37320
caaaatttgc ctgcattacc ggtcgatgca acgagtgatg aggttcgcaa gaacctgatg    37380
gacatgttca gggatcgcca ggcgttttct gagcatacct ggaaaatgct tctgtccgtt    37440
tgccggtcgt gggcggcatg gtgcaagttg aataaccgga aatggtttcc cgcagaacct    37500
gaagatgttc gcgattatct tctatatctt caggcgcgcg gtctggcagt aaaaactatc    37560
cagcaacatt tgggccagct aaacatgctt catcgtcggt ccgggctgcc acgaccaagt    37620
gacagcaatg ctgtttcact ggttatgcgg cggatccgaa agaaaacgt tgatgccggt    37680
gaacgtgcaa acaggctct agcgttcgaa cgcactgatt tcgaccaggt tcgttcactc    37740
atggaaaata gtgatcgctg ccaggatata cgtaatctgg catttctggg gattgcttat    37800
aacaccctgt tacgtatagc cgaaattgcc aggatcaggg ttaaagatat ctcacgtact    37860
gacggtggga gaatgttaat ccatattggc agaacgaaaa cgctggttag caccgcaggt    37920
gtagagaagg cacttagcct gggggtaact aaactggtcg agcgatggat ttccgtctct    37980
ggtgtagctg atgatccgaa taactacctg ttttgccggg tcagaaaaaa tggtgttgcc    38040
gcgccatctg ccaccagcca gctatcaact cgcgccctgg aagggatttt tgaagcaact    38100
catcgattga tttacggcgc taaggtaaat ataaaatttt taagtgtata atgtgttaaa    38160
ctactgattc taattgtttg tgtattttag gatgactctg gtcagagata cctggcctgg    38220
tctggacaca gtgcccgtgt cggagccgcg cgagatatgg cccgcgctgg agtttcaata    38280
ccggagatca tgcaagctgg tggctggacc aatgtaaata ttgtcatgaa ctatatccgt    38340
aacctggata gtgaaacagg ggcaatggtg cgcctgctgg aagatggcga ttgatctaga    38400
taagtaatga tcataatcag ccatatcaca tctgtagagg ttttacttgc tttaaaaaac    38460
ctcccacacc tccccctgaa cctgaaacat aaaatgaatg caattgttgt tgttaaacct    38520
gccctagttg cggccaattc cagctgagcg tgcctccgca ccattaccag ttggtctggt    38580
gtcaaaaata ataataaccg ggcagggggg atctaagctc tagataagta atgatcataa    38640
tcagccatat cacatctgta gaggttttac ttgctttaaa aaacctccca cacctccccc    38700
tgaacctgaa acataaaatg aatgcaattg ttgttgttaa cttgtttatt gcagcttata    38760
atggttacaa ataaagcaat agcatcacaa atttcacaaa taaagcattt ttttcactgc    38820
attctagttg tggtttgtcc aaactcatca atgtatctta tcatgtctgg ataacttcg    38880
tataatgtat gctatacgaa gttatgctag taactataac ggtcctaagg tagcgagcta    38940
gctgcaaccg aggaaaaaac gtgccatgag gtctctgtat ccaagtgtga ct            38992
```

<210> SEQ ID NO 20
<211> LENGTH: 34073
<212> TYPE: DNA
<213> ORGANISM: Artificial Sequence
<220> FEATURE:
<223> OTHER INFORMATION: Recombinant polynucleotide

<400> SEQUENCE: 20

```
gagggagggt ggtgctttgc taatggtgaa ttactaactc ctcaataaag aatattattt      60
gaaataattt ttgaaatttc ataattactt tgggttcttt cttaatgata aataaataat     120
agtatattac aaacatacat taatatttcc tgaatgaata caccacaaat ctcccttaaa     180
atatagcaag aataaaaatt atactatttc tgacaatttt taatttctca aataataata     240
ccactctgat ttttaaacat ctacaccact ctggctttgc caatcttttt aaaaattgaa     300
aagataataa tttatcata attacactga agcatagaac ttttt ctttc aaggaaagca     360
aattttt gaa attctataat ataacctccc ataatcctga ataaattaaa ggttcaacaa     420
cttagtaaag taagactgac cttccctttt attt cttttt cagatcaaaa atcttacttt     480
tataggagca gttttcaact cctaaatgtt gaatataata gtcagttaaa ttcaccagct     540
acacaggaat acaggacttt gagtggaaga attgaatctc tggtaagtta atatttgtct     600
ttgctctttat tccattata aaatgaatat gataataaac ctaatgtttt gtaatatatt     660
ttcagttgct aagtgctcta catattttcc ttccttgaat ggtgaaacat gtgtttctct     720
ctgcttttat ccagttagtt tactcatata ctggttctta ttcacatctt tgtcatgagt     780
aaaaagtgtt agaaaggcca cgagtaaata tgcattttat ttgtttatga attcaaatac     840
taaaagtttt ttatttgttt aattaagcat tgacattgtc ttttt aaatt cttttcattt     900
taccttcttc cctcttcctt atccaactaa agacgcaaag caggaggtgt aaaaaacag      960
gtttaccata tcagcagtaa catagtttgg acaacattac actttggttc aatgatagac    1020
atagaagttt gaacagaaat atgcaaagca agtttgagct ctaacttgaa gagagcctct    1080
gggtgcctgc caggaaacct cacgagtgga cccttaacat tcatgtgtca ccacaaacta    1140
ggggctgccc tttagttttg accagtctca gtgtcactca cttacccta cctttt caaa    1200
aaaaagtcct aagaatataa agtaattcaa tggttctaca atttta gcat gtaactgagt    1260
cacctggcag ggttgctttg gtgagctcaa gataaaattt tatcagcatt tctacatttt    1320
ctggaatatt cctt aatcca ggcttttaat cccttggtgc ttttctgaac cactgcaatg    1380
agcttctaac tgttctcact gtgtgcaggc tcttttcctt ctaatctaat ttacacactt    1440
ctgaacacaa atctctcaca gcctgttt cc ttcatgttac ctccagctca agacttttt g    1500
cctacaaaat aaaattcaaa cttgttagct aagcaccttc tcatgtctat gctttggctc    1560
atatttcagc catcgtgtgc cccacttatt cttatagcca acctgaaaag ccatcttta     1620
taagaaacta cctctgctct ccatgattgg atataattaa tcctccttcc acatcacctc    1680
gccacaaaat tgtatctgtg ttgatctcat gccacatacc tgtatgtatt ttatattata    1740
aatatttgca gacttgttta atttgccatg ttagactaag ttccatgaag acagctccat    1800
atccattcca ttttt atata tccacaacat ttggtcgggt tgatgcttaa taaatgttta    1860
ttgaaggaac aggagtctcc cacttctgac ataatgaact tatttccccc agtgttaacc    1920
ctacatctgg ttcctgtcca agagtctctt cccaaatcat tctgattcaa ctgttcattc    1980
tgatctcatt aaacatttaa atgatatatc taacttcgct tgctttattc tatgctcatc    2040
ctgcagtctc ctcataactt ggtttcaatg atgcttgctt ctagagaaaa aaatgtatta    2100
```

```
aataagctta tgattcagtc ctccagctgt gatggttctc actgaacatt agctcagtgg    2160
ttttcgaagt atggtctcta gcataaccta gaaacttgtt agaaatgcaa attcttgggc    2220
tcaccaagac atactaaatc aaaaattctg acattggggc ctagaaatct gtgttttaac    2280
aagcctgcca gtgcagcctg gtcccttttc ttctcggagc cccactcaaa gctttcagtg    2340
ctcatctccc accaatgaca gggtcctcta tggaaaccgg caggacggtt ccaactcta     2400 actacgtttt agagtttgct tcctagggct atccaggcac caagtatcac aggttagttt    2460
cccagggaag cagactctga gacttgcatg cagggagtgt ctctggggtg ctctcaacca    2520
acaccttcag gaagagaagg aagcagcatt gggcagaggc atagtcaaac tacagtgctg    2580
ttggcacaga agactgaagg gagtcagagc caggggtag aggtgggccc ttagcatcca     2640
tccttcacca ttaggtgtga gttgccccac ctccttgatg gtgtaacctc agtcccaagg    2700
tgggtgggag tgcagcagag cagcccctac aagggccaaa ccagagatac accaggcgcc    2760
agaagtgctg ccagggaata gagaggaaag gatgggctta aggtaggatc cacagaactt    2820
ggcaatggat tagaagacag gatgagaagt gacaggttaa cactaacaca gaaatgtcta    2880
acttcggtag ataatggtgc cattggctag aagaggaaac cgaaatgaaa gcaggttgtt    2940
cagggagaca aaagttcact gtggacatct cagcagagtg attcagtggg gaaaggaatg    3000
gatgcccaga ccacctcaga ggaagatcta agctggagcc agcaataaag atacaagatg    3060
aacaatccct aacgaactgc tcctcagcca tgctccccag acacgctgct tcagatttat    3120
agtccgggtg aggctaggag gtgcgcctcc ctcagtggag gacagcaaag caccagtggc    3180
tccagggagt taaaatcttt tgataatttt tgttctagca tctgtctgca gagctgtctc    3240
tcagccattg cctgccttta cacaggagtg cagtccgaaa ttgggagatg agtgaaattt    3300
attatgccta gagatctgga tccccagttg tttgggagta tattttctga accacttgtt    3360
ggtttaagta atgcagattt attgatgcca cttctcttga atctgtgact ctggacccac    3420
catctaagtg aatgtgcaga gggaacggaa tggctgcaat agatctccat taaaaccagt    3480
gcatcctccc agacacatac agtagtaggg aggtgagtca atgtcaggac agcaccagct    3540
cccgcttcgg tacatttcca aagttctcag tctgtgtaca aaggtttgct ctggggcagc    3600
agaaatagcc ctgggcaggt agtcaaaggc ctggtttgat ttcctccact tccaggcaag    3660
tcactcgaag gctcacaggc ttttttcctca cctgccacat gggtccagtg agatctactg    3720
agctgtaaat aatgaaatga gtgtgtgtgc agtcatctat aagttgtaaa gtactagaaa    3780
atggtgaaac tttgggattt gggctatta aggctgaatg ctaaaaatgt caggcattgt    3840
ggagaaagga atttaaatat aagattgatt gactgggatt taaagacaaa tgaaggcaca    3900
cacgcaagtg cacacccaca ctgacactgc acagctcccg ttggaggcat atcctgacca    3960
tgcagacctg gggctctgcc tgtccaagtg cactcctta ctacataaac cctccttctc     4020 ttttgggct gtcaccccac cagagctggc accgagccct tgctgctgcg cttccctggg     4080
gtgtcagctt ttgacagggt gtttcctccc tctgcaggag ccttaacatc ccttggactt    4140 ccttccccc acccaccccc agcagtttta tctcttccta actcgggacc cttttttcc      4200 cacacaaagt ttattgtcag ttgctggttt catctgtttg agcggctgca acaaaatacc    4260
atagactggg tggcatatgc acgacaaaaa tttatttctc acaggagaag tcaaagatta    4320
atgcaccagc agatctggtg tctgaggggc caccttctgg tttgtagatg atgctttcta    4380
gttaaaacac ctatttaaca cactattaaa cactaagtgt gttaaatagt gcagttgatg    4440
tatttgtcat gtcacctta tcatacacta aatccttctt tgtctttttt tctgtactct     4500
```

```
aatctctttc tgtaagtaat ctttgcttgc agcagtagga tatttagagt actgtggctt    4560
gacaatatat ttagtatttc aagatttcca tgaaattctt ctgatgtatg agttccctag    4620
ttaatcttac atatgtatcc ctttgtaaaa acactttgaa catttaaaat gatacatgaa    4680
tagtactcta atacaatgcc ataaaaatta taaatcattt gtatagactg gtaagtaaag    4740
attgtgagat taagaaacgc atcaaaggcc attgagctgg aaagtggtat aatgagaatt    4800
caaaccaggg tctcttgact caaaatctaa ggatcatacc atttctcatg ataatatgag    4860
tattattgtt atctctatcc catagacaaa gtgttaacac tgaatgagca gtgaaatagt    4920
ctcagaattt tttattttat ttagcaattc acttgtcatt tctggtcctc agtttattca    4980
cgagtaaaat aaaatagttg gactagataa tttctatagt acattcttac acaaaaaatc    5040
tatgattttg ttattttaa tgtgatatac tcatggcact cattcacctc attttcccag    5100
cctgcctcac tggtcattac ttctctgtgt tctttacagg ctccccctcc tctacactgc    5160
cattaaatat tgaaacacct caaagcttta cttatgtcca cctctcctct gacactatca    5220
ttctgtctag atgatcccat acatacatgc ccattacttc aacctgtatt tatacgccaa    5280
tgattcacta tatttccagc ctagacattc ttttgtactc tagttaccag cttgatatcc    5340
ttacatggct gtttcaaaac aactcaaata tattatctct caaaatcaaa ctcatgatgt    5400
ccccacacca tcctagcttt ccaccaacaa tacctatccc tattaatagc aataccattt    5460
attcagttat ccaaatcaaa aacctagaat tcatccttaa aattctacta tcattccaaa    5520
tatcctatcc atcagcagcc actgtattct taatcccctg tatttccttc aaatccattc    5580
acctctctcc atatccattg ctgcatgact atccaagcca tcgcctctac cctagggtac    5640
caaaatagca acaaacctaa tctgttcatt tgcattattt tttctccaaa actgattatc    5700
tatatgtagc aagacagatt gttctcaaat tgcaaatccc actatattat cctcttgctt    5760
caaacacttc catggtttcc cattgtttat gataaaacca aatgcttcaa gttcgaagac    5820
cggcatgatt gggaatttcc tgtcacccta gcctacttgc tctccatggt acagttgcac    5880
tggctttctt tcattcctta agtacaacct gtttcctccc acctcaggac tgtgcatgtg    5940
ccattcattc tgctgaggag cctttttcct tccacttcaa tcagctaagt ctgattcttc    6000
ctgacaatct cagctcaata agcatttcct ctaagaaatg tctctaatat cattaattgg    6060
ctcaggtccc tctactgtat tgctgcactt ttcacagtta taattttact taattatgaa    6120
tgattatttg attaggtcta tttccatcca ttagacataa gcttcatgat ggccagatta    6180
ctgttttcta tccatcgttg tattccaata cctgacagaa ggagggcggg aggtggtggc    6240
acacaagaga tgctcaaaaa caattgttga ataagtaaat gaatgaggcc atttagaaat    6300
aacgaaagta cctgtttaca aagtacatgt atcaaaacta tgaatgcatt ctacttacat    6360
ggttttctcc aaataaaaca aaagacttca atcaggatta atacctggga taaactgagt    6420
cattaaatct ctcctttgcc atcaggagtg acattgaaac aaatgtctgc aaacaacaaa    6480
tacttttttc ccaaaatata ttgaatggca tttccataaa caaactagaa catgggagga    6540
gaaagaaagc aatattaatt taaaattaat cttatcacat aacttatacc atcagggatt    6600
tcgggtaaaa ttcctttcag gcacatccat ttaacaagaa ttgattgtta ctgaaagcct    6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
```

```
aaaatactca aaggtcattt tacatgtatt ttttctctaa attactttc ttaagacaca    6900 gaaaacaaaa aaagaaactt agctttgtta ctttctaaca aatagttaaa tcattaaaca    6960
ggattgacac tagcatcctt gtttggtctt atgccttagg ggaacatgaa atgtgtgaag    7020
acattctgag atctgaggga agggtagaca gtaatacagt gggactgacc aggcttcagc    7080
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaacccccatc   7560 tctacaaaaa tacaaaaatt agccagggat gatggtggat gcttgtagtc ccagctactc    7620
aagaggcaga ggcaggagaa tcacttgaac ctgggaggca gaggttgcag tgagccaaga    7680
tcacccattg cactccagcc tgggcaacag agtgagactc tgtctcaaaa aaaaaaaaat    7740
cactttttag ataaaattca tgctatagag agaagactat gaaaatatgt ttagcaatgt    7800
gtccatcatt aggtgattga gtttcctttt gttttgtttt actgaaaatc atataaagta    7860
tgttatctgt aaaagttctc tgacatgcac acataaaaat ttgggagaaa agattaacta    7920
taatgtttaa tagattttgt acacatttct ttaaaaatat ataaaacaca acacctttca    7980
attggtttgc aagaataacc aattgacatc atggaaaatg gaaattcact tgctgaattt    8040
taacaaaaat ttgcatgatg agtgagactg acaacttagt gtcatgattt aatgaattat    8100
gccaatggta aacttcatgc acatggggcc aggtaattat gtggaaactt tttcaatgct    8160
taaagccaag tattgaaatt aaacttagaa tcagaccttt gaaccatttt atgacaatgt    8220
tcaaaaatta taaattctat ccacttatat tataatatta aaaatatcat tacaaaaaaa    8280
acctgtgttt attttataac tcagccttt taatttctaa tttcataaat atattataat    8340
ggatattgtt agtaatgtag tattattaca tgtatataat ttataagtaa atatacatgt    8400
tttggctact catgcataaa atgtttcacc cataggagca cataatcaga aatgtctgga    8460
gaccattata gtaatagata gatcatattg ccacatattt tatctcctcc ttgacaactg    8520
agctttccag atcttctggt gaaacgaaag agaaagttgt aacagaagag tgattaaaat    8580
gacaaaagca ttacttctat tacttctatt ctaataatat gagcaaagct ataactatca    8640
agtaataatg cactaaagaa ggtgattaat ctgatatatt cacaggcaac taataagacc    8700
tttctattgc agccatgaaa aatatgtgac aattatagat atcctgtgtg cagtgtttca    8760
acctttatgt gacctgttct actaacagat ttagtgatgt tcactttgtt agaattttct    8820
tacacatgcc ataacttgct tcagtctttt gattatgaat attatggata ttaaggattc    8880
tagactattc tagatttaaa aaataatatt gtcacctcaa tcagaaggga aatattaaat    8940
agttctcatt ttttcaatgt ttactcagtt tttgtccaat gtaatgaaag tgtcagcagt    9000
acaggttaca aaataaaatg tgtattaaag taaactcatt tgaacaggtt aataattgta    9060
gagggaggga aaaggctaaa agattgaatg taaaacttat gaaaagtaga tacatcgtct    9120
ctatgatttg cagtagtcaa ctgcatacag atgaatcatt ttaatacacg ttaactactt    9180
tccttttaca gatggagaaa ctgagaggaa gaaagtttat atggttcatt aaactttgtg    9240
```

```
atgcaagcta aactaacctg tctctgtatt ttccatctac tgcccttatc actatctcat   9300
tagaatactc ttcaagcatc tccttactga ttttcttacc aagcatttgt taagttctaa   9360
tgagagttgg tagtaacatt ttcacccact ctgtgaaata tgaaatctta ttcataggcc   9420
tcttctttta ttcttgtatt tgcatatcaa ccaattaatc aacttgcttt ctttatgttg   9480
cttattatct tagtccttac taaattgcct cttaatgttg tccacataac agaaatgtta   9540
aggtggatac ttaacatttt agtccagtct agccggtgcc agtgcaatgc caaatcatga   9600
attaaaatat aattacaaga accacttatc aaattttaac aattccttca gctttgtgac   9660 agtttttttct acttcgatta aagtcaagta aaattaaagt taaatatttt tattaaaata   9720
tctcctttaa cattccatat taataaacat attaaagctc atgcttctaa gtagattact   9780
agaagttact ttatcgaatt acagcaatgg ttaattctag atcatagaat ttagaatgac   9840
tttttgcctt cttctttttt ttcctttttt ttaaacagag tcttgctctg ttgtccaggc   9900
tggagtgtac tggcgcgatc ttgactcact gcgacctctg ccctgcaggt tcaagtgatt   9960
ctcctgcccc agcctcttaa gtagttggga ttacaggtgc ctgccaccac acctggctaa  10020 ttttttttttt gtattttttag gagagacagg gtttcaccat gttggccaga ctggtctcga  10080
actcctgacc tcaagtgatc cacttgcctc agcctcccaa agtgctggga ttacaggtgt  10140
gagccactgt gcctggcctg acttttttgct tcttcttaa tacttactag tatttcttga  10200 attttttaaaa aagaaacata agtactttg ataaaaccaa cagtctcatt gttcttaaaa  10260
ttgttcaaag gttctctgga aaaaaaaaag aaaattatca tttggttaag aatcatgttg  10320
gtctgacatc aatcatccta taggagtgaa tattgaaaaa gtaagatata ttgtggtata  10380
atcgagattg cataaatttt accatttttg agaagaatct gctccaaatc ctggcttaat  10440
gtaatatcca gcatgctact taattttctt gtcttcacct tttcatatcc acatccacct  10500
aggtgccacc tcacagtata agccagcata atccattctt ctcaatgaaa ccacaataca  10560
tctgaccctg catctcagga gaactgtatc agccacagca cttccagttg actatgaatc  10620
tgaatgttat gcctcaggag aaacatcctt gctgggactg agtagtgatt caaggagata  10680
gttatgattc agtcaagaaa ttaataatta gtgttatttt tattattgag acagagtctc  10740
gttctgtagc ccaggctgga gtacagtggc atgatctcgg ctcactgcaa cctctacctc  10800
cccggttcaa gtgattctcc tgcctcagcc tcccaaataa ctgggacagc aggcacttgc  10860
caccacgcct agctaatttt ttgtattttt agtagagacg gagtttcacc gtgttagcca  10920
ggatggtctc gatctcctga cctcaaggtc cacctgcctc agcctcccaa agtgctggga  10980
ttacaggcgt gagccactgc gcccggccat aaattattaa ctgagccagg cacagtggta  11040
cacacttata gtcccagata ctcaggagac tgaggttgga gtatcctttt ttatgttatt  11100 ttattttaa ttattatggg tacataatag gtgtacatac ccatggagta caagtcatgt  11160
tctgatacag acacataatg tttaataatc acatcagggt aattgggata tccatcacct  11220
caagcattta tctttctttg tgttaggaac attccacctc cactcttgga ataggcaccc  11280
tgttgtgcta ttaaatacga ggtcttattc atttcatcta actatatttt tctacccatt  11340
aaccatcacc tcttttcccc tcttccccac tacctttcct gtgaggctgc aggattctta  11400
agcacaacag ttagaggcca gcctggacaa catagtgaga ctcaatttct aaaaaataaa  11460
aaagaaatta ccaactaatg ctaaaaaat agtctctgat gcttaggtat gaattagaaa  11520
tgaccaaaaa aaaaaaaaaa aaaagactg cccttgtcctt ccttctcccc ttctcttcaa  11580
```

-continued

```
gttttccatt gctactcatt ttagtctggt ttaatcaggt ttcatccatt aaaagcaatt    11640
gttgggatca cacattttga gttgtgtcag tggacttccc tcatgctggc atgattcctg    11700
ccccaagccc ttagtaaaag ccaccaagcc atataacata atctctcatt gagtaaaaca    11760
tctgatgtgt ttagaatgac ttctagcaaa aaaccagcct gtccagcatc atctctgtat    11820
aacagataaa ggaataggta ctgcatcaaa aggttataga acctgcccaa atcaatccca    11880
tgtgttttgc aatggaatta ggttgaacta aagtgaaaat tcagttttct actcctcatt    11940
aacatgtctc atgttgcaag gttgagagga aggagaagaa gaactgtatt tacagagaga    12000 ttcccctct ctttctttct acagattact aaaacattca aagaatcaaa tttaagaaat     12060
cagttcatca gagctcatgt tgccaaactg aggtgagtgg aactgtagaa aaaatattta    12120
agtatagata caatgtggca tacttgactt tttgtcacag aatgaatagt aaatgacatg    12180
ttcagataag ttgttgtaat attatgaaaa tagtatttta gtcagcttaa aaaccaatgc    12240 caaaaagcc aaacatatga tctatttagc tactaatgta aataaccata ttatatctat      12300
tcttattggg aagaggaaga aggggtggag agagagttgg ggtgaaggta cagtaacaag    12360
gccatcctat tgtaaaactc cagtggatat cattcacagt gcagcctatg taaacagtcc    12420
ctcctggagt tgtacaatgc tgtggtttgg gtgtatccat ccaagatcaa gacactatga   12480
ccaacatcaa aagtggcttt ttggttttat ctgcctgatg tgctataata aagggtatt     12540 atggccaaat ccaaggcatg tctatcatga attaataata ggaggagtag cagcatgcat    12600
gctagttatt tgccattcct gccttagtta aatatgatgt gataaaacca gcctttccaa    12660
ctgaaatagt cacctttact gactctcccg caaatgtctc aaatgaccac attgctctag    12720
tctttaaata atatgcaata gttctttggt agaagaggaa ttatactaat tctttctcaa    12780
atactagcat cacaagaaaa ttaattcttg ttctctggag agtcacctag taagtatctg    12840
gagcacagat gtctggtcag gtaagttttg atgaggagtt aaagggataa gaagagtcca    12900
tgagaagggt attttccaaa acaccttttcg gtcaattcag tgcacattca cttagtactt    12960
tcttgtcagt atctgtatca gccactaatg ttcaaaagtg agtaagccct gaaaacctgt    13020
aggactacat gagccttctg cctttttctct ccttttgttc acttcccact tatcactcaa   13080
tcctctgcaa cctggcttca ataccaccat aaaatatcaa ctgctcttgc cgattcaaca    13140
atgcatccaa gataacaaaa tccaaagaaa ccacatcagt cctattcttg gacctttcaa    13200
cagtatttgg tcctgttggc ctgtcactcc ttgaaatagg actatccctt ggtttgcatg    13260
gccttgtata ccctgatttt ccccttacct ccctagctat tccttcttag tttcctttac    13320
taggtcttac ttctttgtat attccttaaa tgttgctgaa catcaggctg tgctctaggc    13380
ctctcatctt ctcaggtcac actctctcct ttccttggcc ttcactgcca cccatatgct    13440
gagtgctctc aaagttgtat ctctaggcca gtcctctttt gcctccaaac atgaatatat    13500
gcagccatct acttggtacc atcacatgga taattctcat gatctcttcc agtatgactg    13560
cttctttatt tttttctggg ctctttttta gcattgcttt acatggaact ttatcatgtc    13620
tctcaacctc tattttatct tttatctatg tatgtagagt ctgtgtaatt tcttcatctc    13680
ttttagataa ctaatatctc ttcagctttg acttgtattc tgtgtaaccc atttattgcg    13740
ttttcaattt caatgagtat gttttcctat ctgcaagttc tatttgtttc ttttgagaat    13800
cttcctggtc ttttaaacac atttcttatt ttaattttg ggggtaccta gtagttgtat     13860
gtatttttgg agtacatgag atgttttgat acaagcaaac aatgcataat aatcacattg    13920
tgtaaaatgg ggtatccatc ccctcaagca tttatccttt gtgttacaaa caatccaatt    13980
```

```
atattctttt agttattttt aaatgtacaa ttaaattatt attgaccata gtgactctgt    14040
tgtgctatca gatactaggt gatcttttaa aaataatgtt ttctacttaa tctcattttt    14100
atgattccct cttttacgtc atttgtcatt tcaaatacag tcacttgtct gttgattcta    14160
ttatgtgaag ttttgagga taatctttt gttactttga ttccaccttg gtatggtttg      14220
gctgtgcccc cactaaaatc tcatcttgaa ctctggttcc cataataccc acatgttgtg    14280
ggagggacct tgtgggaggt gattagatta tagggacgtt tccccctttt gctctgttct    14340
ttttcctgcc accatgtaag aaagatgtgt ttgcttcccc ttctgccatg attgtaaatt    14400
tcctgaggcc tccgcagcca tgcaggacct cttttctttg taaattaccc agtctccggc    14460
ggttctttat agctccgtga gaaaaaacta atacacacct catgatgtat tgtttaccac    14520
tgaaattgta tgcttaaatt taatctcact tgggaccctg tacaacctag acttaacata    14580
tctacctcca gagcagttac atctgtcaga cattctagag gaatcagcag cacatggact    14640
tgttgttgt taatttgttg tcggggagg ggggagggat agcattagga gatacaccta      14700
atgctaaatg acgagttaat gggtgcagca caccaacatg gcacatgtat acatatgtaa    14760
caaacctgca cgttgtgcac atataccta aaacttaaag tataataata ataaaattaa     14820
aaaaaaaaag gttctgggag tattcaggta gtattaatga agattcagac atcgtgcagc    14880
caggcccatg cttatgaatt ttcaggtgat acttcttttt cttttttctt aatttaaagc    14940
tggatctcgg aaacagataa atttatttt ttatgacatg acgagcattt ttttcattct      15000
agttcatgct gttattgggt gtttagttct ttgagactcc tggccttttt ctaaaacctc    15060
aagttcaact tcctattttg cactggccca aggtcccatc tccagtctct atgtaaatgc    15120
taaacataag cctgtggaat attctagtct caccacatac tattcacatt cttctttgtt    15180
tttggtcttc caggattttc cttactttc tatgaaccca gtcttgcatt tgaaatggaa      15240
tttattatat attatctatc ctttctattt gttttatgca gaaagtgttt tctaaaatta    15300
tttaggcttc catattgcta gacatggaag ttgtaattat ttgttcagtg cctgtttcta    15360
catctaaact gcaagaccca tatggcaact gtgaatctta gtcccagcta atttctgaag    15420
cttagaatag tgcctagcac aagaagttgt ttatctaaca ttttaaaaa taatattaa       15480
attcatatct ggaatgaata ttaagttaga gctggtcatt gaggtgagag gaggaagcca    15540
agagagaata tgagagcctc aaagccaaat atctttaatg tactttttca gaaagaaga    15600
cagccaatgt caggtggagg aactggttta tgaggtaact ttcctggaag aaaatagaaa    15660
ttactgaggt tttagataat ccaaatattt aatcaagtca ccaaggttta ttgtgggaa     15720
tcttattat taattaaaat gagtgatgaa atcttaatat acgacaaaag ttaaaatttg      15780
cttttgcagg cagatgaatg gtctaggtat caaaaaatta agttgagtct ctaactcaca    15840
caaatttaca accctatcac tttatgaatt tgtttaggag attatttta ataacactgg      15900
tgaagtctaa gaatagctaa aatttatagt acacttattg tgtgctattg actcttcttt    15960
gaagttttgc atatagtgat tcatctaatc ttcataaccc attttacatg tgaagaaact    16020
tagatataga aagattaaga aacttacata acttatccaa agttacacag taaaactctg    16080
gcattataac ttcaaaatca gctatcctac agtgagtaca gtgttctgtg cattgaaatc    16140
aaataagtga gatagcatcg tgatatagta ttacgtatgc aaacactgtt acagagatct    16200
gtctaaagtt aaattccaca aatgaattct ttaaagggt ttaatcaaga agaatatata      16260
aacaggatgg tgaaaattg tcatattatt tgttttttaa aatatcttta tgatttacag      16320
```

```
gcaagatggt agtggtgtga gagcggatgt tgtcatgaaa tttcaattca ctagaaataa    16380
caatggagca tcaatgaaaa gcagaattga gtctgtttta cgacaaatgc tgaataactc    16440
tggaaacctg gaaataaacc cttcaactga gataacatgt aagtataatt tttcataaac    16500
aattttattt caatatatcc ctcaagttta ccaattcaaa ttcatatttt aattgagagg    16560 ctgactttc tttctttgaa actaaactgt gaaaacaatc cattaaaaag ctaaatatac    16620
catatagctc cctaacgtaa atcattctaa gacttaaaga atcatttggc atttatatag    16680 taaatttat ttgctaaaaa ttctcattaa ttatccctgc aacattcctt atgagtgatg    16740
ttactgtcag atgtcattag tggataggcc ataggagggg tacatagatg ctcaaggtca    16800
gagaactatt taattaatga tccacctcag aggcttcttc attttctttt gtaacattta    16860
tcacaattga aattacaaag ttatctgtgt aaattttgta ttgtttggct tcatcctaca    16920
ctgtaatcat cctaaaagaa agaaccagtc aaccttcttc atcctactac cctcctacca    16980
cccagtctcc atcatataac acatattcaa taaataattc ttgcatgact gaaagaaaag    17040
aaataatata tgcatagaat ttaaggacat tcctccaagt tggttacatt ctgctagttt    17100
aataagccat tatttcttct cgatgagctc aagattaaaa ggattttgat gattcccata    17160
ctagactggt aggtaccagt tacagatgta ctaactgtta aatattgaaa tgctttccta    17220
tttgttggta aacaattact gcatcaggcc cacaaagttg tcttccgaga tgtttcaaat    17280
ccactgcccc tgctgctaaa gagttatgct tagcaaagca aagcactcta agacactgct    17340
ccaactccat ggcctgattg catctttat gactggccaa tgctcacgca ctgcagtttg    17400
ttaggtagtt gaatattacc tctgcttcca cacattaagg aatgctcccg aacgcacttc    17460
ccaagtgttt atttatttat cattatacta gacaatatgg tgatacgatg gtcacagaat    17520 agcggttcc acctccagag cccataatct agttgaaggg aaagatattc caacacaaga    17580
gtgttgacaa tcaagataga atatgatcaa gggcccagtg tgaggcccag gcaatgatca    17640
ctgcaggaat ctggggaaga aagagaccag cgtgcttggg atatctagca aaagtttcat    17700
gaaggagaat ggactttgac tttgaaatat gggtaggatt tacatatttt gagatgagaa    17760
aaagaaagtt cccagagaag gaaagcatga aaaggcaaac agtctgtact gaacgcgatg    17820
ctttgacaga ataatgaaga aagggacctg ctggaatgat tgatcagtgt tcatcattca    17880
caccatcatc atcaaaacac ttatttaatg agaacttact gttttttagg catggcttta    17940
atgccctata tgaatttttt tcttgattaa tccttacaac aaacatatcc catagatagt    18000
tttattgtcc cccttagaaa agataaattg cctaggctga cacagtcagt atatgaggca    18060
gtcaggattc aaactaagtc tgtttgttca aaaaattaag aatggccagc ttttaaaat    18120 tttctgtctc cagaagtatg atttggctcc actgaagttt gcaaaacaaa tgtgataccc    18180 aaccttgtg aaactttag tgggaaataa ctttgcataa gtcggtttga gagagcgtgg    18240
aaacctgtct tgaaaagttt taatttaact tgcaggaaat aaaaatgatg ggtttctcaa    18300
ttaaaaattt caatcaagga aggatatgag ctaacataac attttttaa aaagatcagt    18360 ctggtaaggt agaggtgcat aaactgaaaa ggagcaaaag tggtggaatt cagttagaaa    18420
attattgtaa ctgtactgat gtcaaatgat gaaaccatga actaaagtag taccaaaagg    18480
agtgaggagg atgaataat tcaaaagata gaggacagat gtgcagaacc tggagattat    18540
aagatgtgaa aggaggagtt tgagaaaatt tcagattttg gaagtggtgt cattttacta    18600
aaaggatata ataagtagca aattttggat aaagttgggt cccactgagt ttgagatggc    18660
tgttggacat gcagagaaaa ctgtcttgta tgctgttctt aaattgaaat agacagacct    18720
```

```
ttaccctctg atactgacat attttccttt ccaggctcac cctccatttc cctaaacaca    18780
acacatgcac tagctctcct tactttattg ctccacaaac atcttacacc tccaagcatt    18840
tgtgcccact gtaccttcta tctggaatct cttttgtcct cttgtgtgcc tgaaaaattc    18900 cttttcagatc ttcaaaatac agtgcagatg ctatttcttc tagctcaaat attatctcct   18960
ccatataatt taattactct cttttttctt ttctctactt tgcacttaca tttatttgaa    19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaagagata tctattaagt     19260 atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcattttttt aatactagca cttactgacc aggctgcagc aaattggctt   19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg ttcccccttt cctttagaa aaaggaagaa gttgtagtgg aggactaccc     19800
actctgcact caaaattgcc ctcatgaaaa tttctttggc agctttgaga acttttact     19860 gccctggttc taaggtggca tttctgtaga cttacaaatt atgtttgatg acaccgttta    19920
tgtagcttct cctaaccacc agagtagctt gctttgttgt gaattcaggt taatcacaaa    19980
gtataataaa aaagaattgt cagaagtctt cccagctttg ggtctataac ctgaaggaaa    20040
agtcactact cttcaacatc atcctatgta ctctcaggct aggatagcag aaatgcaatc    20100
cctagaaaac agcaacttac ttctctgacc aaaaaaatgc agttaaaaat tagttcaatg    20160
tacctggtag ctggcctatc ttaggtactt cagtgatttt acaaagtgat ggtagtccta    20220
tgggtgtttt tcagcttcac tacgtattta attcatgctt attgttaatg aaactgtgat    20280
aagcaattta ctagggtatt tgtttgggag atgccacaaa ggaacacatg tatctcttaa    20340
tggaagcctg gtcctccttt atccaggaaa tttgctagga aaaaaagcc tttaggtggt     20400 tgtgctatta aaccagggca ctacttaaaa gccagcccag caatagttgt gtgatttacc    20460
attaatttct tagtaataga ccacacaaaa gaagaaaatt atgggaatgc gagttgagag    20520
gaattgggtg atcagcctac cccagcccgt ttcagctctg gccagtagac tattcacgag    20580
ctctttgaaa acatttaaat aaaccttatt tagatactag aaaccctctg tcaccctcaa    20640
gaatattctg tggtatagcg actcctttat gagggcatgt ttggtaatac agcatcagtc    20700
ttggaggtgg actggattct acaaggtgaa ctgcagtcac taaggagtct tttggatgag    20760
accagttttc ctccaacttc aatgtgtgca tgaacctcac atcaaaatgt agctttagat    20820
ttgtcccatg atgtggttcc aagaatcagc acttctaata agtttccagg ggatgcccat    20880
gctgcaggcc cacaaaccac actgagcata gcaagactat tgagaaaaag gaaatttccc    20940
aggagtctgt ggcctgagct ggcacatcca ataatgacct atcttaacct caactcatga    21000
ggaattccag ggaactctga agctgctcaa aatttgaagc ctatatgcca actaaattca    21060
```

```
gaaatgttct ccaaaatgct atctataagc aacagtagtc acaaatgcat tgtagaaata   21120
tatcgatcat gcttttttgga aaatccagca tgtcctgagg aagaatgtat aagacataaa   21180
agtcataaat tatggaaaga ctcttcagct tcttccaaat gtaaaggaat catgatcttc   21240
ccagcacatt aatgcccttt ctcattagaa tgtggggccg gtccagacct aataacattg   21300
tctgagcaga gaatccttgg aggcactgag gctgaggagg gaagctggcc gtggcaagtc   21360
agtctgcggc tcaataatgc ccaccactgt ggaggcagcc tgatcaataa catgtggatc   21420
ctgacagcag ctcactgctt cagaaggtga ggccaccact acctacccat ctgggaacaa   21480
ttagaataga caggtcatga agactgcacc ctctacccta ggattgaatt gagccagaaa   21540
taattcaatg caaaaaaatc agtaagaatt ttcttcctat tcatgaaagg aaaaggattt   21600 ttcccctta gcatgctaat ttagtgctat ttctctgttt caggtaataa tatattagca   21660
cagtaaagaa caaagattta tatgtcagaa tgttttttaa atcctagcta taaaagctta   21720
agaaatttac taaatctcca taagctttat ttttttttcca aattaaggga caacactgtt   21780
atctgtgact tagtgttact ggtagcattg agtcacactaa tgtaaacata cgttaaatgt   21840
tagcgaaacg aattgctgtg aagatttgc acattatatc atgggagctg atggctaacc   21900
tagagactgc cccatgccat taatttattc attcataaag attattgagt atctagtatg   21960
agcacagtgt tatatattgt agaagctact agtataaaca agtattgcc tctgccttca   22020 aagagcttac actcgaatgt tggaatcaga atgcacaaaa ataatgatca attacaatga   22080
gtagcataaa taaaattaat gtaggcaact tacaagaatt cttaattgag gtgactaaac   22140
tattgccaac actagggtga tatgctacca gtggcgagta ggttgcataa acttaccttta   22200 ttggtaaaaa gaaaagttca cattgctcat aaaagaagga ttttagattt cagcataact   22260
aaaatctgtt tcaaacctgc cttgttactg gggcatcgca gaccacaaca gttgttggga   22320
acttaactca aaaagttcac ccagaaaaat aatggagatt tgaactcgtg tgcccctgac   22380
catatcaatt ttcttctcag actcttactc taaactggac ctccttatca cacacacaaa   22440
gccttccata ggcagatcaa tccagtctta tttctcaaag catgtacctt gagcttcaga   22500
taaacagcat tgttctcttc ccctggactc ttcctacatt tccctaccta tgagtatctg   22560
atcaatctgc ttatccttga aatgttaata tatttaccac atctctattt gaattttatg   22620 aaattttga taatttctaa gtagtttttt cagatttata ggcactactt catggtacag   22680
tgactgttac aaacgtattt gttaaattta gaaggaataa agatttaaaa gactagggta   22740
gttactgaac taaagtttta ggaaatccca aattatttca attttttctt atggtaattt   22800
tatgacttaa tatttttata tgcagtgaac aaatttgaaa ctttaaaaga tactcccaga   22860
attatcagtt ttctgatgta gattggcaaa tttattacta tatcccaaat aacccaagag   22920
acaaaattca caaaaacatt tcaattttca ttgccacttg aaaggccaaa aagcagaaat   22980
ggcacgcatt gatttcaatc gtactcttga gtgtgggaac caggaattaa aatacctgga   23040
cttatcaggc acttagcata accaagaacg gaatagaaac ctccctggat tctaagccct   23100
attcagtccc aatcaccaaa aaccaagtaa acgatatcac tataatgaaa gccacagtta   23160
taaatatcga caacgattac caaaggaatc catggaactt tgaattttgc cacccccacat   23220 ccttctattc attaccatga ttgatccact aaagctaaca gactctgtga accttgtatt   23280
ggacccctcc ctaaagacct gattgtcact gagaaccatc agtgaggatt tgtttggggc   23340
atgaccagcc ttacatcaaa gtacatagaa gtgatgaggt cttatcaaag aggattattg   23400
aattatcacc tcttctatgt agctttccct gatactctct ttcctctcca ttgagttcca   23460
```

```
cagaaatttt tttatctgcc tttaacagtt gtcctcatga tttgtgatat ttgacttacc    23520
tcttgtcagt ttccttcact agtgtagagt tcctcaaaga aagagaccat aattacttat    23580 attttattc ctggagactc atactattcc ttatacaaag tagacactta acaatggctt     23640
gttgaactat aattaatgaa aataatagct accttcatga aagttcactt tgtgccaaac    23700
actatagttg acataataca tttgtctcat taatacttaa caattgtgtg agaaggtatc    23760
accaatcaca ttttatatgt aaataaaccc cagagctatt aattaacttg tcataaataa    23820
cacttttcat atgtggcata gccaagattt aaatataaat gttactggtt ccaaaatgat    23880
gctctaattc acttgctgga aagaaggaaa ggaagaaaat aaacgagtgg aaggaagaga    23940
gggagggaag agagaaaagg aaggaaagaa aaaagagtct cttcagaacc ttcactgtaa    24000
agactccgag caaagaagt tgaatataaa acaacatag gtttgtttgt tttctaatat      24060 ttttcttca aaattttaa ctcaggttca ctcttacaca aactactgtg tcttataaaa      24120
gtatttccgg tcatagaatt tttatttct gtattaactc cactatctaa tctccataaa     24180
actcctaaat tggtattatc ggtaacattt tgttttact caacccttag gaacaatgtt     24240
aagttaatca gccctccaca tcacagatcc ttattttcat cagtctgtac aaggcatttc    24300
tctcatttta attttttttc ctcctgtcat ccctggattt cactttcact gccctccttc    24360
cacccatatg cctcatacta atatattcga aatatacatg tcttaaaggt acatgcacgc    24420
acctacaaaa cctatagtgt tttttgtat gtatatgtct ttaatttaaa taagtagcat     24480
tgtgtaaaag tctaatattg tttcttactg ttttcactca attcttggaa ttttcatctg    24540
atgcactgct gcatagcacc ccatggtatg cagccaccat atttccttca tccaattagg    24600
ttgcatgacc taccttccca ttgccacaaa gagtacacac aaaatatttg tacttatctt    24660
tctgtaaacc ttcaggaatt tcagaagcac acatgcaggc tgctaaatat accagaatac    24720
tttccagcca cttaaatctt taccagtatt gcaaaagagg ccccatttcc ctccacatca    24780
acatttagta ttattctttt gtttaagttt tatcaatctt ttaaatgtac acaagatgct    24840 cattttata atttaatttt ctcagattac tagtttgagt atcttttcat atatctaaga    24900
gctgttttga tctcccctac catgaactgc cactaatatt ctttgcctat tttacaatgg    24960
tttttctgct tatttattac tggtttacag acttttaaaa tatattctac aaaaatttta    25020
gacattaaac attaccaata ttttcccatg gttcctcatc catctggtaa acttgtctat    25080
ggtatatcta attttgattt aatagaattc attctatttt taccttttag tttgtgtttt    25140
tgttgtttag ccaaaaagtc cccattccta ggtcataaag gtaatgtcct ttttttttt    25200 ttaacgctac tgttctctct ctgtctcccc ctatgtatat aggtgcacat atacttgtac    25260
acacatacat ataccatat atgaggggag ttcgataagt ttatggaaaa taaaattaaa     25320
agataaaata aaaaattata aactttattt ctcaacataa gctccttcaa gttcaagaca    25380
cttttgtaag caataatacc agccatatcg tccatcccta aagaactgag ggtcctgaga    25440
atttaactat gtcaatgcag tcttttttac attacttttt tacagtactt attgatgaaa    25500
aatgggtgcc ttttaaagat tgttttaaga ttagggaaca aaaataagtc agaggaagtc    25560
aaatcaggac tgaaggtgg atgcctagtg atttattgct gaaacttca taaaactaac      25620 cttatttgat gagaggaatg agcatgagca tggttgtgat ggagaagaac tctggtggag    25680
ctttcctgga cacttttct actaaagctt tggctaactt tcttactctc ataagaagaa     25740
gatgttattt ttcactgacc ctttagaagg tcaacaagca aaatgccttc agcatcccaa    25800
```

```
atgtctgttg tcatgacttt tgttcttgac tagtctggtt ttgctttgac tggaccactt   25860
ctacctcttt atagccattg ctttgatggt gctttgtctt caagattgta ttagtaaagc   25920
catatttcat cttctgttac aattcttcaa agaaatactt cagaatcttg atctgacatg   25980
tttaaaattt ctattggaag ctctgacctt gggtgcagct gatctgggcg aaacagtttt   26040
ggcatccatc aagtagaaag tttgctcaac tttagttttt cagtcagaat tgtataagct   26100
gaaccagttg agatgtctat ggtgttgtct attgtttctc acagttaatt gttggtcctc   26160
tttgagacat gaacaagatg aaattttttcc tagcaaactg atgtggatga tctgttgctg   26220
cgggcttcac cctcaacaac atctctttct ttcttgaaac aaattatcca ttagtaaact   26280
gatgattggg ggagatgctg tccccataaa cttttttgtaa ggcataaata atttcaccat   26340
tcttccagtt tcaccataaa tttgacgttt ttttgcttca atttttagcag cattcatgtt   26400 gctttgataa gagctctttt caaattcatg tcttattcct cttagtgcct caaactagat   26460
cttgttcagt atgacaagtt agtatgagtt tatctgcatg caaaaatctt tgaaatccat   26520
gcatagtttg tttataatat acattttcaa tgaactttg aagaccccat acatacatat   26580
gtatatatat gcacacacac acacacacac acaccaaaat cttcaaccat tatcagactt   26640
agtgcagaaa aattattcat ccattaacaa gataagaatg ccccttatca tcactactat   26700
ttaaatggag ctcctggcta aaggaaaaga cagggattga aaaaaattag ttaaatctaa   26760
aatgtttatt atttcaggtt tcttagttgc ttaaatggga agggaggtat ggacaaaaga   26820
gaaatcaaag atatttgtgt tatgctactt atcattaaag tatcagaata acttcattgg   26880
aatagaaaaa caccaagatc accccacgat atgttttcta aaatcttctc catttcttta   26940
gacaagtgac catgtattcg gccagtgaag aattaaactc acttgccagc ttataatgca   27000
ggaaaatata gcaaagagat gtggatccaa tagtttctag atagtggtac aggatggcta   27060
agatgaattt atatatctga aatgttcaca aattccctac tcatatagca tgtttttcata   27120 atgttttagc aactctaatc ctcgtgactg gattgccacg tctggtattt ccacaacatt   27180
tcctaaacta agaatgagag taagaaatat tttaattcat aacaattata aatctgcaac   27240
tcatgaaaat gacattgcac ttgtgagact tgagaacagt gtcaccttta ccaaagatat   27300
ccatagtgtg tgtctcccag ctgctaccca gaatattcca cctggctcta ctgcttatgt   27360
aacaggatgg ggcgctcaag aatatgctgg taagtgtctc ggaaaaaaaa attaacaata   27420
gaaatgtctt atatttgcta ttaggtaatt ttttaaatta ggaaacatct ggaataggtg   27480
tttctattct tctacagaca gaaccattct atattctgct cagcccaagc tctggctacc   27540
cctgagtctc cttagcaaag caaagcaatg ctccagaaac tatgggaatt ctcaaatata   27600
gtaataggaa aatgtaaaag aaagttatga agacacgagt tctttaataa tccagagatt   27660
ctataagatt caaatagctt ccctataaac aataaaaaag attttgtttg tttgtttgtt   27720
tgcttgtttt ttagagacaa agactttctc agactggagt gcagtggtgc aatcatggct   27780
tactgcagcc tcaaactctg gtcttaagaa atcctcttgc ttcagcctcc caagtagcta   27840
gaattataaa taagtgtgta ccaccatacc cagctttttt ttttttttc tacagacagg   27900 ttcttgctct gttgcccagg ctggtctgga attcctgccc tcaagccatc ctcctgcctt   27960
gttggcctcc caaagcaatg ggaggattta gattagacat tgtatgaggg cttaataatc   28020
cttaaggtat taactgccct ttaaagtatt ctgggatatg gcaaaactc gatgtgtata   28080 taaacattgg tcatatttgt ttattgaatg aataaaatgg aaactaaaat gaggacaatg   28140
cacaagagct actagaacca gtaagagtat cagcgaagga gtggaagggt agcattgaca   28200
```

```
atttccctgg gcttttaccc atgttgtaga ttgtctctcc aaggaataat acaaagcctt    28260
aatagtccta gaacacattc tattgtgttc ttatggccca aagtaaattg gtgtagtaga    28320
taacatttgc accagtcatg aaaaactatt ggtgtcattc tgagagtaca tcaatataaa    28380
atagactagt tctttagcct tgaaactaga ctggtttctc ttttgctgct aggttaaagg    28440
ttattcaata tgtaatcttc caatccaaaa tctgtcagtg gataatttaa aagcttttag    28500
tcaattttaa gatatttgtt ttcttaaaat tttaaggggc actgtgtcac aaagctaaag    28560 aaaaaaaga aaaaaaaact gatctgtgaa aggggttatc ctcatctact tggggaattt    28620
tggctgcgaa gaaactccaa agtaaatctt tagaagcctt cattgttaaa tatgaaataa    28680
tgtttggagt acatttattt cttctcaaat ttattatagg gtcaataatg tacacatctt    28740
gaagtccatt ttttcctgc ttttataaca acaggccac acagttccag agctaaggca     28800
aggacaggtc agaataataa gtaatgatgt atgtaatgca ccacatagtt ataatggagc    28860
catcttgtct ggaatgctgt gtgctggagt acctcaaggt ggagtggacg catgtcaggt    28920
aagctcaaga caatctcatc catgtcatca tccaagaagt gtataagcac ttcctagtat    28980
gtgataatgt gatagacata agtgtaacag ttacaataca cagccctgtt cctctaaaat    29040
ttataatcta gattttagaa ataaattttt ttatgaatga agtttatcta tcatgaaagc    29100
attaactctg agaggccaaa ttacagagta gttaaccatc caaagctcaa gaatcagaaa    29160
gacctcgatt tgaattcctt aacctctatt accaagtctc taactaaaag ctggggataa    29220
tcataatagc acctaacttt tgggtacta agaaaagtta aatgaagact aaatatatca     29280
ggcacatggt aaacaacaaa gaaatctcat ctatttcact attattaatg tagaccatgg    29340
tcactcgtgt taataacttt aacctcaacc ttttaactgc tgtgaaggat taaataaaaa    29400
attaatcact atattataaa aattaattga tatataataa atgaattta agagatacgt     29460 aataattcat ggactccttg aagatagaaa atttatacaa atcctagta atttgagtca     29520 caaaagctcc tacaataatg aaacagtatg aatgaaaaag aaaagaaata actattatat    29580
ttggatctag cccataattt ttaaccaaat gcacaaaaac aaacaacaaa tatgaaattc    29640
tcactgtaaa gtgattaaaa tcaaatttga attctaaaat tttaaattaa attatctaaa    29700
cataattgat gcagttatat gtttttaatag gttttgttca catatctgaa atccaactcc    29760
acacagtagc aggaacagct ggtgtcagaa attaaatatt cttttagtct ggagttttaa    29820
aaaatcaatc tgtttacttg agtaatttgt tgctgttttc atgggtgaat tgtatacaga    29880
aggataagaa ttattcttcg catcaaaagg tcactgactt tcatatttag tgctcatggt    29940
ctttaaaaag tggataaaaa gtagttctca catttcatgg aaagccccca atccatgagc    30000
acatttccca aaatgaaaca ttttttatcaa ctgcaagttg tgtgtaggtg gagatttgtt    30060
tttcaattgt caagatactg ttaattaccc agtcctttat ctccttttgg tggagatgtc    30120
tctgtgctag gaaaccctcc ttgctctcct tcctgtttct cttttactac tggccctgaa    30180
acaacaaatt ctcaagtttc atgacagctt tccaaagaat ccatcaatca aataagcaac    30240
acaactcgac actgacaatt ccagacctac taagagcatt aattaagact aaaaataaa     30300 catgagtttt aaagggtgt tattcattat tttcccattt ataacgtccc ttaccttctg     30360
tccttcagtg catacaaatt attatcttcc ttgaagccca gttcaagccg tacctcacca    30420
tgataccttc catgtatatt ccactctagg cctcactgat ttttaactga atactataa     30480 tgcatagttc acacttaaaa aaaaaaaaaa aacacagcac tttacataag agcttacagg    30540
```

```
atcctatttg ttttatccat tcttttgttc attttacaa tcattaattc aaaggaatta    30600
tattaattac tttctatgca cccgacgttg tgttaacaca acaatactat ccctgcattc    30660
agcaagtcta tggtctacaa gagaggacac aaattcaaat gtctgtagtc aagcagtgaa    30720
gctggctaga tatggaaaaa ttacaagtcc ctccttgcttt aacatttgct tgcccacatt    30780
tggtcagaca tcatgcaaaa taatttctca ctatagaaaa aaaacacta caaaacaat     30840 aatataaaga actgagaact ggttaactga agcatgcata tgtcatctaa agaagcagg    30900 tgacgaccag cttcatgaag tacttgccat gcatattggc acttcacaca ctgacccttc    30960
tccccaccta gaccagtaat taaacaggta tggatgagct agctactaag agcagccaac    31020
tgaatagctg actaacttag aagcacactt ggtaataata gctgactttt attagtactg    31080
actatactat atgctaagct gtactcaaag tgctttgagt tttaaactga tacaaacatt    31140
atatgaggaa acagaggtac agagagctat tcaccagctt accaaaggtc acatagctgg    31200
taagtggagg acttaaaccc agactatcta gtttcagaac ccacagactt aatccatcgt    31260
gcagaacata agacatactc catctgtctc cccaactagg ttattatgtg cacaaatatt    31320
tattggttgg ttggttcatt attatgactg ggtggtaagt atgtcattag gagtgtttg    31380 cttatgacta tataaatttc ttcaccaaaa gaagactttc tgatgatata ctatgcatca    31440
gacaccacgc agggtgctaa ggttaggaag ataagtgaga cttctagaaa ctcattcatt    31500
caacaaatat ctcctaaggg ctagaagctt aggtttcagc agtgaacaga ataggtatgt    31560
tctctttcgt gttggacctt atagtatatc tgggaaaaca gacattgaat aaatatcaca    31620
aatgcaagtg agtgtttcag agacatgcag ctgctcatcc aaaacaaaac agaacaaaac    31680
aaacaaacaa aaactgacca gtgggattaa gtgtaaatag gcacacaaat gcacaaatat    31740
gcttttataa aatagtgaag cagtgacaga gacacacaca agatataaag acacaatgaa    31800
gaacaattga gcccaaagct ggaaagggtg agagtgtgaa ggaaaaggt tgatcagaga     31860 agttttcccg aaggagagaa agcctggatg attaggaggc aaccactcgg tgactgaggg    31920
aaatctgaaa aatgtatttg tcatcttctc agacttgctg aaggaatgac ttgggtactt    31980
tgaggatttc agtaattttt ccatgacttg gtataatatt tcaaaggaa ataggctgac     32040 tttatttgta taatgaatgt gactccttcc tcgactgcca tagaaataaa ctccttaata    32100
ttttgggttt gtcttttgcac ttaagtaatc agtcattctg ttttttttaca gggtgactct   32160 ggtggcccac tagtacaaga agactcacgg cggctttggt ttattgtggg gatagtaagc    32220
tggggagatc agtgtggcct gccggataag ccaggagtgt atactcgagt gacagcctac    32280
cttgactgga ttaggcaaca aactgggatc tagtgcaaca agtgcatccc tgttgcaaag    32340
tctgtatgca ggtgtgcctg tcttaaattc caaagcttta catttcaact gaaaagaaa    32400 ctagaaatgt cctaatttaa catcttgtta cataaatatg gtttaacaaa cactgtttaa    32460 cctttctttta ttattaaagg ttttctattt tctccagaga actatatgaa tgttgcatag   32520
tactgtggct gtgtaacaga agaaacacac taaactaatt acaaagttaa caatttcatt    32580
acagttgtgc taaatgcccg tagtgagaag aacaggaacc ttgagcatgt atagtagagg    32640
aacctgcaca ggtctgatgg gtcagagggg tcttctctgg gtttcactga ggatgagaag    32700
taagcaaact gtggaaacat gcaaaggaaa aagtgataga ataatattca agacaaaag    32760 aacagtatga ggcaagagaa ataatatgta tttaaaattt ttggttactc aatatcttat    32820
acttagtatg agtcctaaaa ttaaaaatgt gaaactgttg tactatacgt ataacctaac    32880
cttaattatt ctgtaagaac atgcttccat aggaaatagt ggataatttt cagctattta    32940
```

-continued

```
aggcaaaagc taaaatagtt cactcctcaa ctgagaccca agaattata gatattttc    33000
atgatgaccc atgaaaaata tcactcatct acataaagga gagactatat ctattttata   33060
gagaagctaa gaaatatacc tacacaaact tgtcaggtgc tttacaacta catagtactt   33120
tttaacaaca aaataataat tttaagaatg aaaaatttaa tcatcgggaa gaacgtccca   33180
ctacagactt cctatcactg gcagttatat ttttgagcgt aaaagggtcg tcaaacgcta   33240
aatctaagta acgaattgaa agtttaaaga gggggaagag ttggtttgca aaggaaaagt   33300
ttaaatagct taatatcaat agaatgatcc tgaagacaga aaaaactttg tcactcttcc   33360
tctctcattt tctttctctc tctctcccct tctcatacac atgcctcccc caccaaagaa   33420
tataatgtaa attaaatcca ctaaaatgta atggcatgaa atctctgta gtctgaatca    33480
ctaatattcc tgagttttta tgagctccta gtacagctaa agtttgccta tgcatgatca   33540
tctatgcgtc agagcttcct ccttctacaa gctaactccc tgcatctggg catcaggact   33600
gctccataca tttgctgaaa acttcttgta tttcctgatg taaaattgtg caaacaccta   33660
caataaagcc atctactttt agggaagggg agttgaaaat gcaaccaact cttggcgaac   33720
tgtacaaaca aatctttgct atactttatt tcaaataaat tcttttaaaa ataatttccc   33780
tgcctaatta tttatggaag ttatgacttt tgaaggacaa ttcaaaacca tttatttaat   33840
tggttctgca atgaaagaac tgccccatat actctactaa aggcttggca ctttctgctg   33900
ccttttaatc cagcgctata attgaggcaa gcgtccagct tgacacctcg agataacttc   33960
gtataatgta tgctatacga agttatgcta gtaactataa cggtcctaag gtagcgagct   34020
agctgcaacc gaggaaaaaa cgtgccatga ggtctctgta tccaagtgtg act          34073
```

<210> SEQ ID NO 21
<211> LENGTH: 418
<212> TYPE: PRT
<213> ORGANISM: Artificial Sequence
<220> FEATURE:
<223> OTHER INFORMATION: Recombinant protein

<400> SEQUENCE: 21

```
Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
            20                  25                  30

Met Ala Gly Leu Leu Ile His Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160
```

```
Thr Asp Gln Ala Ala Ala Asn Trp Leu Ile Asn Glu Cys Gly Ala Gly
                165                 170                 175
Pro Asp Leu Ile Thr Leu Ser Glu Gln Arg Ile Leu Gly Gly Thr Glu
            180                 185                 190
Ala Glu Glu Gly Ser Trp Pro Trp Gln Val Ser Leu Arg Leu Asn Asn
        195                 200                 205
Ala His His Cys Gly Gly Ser Leu Ile Asn Asn Met Trp Ile Leu Thr
    210                 215                 220
Ala Ala His Cys Phe Arg Ser Asn Ser Asn Pro Arg Asp Trp Ile Ala
225                 230                 235                 240
Thr Ser Gly Ile Ser Thr Thr Phe Pro Lys Leu Arg Met Arg Val Arg
                245                 250                 255
Asn Ile Leu Ile His Asn Asn Tyr Lys Ser Ala Thr His Glu Asn Asp
            260                 265                 270
Ile Ala Leu Val Arg Leu Glu Asn Ser Val Thr Phe Thr Lys Asp Ile
        275                 280                 285
His Ser Val Cys Leu Pro Ala Ala Thr Gln Asn Ile Pro Pro Gly Ser
    290                 295                 300
Thr Ala Tyr Val Thr Gly Trp Gly Ala Gln Glu Tyr Ala Gly His Thr
305                 310                 315                 320
Val Pro Glu Leu Arg Gln Gly Gln Val Arg Ile Ile Ser Asn Asp Val
                325                 330                 335
Cys Asn Ala Pro His Ser Tyr Asn Gly Ala Ile Leu Ser Gly Met Leu
            340                 345                 350
Cys Ala Gly Val Pro Gly Gly Val Asp Ala Cys Gln Gly Asp Ser
        355                 360                 365
Gly Gly Pro Leu Val Gln Glu Asp Ser Arg Arg Leu Trp Phe Ile Val
    370                 375                 380
Gly Ile Val Ser Trp Gly Asp Gln Cys Gly Leu Pro Asp Lys Pro Gly
385                 390                 395                 400
Val Tyr Thr Arg Val Thr Ala Tyr Leu Asp Trp Ile Arg Gln Gln Thr
                405                 410                 415
Gly Ile

<210> SEQ ID NO 22
<211> LENGTH: 257
<212> TYPE: DNA
<213> ORGANISM: Artificial Sequence
<220> FEATURE:
<223> OTHER INFORMATION: synthetic oligonucleotide

<400> SEQUENCE: 22
agcacccctc tcttccgcag agtctaagaa atcgctgtgt ttagccctcg ccctgggcac    60
tgtcctcacg ggagctgctg tggctgctgt cttgctttgg aagttcagta agtgcaggga   120
gcctcgatcc caccatgtgc tcctgcagtc cccagtgctc tgagccagac cctgctctct   180
gggctattga gacctctgga ggccctccgt gaggttcctc tcttacataa cgaggctgtc   240
tctcttccct tctcttg                                                  257

<210> SEQ ID NO 23
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 23
```

```
ggtcagagga ccaaaggtga ggcaaggcca gacttggtgc tcctgtggtt ctcgagataa    60
cttcgtataa tgtatgctat acgaagttat atgcatggcc tccgcgcgg gttttggcgc    120 ctcccgcggg cgccccctc ctcacggcga gcgctgccac gtcagacgaa gggcgcagcg   180
agcgtcctga                                                         190
```

```
<210> SEQ ID NO 24
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 24
attgttttgc caagttctaa ttccatcaga cctcgacctg cagcccctag ataacttcgt    60
ataatgtatg ctatacgaag ttatgctagt aactataacg gtcctaaggt agcgagctag   120
ctccacgtgg ctttgtccca gacttccttt gtcttcaaca accttctgca a            171
```

```
<210> SEQ ID NO 25
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 25
ggtcagagga ccaaaggtga ggcaaggcca gacttggtgc tcctgtggtt ctcgagataa    60
cttcgtataa tgtatgctat acgaagttat gctagtaact ataacggtcc taaggtagcg   120
agctagctcc acgtggcttt gtcccagact cctttgtct tcaacaacct tctgcaa      177
```

```
<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gccgtgactg tgaccttctc                                               20
```

```
<210> SEQ ID NO 27
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 27
tggaggagcc acctgatgcc tc                                            22
```

```
<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gccttgccct caatggaaac                                               20
```

```
<210> SEQ ID NO 29
```

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
ggttgcacag caaggaagaa g                                            21

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
ccaggagttc ctgtgagcct accc                                         24

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
tggaatggaa ggagctggag                                              20

<210> SEQ ID NO 32
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 32
gtcccacctc ctgcaactg                                               19

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
tgagccttcc catcagcctg gg                                           22

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
ccacaatggc acatgggtct g                                            21

<210> SEQ ID NO 35
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 35
```
ggtgcttgct ccccaaga                                                   18

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cctaaaaggt gttgtaatgg                                                 20

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37
ggcaataaag aaggaagacg tttt                                            24

<210> SEQ ID NO 38
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 38
ccagtcaggg acacacatgc tcacacgccc gcccacccgc acacactaca gtcgagataa     60
cttcgtataa tgtatgctat acgaagttat atgcatggcc tccgcgccgg gttttggcgc    120

<210> SEQ ID NO 39
<211> LENGTH: 198
<212> TYPE: DNA
<213> ORGANISM: Artificial Sequence
<220> FEATURE:
<223> OTHER INFORMATION: synthetic oligonucleotide

<400> SEQUENCE: 39
attctagttg tggtttgtcc aaactcatca atgtatctta tcatgtctgg aataacttcg     60
tataatgtat gctatacgaa gttatgctag taactataac ggtcctaagg tagcgagcta    120
gccaagtctg tgtgctacca agtagcaaaa ctgagcctgg aactcacaca tgcgtgtctg    180
agagcccagc actatcgc                                                  198

<210> SEQ ID NO 40
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 40
taatctgact ttctcttcat cggtctctct tattctaggc tgagctgtaa cgctgccgtc     60
ccccacatcc agaagctgct tcccttcaga cctacctacg                          100

<210> SEQ ID NO 41
<211> LENGTH: 177
<212> TYPE: DNA
<213> ORGANISM: Artificial Sequence
<220> FEATURE:

-continued

<223> OTHER INFORMATION: synthetic oligonucleotide

<400> SEQUENCE: 41
ccagtcaggg acacacatgc tcacacgccc gcccacccgc acacactaca gtcgagataa    60
cttcgtataa tgtatgctat acgaagttat gctagtaact ataacggtcc taaggtagcg   120
agctagccaa gtctgtgtgc taccaagtag caaaactgag cctggaactc acacatg      177

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 42
gagcagggcc atgacacat                                                 19

<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43
accattagat cccagcactg gaca                                           24

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
aaacccttcc cgagagagaa                                                20

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gaggaacact gtgtcaagga ctt                                            23

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
cctgaaaagc ccggagtggc ag                                             22

<210> SEQ ID NO 47
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 47

```
gggcagagac cacatctga                                              19

<210> SEQ ID NO 48
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 48
ggaagccctc tctcgatact tg                                          22

<210> SEQ ID NO 49
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 49
ttctaccctg agggcatgca gc                                          22

<210> SEQ ID NO 50
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 50
tgggatgtag aaggttgtca ga                                          22

<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51
ctgagcctgg aactcacaca tg                                          22

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
tctgagagcc cagcactatc gcc                                         23

<210> SEQ ID NO 53
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 53
gctgagggtc aggcttgag                                              19

<210> SEQ ID NO 54
<211> LENGTH: 21
<212> TYPE: DNA
```

```
<213> ORGANISM: Artificial Sequence
<220> FEATURE:
<223> OTHER INFORMATION: synthetic oligonucleotide

<400> SEQUENCE: 54
tctgcagggt agggagagaa g                                              21

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 55
tgtttcagaa aaggaagact cacgttaca                                      29

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
gagaccgatg aagagaaagt caga                                           24

<210> SEQ ID NO 57
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 57
gaccatttta aggttttgct tggttgtttt ggagggaggg tggtgctttg ctaatggtga    60
attactaact cctcaataaa gaatattatt tgaaataatt                         100

<210> SEQ ID NO 58
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 58
gctgcctttt aatccagcgc tataattgag gcaagcgtcc agcttgacac ctcgagataa    60
cttcgtataa tgtatgctat acgaagttat atgcatggcc tccgcgccgg gttttggcgc   120
ctcccgcggg cgcccccctc ctcacggcga gcgctgccac gtcagacgaa gggcgcagcg   180
agcgtcctga                                                         190

<210> SEQ ID NO 59
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 59
attgttttgc caagttctaa ttccatcaga cctcgacctg cagcccctag ataacttcgt    60
ataatgtatg ctatacgaag ttatgctagt aactataacg gtcctaaggt agcgagctag   120
ctgcaaccga ggaaaaaacg tgccatgagg tctctgtatc caagtgtgac t            171
```

```
<210> SEQ ID NO 60
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 60
ccagtcaggg acacacatgc tcacacgccc gcccacccgc acacactaca ctcgagataa      60
cttcgtataa tgtatgctat acgaagttat gctagtaact ataacggtcc taaggtagcg     120
agctagctgc aaccgaggaa aaaacgtgcc atgaggtctc tgtatccaag tgtgact       177

<210> SEQ ID NO 61
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 61
tcctctccag acaagaaagc t                                                21

<210> SEQ ID NO 62
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 62
tcatagcagc tttcaaatcc taaacgttga                                       30

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
tcgtgtgtag ctggtgagtt                                                  20

<210> SEQ ID NO 64
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 64
catgcgatca caggaggaga tc                                               22

<210> SEQ ID NO 65
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 65
aattgggccc gaagccagat gc                                               22

<210> SEQ ID NO 66
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
cggaaggctt ctgtgacttc                                              20

<210> SEQ ID NO 67
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 67
gtctcccact tctgacataa tgaac                                        25

<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68
cccagtgtta accctacatc tggttcc                                      27

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
tgggaagaga ctcttggaca                                              20

<210> SEQ ID NO 70
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 70
atgagctcct agtacagcta aagtt                                        25

<210> SEQ ID NO 71
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 71
atgcatgatc atctatgcgt cagagc                                       26
```

```
<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72
tgcccagatg cagggagtta g                                              21
```

RODENTS HAVING A HUMANIZED *TMPRSS* GENE

CROSS REFERENCE TO RELATED APPLICATIONS

This application is a continuation of U.S. patent application Ser. No. 15/442,857, filed Feb. 27, 2017, which claims the benefit of priority from U.S. Provisional Application No. 62/301,023, filed Feb. 29, 2016, the entire contents of which are incorporated herein by reference.

INCORPORATION BY REFERENCE OF SEQUENCE LISTING

The Sequence Listing in the ASCII text file, named as 33093Y_10234US03_SequenceListing.txt of 275 KB, created on Jun. 4, 2018, and submitted to the United States Patent and Trademark Office via EFS-Web, is incorporated herein by reference.

BACKGROUND

Type II transmembrane serine proteases are a family of proteases characterized by an N-terminal transmembrane domain (Bugge et al., *J. Biol. Chem.* 284 (35): 23177-23181, 2009; Hooper et al., *J. Biol. Chem.* 272 (2): 857-860, 2001). All members of this family are expressed as single-chain zymogens and are proteolytically activated by cleavage within a highly conserved R/(IV)VGG motif. One member of the family, transmembrane protease, serine type 4 (TMPRSS4), has been shown to activate the epithelial sodium channel (ENaC) regulating the sodium and water flux across epithelia (Guipponi et al. 2002 *Hum. Mol. Genet.* 11:2829; Vuagniaux et al. 2002 *Gen. Physiol.* 120:191). The proteolytical activators of TMPRSS4 are unknown; however, data available to date suggests that the protein is autoactivated. When activated, the catalytic domain of TMPRSS4 remains bound to the N-terminus of the protein via a disulphide linkage. TMPRSS4, TMPRSS2 and TMPRSS11D (or Human Airway Trypsin-like protease; "HAT") have been shown in vitro to cleave influenza A hemagglutinin (HA), which is the first essential step in the viral life cycle. This cleavage is essential for activity of HA, as the protein is synthesized as a precursor protein (HA0) and requires cleavage into HA1 and HA2 for activity. RNAi knock-down of TMPRSS4 in Caco-2 cells resulted in reduced spread of the virus. In addition, TMPRSS4 was shown to be strongly upregulated in the lungs of mice infected with influenza (Böttcher et al. 2006 *J. Virol.* 80:9896; Böttcher et al. 2009 *Vaccine* 27: 6324; Böttcher-Friebershäusser et al. 2010 *J. Virol.* 84: 5604; Bertam et al. 2010 *J. Virol.* 84:10016; Bertam et al. 2010 *J. Virol.* 84:10016; Böttcher-Friebershäusser et al. 2011 *J. Virol.* 85: 1554; Bahgat et al. 2011 *Virol. J.* 8:27).

Development of an in vivo system, e.g., a rodent model of infection, is needed in order to identify and test compounds including antibodies that specifically target human type II transmembrane serine proteases for the treatment and prevention of viral infection and other diseases.

SUMMARY

The present invention encompasses the recognition that it is desirable to engineer rodent animals to provide in vivo systems for identifying and developing new therapeutics. For example, the present invention encompasses the recognition that rodents having a humanized Tmprss gene are desirable for use in identifying and developing therapeutics for the treatment and prevention of viral infections.

In one aspect, the invention provides a rodent whose genome contains a humanized Tmprss gene that includes a nucleotide sequence of an endogenous rodent Tmprss gene and a nucleotide sequence of a cognate human TMPRSS gene, wherein the humanized Tmprss gene is under control of a 5' regulatory sequence(s), such as the promoter and/or enhancer(s), of the endogenous rodent Tmprss gene.

In some embodiments, the humanized Tmprss gene in rodents disclosed herein encodes a humanized Tmprss protein that contains an ectodomain substantially identical (e.g., at least 85%, 90%, 95%, 98%, 99% or 100% identical in sequence) to the ectodomain of a human TMPRSS protein. In some embodiments, the humanized Tmprss protein contains a cytoplasmic and transmembrane portion that is substantially identical (e.g., at least 85%, 90%, 95%, 98%, 99% or 100% identical in sequence) to the cytoplasmic and transmembrane portion of an endogenous rodent Tmprss protein.

In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical (e.g., at least 85%, 90%, 95%, 98%, 99% or 100% identical in sequence) to the ectodomain of the human TMPRSS protein encoded by the cognate human TMPRSS gene. In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the endogenous rodent Tmprss gene encodes a polypeptide substantially identical (e.g., at least 85%, 90%, 95%, 98%, 99% or 100% identical in sequence) to the cytoplasmic and transmembrane portion of the endogenous rodent Tmprss protein encoded by the endogenous rodent Tmprss gene.

In some embodiments, a rodent disclosed herein contains a humanized Tmprss gene located at an endogenous rodent Tmprss locus that results from a replacement of a contiguous genomic sequence of an endogenous rodent Tmprss gene with a contiguous genomic sequence of a cognate human TMPRSS gene. In specific embodiments, the contiguous genomic sequence of a cognate human TMPRSS gene being inserted includes exon sequences encoding an ectodomain substantially identical with the ectodomain of the human TMPRSS protein encoded by human TMPRSS gene. In some embodiments, the contiguous genomic sequence of a cognate human TMPRSS gene also includes the 3'UTR of the cognate human TMPRSS gene.

In some embodiments, a rodent disclosed herein is heterozygous for a humanized Tmprss gene at an endogenous rodent Tmprss locus. In other embodiments, a rodent is homozygous for a humanized Tmprss gene at an endogenous rodent Tmprss locus.

In further embodiments, a rodent contains two or more humanized Tmprss genes at different endogenous rodent Tmprss loci with each endogenous rodent Tmprss locus being humanized with a respective cognate human TMPRSS gene; for example, two or more of humanized Tmprss2, humanized Tmprss4, and humanized Tmprss11d genes.

In some embodiments, a rodent disclosed herein contains a humanized Tmprss2 gene that includes a nucleotide sequence of an endogenous rodent Tmprss2 gene and a nucleotide sequence of a human TMPRSS2 gene, wherein the humanized Tmprss2 gene is under control of the promoter of the endogenous rodent Tmprss2 gene.

In some embodiments, the humanized Tmprss2 gene encodes a humanized Tmprss2 protein that contains an ectodomain substantially identical (e.g., at least 85%, 90%, 95%, 98%, 99% or 100% identical in sequence) with the ectodomain of the human TMPRSS2 protein encoded by the human TMPRSS2 gene used in humanization. The human TMPRSS2 protein contains, in some embodiments, an amino acid sequence at least 85% identical (e.g., at least 90%, 95%, 98%, 99% or 100% identical) with the amino acid sequence as set forth in SEQ ID NO: 4. In some embodiments, a humanized Tmprss2 protein contains an ectodomain substantially identical (e.g., at least 85%, 90%, 95%, 98%, 99% or 100% identical) with the amino acid sequence composed of residues W106 to G492 or the C-terminal 387 amino acids of a human TMPRSS2 protein as set forth in, e.g., SEQ ID NO: 4. In some embodiments, the humanized Tmprss2 gene encodes a humanized Tmprss2 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss2 protein encoded by the endogenous rodent Tmprss2 gene being humanized. An exemplary endogenous rodent Tmprss2 protein is set forth in SEQ ID NO: 2.

In some embodiments, a rodent contains a humanized Tmprss2 gene that includes a nucleotide sequence of an endogenous rodent Tmprss2 gene and a nucleotide sequence of a human TMPRSS2 gene, wherein the nucleotide sequence of the human TMPRSS2 gene encodes an ectodomain substantially identical (e.g., at least 85%, 90%, 95%, 98%, 99% or 100% identical in sequence) with the ectodomain of the human TMPRSS2 protein encoded by the human TMPRSS2 gene. In specific embodiments, the nucleotide sequence of a human TMPRSS2 gene is a contiguous genomic sequence of a human TMPRSS2 gene containing coding exon 4 through the stop codon in coding exon 13 of the human TMPRSS2 gene. In particular embodiments, the contiguous genomic sequence of a human TMPRSS2 gene further contains the 3' UTR of the human TMPRSS2 gene. In some embodiments, the nucleotide sequence of an endogenous rodent Tmprss2 gene included in a humanized Tmprss2 gene encodes a cytoplasmic and transmembrane portion that is substantially identical (e.g., at least 85%, 90%, 95%, 98%, 99% or 100% identical) with the cytoplasmic and transmembrane portion of the endogenous rodent Tmprss2 protein encoded by the endogenous rodent Tmprss2 gene.

In particular embodiments, a humanized Tmprss2 gene contains coding exons 1-2 of an endogenous rodent Tmprss2 gene, and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein encoded by the endogenous rodent Tmprss2 gene, and an ectodomain that is substantially identical with the ectodomain of the human TMPRSS2 protein encoded by the human TMPRSS2 gene. The humanized Tmprss2 gene contains an exon 3 that in some embodiments is coding exon 3 of a human TMPRSS2 gene, and in other embodiments is coding exon 3 of an endogenous rodent Tmprss2 gene. In some embodiments, the humanized Tmprss2 gene contains an exon 3 that includes a 5' portion of coding exon 3 of an endogenous rodent Tmprss2 gene and a 3' portion of coding exon 3 of a human TMPRSS2 gene.

In some embodiments, a rodent disclosed herein contains a humanized Tmprss4 gene that includes a nucleotide sequence of an endogenous rodent Tmprss4 gene and a nucleotide sequence of a human TMPRSS4 gene, wherein the humanized Tmprss4 gene is under control of the promoter of the endogenous rodent Tmprss4 gene.

In some embodiments, the humanized Tmprss4 gene encodes a humanized Tmprss4 protein that contains an ectodomain substantially identical (e.g., at least 85%, 90%, 95%, 98%, 99% or 100% identical in sequence) with the ectodomain of the human TMPRSS4 protein encoded by the human TMPRSS4 gene used in humanization. The human TMPRSS4 protein contains, in some embodiments, an amino acid sequence at least 85% identical (e.g., at least 90%, 95%, 98%, 99% or 100% identical) with the amino acid sequence as set forth in SEQ ID NO: 11. In some embodiments, a humanized Tmprss4 protein contains an ectodomain substantially identical (e.g., at least 85%, 90%, 95%, 98%, 99% or 100% identical) with the amino acid sequence composed of residues K54 to L437 or the C-terminal 384 amino acids of a human TMPRSS4 protein as set forth in, e.g., SEQ ID NO: 11. In some embodiments, the humanized Tmprss4 gene encodes a humanized Tmprss4 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss4 protein encoded by the endogenous rodent Tmprss4 gene being humanized. An exemplary endogenous rodent Tmprss4 protein is set forth in SEQ ID NO: 9.

In some embodiments, a rodent contains a humanized Tmprss4 gene that includes a nucleotide sequence of an endogenous rodent Tmprss4 gene and a nucleotide sequence of a human TMPRSS4 gene, wherein the nucleotide sequence of a human TMPRSS4 gene encodes an ectodomain substantially identical with the ectodomain of the human TMPRSS4 protein encoded by the human TMPRSS4 gene. In specific embodiments, the nucleotide sequence of a human TMPRSS4 gene is a contiguous genomic sequence containing coding exon 4 through the stop codon in coding exon 13 of a human TMPRSS4 gene. In some embodiments, the nucleotide sequence of an endogenous rodent Tmprss4 gene included in a humanized Tmprss4 gene encodes a cytoplasmic and transmembrane portion that is substantially identical with the cytoplasmic and transmembrane portion of the rodent Tmprss4 protein encoded by the endogenous rodent Tmprss4 gene.

In particular embodiments, a humanized Tmprss4 gene contains coding exon 1 through coding exon 3 of an endogenous rodent Tmprss4 gene, and coding exon 4 through the stop codon in coding exon 13 of a human TMPRSS4 gene.

In some embodiments, a rodent disclosed herein contains a humanized Tmprss11d gene that includes a nucleotide sequence of an endogenous rodent Tmprss11d gene and a nucleotide sequence of a human TMPRSS11D gene, wherein the humanized Tmprss11d gene is under control of the promoter of the endogenous rodent Tmprss11d gene.

In some embodiments, the humanized Tmprss11d gene encodes a humanized Tmprss11d protein that contains an ectodomain substantially identical (e.g., at least 85%, 90%, 95%, 98%, 99% or 100% identical in sequence) with the ectodomain of the human TMPRSS11D protein encoded by the human TMPRSS11D gene used in humanization. The human TMPRSS11D protein contains, in some embodiments, an amino acid sequence at least 85% identical (e.g., at least 90%, 95%, 98%, 99% or 100% identical) with the amino acid sequence as set forth in SEQ ID NO: 18. In some embodiments, a humanized Tmprss11d protein contains an ectodomain substantially identical (e.g., at least 85%, 90%, 95%, 98%, 99% or 100% identical) with the amino acid sequence composed of residues A42-I418 or the C-terminal 377 amino acids of a human TMPRSS11D protein as set forth in, e.g., SEQ ID NO: 18. In some embodiments, the humanized Tmprss11d gene encodes a humanized Tmprss11d protein that further contains a cytoplasmic and transmembrane portion that is substantially identical (e.g., at least 85%, 90%, 95%, 98%, 99% or 100% identical) with the cytoplasmic and transmembrane portion of the endogenous rodent Tmprss11d protein encoded by the endogenous rodent Tmprss11d gene being humanized. An exemplary endogenous rodent Tmprss11d protein is set forth in SEQ ID NO: 16.

In some embodiments, a rodent contains a humanized Tmprss11d gene that includes a nucleotide sequence of an endogenous rodent Tmprss11d gene and a nucleotide sequence of a human TMPRSS11D gene, wherein the nucleotide sequence of the human TMPRSS11D gene encodes an ectodomain substantially identical with the ectodomain of the human TMPRSS11D protein encoded by the human TMPRSS11D gene. In specific embodiments, the nucleotide sequence of a human TMPRSS11d gene is a contiguous genomic sequence containing coding exon 3 through the stop codon in coding exon 10 of a human TMPRSS11D gene. In particular embodiments, the contiguous genomic sequence of a human TMPRSS11D gene further contains the 3' UTR of the human TMPRSS11D gene. In some embodiments, the nucleotide sequence of an endogenous rodent Tmprss11d gene included in a humanized Tmprss11d gene encodes a cytoplasmic and transmembrane portion that is substantially identical with the cytoplasmic and transmembrane portion of the rodent Tmprss11d protein encoded by the endogenous rodent Tmprss11d gene.

In particular embodiments, a humanized Tmprss11d gene contains coding exons 1-2 of an endogenous rodent Tmprss11d gene, and coding exon 3 through coding exon 13 of a human TMPRSS11D gene.

In another aspect, the invention provides an isolated rodent cell or tissue whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In still another aspect, the invention provides a rodent embryonic stem cell whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In another aspect, a rodent embryo generated from the rodent embryonic stem cell disclosed herein is also provided.

In one aspect, the invention provides a nucleic acid vector suitable for use in humanizing an endogenous Tmprss gene in a rodent. In some embodiments, the nucleic acid vector includes a human Tmprss nucleic acid sequence (e.g., a human genomic DNA encoding the ectodomain of a human TMPRSS protein), flanked by a 5' homology arm and a 3' homology arm. The 5' and 3' homology arms are nucleic acid sequences that are placed at 5' and 3', respectively, to the human Tmprss nucleic acid sequence and are homologous to genomic DNA sequences at an endogenous Tmprss locus in a rodent that flank a rodent genomic DNA encoding the ectodomain of a cognate rodent Tmprss protein. Thus, the 5' and 3' homology arms are capable of mediating homologous recombination and replacement of the rodent genomic DNA encoding the ectodomain of the cognate rodent Tmprss protein with the human Tmprss nucleic acid sequence to form a humanized Tmprss gene as described herein.

In a further aspect, the invention is directed to a method of providing a rodent whose genome contains a humanized Tmprss gene. The method includes modifying the genome of a rodent to replace a genomic sequence of an endogenous rodent Tmprss gene with a genomic sequence of a cognate human TMPRSS gene to form a humanized Tmprss gene.

In some embodiments, the invention provides a method of making a rodent (such as a mouse or a rat) having a humanized Tmprss gene, the method including the steps of (a) inserting a genomic fragment into an endogenous rodent Tmprss locus in a rodent embryonic stem cell, wherein the genomic fragment contains a nucleotide sequence of a cognate human TMPRSS gene, thereby forming a humanized Tmprss gene (such as those described herein); (b) obtaining a rodent embryonic stem cell comprising the humanized Tmprss gene of (a); and (c) creating a rodent using the rodent embryonic stem cell of (b).

In some embodiments, the humanized Tmprss gene is selected from the group consisting of a humanized Tmprss2 gene, a humanized Tmprss4 gene, and a humanized Tmprss11d gene. In various embodiments, the humanized Tmprss gene encodes a humanized Tmprss protein that contains an ectodomain substantially identical (e.g., at least 90%, 95%, 98%, 99% or 100% identical in sequence) to the ectodomain of the human TMPRSS protein encoded by the human TMPRSS gene used for humanization. In specific embodiments, the humanized Tmprss protein contains the ectodomain of a human TMPRSS protein selected from the group consisting of a human TMPRSS2 protein, a human TMPRSS4 protein, and a human TMPRSS11D protein. In specific embodiments, the humanized Tmprss protein further contains a cytoplasmic and transmembrane portion that is substantially identical with the cytoplasmic and transmembrane portion of the rodent Tmprss protein encoded by the endogenous rodent Tmprss gene being humanized.

In another aspect, the invention provides a method of using a rodent disclosed herein to assess the therapeutic efficacy of a compound (e.g., candidate inhibitors that specifically target a human TMPRSS protein) in treating influenza virus infection. The method can include the steps of providing a rodent described herein, administering an influenza virus and a candidate compound to the rodent; and monitoring the presence and severity of influenza virus infection in the rodent to determine the therapeutic efficacy of the drug candidate.

In some embodiments, the influenza virus is administered to the rodent before the compound. In other embodiments, the influenza virus is administered to the rodent after the compound.

In some embodiments, the candidate compound is an antibody or antigen-binding fragment thereof specific for a human TMPRSS protein. In specific embodiments, the candidate compound is an antibody or antigen-binding fragment thereof specific for a human TMPRSS protein selected from the group consisting of a human TMPRSS2 protein, a human TMPRSS4 protein, and a human TMPRSS11D protein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Drawings included herein, which are composed of the following Figures, are for illustration purposes only and not for limitation.

FIGS. 1A-1D. Exemplary strategy for humanization of mouse Tmprss2.

FIG. 1A shows a diagram, not to scale, of the genomic organization of mouse Tmprss2 and human TMPRSS2 genes. Exons are represented by thin bars placed across the genomic sequences, with the first coding exon for both genes indicated by the start codon "ATG" above the exon, and the last coding exon indicated by the "Stop" codon above the exon. A mouse genomic fragment of about 25,291 bp to be deleted and a human genomic fragment of about 25,091 bp to be inserted are indicated. Locations of probes used in an assay described in Example 1 are indicated. TM: transmembrane domain; SRCR: scavenger receptor cysteine-rich like domain; LDLRa: low density lipoprotein receptor class A.

FIG. 1B illustrates, not to scale, an exemplary modified BAC vector for humanization of an endogenous mouse Tmprss2 gene, along with the junction sequences (SEQ ID NOS: 22, 23 and 24).

FIG. 1C illustrates, not to scale, a humanized Tmprss2 allele after the neomycin cassette has been deleted, along with the junction sequences (SEQ ID NOS: 22 and 25), FIG. 1D sets forth a sequence alignment of a human TMPRSS2 protein (SEQ ID NO: 4), a mouse Tmprss2 protein (SEQ ID NO: 2), and a humanized Tmprss2 protein ("7010 mutant pro") (SEQ ID NO: 7).

FIGS. 2A-2D, Exemplary strategy for humanization of mouse Tmprss4.

FIG. 2A shows a diagram, not to scale, of the genomic organization of mouse Tmprss4 and human TMPRSS4 genes. Exons are represented by thin bars placed across the genomic sequences, with the first exon (also the first coding exon) for both genes indicated by the start codon "ATG" above the exon, and the last coding exon indicated by the "Stop" codon above the exon. The mouse genomic fragment of about 11,074 bp to be deleted and the human genomic fragment of about 14,963 bp to be inserted are indicated. Locations of probes used in an assay described in Example 2 are indicated. TM: transmembrane domain; SRCR: scavenger receptor cysteine-rich like domain; LDLRa: low density lipoprotein receptor class A.

FIG. 2B illustrates, not to scale, an exemplary modified BAC vector for humanization of an endogenous mouse Tmprss4 gene, along with the junction sequences (SEQ ID NOS: 38, 39 and 40).

FIG. 2C illustrates, not to scale, a humanized Tmprss4 allele after the neomycin cassette has been deleted, along with the junction sequences (SEQ ID NOS: 41 and 40).

FIG. 2D sets forth a sequence alignment of a human TMPRSS4 protein (SEQ ID NO: 11), a mouse Tmprss4 protein (SEQ ID NO: 9), and a humanized Tmprss4 protein ("7224 mutant pro") (SEQ ID NO: 14).

FIG. 3A shows a diagram, not to scale, of the genomic organization of mouse Tmprss11d and human TMPRSS11D genes. Exons are represented by thin bars placed across the genomic sequences, with the first exon (also the first codon exon) for both genes indicated by the start codon "ATG" above the exon, and the last coding exon indicated by the "Stop" codon above the exon. A mouse genomic fragment of about 35,667 bp to be deleted and a human genomic fragment of about 33,927 bp to be inserted are indicated. Locations of probes used in an assay described in Example 3 are indicated. TM: transmembrane domain; SEA: domain found in sea urchin sperm protein, enterokinase and agrin.

FIG. 3B illustrates, not to scale, an exemplary modified BAC vector for humanization of an endogenous mouse Tmprss11d gene, along with the junction sequences (SEQ ID NOS: 57, 58 and 59).

FIG. 3C illustrates, not to scale, a humanized Tmprss11 allele after the neomycin cassette has been deleted, along with the junction sequences (SEQ ID NOS: 57 and 60).

FIG. 3D sets forth a sequence alignment of a human TMPRSS11D protein (SEQ ID NO: 18), a mouse Tmprss11d protein (SEQ ID NO: 16), and a humanized Tmprss11d protein ("7226 mutant pro") (SEQ ID NO: 21).

DETAILED DESCRIPTION OF CERTAIN EMBODIMENTS

Figure 1A:
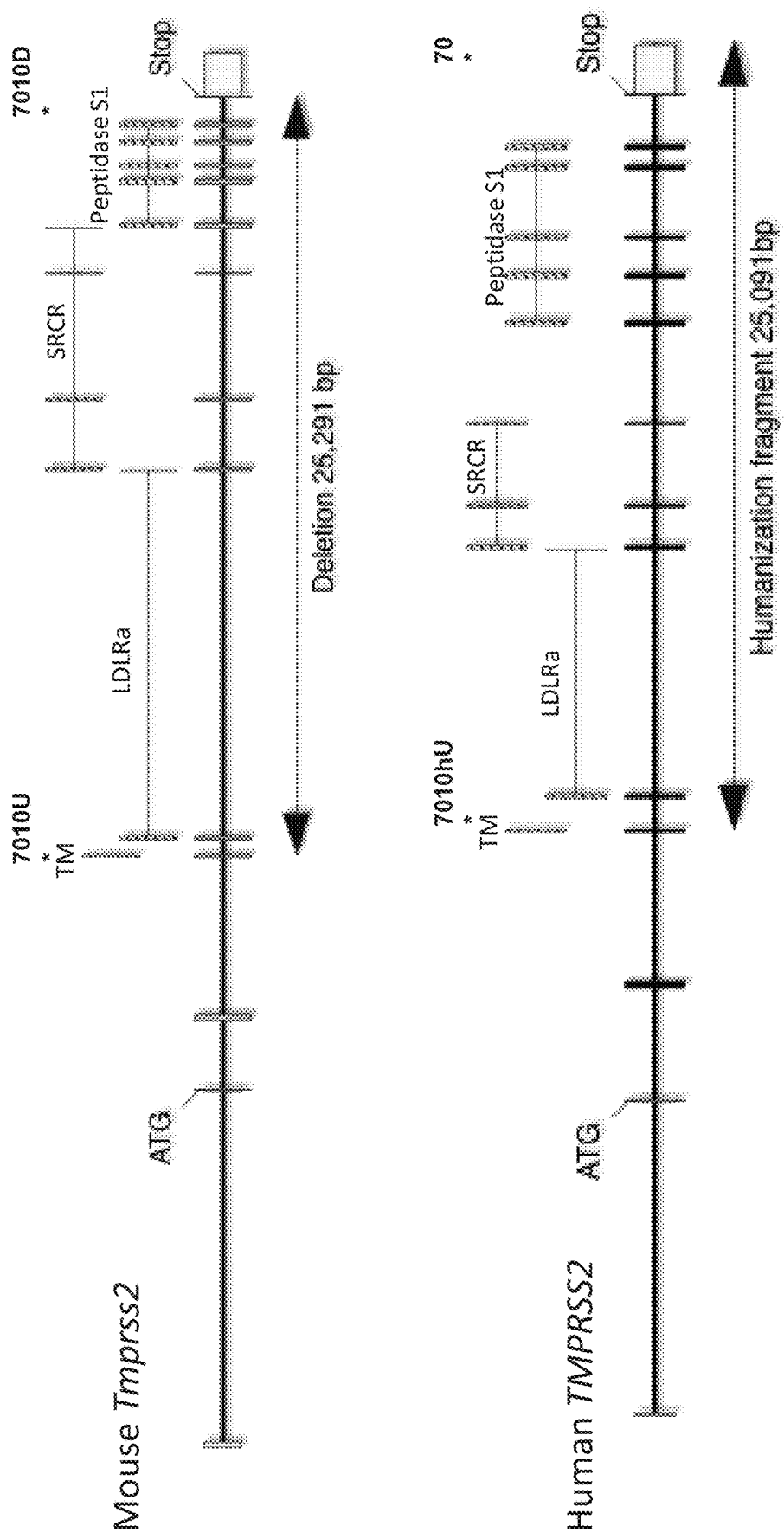

The present invention relates to genetically modified rodents (e.g., mice and rats) having a humanized gene encoding a type II transmembrane serine protease (or "Tmprss", for transmembrane protease/serine). The genetically modified rodents are suitable for use in screening for candidate compounds that specifically target a human TMPRSS molecule for the treatment and prevention of diseases such as influenza virus infection. Accordingly, the present invention provides genetically modified rodents having a humanized Tmprss gene, cells and tissues isolated from the genetically modified rodents, methods and compositions for making the genetically modified rodents, and use of the genetically modified rodents for screening and testing therapeutic compounds. The various embodiments of the present invention are further described below.

Type II Transmembrane Serine Proteases ("Tmprss")

Type II transmembrane serine proteases; also referred to herein as "Tmprss" for non-human molecules or "TMPRSS" for human molecules ("transmembrane protease/serine"), are a family of proteins characterized by an N-terminal transmembrane domain and a C-terminal extracellular serine protease domain. At least 18 members have been identified in the family, which are grouped into four subfamilies (Bugge et al. (2009), supra). All members share several common structural features that define the family, including (i) a short N-terminal cytoplasmic domain, (ii) a transmembrane domain, and (iii) an ectodomain that contains a protease domain and a stem region that links the transmembrane domain with the protease domain. The stem region contains a combination of modular structural domains of six different types: a SEA (sea urchin sperm protein/enteropeptidase/agrin) domain, a group A scavenger receptor domain, a LDLA (low-density lipoprotein receptor class A) domain, a CUB (Cls/Clr urchin embryonic growth factor, hone morphogenetic protein-1) domain, a MAM (meprin/A5 antigen/receptor protein phosphatase mu) domain, and a frizzled domain. See review by Bugge et al. (2009), supra. For example, TMPRSS2 and TMPRSS4, both of which belong to the hepsin/TMPRSS subfamily, have a group A scavenger receptor domain, preceded by a single LDLA domain in the stem region. TMPRSS11D, also known as "HAT" for human airway trypsin-like protease that belongs to the HAT/DESC subfamily, has a single SEA domain. See FIG. 1 of Bugge et al. (2009), supra.

Type II transmembrane serine proteases are produced initially as inactive proenzymes that require activation by cleavage following a basic amino acid residue in a consensus activation motif preceding the protease domain. Some of the activated proteases remain membrane bound as a result of a disulfide bond between the prodomain and the protease domain. The extracellular domains are considered to be critical for cellular localization, activation, inhibition, and/or substrate specificity of these proteases (Bugge et al. (2009), supra; Szabo et al., *Int. J. Biochem. Cell Biol.* 40: 1297-1316 (2008)).

Various biochemical and pathophysiological information has been documented for members of the type ft transmembrane serine proteases. TMPRSS2, TMPRSS4 and TMPRSS11D have been shown in vitro to cleave influenza A hemagglutinin (HA), which is the first essential step in the viral life cycle. Genetically modified rodent animals having a humanized Tmprss gene disclosed herein provide useful in vivo systems that allow for a thorough understanding of the biological functions of the TMPRSS molecules, as well as for screening therapeutic compounds that specifically target human TMPRSS molecules.

Exemplary Tmprss sequences, including mouse, human and humanized Tmprss nucleic acid and protein sequences, are provided in this application and are summarized in the following table. Primer and probe sequences used in the assays described in the examples section, and insertion junction sequences of exemplary humanized Tmprss alleles, are also included in the table.

Summary Description of Sequences

| SEQ ID NO | Description | Features |
|---|---|---|
| 1 | *Mus musculus* Tmprss2, mRNA, NM_015775.2 | Length: 3175 bp<br>CDS: 231-1703<br>Exons: 1-177; 178-245 (second exon, and first coding exon); 246-465; 466-552; 553-672; 673-799; 800-910; 911-954; 955-1123; 1124-1299; 1300-1395; 1396-1538; 1539-1691; 1692-3161. |
| 2 | *Mus musculus* Tmprss2, protein | Length: 490 aa |
| 3 | *Homo sapiens* TMPRSS2, transcript, variant 2, mRNA, NM_005656.3 | Length: 3212 bp<br>CDS: 135-1613<br>Exons: 1-78; 79-149 (second exon, and first coding exon); 150-372; 373-459; 460-579; 580-706; 707-817; 818-861; 862-1033; 1034-1209; 1210-1305; 1306-1448; 1449-1601; 1602-3204, |
| 4 | *Homo sapiens* TMPRSS2, transcript variant 2, protein | Length: 492 aa<br>Ectodomain: begins at W106. |
| 5 | Humanization Tmprss2 genomic fragment | Length: 27,947 bp<br>1-84: mouse sequence<br>85-25175: human sequence (total 25091 bp)<br>25176-27866: XhoI-LoxP-Cassette-loxP-ICeUI-NheI (total 2691 bp)<br>27867-27947: mouse sequence |
| 6 | Humanization Tmprss2 genomic fragment with cassette deleted | Length: 25,333 bp<br>1-84: mouse sequence<br>85-25175: human sequence (total 25091 bp)<br>25176-25252: XhoI-loxP-ICeUI-NheI (77 bp)<br>25253-25333: mouse sequence |
| 7 | Humanized Tmprss2 protein | Length: 491 aa |
| 8 | *Mus musculus* Tmprss4, mRNA, NM_145403.2 | Length: 2267 bp<br>CDS: 289-1596<br>Exons: 1-291 (first exon and first coding exon); 292-325; 326-439; 440-592; 593-722; 723-824; 825-865; 866-1025; 1026-1192; 1193-1291; 1292-1434; 1435-1584; 1585-2267. |
| 9 | *Mus musculus* Tmprss4, protein | Length: 435 aa |
| 10 | *Homo sapiens* TMPRSS4, transcript variant 4, mRNA, NM_001173551.1 | Length: 3543 bp<br>CDS: 292-1599<br>Exons: 1-294 (first exon and first coding exon); 295-328; 329-442; 443-595; 596-725; 726-827; 828-868; 869-1028; 1029-1195; 1196-1294; 1295-1437; 1438-1587; 1588-3529. |
| 11 | *Homo sapiens* TMPRSS4, transcript variant 4, protein | Length: 437 aa<br>Ectodomain: begins at K54. |
| 12 | Humanization Tmprss4 genomic fragment containing cassette | Length: 20,078 bp<br>1-18: mouse sequence<br>19-5014: SalI/XhoI-LoxP-hUbi-EM7-Neo-Pm-Cre-loxP-ICeuI-NheI (total 4996 bp)<br>5015-19977: HUMAN sequence (total 14963 bp)<br>19978-20078: mouse sequence |
| 13 | Humanization Tmprss4 genomic fragment with cassette deleted | Length: 15159 bp<br>1-18: mouse sequence<br>19-95: SalI/XhoI-LoxP-ICeuI-NheI (total 77 bp)<br>96-15058: HUMAN sequence (total 14963 bp)<br>15059-15159: mouse sequence |
| 14 | Humanized Tmprss4 Protein | Length: 435 aa |
| 15 | *Mus musculus* Tmprss11d, mRNA, NM_145561.2 | Length: 2046 bp<br>CDS: 36-1289<br>Exons: 1-43 (first exon and first coding exon), 44-165, 166-284; 285-352; 353-507; 508-546; 547-724; 725-984; 985-1127; 1128-2046. |
| 16 | *Mus musculus* Tmprss11d, protein | Length: 417 aa |
| 17 | *Homo sapiens* TMPRSS11D, mRNA, NM_004262.2 | Length: 2800 bp<br>CDS: 66-1322<br>Exons: 1-73 (first exon and first coding exon); 74-195; 196-314; 315-382; 383-540; 541-579; 580-757; 758-1017; 1018-1160; 1161-2783. |

-continued

| SEQ ID NO | Description | Features |
|---|---|---|
| 18 | Homo sapiens TMPRSS11D, protein | Length: 418 aa Ectodomain begins at A42. |
| 19 | Humanization Tmprss11d genomic fragment containing cassette | Length: 38,992 1-19: mouse sequence 20-33,946: HUMAN sequence (total 33,927 bp) 33,947-38,942: XhoI-LoxP-hUbi-EM7-Neo-Pm-Cre-loxP-ICeuI-NheI (total 4,996 bp) 38,943-38,992: mouse sequence |
| 20 | Humanization Tmprss11d genomic fragment with cassette deleted | Length: 34,073 bp 1-19: mouse sequence 20-33,946: HUMAN sequence (total 33,927 bp) 33,947-34,023: XhoI-LoxP-ICeuI-NheI (77 bp) 34,024-34,073: mouse sequence |
| 21 | Humanized Tmprss11d Protein | 418 aa |
| 22 | 5' mouse/5' human junction sequence for Tmprss2 humanization | 5' mouse//5' human |
| 23 | 3' human/cassette junction sequence for Tmprss2 humanization | Human//XhoI//loxP Cassette |
| 24 | Cassette/3' mouse junction sequence for Tmprss2 humanization | Cassette (loxP)/ICEUI//NheI//mouse |
| 25 | 3' human/loxP/3' mouse junction for Tmprss2 humanization | 3' human//XhoI//(loxP)/ICEUI//NheI//3' mouse |
| 26-37 | Primers and probes for loss of allele and gain of allele assays for Tmprss2 humanization | Table 1 |
| 38 | 5' mouse/Cassette junction sequence for Tmprss4 humanization | 5' mouse//SalI-XhoI//(loxP) Cassette |
| 39 | Cassette/5' human junction sequence for Tmprss4 humanization | Cassette (loxP)/ICEUI//NheI//5' human |
| 40 | 3' human/3' mouse junction sequence for Tmprss4 humanization | 3' human/3' mouse |
| 41 | 5' mouse/loxP/5' human junction for Tmprss4 humanization | 5' mouse//SalI/XhoI//(loxP)/ICEUI//NheI//5' human |
| 42-56 | Primers and probes for loss of allele and gain of allele assays for Tmprss4 humanization | Table 2 |
| 57 | 5' mouse/5' human junction sequence for Tmprss11d humanization | 5' mouse//5' human |
| 58 | 3' human/cassette junction sequence for Tmprss11d humanization | 3' human//XhoI//(loxP) Cassette |
| 59 | Cassette/3' mouse junction sequence for Tmprss11d humanization | Cassette (loxP)/ICEUI//NheI//3' mouse |
| 60 | 3' human/loxP/3' mouse junction for Tmprss11d humanization | 3' human//XhoI//(loxP)/ICEUI//NheI//3' mouse |
| 61-72 | Primers and probes for loss of allele and gain of allele assays for Tmprss11d humanization | Table 3 |

Humanized Tmprss Rodent Animals

In one aspect, the present invention provides rodent animals that contain in the germline a humanized Tmprss gene encoding a humanized Tmprss protein.

The term "humanized", when used in the context of nucleic acids or proteins, refers to nucleic acids or proteins whose structures (i.e., nucleotide or amino acid sequences) include portions that correspond substantially or identically with structures of a particular gene or protein found in nature in a rodent animal, and also include portions that differ from that found in the relevant rodent gene or protein and instead correspond more closely or identically with structures found in a corresponding human gene or protein. A rodent containing a humanized gene or expressing a humanized protein is a "humanized" rodent.

In some embodiments, a rodent of the present invention is selected from a mouse, a rat, and a hamster, in some embodiments, a rodent of the present invention is selected from the superfamily Muroidea. In some embodiments, a genetically modified rodent of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae.

In some embodiments, the rodent disclosed herein contains a humanized Tmprss gene in the genome that includes a nucleotide sequence of an endogenous rodent Tmprss gene and a nucleotide sequence of a human TMPRSS gene, wherein the nucleotide sequence of the endogenous rodent Tmprss gene and the nucleotide sequence of the human TMPRSS gene are operably linked to each other such that the humanized Tmprss gene encodes a Tmprss protein and is under control of a 5' regulatory element(s), such as the promoter and/or enhancer(s), of the endogenous rodent Tmprss gene.

The present invention is particularly directed to like-for-like humanization; in other words, a nucleotide sequence of an endogenous rodent Tmprss gene is operably linked to a nucleotide sequence of a cognate human TMPRSS gene to form a humanized gene. For example, in some embodiments, a nucleotide sequence of an endogenous rodent Tmprss2 gene is operably linked to a nucleotide sequence of a human TMPRSS2 gene to form a humanized Tmprss2 gene. In other embodiments, a nucleotide sequence of an endogenous rodent Tmprss4 gene is operably linked to a nucleotide sequence of a human TMPRSS4 gene to form a humanized Tmprss4 gene. In still other embodiments, a nucleotide sequence of an endogenous rodent Tmprss11d gene is operably linked to a nucleotide sequence of a human TMPRSS11D gene to form a humanized Tmprss11d gene.

In some embodiments, a genetically modified rodent of this invention contains a humanized Tmprss gene in its genome, wherein the humanized Tmprss gene encodes a humanized Tmprss protein that contains an ectodomain that is substantially identical with the ectodomain of a human TMPRSS protein. The term "ectodomain" refers to the portion of a transmembrane protein that extends outside of the cell membrane, i.e., the extracellular portion of a transmembrane protein. The ectodomain of a TMPRSS molecule includes a protease domain and a stem region that links the transmembrane domain with the protease domain. By an ectodotnain or polypeptide that is "substantially identical with the ectodomain of a human TMPRSS protein", it is meant in some embodiments, a polypeptide that is at least 85%, 90%, 95%, 95?/k, 99% or 100% identical in sequence with the ectodomain of a human TMPRSS protein; in some embodiments, a polypeptide that differs from the ectodomain of a human TMPRSS protein by not more than 10, 9, 8, 7, 6, 5, 4, 3, 2 or 1 amino acid(s); in some embodiments, a polypeptide that differs from the ectodomain of a human TMPRSS protein only at the N- or C-terminus of the ectodomain, e.g., by lacking amino acids or having additional amino acids at the at the N- or C-terminus of the ectodomain; and in some embodiments, a polypeptide that is substantially the ectodomain of a human TMPRSS protein. By "substantially the ectodomain" of a human TMPRSS protein, it is meant a polypeptide that is identical with the ectodomain, or differs from the ectodomain by lacking 1-5 (i.e., 1, 2, 3, 4 or 5) amino acids or having additional 1-5 amino acids at the N- or C-terminus.

In some embodiments, the humanized Tmprss gene encodes a humanized Tmprss protein that further contains a cytoplasmic and transmembrane portion that is substantially identical with the cytoplasmic and transmembrane portion of an endogenous rodent Tmprss protein. By a cytoplasmic and transmembrane portion or polypeptide that is "substantially identical with the cytoplasmic and transmembrane portion of an endogenous rodent Tmprss protein", it is meant in some embodiments, a polypeptide that is at least 85%, 90%, 95%, 95%, 99% or 100% identical in sequence with the cytoplasmic and transmembrane portion of an endogenous rodent Tmprss protein; in some embodiments, a polypeptide that differs from the cytoplasmic and transmembrane portion of an endogenous rodent Tmprss protein by not more than 10, 9, 8, 7, 6, 5, 4, 3, 2 or 1 amino acid(s); in some embodiments, a polypeptide that differs from the cytoplasmic and transmembrane portion of an endogenous rodent Tmprss protein only at the C-terminus, e.g., by lacking amino acids or having additional amino acids at the at the C-terminus of the transmembrane domain; and in some embodiments, a polypeptide composed of the cytoplasmic domain and substantially the transmembrane domain of an endogenous rodent Tmprss protein. By "substantially the transmembrane domain" of an endogenous rodent Tmprss protein, it is meant a polypeptide that is identical with the transmembrane domain, or differs from the transmembrane domain by lacking 1-5 amino acids or having additional 1-5 amino acids at the C-terminus.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical to the ectodomain of the human TMPRSS protein encoded by the human TMPRSS gene. In certain embodiments, the nucleotide sequence of a cognate human TMPRSS gene in a humanized Tmprss gene encodes the ectodomain of the human TMPRSS protein encoded by the human TMPRSS gene.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of an endogenous rodent Tmprss gene encodes a polypeptide substantially identical to the cytoplasmic and transmembrane portion of the endogenous rodent Tmprss protein encoded by the rodent Tmprss gene. In specific embodiments, the nucleotide sequence of an endogenous rodent Tmprss gene present in a humanized Tmprss gene encodes the cytoplasmic and transmembrane domains of the endogenous rodent Tmprss protein encoded by the endogenous rodent Tmprss gene.

In some embodiments, a humanized Tmprss gene results from a replacement of a nucleotide sequence of an endogenous rodent Tmprss gene at an endogenous rodent Tmprss locus with a nucleotide sequence of a cognate human TMPRSS gene.

In some embodiments, a contiguous genomic sequence of a rodent Tmprss gene at an endogenous rodent Tmprss locus has been replaced with a contiguous genomic sequence of a cognate human TMPRSS gene to form a humanized Tmprss gene.

In specific embodiments, a contiguous genomic sequence of a human TMPRSS gene inserted into an endogenous rodent Tmprss gene includes exons, in full or in part, of a human TMPRSS gene, that encode an ectodomain that is substantially identical with the ectodomain of the human TMPRSS protein encoded by the human TMPRSS gene.

In certain embodiments, the genomic sequence of an endogenous rodent Tmprss gene that remains at an endogenous rodent Tmprss locus after the humanization replacement and is operably linked to the inserted contiguous human TMPRSS genomic sequence encodes a cytoplasmic and transmembrane portion that is substantially identical with the cytoplasmic and transmembrane portion of the endogenous rodent Tmprss protein encoded by the endogenous rodent Tmprss gene.

In circumstances where an endogenous Tmprss protein and a human TMPRSS protein share common amino acids near the junction between the transmembrane domain and the ectodomain, it may not be necessary to insert a human TMPRSS genomic sequence that encodes precisely the ectodomain of the human TMPRSS protein. It is possible to insert a slightly longer or shorter genomic sequence of a human TMPRSS gene, which encodes substantially the ectodomain of the human TMPRSS protein, in operable linkage to a genomic sequence of an endogenous rodent Tmprss gene that encodes the cytoplasmic domain and substantially the transmembrane domain of the endogenous rodent Tmprss protein, such that the humanized Tmprss protein encoded by the resulting humanized Tmprss gene includes an ectodomain that is identical with the ectodomain of the human TMPRSS protein and a transmembrane domain that is identical with the transmembrane domain of the endogenous rodent Tmprss protein.

In some embodiments, the nucleotide sequence of a human TMPRSS gene included in a humanized Tmprss gene also includes the 3' untranslated region ("UTR") of the human TMPRSS gene. In certain embodiments, in addition to the 3' UTR of a human TMPRSS gene, a humanized Tmprss gene also includes an additional human genomic sequence from the human TMPRSS gene locus, following the human TMPRSS3' UTR. The additional human genomic sequence can consist of at least 10-200 bp, e.g., 50 bp, 75 bp, 100 bp, 125 bp, 150 bp, 175 bp, 200 bp, or more, found in the human TMPRSS gene locus immediately downstream of the 3' UTR of the human TMPRSS gene. In other embodiments, the nucleotide sequence of a human TMPRSS gene present in a humanized Tmprss gene does not include a human 3' UTR; instead, the 3' UTR of an endogenous rodent Tmprss gene is included and follows immediately the stop codon of the humanized Tmprss gene. For example, a humanized Tmprss gene can include a nucleotide sequence of an endogenous rodent Tmprss gene containing exon sequences encoding the cytoplasmic and transmembrane domains of the endogenous rodent Tmprss protein, followed by a nucleotide sequence of a human TMPRSS gene containing exon sequences encoding the ectodomain through the stop codon of the human TMPRSS protein, with the 3' UTR of the endogenous rodent Tmprss gene following immediately after the stop codon.

In some embodiments, a humanized Tmprss gene results in an expression of the encoded humanized Tmprss protein in a rodent. In some embodiments, a humanized Tmprss protein is expressed in a pattern comparable with, or substantially the same as, a counterpart rodent Tmprss protein in a control rodent (e.g., a rodent without the humanized Tmprss gene). In some embodiments, a humanized Tmprss protein is expressed at a level comparable with, or substantially the same as, a counterpart rodent Tmprss protein in a control rodent (e.g., a rodent without the humanized Tmprss gene). In certain embodiments, a humanized Tmprss protein is expressed and detected at the cell surface. In certain embodiments, a humanized. Tmprss protein or a soluble form (e.g., a shed ectodomain form) is expressed and detected in serum of a rodent, e.g., at a level comparable with, or substantially the same as, a counterpart rodent Tmprss protein or a soluble form thereof in a control rodent. In the context of comparing a humanized gene or protein in a humanized rodent with an endogenous rodent gene or protein in a control rodent, the term "comparable" means that the molecules or levels being compared may not be identical to one another but are sufficiently similar to permit comparison there between so that conclusions may reasonably be drawn based on differences or similarities observed; and the term "substantially the same" in referring to expression levels means that the levels being compared are not different from one another by more than 20%, 19%, 18%, 17%, 16%, 15%, 14%, 13%, 17%, 11%, 10%, 9%, 8%, 7%, 6%, 5%, 4%, 3%, 2%, or 1%.

In some embodiments, the present invention further provides an isolated cell or tissue from a rodent animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a rodent embryonic stem whose genome contains a humanized Tmprss gene as described herein. In some embodiments, a rodent embryonic stem cell is a mouse embryonic stem cell. In other embodiments, a rodent embryonic stem cell is a rat embryonic stem cell. A rodent embryonic stem cell containing a humanized Tmprss gene in its genome can be used to make a humanized rodent animal, as further described herein below.

In some embodiments, a rodent provided herein is heterozygous for a humanized Tmprss gene in its genome. In other embodiments, a rodent provided herein is homozygous for a humanized Tmprss gene in its genome.

In certain embodiments, a rodent includes multiple, i.e., two or more, humanized Tmprss genes in its genome. In other words, two or more different endogenous Tmprss loci in a rodent have been humanized using nucleotide sequences of cognate human TMPRSS genes. For example, a rodent has been humanized at two or more of the gene loci selected from: Tmprss2, Tmprss4, and Tmprss11d.

Exemplary humanized Tmprss2 rodents (such as mice), humanized Tmprss4 rodents (such as mice), and humanized Tmprss11d rodents (such as mice) are further described below.

Humanized Tmprss2 Rodents

In some embodiments, this invention provides a rodent whose genome contains a humanized Tmprss2 gene that includes a nucleotide sequence of an endogenous rodent Tmprss2 gene and a nucleotide sequence of a human TMPRSS2 gene, and that is under control of a 5' regulatory element(s), such as the promoter and/or enhancer(s), of the endogenous rodent Tmprss2 gene. Examples of rodents include mice and rats.

In some embodiments, a humanized Tmprss2 gene encodes a humanized Tmprss2 protein that contains an ectodomain that is substantially identical with the ectodomain of a human TMPRSS2 protein.

In specific embodiments, the human TMPRSS2 protein has an amino acid sequence having at least 85%, 90%, 95%, 98%, 99% or 100% identity with the amino acid sequence as set forth in SEQ ID NO: 4.

In some embodiments, a humanized Tmprss2 protein contains the C-terminal 387 amino acids of a human TMPRSS2 protein, for example, amino acids 106 to 492 of a human TMPRSS2 protein. In some embodiments, a humanized Tmprss2 protein contains an ectodomain that is substantially identical with the amino acid sequence composed of W106 to G492 of SEQ ID NO: 4. In specific embodiments, a humanized Tmprss2 protein contains an ectodomain having at least 85%, 90%, 95%, 98%, 99% or 100% identity with the amino acid sequence composed of W106 to G492 of SEQ ID NO: 4; an ectodomain that differs from the amino acid sequence composed of W106 to G492 of SEQ ID NO: 4 by not more than 10, 9, 8, 7, 6, 5, 4, 3, 2 or 1 amino acid(s); or an ectodomain that differs from the amino acid sequence composed of W106 to G492 of SEQ ID NO: 4 only at the N- or C-terminus of the ectodomain, e.g., lacking 1-5 amino acids or having additional 1-5 amino acids at the at the N- or C-terminus.

In some embodiments, a humanized Tmprss2 protein further contains a cytoplasmic and transmembrane portion that is substantially identical with the cytoplasmic and transmembrane portion of an endogenous rodent Tmprss2 protein. In some embodiments, a humanized. Tmprss2 protein further includes the transmembrane domain and the cytoplasmic domain of an endogenous rodent Tmprss2 protein.

In specific embodiments, a humanized Tmprss2 protein contains the transmembrane domain and the cytoplasmic domain of an endogenous rodent Tmprss2 protein, and the ectodomain of a human TMPRSS2 protein. In particular embodiments, a humanized Tmprss2 gene encodes a humanized Tmprss2 protein having the amino acid sequence as set forth in SEQ ID NO: 7.

In some embodiments, a humanized Tmprss2 gene results from a replacement of a nucleotide sequence of an endogenous rodent Tmprss2 gene at an endogenous rodent Tmprss2 locus with a nucleotide sequence of a human TMPRSS2 gene.

In some embodiments, a contiguous genomic sequence of an endogenous rodent Tmprss2 gene at an endogenous rodent Tmprss2 locus has been replaced with a contiguous genomic sequence of a human TMPRSS2 gene to form a humanized Tmprss2 gene.

In specific embodiments, the contiguous genomic sequence of a human TMPRSS2 gene inserted into an endogenous rodent Tmprss2 gene includes exon sequences, i.e., exons in full or in part, of a human TMPRSS2 gene, that encode an ectodomain that is substantially identical to the ectodomain of the human TMPRSS2 protein encoded by the human TMPRSS2 gene. In circumstances where an endogenous Tmprss2 protein and a human TMPRSS2 protein share common amino acids near the junction of the transmembrane domain and the ectodomain, it may not be necessary to insert a human TMPRSS2 genomic sequence that encodes precisely the ectodomain of the human TMPRSS2 protein, and it is possible to use a slightly longer or shorter human TMPRSS2 genomic sequence that encodes substantially the ectodomain of a human TMPRSS2 protein in order to make a humanized Tmprss2 protein having an ectodomain that is identical with the ectodomain of the human TMPRSS2 protein.

In specific embodiments, a contiguous genomic sequence of a human TMPRSS2 gene being inserted into an endogenous rodent Tmprss2 gene contains at least coding exon 4 through the stop codon in coding exon 13 of the human TMPRSS2 gene.

In certain embodiments, a contiguous genomic sequence of a human TMPRSS2 gene being inserted into an endogenous rodent Tmprss2 gene contains intron 3 and coding exon 4 through the stop codon in coding exon 13 of the human TMPRSS2 gene. In particular embodiments, a contiguous genomic sequence of a human TMPRSS2 gene being inserted into an endogenous rodent Tmprss2 gene contains a 3' portion of coding exon 3, intron 3, and coding exon 4 through the stop codon in coding exon 13 of the human TMPRSS2 gene. In specific embodiments, the 3' portion of coding exon 3 of a human TMPRSS2 gene included in the humanization is about 5-10 base pair in length, i.e., about 5, 6, 7, 8, 9 or 10 base pair of the 3' end of coding exon 3.

In some embodiments, a contiguous genomic sequence of a human TMPRSS2 gene being inserted into an endogenous rodent Tmprss2 gene also contains the 3' UTR of the human TMPRSS2 gene. In specific embodiments, the entire coding exon 13 of a human TMPRSS2 gene is included in the contiguous human TMPRSS2 genomic sequence for humanization, which includes the 3' UTR of the human TMPRSS2 gene. In particular embodiments, a contiguous genomic sequence of a human TMPRSS2 gene includes an additional human genomic sequence downstream of the 3' UTR of the human TMPRSS2 gene. The additional human genomic sequence can be a sequence of at least 10-200 bp, or at least 10, 20, 30, 40, 50, 75, 100, 125, 150, 175, or 200 bp, that is found immediately downstream of the 3' UTR of the human TMPRSS2 gene at a human TMPRSS2 locus.

In some embodiments, the nucleotide sequence of an endogenous rodent Tmprss2 gene remaining at a humanized Tmprss2 locus encodes a polypeptide that is substantially identical with the cytoplasmic and transmembrane portion of the endogenous rodent Tmprss2 protein. In circumstances where an endogenous Tmprss2 protein and a human TMPRSS2 protein share common amino acids near the junction of the transmembrane domain and the ectodomain, it may not be necessary to maintain the endogenous rodent Tmprss2 genomic sequence that encodes precisely the transmembrane domain of the endogenous rodent Tmprss2 protein, and it is possible to maintain a slightly longer or shorter rodent Tmprss2 genomic sequence that encodes substantially the transmembrane domain of the endogenous rodent Tmprss2 protein in the humanization replacement in order to encode a humanized Tmprss2 protein having a transmembrane domain that is identical with the transmembrane of the endogenous rodent Tmprss2 protein. In some embodiments, the nucleotide sequence of an endogenous rodent Tmprss2 gene remaining at a humanized Tmprss2 locus includes exons 1-2 and a 5' portion of coding exon 3 of an endogenous rodent Tmprss2 gene, wherein the 5' portion of coding exon 3 is a substantial portion of codon exon 3, e.g., the entire coding exon 3 except 5-10 base pairs at the 3' end of coding exon 3.

In specific embodiments, a humanized Tmprss2 gene contains coding exons 1-2 and a 5' portion of coding exon 3 of an endogenous rodent Tmprss2 gene, and a 3' portion of coding exon 3 and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein, and an ectodomain that is substantially identical with the ectodomain of the human TMPRSS2 protein. In certain embodiments, the humanized Tmprss2 gene encodes a humanized Tmprss2 protein that contains the cytoplasmic domain and the transmembrane domain of the rodent Tmprss2 protein encoded by an endogenous rodent Tmprss2 gene, and the ectodomain of the human TMPRSS2 protein encoded by a human TMPRSS2 gene. In particular embodiments, a humanized Tmprss2 gene encodes a humanized Tmprss2 protein having the amino acid sequence as set forth in SEQ ID NO: 7.

In some embodiments, the exons and introns of a human TMPRSS2 gene and a rodent Tmprss2 gene used in the humanization are those found in SEQ ID NOS: 1, 3 and 5-6.

In some embodiments, a humanized Tmprss2 gene results in an expression of the encoded humanized Tmprss2 protein in a rodent. In some embodiments, a humanized Tmprss2 protein is expressed in a pattern comparable with, or substantially the same as, a counterpart rodent Tmprss2 protein in a control rodent (e.g., a rodent without the humanized Tmprss2 gene). In some embodiments, a humanized Tmprss2 protein is expressed at a level comparable with, or substantially the same as, a counterpart rodent Tmprss2 protein in a control rodent (e.g., a rodent without the humanized Tmprss2 gene). In certain embodiments, a humanized. Tmprss2 protein is expressed and detected at the cell surface. In certain embodiments, a humanized Tmprss2 protein or a soluble form (e.g., a shed ectodomain form) is expressed and detected in serum of a rodent, e.g., at a level comparable with, or substantially the same as, a counterpart rodent Tmprss2 protein or a soluble form thereof in a control rodent.

Humanized Tmprss4 Rodents

In some embodiments, this invention provides a rodent whose genome contains a humanized Tmprss4 gene that includes a nucleotide sequence of an endogenous rodent Tmprss4 gene and a nucleotide sequence of a human TMPRSS4 gene, and that is under control of a 5' regulatory element(s), such as the promoter and/or an enhancer(s), of the endogenous rodent Tmprss4 gene. Examples of rodents include mice and rats.

In some embodiments, a humanized Tmprss4 gene encodes a humanized Tmprss4 protein that contains an ectodomain that is substantially identical with the ectodomain of a human TMPRSS4 protein. In specific embodiments, the human TMPRSS4 protein has an amino acid sequence having at least 85%, 90%, 95%, 98%, 99% or 100% identity with the amino acid sequence as set forth in SEQ ID NO: 11.

In some embodiments, a humanized Tmprss4 protein contains the C-terminal 384 amino acids of a human TMPRSS4 protein, for example, amino acids 54 to 437 of a human TMPRSS4 protein. In some embodiments, a humanized Tmprss4 protein contains an ectodomain that is substantially identical with the amino acid sequence composed of K54 to L437 of SEQ ID NO: 11. In specific embodiments, a humanized Tmprss4 protein contains an ectodomain having at least 85%, 90%, 95%, 98%, 99% or 100% identity with the amino acid sequence composed of K54 to L437 of SEQ ID NO: 11; an ectodotnain that differs from the amino acid sequence composed of K54 to L437 of SEQ II) NO: 11 by not more than 10, 9, 8, 7, 6, 5, 4, 3, 2 or 1 amino acid(s); or an ectodomain that differs from the amino acid sequence composed of K54 to L437 of SEQ ID NO: 11 only at the N- or C-terminus of the ectodomain, e.g., lacking 1-5 amino acids or having additional 1-5 amino acids at the N- or C-terminus.

In some embodiments, a humanized Tmprss4 protein further contains a cytoplasmic and transmembrane portion that is substantially identical with the cytoplasmic and transmembrane portion of an endogenous rodent Tmprss4 protein. In some embodiments, a humanized Tmprss4 protein further includes the transmembrane domain and the cytoplasmic domain of an endogenous rodent Tmprss4 protein.

In specific embodiments, a humanized Tmprss4 protein contains the transmembrane domain and the cytoplasmic domain of an endogenous rodent Tmprss4 protein, and the ectodomain of a human TMPRSS4 protein. In particular embodiments, a humanized Tmprss4 gene encodes a humanized Tmprss4 protein having the amino acid sequence as set forth in SEQ ID NO: 14.

In some embodiments, a humanized Tmprss4 gene results from a replacement of a nucleotide sequence of an endogenous rodent Tmprss4 gene at an endogenous rodent Tmprss4 locus with a nucleotide sequence of a human TMPRSS4 gene.

In some embodiments, a contiguous genomic sequence of an endogenous rodent Tmprss4 gene at an endogenous rodent Tmprss4 locus has been replaced with a contiguous genomic sequence of a human TMPRSS4 gene to form a humanized Tmprss4 gene.

In specific embodiments, the contiguous genomic sequence of a human TMPRSS4 gene inserted into an endogenous rodent Tmprss4 gene includes exon sequences, i.e., exons in full or in part, of a human TMPRSS4 gene that encode an ectodomain that is substantially identical with the ectodomain of the human TMPRSS4 protein encoded by the human TMPRSS4 gene. In circumstances where an endogenous Tmprss4 protein and a human TMPRSS4 protein share common amino acids near the junction of the transmembrane domain and the ectodomain, it may not be necessary to insert a human TMPRSS4 genomic sequence that encodes precisely the ectodomain of the human TMPRSS4 protein, and it is possible to use a slightly longer or shorter human TMPRSS4 genomic sequence that encodes substantially the ectodomain of a human TMPRSS4 protein in order to make a humanized Tmprss4 protein having an ectodomain that is identical with the ectodomain of the human TMPRSS4 protein.

In specific embodiments, a contiguous genomic sequence of a human TMPRSS4 gene being inserted into an endogenous rodent Tmprss4 gene contains at least coding exon 4 through the stop codon in coding exon 13 of the human TMPRSS4 gene.

In certain embodiments, a contiguous genomic sequence of a human TMPRSS4 gene being inserted into an endogenous rodent Tmprss4 gene includes a 3' portion of intron 3, and coding exon 4 through the stop codon in coding exon 13 of a human TMPRSS4 gene. In specific embodiments, the 3' portion of intron 3 of a human TMPRSS4 gene included in the humanization is about 140-160 base pair in length, i.e., about 140, 145, 150, 155, 160 base pair of the 3' end of intron 3.

In some embodiments, a contiguous genomic sequence of a human TMPRSS4 gene being inserted into an endogenous rodent Tmprss4 gene contains the 3' UTR of the human TMPRSS4 gene. In specific embodiments, a contiguous genomic sequence of a human TMPRSS4 gene being inserted into an endogenous rodent Tmprss4 gene does not contain the 3' UTR of the human TMPRSS4 gene, and the 3' UTR of the endogenous rodent Tmprss4 gene follows immediately after the stop codon in the humanized Tmprss4 gene.

In some embodiments, the nucleotide sequence of an endogenous rodent Tmprss4 gene remaining at a humanized Tmprss4 locus encodes a polypeptide that is substantially identical with the cytoplasmic and transmembrane portion of the endogenous rodent Tmprss4 protein. In circumstances where an endogenous Tmprss4 protein and a human TMPRSS4 protein share common amino acids near the junction of the transmembrane domain and the ectodomain, it may not be necessary to maintain the endogenous rodent Tmprss4 genomic sequence that encodes precisely the transmembrane domain of the endogenous rodent Tmprss4 protein, and it is possible to maintain a slightly longer or shorter rodent Tmprss4 genomic sequence that encodes substantially the transmembrane domain of the endogenous rodent Tmprss4 protein in the humanization replacement in order to encode a humanized Tmprss4 protein having a transmembrane domain that is identical with the transmembrane of the endogenous rodent Tmprss4 protein.

In specific embodiments, a humanized Tmprss4 gene contains coding exons 1-3 of an endogenous rodent Tmprss4 gene, and coding exon 4 through the stop codon of coding exon 13 of a human TMPRSS4 gene. In particular embodiments, a humanized Tmprss4 gene contains coding exons 1-3 and a 5' portion of intron 3 of an endogenous rodent Tmprss4 gene, and a 3' portion of intron 3 and coding exon 4 through the stop codon of coding exon 13 of a human TMPRSS4 gene. In certain embodiments, the humanized Tmprss4 gene encodes a humanized Tmprss4 protein that contains the cytoplasmic domain and the transmembrane domain of the rodent Tmprss4 protein encoded by an endogenous rodent Tmprss4 gene, and the ectodomain of the human TMPRSS4 protein encoded by a human TMPRSS4 gene. In particular embodiments, a humanized Tmprss4 gene encodes a humanized Tmprss4 protein having the amino acid sequence as set forth in SEQ ID NO: 14.

In some embodiments, the exons and introns of a human TMPRSS4 gene and a rodent Tmprss4 gene used in the humanization are those found in SEQ ID NOS: 8, 10 and 12-13.

In some embodiments, a humanized Tmprss4 gene results in an expression of the encoded humanized Tmprss4 protein in a rodent. In some embodiments, a humanized Tmprss4 protein is expressed in a pattern comparable with, or substantially the same as, a counterpart rodent Tmprss4 protein in a control rodent (e.g., a rodent without the humanized Tmprss4 gene encoding the humanized Tmprss4 protein). In some embodiments, a humanized. Tmprss4 protein is expressed at a level comparable with, or substantially the same as, a counterpart rodent Tmprss4 protein in a control rodent (e.g., a rodent without the humanized Tmprss4 gene encoding the humanized Tmprss4 protein). In certain embodiments, a humanized Tmprss4 protein is expressed and detected at the cell surface. In certain embodiments, a humanized Tmprss4 protein or a soluble form (e.g., a shed ectodomain form) is expressed and detected in serum of a rodent, e.g., at a level comparable with, or substantially the same as, a counterpart rodent Tmprss4 protein or a soluble form thereof in a control rodent.

Humanized Tmprss11d Rodents

In some embodiments, this invention provides a rodent whose genome contains a humanized Tmprss11d gene that includes a nucleotide sequence of an endogenous rodent Tmprss11d gene and a nucleotide sequence of a human TMPRSS11D gene, and that is under control of a 5' regulatory element(s), such as the promoter and/or enhancer(s) of the endogenous rodent Tmprss11d gene. Examples of rodents include mice and rats.

In some embodiments, a humanized Tmprss11d gene encodes a humanized Tmprss11d protein that contains an ectodomain that is substantially identical with the ectodomain of a human TMPRSS11D protein.

In specific embodiments, the human TMPRSS11D protein has an amino acid sequence having at least 85%, 90%, 95%, 98%, 99% or 100% identity with the amino acid sequence as set forth in SEQ ID NO: 18.

In some embodiments, a humanized Tmprss11d protein contains the C-terminal 377 amino acids of a human TMPRSS11D protein, for example, amino acids 42 to 418 of a human TMPRSS11D protein. In some embodiments, a humanized Tmprss11d protein contains an ectodomain that is substantially identical with the amino acid sequence composed of A42 to 1418 of SEQ ID NO: 18. In specific embodiments, a humanized Tmprss11d protein contains an ectodotnain having at least 85%, 90%, 95%, 98?, 99% or 100% identity with the amino acid sequence composed of A42 to 1418 of SEQ ID NO: 18; an ectodomain that differs from the amino acid sequence composed of A42 to 1418 of SEQ ID NO: 18 by not more than 10, 9, 8, 7, 6, 5, 4, 3, 2 or 1 amino acid(s); or an ectodomain that differs from the amino acid sequence composed of A42 to 1418 of SEQ ID NO: 18 only at the N- or C-terminus, e.g., by lacking 1-5 amino acids or having additional 1-5 amino acids at the N- or C-terminus.

In some embodiments, a humanized Tmprss11d protein further contains a cytoplasmic and transmembrane portion that is substantially identical with the cytoplasmic and transmembrane portion of an endogenous rodent Tmprss11d protein. In some embodiments, a humanized Tmprss11d protein includes the transmembrane domain and the cytoplasmic domain of an endogenous rodent Tmprss11d protein.

In specific embodiments, a humanized Tmprss11d protein contains the transmembrane domain and the cytoplasmic domain of an endogenous rodent Tmprss11d protein, and the ectodomain of a human TMPRSS11D protein. In particular embodiments, a humanized Tmprss11d gene encodes a humanized Tmprss11d protein having the amino acid sequence as set forth in SEQ ID NO: 21.

In some embodiments, a humanized Tmprss11d gene results from a replacement of a nucleotide sequence of an endogenous rodent Tmprss11d gene at an endogenous rodent Tmprss11d locus with a nucleotide sequence of a human TMPRSS11D gene.

In some embodiments, a contiguous genomic sequence of an endogenous rodent Tmprss11d gene at an endogenous rodent Tmprss11d locus has been replaced with a contiguous genomic sequence of a human TMPRSS11D gene to form a humanized Tmprss11d gene. In specific embodiments, the contiguous genomic sequence of a human TMPRSS11D gene inserted into an endogenous rodent Tmprss11d gene includes exon sequences, i.e., exons in full or in part, of a human TMPRSS11D gene that encode an ectodomain that is substantially identical with the ectodomain of the human TMPRSS11D protein encoded by the human TMPRSS11D gene. In circumstances where an endogenous Tmprss11d protein and a human TMPRSS11D protein share common amino acids near the junction of the transmembrane domain and the ectodomain, it may not be necessary to insert a human TMPRSS11D genomic sequence that encodes precisely the ectodomain of the human TMPRSS11D protein, and it is possible to use a slightly longer or shorter human TMPRSS11D genomic sequence that encodes substantially the ectodomain of a human TMPRSS11D protein in order to make a humanized Tmprss11d protein having an ectodomain that is identical with the ectodomain of the human TMPRSS11D protein.

In specific embodiments, a contiguous genomic sequence of a human TMPRSS11D gene being inserted into an endogenous rodent Tmprss11d gene contains at least coding exon 3 through the stop codon in coding exon 10 of a human TMPRSS11D gene.

In certain embodiments, a contiguous genomic sequence of a human TMPRSS11D gene being inserted into an endogenous rodent Tmprss11d gene contains at least a 3' portion of intron 2 and coding exon 3 through the stop codon in coding exon 10 of the human TMPRSS11D gene. In specific embodiments, the 3' portion of intron 2 of a human TMPRSS2 gene included in the humanization is about 444 base pairs in length.

In some embodiments, a contiguous genomic sequence of a human TMPRSS11D gene being inserted into an endogenous rodent Tmprss11d gene contains the 3' UTR of the human TMPRSS11D gene. In specific embodiments, the entire coding exon 10 of a human TMPRSS11D gene is included in the contiguous human TMPRSS11D genomic sequence for humanization, which includes the 3' UTR of a human TMPRSS11D gene. In particular embodiments, a contiguous genomic sequence of a human TMPRSS11D gene includes an additional human genomic sequence downstream of the 3' UTR of the human TMPRSS11D gene. The additional human genomic sequence can be a sequence of 10-200 bp, 50-200 bp, or about 150, 160, 170, 180 bp, that is found immediately downstream of the 3' UTR of the human TMPRSS11D gene at a human TMPRSS11D locus.

In some embodiments, the nucleotide sequence of an endogenous rodent Tmprss11d gene remaining at a humanized Tmprss11d locus encodes a polypeptide that is substantially identical with the cytoplasmic and transmembrane portion of the endogenous rodent Tmprss11d protein encoded by the endogenous rodent Tmprss11d gene. In circumstances where an endogenous Tmprss11d protein and a human TMPRSS11D protein share common amino acids near the junction of the transmembrane domain and the ectodomain, it may not be necessary to maintain the endogenous rodent Tmprss11d genomic sequence that encodes precisely the transmembrane domain of the endogenous rodent Tmprss11 d protein, and it is possible to maintain a slightly longer or shorter rodent Tmprss11d genomic sequence that encodes substantially the transmembrane domain of the endogenous rodent Tmprss11d protein in the humanization replacement in order to encode a humanized Tmprss11d protein having a transmembrane domain that is identical with the transmembrane of the endogenous rodent Tmprss11d protein.

In specific embodiments, a humanized Tmprss11d gene contains coding exons 1-2 of an endogenous rodent Tmprss11d gene, and coding exon 3 through coding exon 10 of a human TMPRSS11D gene. In certain embodiments, the humanized Tmprss11d gene encodes a humanized Tmprss11d protein that contains the cytoplasmic domain and the transmembrane domain of the rodent Tmprss11d protein encoded by an endogenous rodent Tmprss11d gene, and the ectodomain of the human TMPRSS11D protein encoded by a human TMPRSS11D gene. In particular embodiments, a humanized Tmprss11d gene encodes a humanized Tmprss11d protein having the amino acid sequence as set forth in SEQ ID NO: 21.

In some embodiments, the exons and introns of a human TMPRSS11D gene and a rodent Tmprss11d gene used in the humanization are those found in SEQ ID NOS: 15, 17 and 19-20.

In some embodiments, a humanized Tmprss11D gene results in an expression of the encoded humanized Tmprss11d protein in a rodent. In some embodiments, a humanized Tmprss11d protein is expressed in a pattern comparable with, or substantially the same as, a counterpart rodent Tmprss11d protein in a control rodent (e.g., a rodent without the humanized Tmprss11d gene encoding the humanized Tmprss11d protein). In some embodiments, a humanized Tmprss11d protein is expressed at a level comparable with, or substantially the same as, a counterpart rodent Tmprss11d protein in a control rodent (e.g., a rodent without the humanized Tmprss11d gene encoding the humanized Tmprss11d protein). In certain embodiments, a humanized Tmprss11d protein is expressed and detected at the cell surface. In certain embodiments, a humanized Tmprss11d protein or a soluble form (e.g., a shed ectodomain form) is expressed and detected in serum of a rodent, e.g., at a level comparable with, or substantially the same as, a counterpart rodent Tmprss11d protein or a soluble form thereof in a control rodent.

Methods of Making Humanized Tmprss Rodent Animals

Further aspects of this disclosure are directed to methods for making a humanized Tmprss rodent described above, as well as nucleic acid vectors and non-human embryonic stem cells suitable for use in making a humanized Tmprss rodent.

The rodents provided herein can be made using methods known in the art. In exemplary embodiments, a bacterial artificial chromosome (BAC) clone carrying a rodent Tmprss gene can be modified using bacterial homologous recombination and VELOCIGENE® technology (see, e.g., U.S. Pat. No. 6,586,251 and Valenzueia et al. (2003), High-throughput engineering of the mouse genome coupled with high-resolution expression analysis, *Nature Biotech.* 21(6): 652-659). As a result, a rodent Tmprss nucleotide sequence has been deleted from the original BAC clone, and a human Tmprss nucleotide sequence has been inserted, resulting in a modified BAC clone carrying a humanized Tmprss gene, flanked with 5' and 3' rodent homology arms. The modified BAC clone, once linearized, can be introduced into rodent embryonic stem (ES) by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference') describe mouse ES cells and the VELOCI-MOUSE® method for making a genetically modified mouse; US 2014/0235933 A1, US 2014/0310828 A1, Tong et al. (2010) *Nature* 467:211-215, and Tong et al. (2011) *Nat Protoc.* 6(6): doi:10.1038/nprot.2011.338 (all of which are incorporated herein by reference) describe rat ES cells and methods for making a genetically modified rat.

ES cells having a humanized Tmprss gene integrated in the genome can be selected. In some embodiments, ES cells having a humanized Tmprss integrated into an endogenous rodent Tmprss locus can be selected based on loss of rodent allele and/or gain of human allele assays. Selected ES cells are then used as donor ES cells for injection into a pre-morula stage embryo (e.g., 8-cell stage embryo) by using the VELOCIMOUSE® method (see, e.g., U.S. Pat. Nos. 7,576, 259, 7,659,442, 7,294,754, and US 2008-0078000 A1), or methods described in US 2014/0235933 A1 and US 2014/ 0310828 A1. The embryo comprising the donor ES cells is incubated until blastocyst stage and then implanted into a surrogate mother to produce an F0 rodent fully derived from the donor ES cells. Rodent pups bearing the humanized Tmprss gene can be identified by genotyping of DNA isolated from tail snips using loss of rodent allele and/or gain of human allele assays.

Rodents heterozygous for a humanized Tmprss gene can be crossed to generated homozygous rodents, Rodents containing one humanized Tmprss gene can be crossed with rodents containing another humanized Tmprss gene to make rodents containing multiple humanized Tmprss genes. For example, rodents containing a humanized Tmprss2 gene can be crossed with rodents containing a humanized Tmprss4 gene to make rodents containing a humanized Tmprss2 gene and a humanized Tmprss4 gene.

Methods Employing Rodents Having Humanized Tmprss Genes

Rodents disclosed herein provide a useful in vivo system and source of biological materials (e.g., cells) expressing humanized Tmprss proteins for identifying and testing compounds that specifically target human TMPRSS proteins.

In one aspect, a rodent disclosed herein is used to determine the ability of a candidate compound, such as an inhibitor of a human TMPRSS protein, to treat and/or prevent influenza virus infection.

In some embodiments, a rodent containing a humanized Tmprss gene and expressing a humanized Tmprss protein disclosed herein is administered with a candidate compound prior to experimental influenza virus infection. The prophylactic efficacy of the compound can be evaluated by determining whether the rodent exhibits fewer and/or less severe symptoms of influenza virus infection, and/or improved viability, as compared to control rodent(s).

In other embodiments, a rodent containing a humanized Tmprss gene and expressing a humanized Tmprss protein comprising the ectodomain of a human TMPRSS protein is administered with a candidate inhibitor of that human TMPRSS protein after experimental influenza virus infection. The treatment efficacy of the candidate inhibitor can be evaluated by determining whether the rodent exhibits fewer and/or less severe symptoms of influenza virus infection, and/or improved viability, as compared to control rodent(s).

Suitable control rodents include, e.g., rodents containing a humanized Tmprss gene without being subjected to the experimental infection; and rodents containing a humanized Tmprss gene subjected to the experimental infection without any compound; and rodents containing a humanized Tmprss gene subjected to the experimental infection and a compound known to be therapeutically effective.

Compounds that can be evaluated in the methods of this invention include candidate TMPRSS inhibitors, for example, a small molecule protease inhibitor, a nucleic acid-based inhibitor (e.g., siRNA, ribozyme, anti sense construct, etc.), antigen-binding protein (e.g., antibody or antigen-binding fragment thereof), or a blocking peptide/peptide inhibitor. A TMPRSS inhibitor may function by inhibiting or reducing the ability of a TMPRSS protein to proteolytically cleave hemagglutinin precursor protein (HA0) into the HA1 and HA2 subunits.

In some embodiments, a candidate inhibitor is an antibody or antigen-binding fragment thereof. Both monoclonal and polyclonal antibodies are suitable for purposes of this invention. In specific embodiments, the antibody specifically binds to a TMPRSS protein and inhibits the protease activity of that TMPRSS protein and does not substantially inhibit the protease activity of another TMPRSS protein. For example, an anti-TMPRSS2 antibody inhibitor specifically binds to a TMPRSS2 protein and inhibits the protease activity of the TMPRSS2 protein, and has no effect on the proteolytic activity of TMPRSS4 or TMPRSS11D, or reduces the proteolytic activity of TMPRSS4 or TMPRSS11D by no more than 25% (e.g., by 20%, 15%, 10%, 5%, or less) relative to a non-inhibitory control molecule tested under identical or substantially identical experimental conditions.

In some embodiments, the inhibitor is an anti-TMPRSS2 antibody or antigen-binding fragment thereof. In some embodiments, the inhibitor is an anti-TMPRSS4 antibody or antigen-binding fragment thereof. In other embodiments, the inhibitor is an anti-TMPRSS11D antibody or antigen-binding fragment thereof.

Experimental influenza virus infection can be induced and monitored following known protocols. See, e.g., US 2013/0273070 A1. For example, rodent animals can be administered intranasally with influenza virus. The infected animals can be evaluated to determine the symptoms and severity of the infection. For example, the animals can be analyzed for (1) weight change and survival, (2) cellular changes via flow cytometry, (3) immunochemistry, PAS and H&E staining of whole lungs, and (4) cytokine levels in serum. Control animals known to be susceptible to the virus exhibit a significant increase in the frequency of dendritic cells, the levels influenza-positive alveolar macrophages, neutrophils or epithelial cells in the lungs, and the levels of as compared to uninfected animals.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Tmprss2 Gene

This example illustrates exemplary methods of humanizing an endogenous gene encoding Tmprss2 in a rodent (e.g., a mouse). The methods described in this example can be employed to humanize an endogenous Tmprss2 gene of a rodent using any human sequence, or combination of human sequences (or sequence fragments) as desired.

A targeting vector for humanization of an endogenous Tmprss2 gene was constructed using bacterial artificial chromosome (BAC) clones and VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659; incorporated herein by reference).

Briefly, mouse bacterial artificial chromosome (BAC) clone bMQ-264A15 containing a mouse Tmprss2 gene was used and modified as follows. A DNA fragment was generated to include a 5' mouse homology nucleotide sequence, a human TMPRSS2 genomic DNA of about 25,091 bp (containing the last 7 bp of coding exon 3, intron 3, and coding exon 4 through coding exon 13 (including the 3' UTR which is part of coding exon 13), of a human TMPRSS2 gene), a self-deleting neomycin cassette of about 2,691 bp, and a 3' mouse homology sequence. This DNA fragment was used to modify BAC clone bMQ-264A15 through homologous recombination in bacterial cells. As a result, an ectodomain-encoding mouse Tmprss2 genomic fragment (of about 25,291 bp) in the BAC clone was replaced with the human TMPRSS2 genomic fragment of about 25,091 bp, followed by a self-deleting neomycin cassette of about 2691 bp. Specifically, the mouse Tmprss2 genomic fragment that was replaced included the last 7 bp of coding exon 3, intron 3, and coding exon 4 through the stop codon in coding exon 13 of the mouse Tmprss2 gene (FIGS. 1A-1B). The human TMPRSS2 genomic fragment that was inserted included the last 7 bp of coding exon 3, intron 3, and coding exon 4 through coding exon 13 of a human TMPRSS2 gene (including the 3' UTR of human TMPRSS2), and a human 3' genomic sequence of 131 bp downstream of the 3' UTR of human TMPRSS2 (FIGS. 1A-1B). The resulting modified BAC clone included, from 5' to 3', (i) a 5' mouse homology arm containing about 12 kb of mouse genomic DNA including a mouse Tmprss2 5' UTR, mouse Tmprss2 exon 1 (non-coding), coding exons 1-3 (except the last 7 bp of coding exon 3); (ii) a human TMPRSS2 genomic fragment of about 25,091 bp including the last 7 bp of human coding exon 3, intron 3, human coding exons 4 through 13 (including the 3' UTR of human TMPRSS2), and a human 3' genomic sequence; (iii) a self-deleting neomycin cassette of about 2691 bp, followed by (iv) a 3' mouse homology arm of 45 kb containing the mouse Tmprss2 3'UTR and the remaining mouse genomic DNA in the original BAC clone. See FIGS. 1A-1B. The junction sequences are also set forth at the bottom of FIG. 1B. The part of the modified BAC clone containing the human TMPRSS2 genomic fragment and the neomycin cassette, as well as the upstream and downstream insertion junctions, is set forth in SEQ ID NO: 5. The amino acid sequence of the protein encoded by the humanized Tmprss2 gene is set forth in SEQ ID NO: 7. An alignment of this humanized Tmprss2 protein ("7010 mutant protein"), a mouse Tmprss2 protein (SEQ ID NO: 2), and a human TMPRSS2 protein (SEQ ID NO: 4), is provided in FIG. 1D.

Figure 1C:
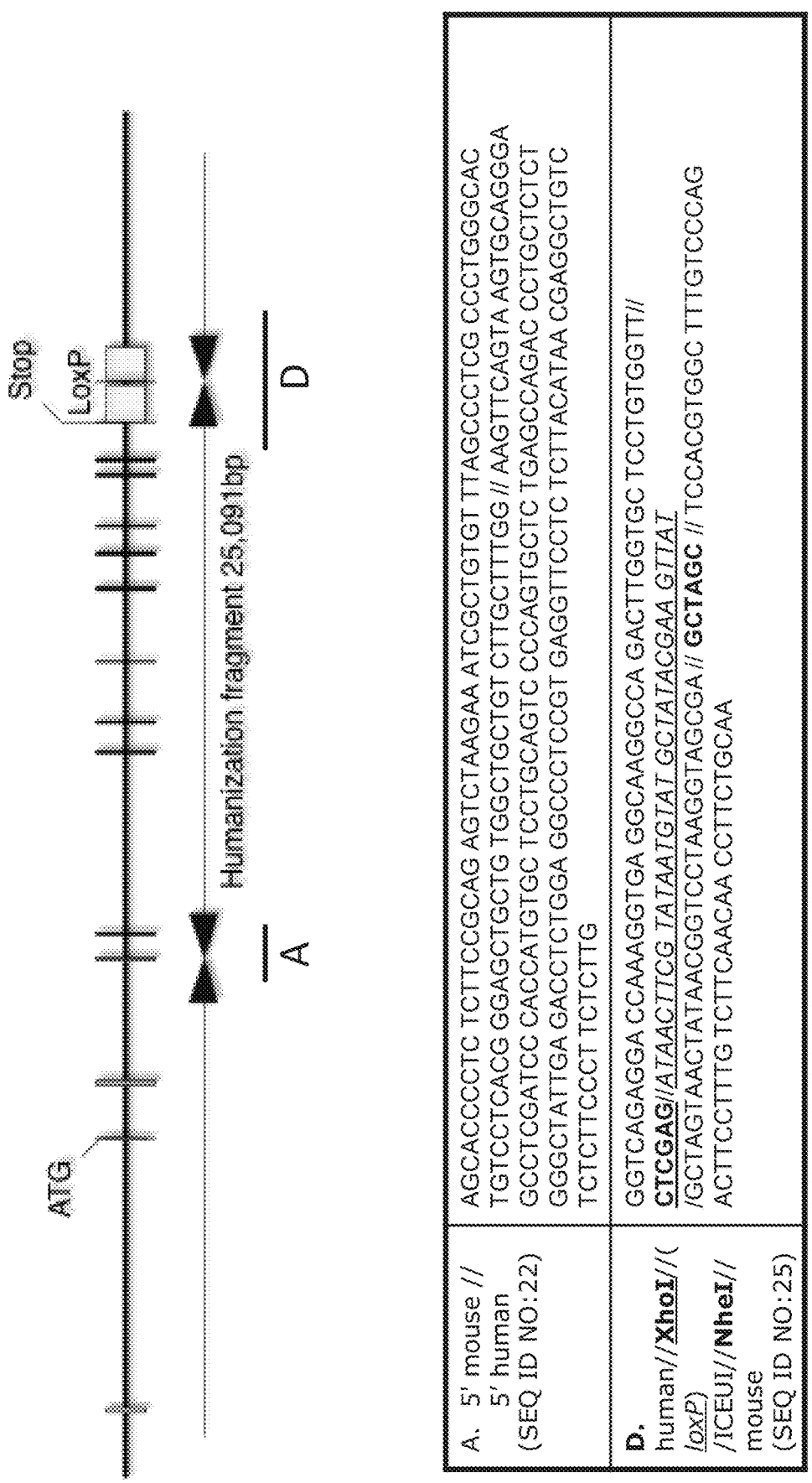
Figure 1D:
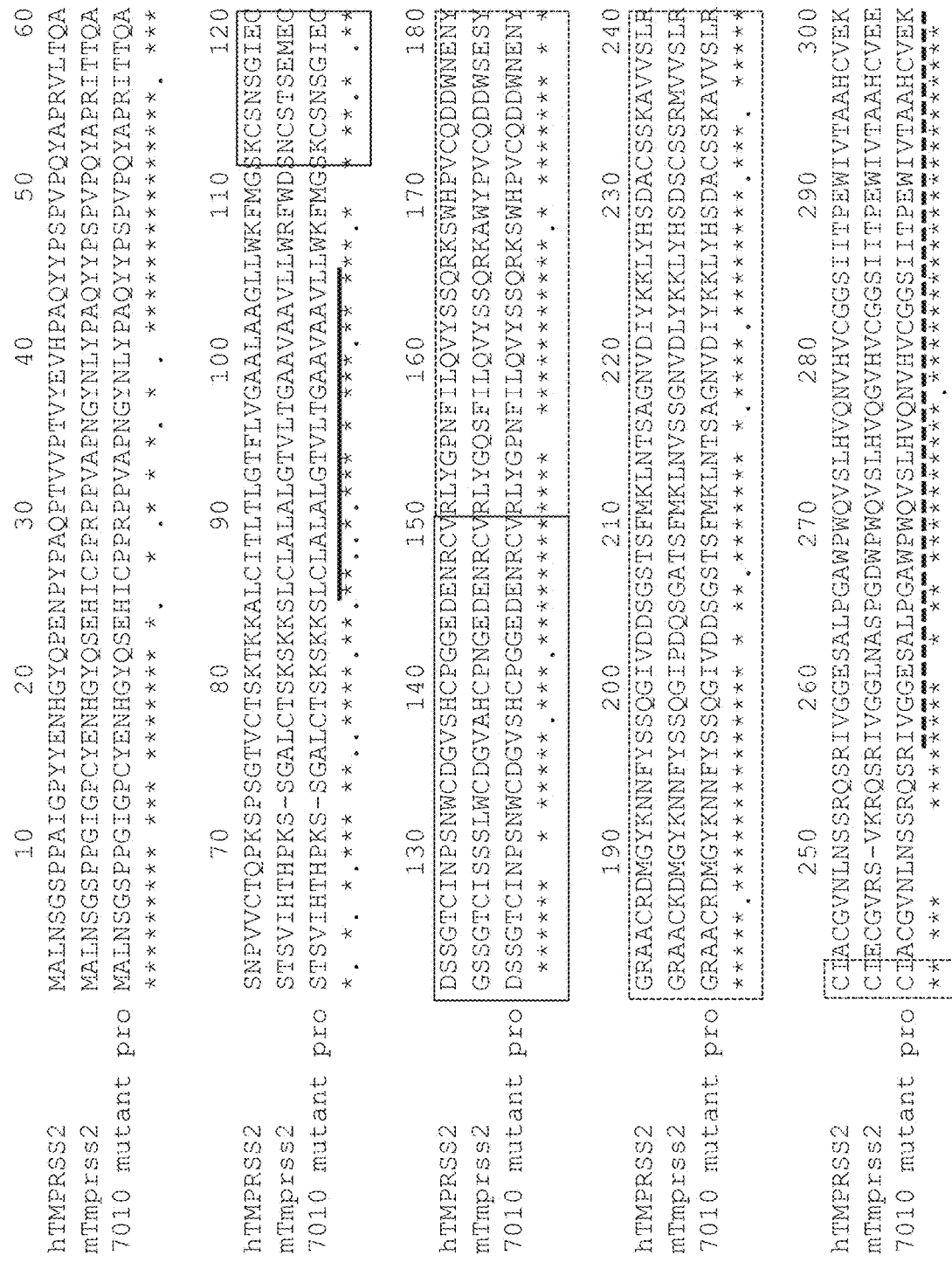

The modified BAC clone containing the humanized Tmprss2 gene, as described above, was used to electroporate mouse embryonic stem (ES) cells to create modified ES cells comprising a humanized Tmprss2 gene. Positively targeted ES cells containing a humanized Tmprss2 gene were identified by an assay (Valenzuela et al., supra) that detected the presence of the human TMPRSS2 sequences (e.g., coding exons 4-13 of human TMPRSS2) and confirmed the loss and/or retention of mouse Tmprss2 sequences (e.g., loss of coding exons 4-13 of mouse Tmprss2). Table 1 sets forth the primers and probes that were used to confirm humanization of an endogenous Tmprss2 gene as described above (FIGS. 1A-1B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss2 locus after the deletion of the cassette is depicted in FIG. 1C, with the junction sequences shown at the bottom of FIG. 1C.

Selected ES cell clones (with or without the cassette) were used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, *Nature Biotech*, 25(1):91-99) to generate a litter of pups containing a humanized Tmprss2 allele in the genome. Mice bearing a humanized Tmprss2 allele can be again confirmed and identified by genotyping of DNA isolated from tail snips using a modification of allele assay (Valenzuela et al., supra) that detects the presence of the human TMPRSS2 gene sequences. Pups are genotyped and cohorts of animals heterozygous for the humanized Tmprss2 locus are selected for characterization. Animals homozygous for the humanized Tmprss2 locus are made by crossing heterozygous animals.

Figure 2A:
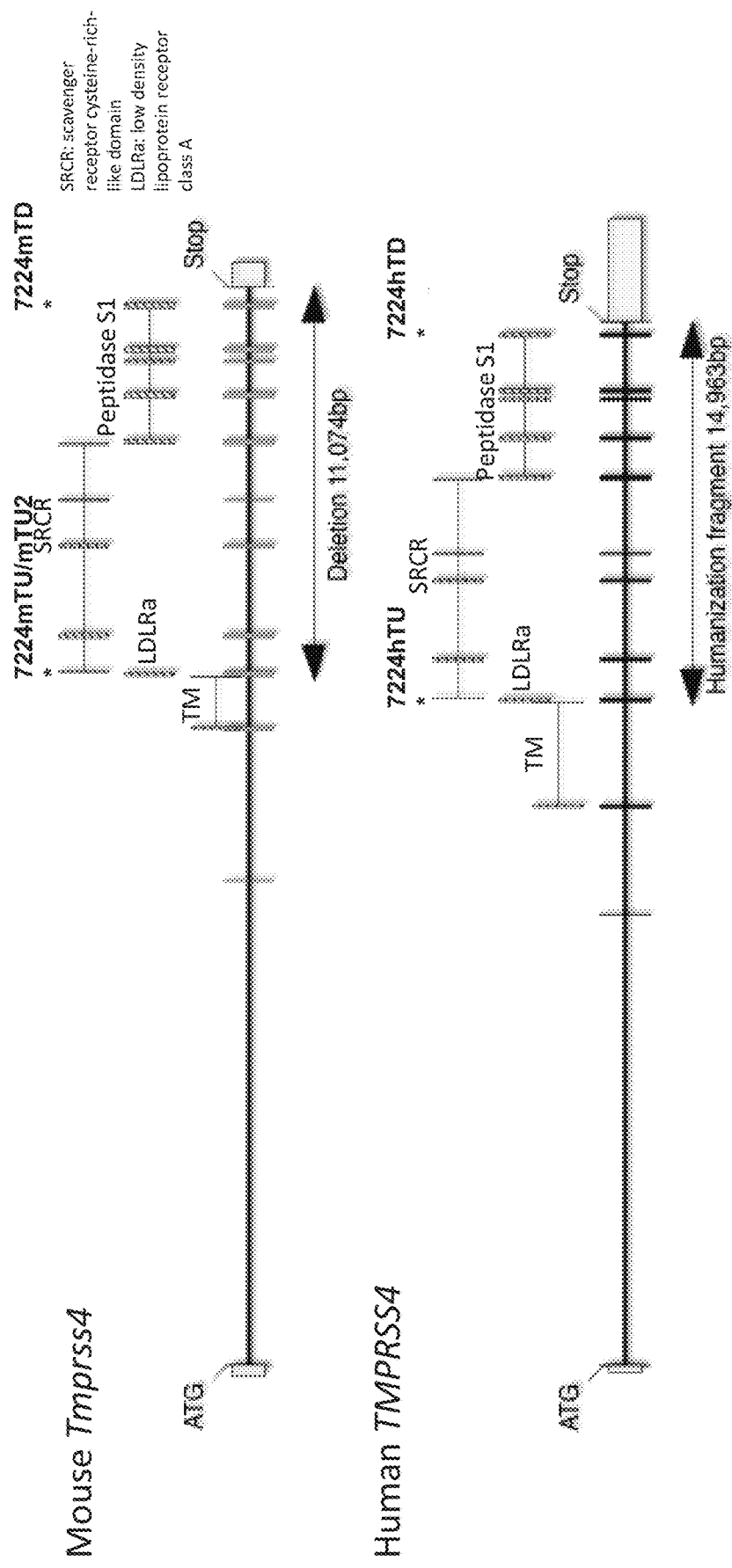
Figure 2B:
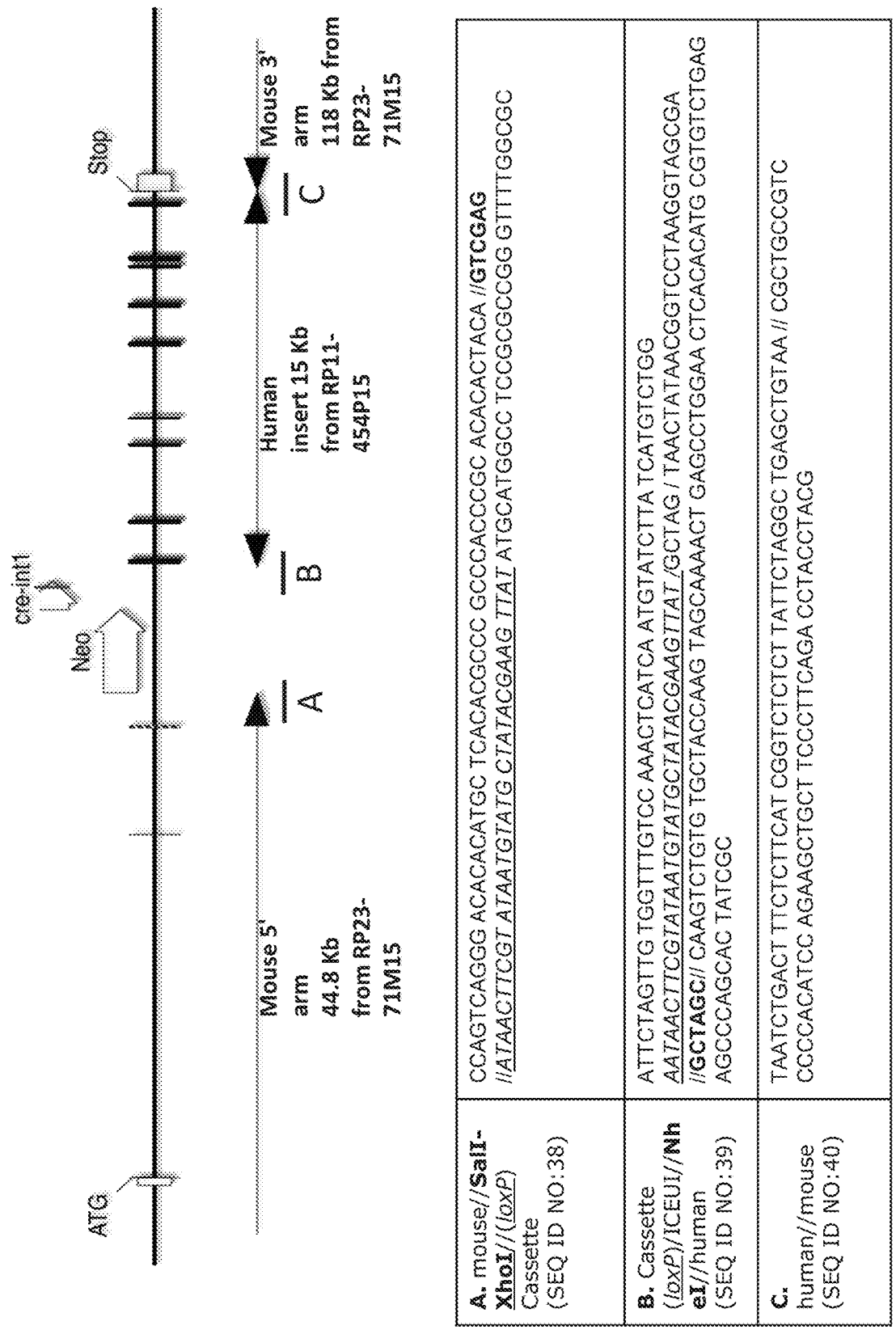

Briefly, mouse bacterial artificial chromosome (BAC) clone RP23-71M15 containing a mouse Tmprss4 gene was used and modified as follows. A DNA fragment was generated to include a 5' mouse homology nucleotide sequence, a self-deleting neomycin cassette of about 4,996 bp, a human genomic DNA of about 14,963 bp (containing coding exon 4 through the stop codon in coding exon 13 of a human TMPRSS4 gene), and a 3' mouse homology sequence. This DNA fragment was used to modify BAC clone RP23-71M15 through homologous recombination in bacterial cells. As a result, an ectodomain-encoding mouse genomic fragment (of about 11,074 bp) in the BAC clone was replaced with a self-deleting neomycin cassette of about 4,996 bp, followed by the human genomic DNA of about 14,963 bp. Specifically, the mouse genomic fragment that was deleted and replaced included the 3' 130 bp of mouse intron 3, coding exon 4 through the stop codon in coding exon 13 of the mouse Tmprss4 gene (FIGS. 2A-2B). The human genomic fragment that was inserted included a 3' portion of human TMPRSS4 intron 3 of about 150 bp, and human TMPRSS4 coding exon 4 through the stop codon in coding exon 13 (FIGS. 2A-2B). The resulting modified BAC clone included, from 5' to 3', a 5' mouse homology arm containing about 44.8 kb of mouse genomic DNA (including a mouse Tmprss4 5' UTR, mouse Tmprss4 coding exons 1 through 3, mouse Tmprss4 intron 3 in part (without the 3' 130 bp), a self-deleting neomycin cassette of about 4996 bp, a 3' portion of human TMPRSS4 intron 3 of about 150 bp, human TMPRSS4 coding exons 4 through the stop codon in coding exon 13, followed directly by the mouse Tmprss4 3' UTR and the remaining mouse genomic DNA in the original BAC clone (a 3' mouse homology arm of about 118 kb in total). See FIGS. 2A-2B. The junction sequences are also set forth at the bottom of FIG. 2B. The part of the modified BAC clone containing the neomycin cassette and the human

TABLE 1

| Name | Primer | Sequence (5'-3') | SEQ ID NO |
|---|---|---|---|
| 7010U | Forward | GCCGTGACTGTGACCTTCTC | (SEQ ID NO: 26) |
|  | Probe (BHQ) | TGGAGGAGCCACCTGATGCCTC | (SEQ ID NO: 27) |
|  | Reverse | GCCTTGCCCTCAATGGAAAC | (SEQ ID NO: 28) |
| 7010D | Forward | GGTTGCACAGCAAGGAAGAAG | (SEQ ID NO: 29) |
|  | Probe (BHQ) | CCAGGAGTTCCTGTGAGCCTACCC | (SEQ ID NO: 30) |
|  | Reverse | TGGAATGGAAGGAGCTGGAG | (SEQ ID NO: 31) |
| 7010hU | Forward | GTCCCACCTCCTGCAACTG | (SEQ ID NO: 32) |
|  | Probe (BHQ) | TGAGCCTTCCCATCAGCCTGGG | (SEQ ID NO: 33) |
|  | Reverse | CCACAATGGCACATGGGTCTG | (SEQ ID NO: 34) |
| 7010hTD | Forward | GGTGCTTGCTCCCCAAGA | (SEQ ID NO: 35) |
|  | Probe (BHQ) | CCTAAAAGGTGTTGTAATGG | (SEQ ID NO: 36) |
|  | Reverse | GGCAATAAAGAAGGAAGACGTTTT | (SEQ ID NO: 37) |

Example 2. Humanization of an Endogenous Tmprss4 Gene

This example illustrates exemplary methods of humanizing an endogenous gene encoding Tmprss4 in a rodent (e.g., a mouse). The methods described in this example can be employed to humanize an endogenous Tmprss4 gene of a rodent using any human sequence, or combination of human sequences (or sequence fragments) as desired.

A targeting vector for humanization of an endogenous Tmprss4 gene was constructed using bacterial artificial chromosome (BAC) clones and VELOCIGENE® technology (see, e.g., U.S. Pat. No. 6,586,251 and Valenzuela et al. (2003), supra).

TMPRSS4 genomic fragment, as well as the upstream and downstream insertion junctions, is set forth in SEQ ID NO: 12. The amino acid sequence of the protein encoded by the humanized Tmprss4 gene is set forth in SEQ ID NO: 14. An alignment of this humanized Tmprss4 protein ("7224 mutant pro"), a mouse Tmprss4 protein (SEQ ID NO: 9), and a human TMPRSS4 protein (SEQ ID NO: 11), is provided in FIG. 2D.

Figure 2C:
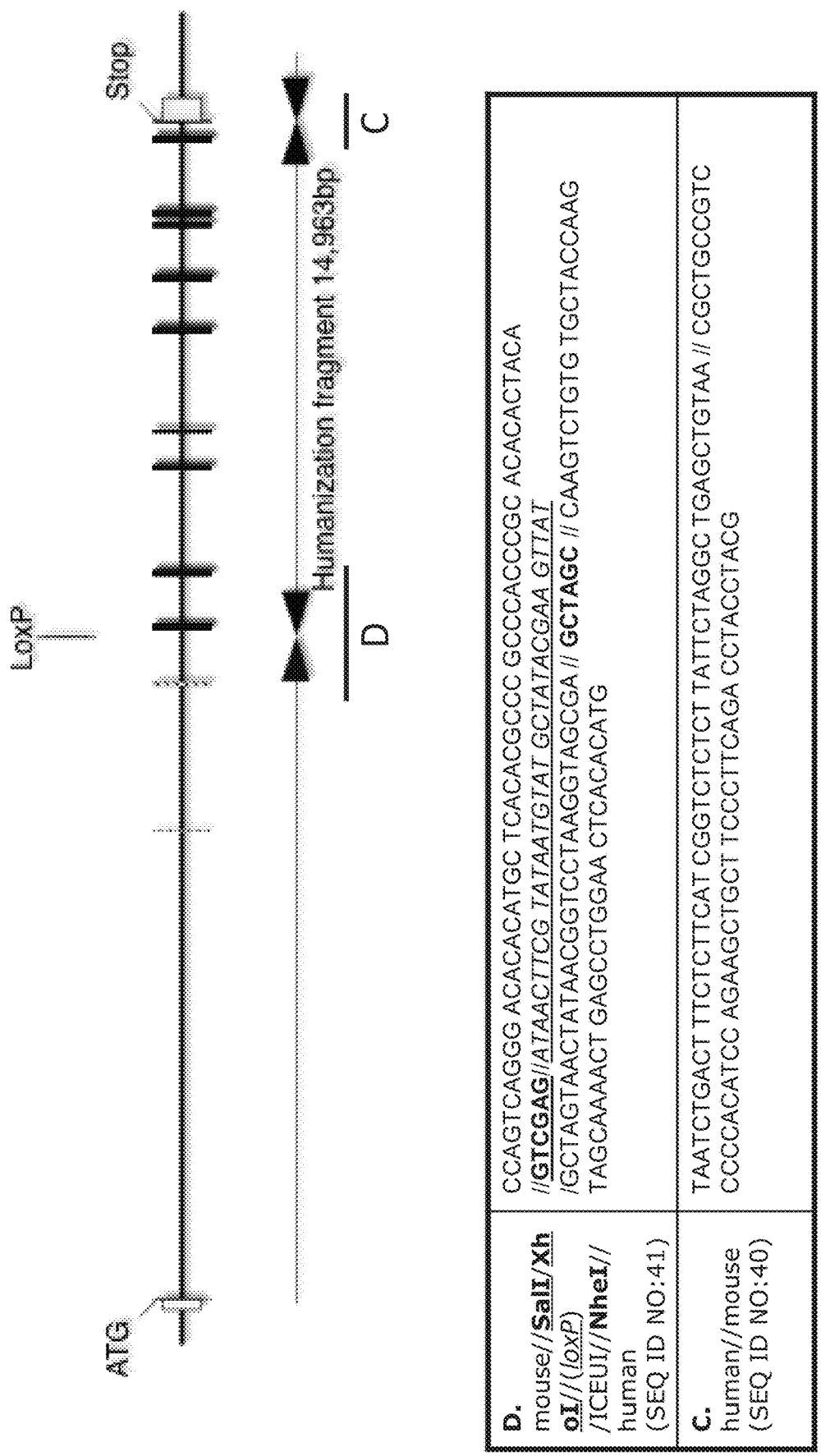
Figure 2D:
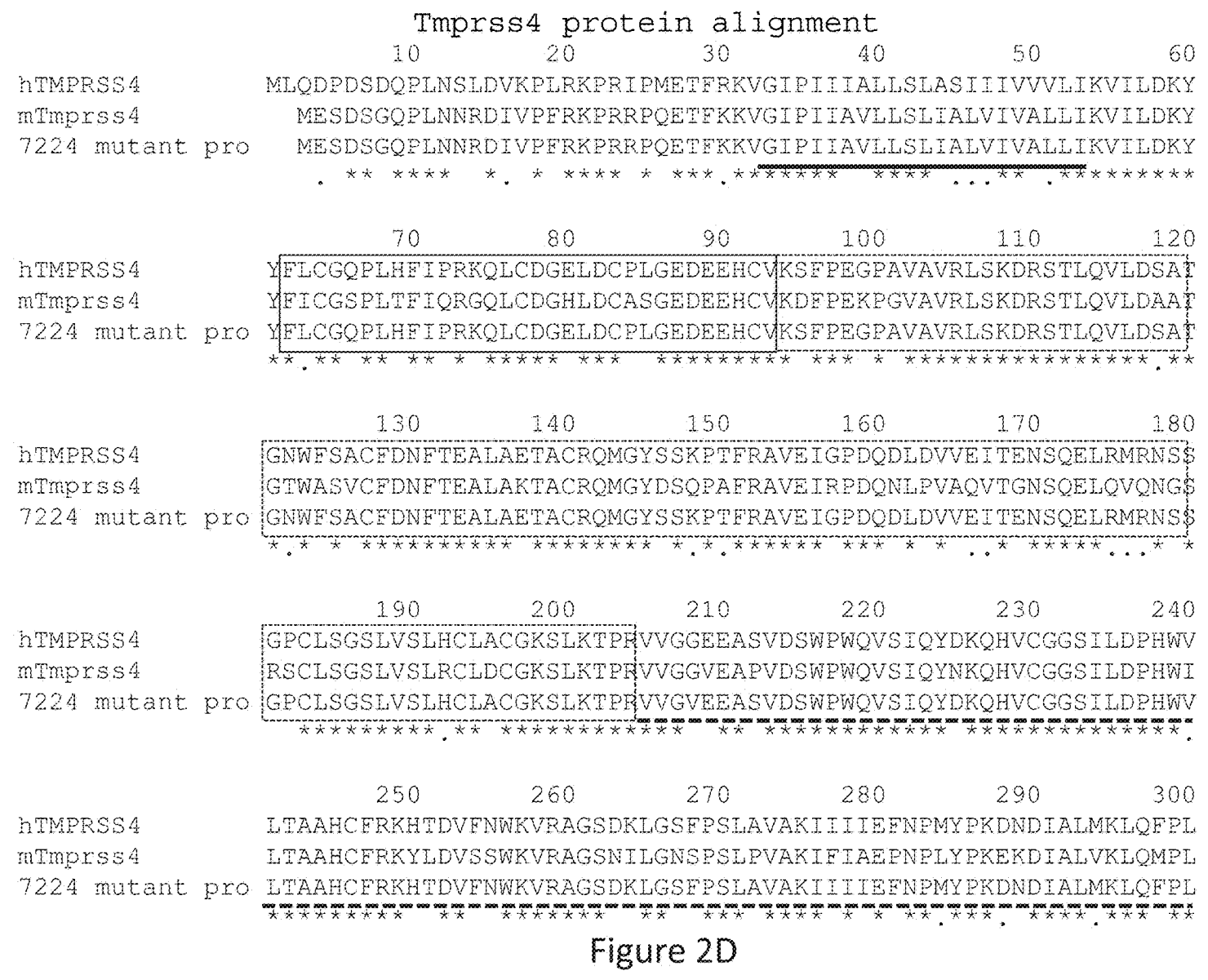

The modified BAC clone containing the humanized Tmprss4 gene, as described above, was used to electroporate mouse embryonic stem (ES) cells to create modified ES cells comprising a humanized Tmprss4 gene. Positively targeted ES cells containing a humanized Tmprss4 gene were identified by an assay (Valenzuela et al., supra) that detected the presence of the human TMPRSS4 sequences (e.g., coding exons 4-13 of human TMPRSS4) and confirmed the loss and/or retention of mouse Tmprss4 sequences (e.g., loss of coding exons 4-13 of mouse Tmprss4). Table 2 sets forth the primers and probes that were used to confirm humanization of an endogenous Tmprss4 gene as described above (FIGS. 2A-2B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss4 locus after the deletion of the cassette is depicted in FIG. 2C, with the junction sequences shown at the bottom of FIG. 2C.

Figure 3A:
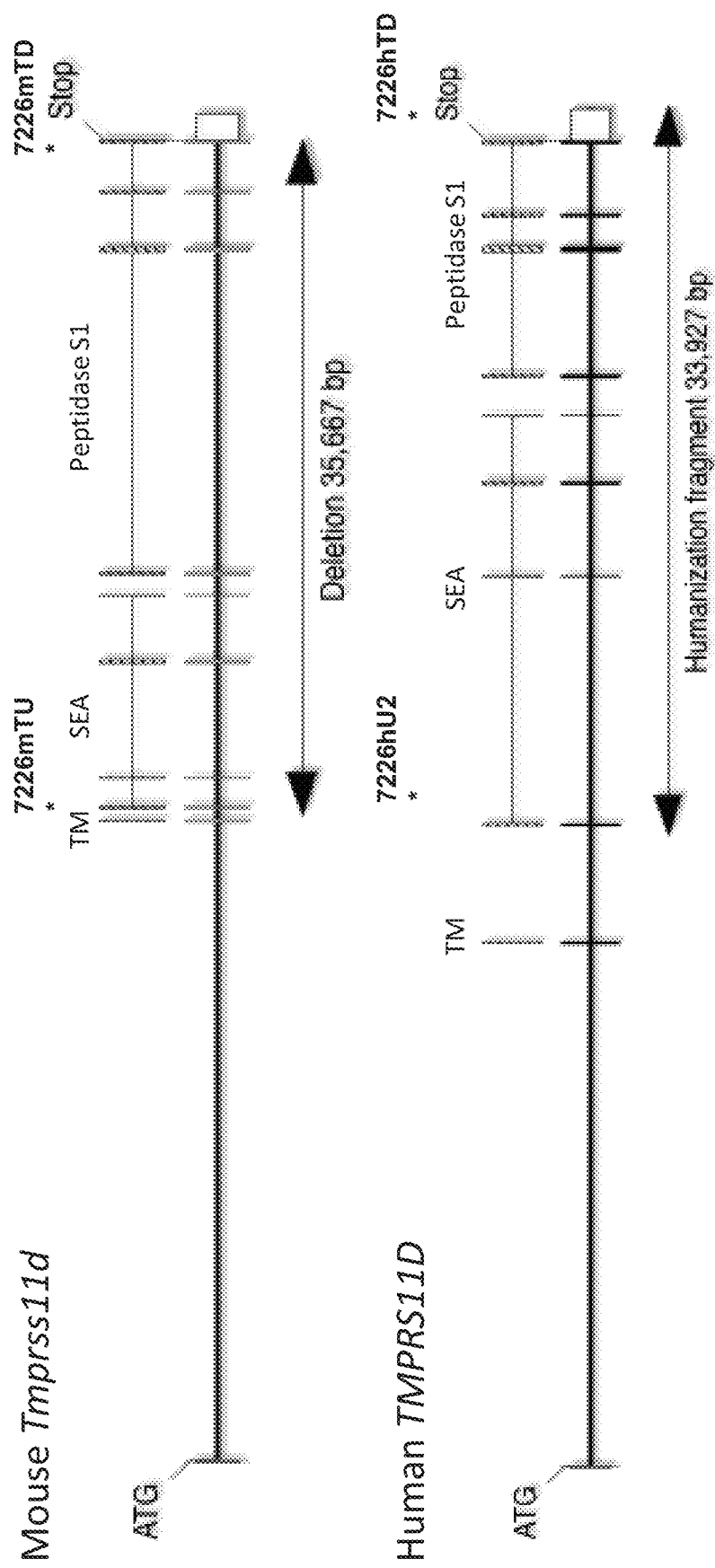
FIGS. 3A-3D. Exemplary strategy for humanization of mouse Tmprss11d.
Figure 3B:
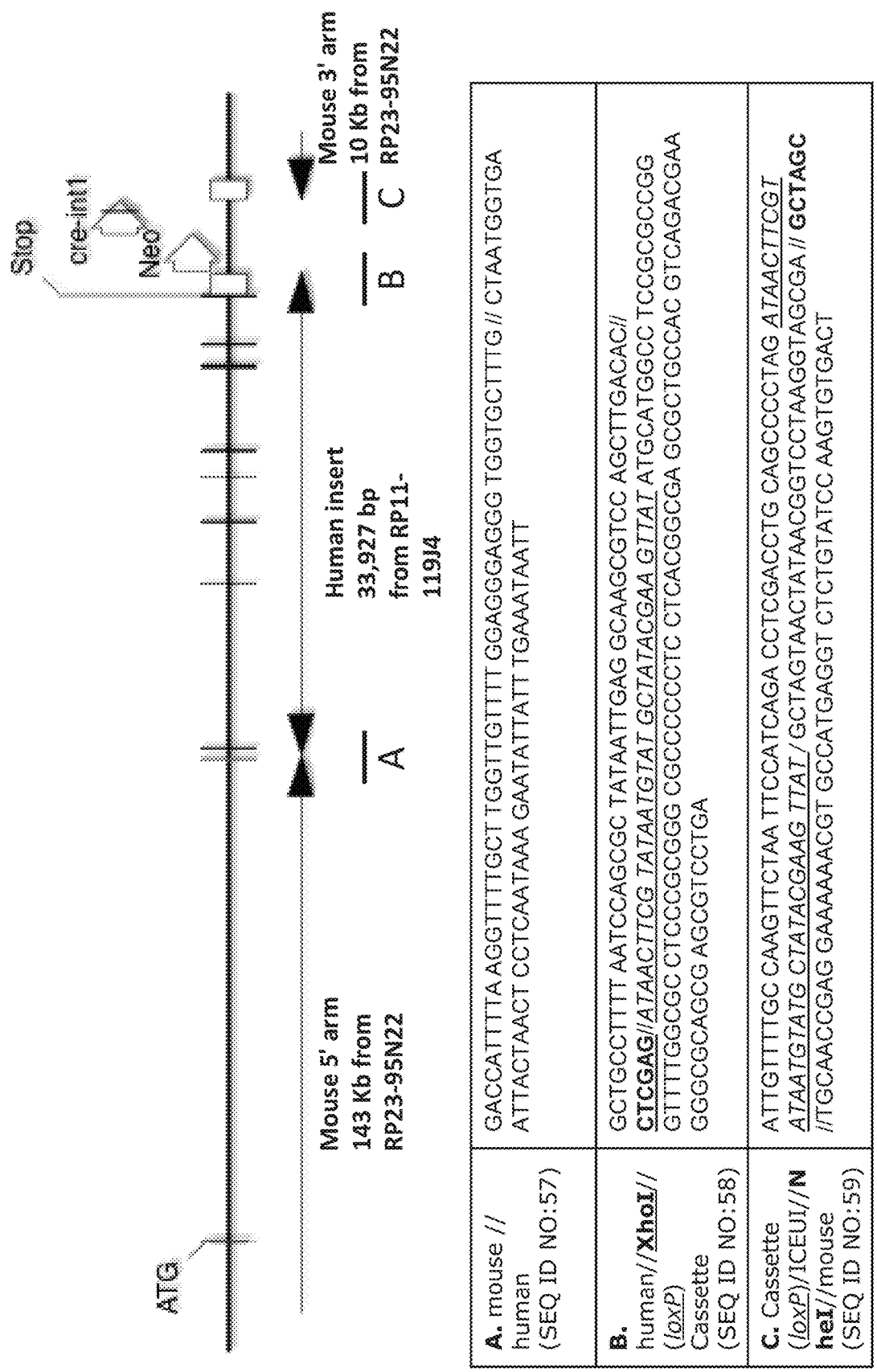

Selected ES cell clones or without the cassette) were used to implant female mice using the VELOCIMOUSE® method (see, e.g., U.S. Pat. No. 7,294,754 and Poueymirou et al. (2007), supra) to generate a litter of pups containing a humanized Tmprss4 allele in the genome. Mice bearing a humanized Tmprss4 allele were again confirmed and identified by genotyping of DNA isolated from tail snips using a modification of allele assay (Valenzuela et al., supra) that detected the presence of the human TMPRSS4 gene sequences. Pups were genotyped and cohorts of animals heterozygous for the humanized Tmprss4 locus were selected for characterization. Animals homozygous for the humanized Tmprss4 locus were made by crossing heterozygous animals.

was used and modified as follows. A DNA fragment was generated to include a 5' mouse homology nucleotide sequence, a human TMPRSS11D genomic DNA of about 33,927 bp (containing 444 bp at the 3' end of intron 2, and coding exon 3 through coding exon 10 (including the 3' UTR which is part of coding exon 10), of a human TMPRSS11D gene), a self-deleting neomycin cassette of about 4,996 bp, and a 3' mouse homology sequence. This DNA fragment was used to modify BAC clone RP23-95N22 through homologous recombination in bacterial cells. As a result, an ectodomain-encoding mouse Tmprss11d genomic fragment (of about 35,667 bp) in the BAC clone was replaced with the human TMPRSS11D genomic fragment of about 33,927 bp, followed by a self-deleting neomycin cassette of about 4,996 bp. Specifically, the mouse Tmprss11d genomic fragment that was replaced included a 3' portion of intron 2, and coding exon 3 through the stop codon in coding exon 10 of the mouse Tmprss11d gene (FIGS. 3A-3B). The human TMPRSS11D genomic fragment that was inserted included 444 bp at the 3' end of intron 2, and coding exon 3 through coding exon 10 of a human TMPRSS11D gene (including the 3' UTR of human TMPRSS11D), and a human 3' genomic sequence of about 172 bp downstream of the 3' UTR of human TMPRSS11D (FIGS. 3A-3B). The resulting modified BAC clone included, from 5' to 3', (i) a 5' mouse homology arm containing about 143 kb of mouse genomic DNA including a mouse Tmprss11d 5' UTR, mouse Tmprss11d coding exons 1-2 and a 5' portion of intron 2; (ii) a human TMPRSS11D genomic fragment including a 3'

TABLE 2

| Name | Primer | Sequence (5'-3') | SEQ ID NO |
|---|---|---|---|
| 7224mTU | Forward | GAGCAGGGCCATGACACAT | (SEQ ID NO: 42) |
| | Probe (BHQ) | ACCATTAGATCCCAGCACTGGACA | (SEQ ID NO: 43) |
| | Reverse | AAACCCTTCCCGAGAGAGAA | (SEQ ID NO: 44) |
| 7224mTU2 | Forward | GAGGAACACTGTGTCAAGGACTTT | (SEQ ID NO: 45) |
| | Probe (BHQ) | CCTGAAAAGCCCGGAGTGGCAG | (SEQ ID NO: 46) |
| | Reverse | GGGCAGAGACCACATCTGA | (SEQ ID NO: 47) |
| 7224mTD | Forward | GGAAGCCCTCTCTCGATACTTG | (SEQ ID NO: 48) |
| | Probe (BHQ) | TTCTACCCTGAGGGCATGCAGC | (SEQ ID NO: 49) |
| | Reverse | TGGGATGTAGAAGGTTGTCAGA | (SEQ ID NO: 50) |
| 7224hTU | Forward | CTGAGCCTGGAACTCACACATG | (SEQ ID NO: 51) |
| | Probe (BHQ) | TCTGAGAGCCCAGCACTATCGCC | (SEQ ID NO: 52) |
| | Reverse | GCTGAGGGTCAGGCTTGAG | (SEQ ID NO: 53) |
| 7224hTD | Forward | TCTGCAGGGTAGGGAGAGAAG | (SEQ ID NO: 54) |
| | Probe (BHQ) | TGTTTCAGAAAAGGAAGACTCACGTTACA | (SEQ ID NO: 55) |
| | Reverse | GAGACCGATGAAGAGAAAGTCAGA | (SEQ ID NO: 56) |

Example 3. Humanization of an Endogenous Tmprss11d Gene

This example illustrates exemplary methods of humanizing an endogenous gene encoding Tmprss11d in a rodent (e.g., a mouse). The methods described in this example can be employed to humanize an endogenous Tmprss11d gene of a rodent using any human sequence, or combination of human sequences (or sequence fragments) as desired.

A targeting vector for humanization of an endogenous Tmprss11d gene was constructed using bacterial artificial chromosome (BAC) clones and VELOCIGENE® technology (see, e.g., U.S. Pat. No. 6,586,251 and Valenzuela et al. (2003), supra).

Briefly, mouse bacterial artificial chromosome (BAC) clone RP23-95N22 containing a mouse Tmprss11d gene portion of intron 2 and coding exons 3 through 10 (including the 3' UTR) of human TMPRSS11D, and a human 3' genomic sequence; (iii) a self-deleting neomycin cassette of about 4,996 bp, followed by (iv) a 3' mouse homology arm of 10 kb containing the mouse Tmprss11d 3' UTR and the remaining mouse genomic DNA in the original BAC clone. See FIGS. 3A-3B. The junction sequences are also set forth at the bottom of FIG. 3B. The part of the modified BAC clone containing the human TMPRSS11D genomic fragment and the neomycin cassette, as well as the upstream and downstream insertion junctions, is set forth in SEQ ID NO: 19. The amino acid sequence of the protein encoded by the humanized Tmprss11d gene is set forth in SEQ ID NO: 21. An alignment of this humanized Tmprss11d protein ("7226 mutant pro"), a mouse Tmprss11d protein (SEQ ID NO: 16), and a human TMPRSS11D protein (SEQ ID NO: 18), is provided in FIG. 3D.

Figure 3C:
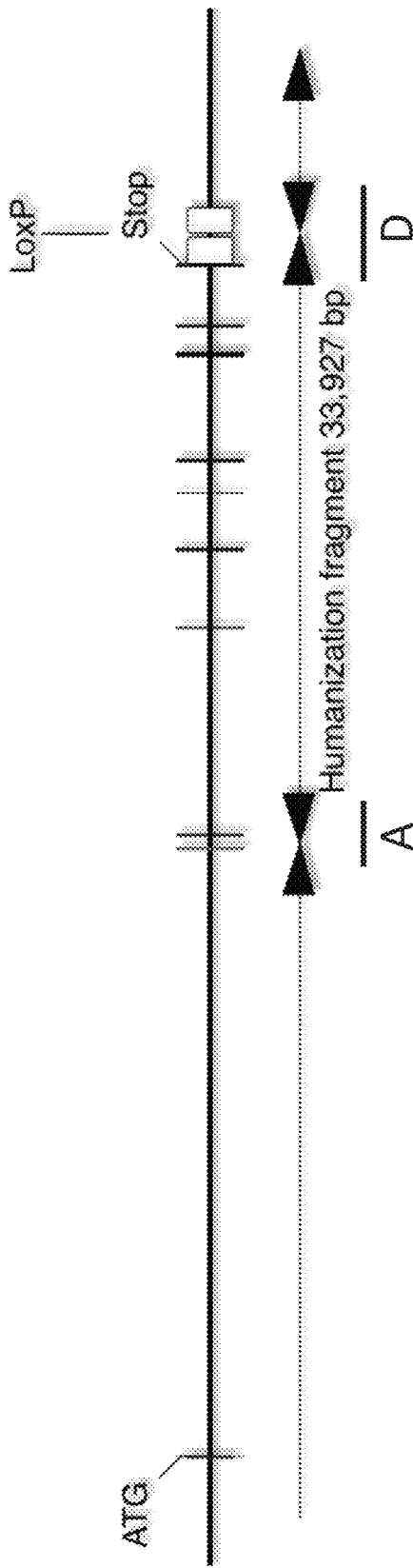
Figure 3D:
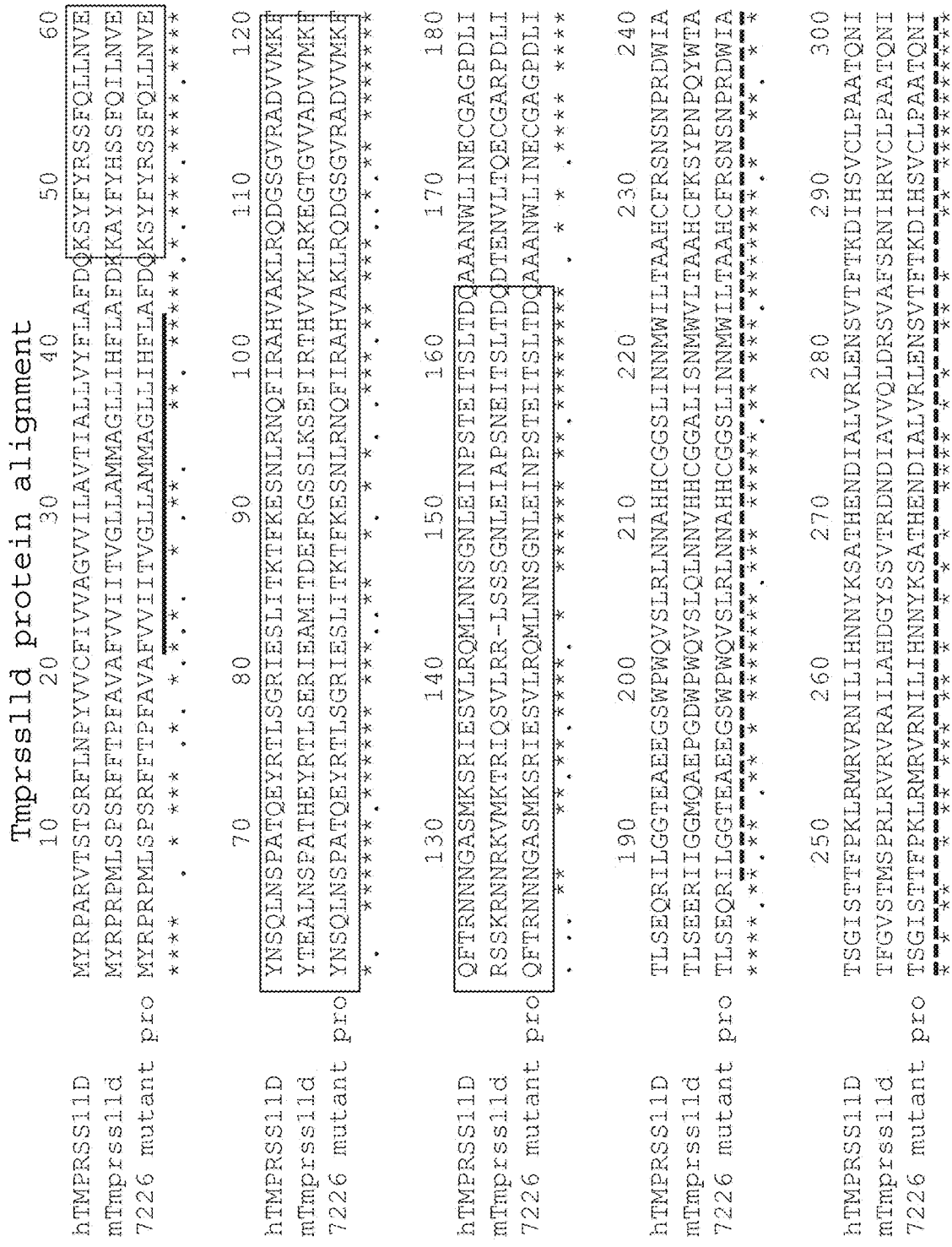

The modified BAC clone containing the humanized Tmprss11d gene, as described above, is used to electroporate mouse embryonic stem (ES) cells to create modified ES cells comprising a humanized Tmprss11d gene. Positively targeted ES cells containing a humanized Tmprss11d gene are identified by an assay (Valenzuela et al., supra) that detects the presence of the human TMPRSS11D sequences (e.g., coding exons 3-40 of human TMPRSS11D) and confirms the loss and/or retention of mouse Tmprss11d sequences (e.g., loss of coding exons 3-10 of mouse Tmprss11d). Table 3 sets forth the primers and probes that were used to confirm humanization of an endogenous Tmprss11d gene as described above (FIGS. 3A-3B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss11d locus after the deletion of the cassette is depicted in FIG. 3C, with the junction sequences shown at the bottom of FIG. 3C.

Selected ES cell clones (with or without the cassette) are used to implant female mice using the VELOCIMOUSE® method (see, e.g., U.S. Pat. No. 7,294,754 and Poueymirou et al. (2007), supra) to generate a litter of pups containing a humanized. Tmprss11d allele in the genome. Mice bearing a humanized Tmprss11d allele are again confirmed and identified by genotyping of DNA isolated from tail snips using a modification of allele assay (Valenzuela et al., supra) that detects the presence of the human TMPRSS11D gene sequences. Pups are genotyped and cohorts of animals heterozygous for the humanized Tmprss11d locus are selected for characterization. Animals homozygous for the humanized Tmprss11d locus are made by crossing heterozygous animals.

MAID7225 HumIn TMPRSS4 mice are homozygous for a humanized Tmprss4 gene in its genome and were generated as described in Example 2, The viral strains used in these studies included the historical A/Puerto Rico/08/1934 (H1N1) influenza A virus group 1 isolate and an in-house mouse-adapted A/Aichi/02/1968 (HA, NA) X-31 (H3N2) influenza. A virus group 2 isolate. All experiments were performed in 6-8 week-old male and female MAID7225 HumIn TMPRSS4 mice or WI littermates. Mice were challenged with 1150 plaque-forming units (PFUs) of A/Puerto Rico/08/1934 (H1NT) or 10,000 PFUs of A/Aichi/02/1968-X31 (H3N2). In these survival models, mice were challenged intranasally (IN) on day 0 post-infection (p.i.). Mice were weighed and observed daily up to day 14 p.i. and were sacrificed when they lost 20% of their starting weight. Results are reported as percent survival (Table 4).

TABLE 4

| Group ID | Number of mice per group | Percent survival (no. of surviving mice/total no. of mice in the group) |
| --- | --- | --- |
| Uninfected control (2 HumIn, 2 WT mice) | 4 | 100 (4/4) |
| WT TMPRSS4; H1_PR34 infected | 10 | 20 (2/10) |
| HumIn TMPRSS4; H1_PR34 infected | 8 | 25 (2/8) |
| WT TMPRSS4; H3_X31 infected | 9 | 11.1 (1/9) |
| HumIn TMPRSS4; H3_X31 infected | 8 | 25 (2/8) |

The survival of MAID7225 HumIn TMPRSS4 mice was compared to WT littermates after challenge with both severe Influenza A group 1 virus [A/Puerto Rico/08/1.934 (H1N1)] and a severe, mouse-adapted influenza A group 2 virus

TABLE 3

| Name | Primer | Sequence (5'-3') | SEQ ID NO |
| --- | --- | --- | --- |
| 7226mTU | Forward | TCCTCTCCAGACAAGAAAGCT | (SEQ ID NO: 61) |
|  | Probe (BHQ) | TCATAGCAGCTTTCAAATCCTAAACGTTGA | (SEQ ID NO: 62) |
|  | Reverse | TCGTGTGTAGCTGGTGAGTT | (SEQ ID NO: 63) |
| 7226mTD | Forward | CATGCGATCACAGGAGGAGATC | (SEQ ID NO: 64) |
|  | Probe (BHQ) | AATTGGGCCCGAAGCCAGATGC | (SEQ ID NO: 65) |
|  | Reverse | CGGAAGGCTTCTGTGACTTC | (SEQ ID NO: 66) |
| 7226hTU | Forward | GTCTCCCACTTCTGACATAATGAAC | (SEQ ID NO: 67) |
|  | Probe (BHQ) | CCCAGTGTTAACCCTACATCTGGTTCC | (SEQ ID NO: 68) |
|  | Reverse | TGGGAAGAGACTCTTGGACA | (SEQ ID NO: 69) |
| 7226hTD | Forward | ATGAGCTCCTAGTACAGCTAAAGTT | (SEQ ID NO: 70) |
|  | Probe (MGB) | ATGCATGATCATCTATGCGTCAGAGC | (SEQ ID NO: 71) |
|  | Reverse | TGCCCAGATGCAGGGAGTTAG | (SEQ ID NO: 72) |

Example 4. Evaluation of Group 1 and Group 2 Influenza A Viruses in MAID7225 HumIn vs. Wild-Type Tmprss4 Mice To validate the use of humanized Tmprss rodents as an animal model of infection, experiments were conducted to evaluate the survival of MAID7225 HumIn TMPRSS4 mice versus wild-type (WT) littermates in an influenza A group 1 and group 2 model of severe influenza infection.

Figure 4:
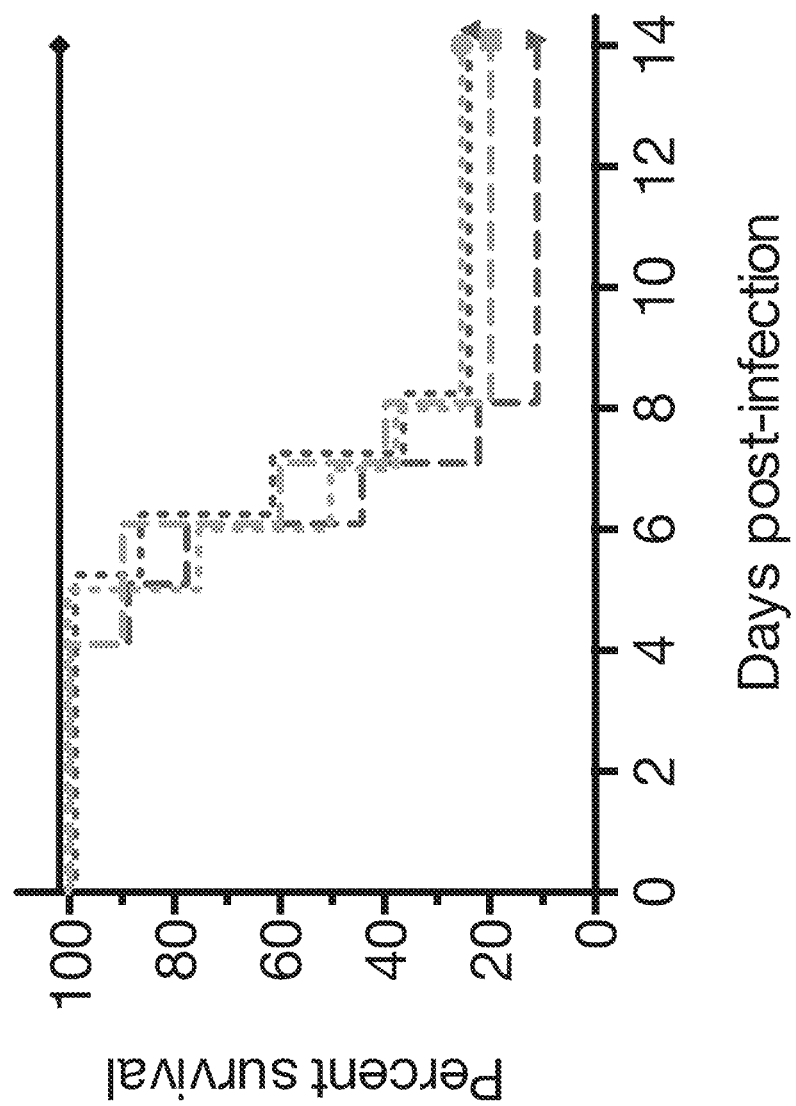
FIG. 4 depicts the results of an experiment showing that MAID7225 HumInTMPRSS4 mice do not differ in their susceptibility to challenge with high doses of severe influenza A H1N1 or severe, mouse-adapted H3N2. MAID7225 HumIn TMRPSS4 mice challenged with A/Puerto Rico/08/1934 (H1N1) (light gray circles, dotted line) showed similar survival rates compared to wild-type mice (light gray squares, dotted line). Likewise, MAID7225 HumIn TMRPSS4 mice challenged with A/Aichi/02/1968-X31 (H3N2) (dark gray triangles, dotted line) showed similar survival rates compared to wild-type mice (light gray inverse triangles, dashed line). Mice were infected IN on day 0 with either 1150 PFUs of A/Puerto Rico/08/1934 (H1N1) or 10,000 PFUs of A/Aichi/02/1968-X31 (H3N2). The control group included uninfected negative control MAID7225 HumIn TMPRSS4 and wild-type mice (black diamonds, solid line).

[A/Aichi/02/1968-X31 (H3N2)] (FIG. 4). Survival of MAID7225 HumIn TMPRSS4 mice was no different from wild-type mice with either the H1N1 challenge (25%; n=8 and 20%; n=10, respectively) or the H3N2 challenge (25%; n=8 and 11.1%; n=9, respectively).

The publications, websites and other reference materials referenced herein to describe the background of the invention and to provide additional detail regarding its practice are hereby incorporated by reference.

What is claimed is:

1. A rodent embryonic stem (ES) cell, comprising a replacement of a nucleotide sequence of an endogenous rodent Tmprss2 gene at an endogenous Tmprss2 locus with a nucleotide sequence of a human TMPRSS2 gene to form a humanized Tmprss2 gene,
wherein the humanized Tmprss2 gene is under control of the promoter of the endogenous rodent Tmprss2 gene at the endogenous Tmprss2 locus, and
wherein the humanized Tmprss2 gene encodes a humanized Tmprss2 protein that comprises (i) an ectodomain of the human TMPRSS2 protein encoded by the human TMPRSS2 gene, and (ii) a cytoplasmic and transmembrane portion encoded by the endogenous rodent Tmprss2 gene.

2. The rodent ES cell of claim 1, wherein the ectodomain comprises amino acid residues W106 to G492 of SEQ ID NO: 4.

3. The rodent ES cell of claim 1, wherein the nucleotide sequence of the human TMPRSS2 gene comprises coding exon 4 through the stop codon in coding exon 13 of the human TMPRSS2 gene.

4. The rodent ES cell of claim 3, further comprising the 3' UTR of the human TMPRSS2 gene.

5. The rodent ES cell of claim 4, wherein the humanized Tmprss2 gene comprises coding exons 1-2 of the endogenous rodent Tmprss2 gene, and coding exon 4 through coding exon 13 of the human TMPRSS2 gene.

6. The rodent ES cell of claim 5, wherein the humanized Tmprss2 gene comprises an exon 3 that comprises a 5' portion of coding exon 3 of the endogenous rodent Tmprss2 gene and a 3' portion of coding exon 3 of the human TMPRSS2 gene.

7. The rodent ES cell of claim 1, wherein the rodent ES cell is a mouse ES cell.

8. The rodent ES cell of claim 2, wherein the rodent ES cell is a mouse ES cell.

9. The rodent ES cell of claim 3, wherein the rodent ES cell is a mouse ES cell.

10. The rodent ES cell of claim 4, wherein the rodent ES cell is a mouse ES cell.

11. The rodent ES cell of claim 5, wherein the rodent ES cell is a mouse ES cell.

12. The rodent ES cell of claim 6, wherein the rodent ES cell is a mouse ES cell.

13. The rodent ES cell of claim 1, wherein the rodent ES cell is a rat ES cell.

14. The rodent ES cell of claim 2, wherein the rodent ES cell is a rat ES cell.

15. The rodent ES cell of claim 3, wherein the rodent ES cell is a rat ES cell.

16. The rodent ES cell of claim 4, wherein the rodent ES cell is a rat ES cell.

* * * * *